US012559766B2

(12) United States Patent
Dodo et al.

(10) Patent No.: US 12,559,766 B2
(45) Date of Patent: Feb. 24, 2026

(54) PEANUT WITH REDUCED ALLERGEN LEVELS

(71) Applicant: INGATEYGEN LLC, Elizabeth City, NC (US)

(72) Inventors: Hortense Dodo, Elizabeth City, NC (US); Koffi N'da Konan, Elizabeth City, NC (US)

(73) Assignee: INGATEYGEN LLC, Elizabeth City, NC (US)

( * ) Notice: Subject to any disclaimer, the term of this patent is extended or adjusted under 35 U.S.C. 154(b) by 0 days.

(21) Appl. No.: 16/634,220

(22) PCT Filed: Jul. 30, 2018

(86) PCT No.: PCT/US2018/044312
§ 371 (c)(1),
(2) Date: Jan. 27, 2020

(87) PCT Pub. No.: WO2019/027871
PCT Pub. Date: Feb. 7, 2019

(65) Prior Publication Data
US 2021/0010014 A1 Jan. 14, 2021

Related U.S. Application Data

(60) Provisional application No. 62/539,308, filed on Jul. 31, 2017.

(51) Int. Cl.
*C12N 15/82* (2006.01)
*C12N 9/22* (2006.01)
*C12N 15/63* (2006.01)

(52) U.S. Cl.
CPC ..... *C12N 15/8242* (2013.01); *C12N 15/8213* (2013.01); *C12N 15/8218* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 6,943,010 B1 * | 9/2005 | Dodo | C07K 14/415 |
| | | | 435/320.1 |
| 2005/0114924 A1 | 5/2005 | Dodo et al. | |
| 2016/0317677 A1 | 11/2016 | Bhatia et al. | |

OTHER PUBLICATIONS

Brazelton, 2015, "Enabling broad use of genome modification technologies to solve real world problems: a specific application in peanut", Graduate Theses and Dissertations 14795, p. 1-44.*
Anderson et al, 2015, Journal of Biotechnology, 211:56-65.*
Brazelton, 2015, "Enabling broad use of genome modification technologies to solve real world problems: a specific application in peanut", Graduate Theses and Dissertations, 14795:1-50.*
Dodo et al, 2008, Plant Biotechnology Journal, 6:135-145.*
Kumar et al, 2015, Journal of Experimental Botany, 66:47-57.*
Liu et al, 2016, Scientific Reports, 6:1-9.*
Zhou et al, 2014, Nucleic Acids Research, 42:10903-10914.*
Khamsi, 2016, "Is It Possible to Make a Less Allergenic Peanut?", The New York Times Magazine.*
Ramos et al, 2006, Mol Gen Genomics, 275:578-592.*
International Preliminary Report on Patentability corresponding to PCT/US2018/044312, dated Feb. 4, 2020, 8 pages.
International Search Report and Written Opinion corresponding to International Patent Application No. PCT/US2018/044312, mailed Jan. 2, 2019, 11 pages.
Stoutjesdijk et al. "hpRNA-Mediated Targeting of the Arabidopsis FAD2 Gene Gives Highly Efficient and Stable Silencing" Plant Physiol, 129(4):1723-1731(2002).
Brazelton "Enabling broad use of genome modification technologies to solve real world problems: A specific application in peanut" MS Thesis Dissertation, pp. 1-44, URL: https://lib.dr.iastate.edu/etd/14795, (2015).
Liu et al. "Sequence features associated with the cleavage efficiency of CRISPR/Cas9 system" Scientific Report, 6:19675, 9 pages 2015.
Shu et al. "The application of CRISPR/Cas9 in hairy roots to explore the functions of AhNFR1 and AhNFR5 genes during peanut nodulation" BMC Plant Biology, 20:417 15 pages 2020.
Stephan and Vieths "Development of a Real-Time PCR and a Sandwich ELISA for Detection of Potentially Allergenic Trace Amounts of Peanut (*Arachis hypogaea*) in Processed Foods" J. Agric. Food Chem., 52:3754-3760 2004.

* cited by examiner

*Primary Examiner* — Jason Deveau Rosen
(74) *Attorney, Agent, or Firm* — Barnes & Thornburg LLP

(57) ABSTRACT

Genetic constructs are provided to reduce or eliminate the allergenicity of peanuts. The constructs function by generating interfering RNA and/or by directing deletion using the CRISPR/Cas9 system. The constructs may be used in the production of genetically modified plants, plant parts and cells with reduced allergenicity.

14 Claims, 18 Drawing Sheets

Specification includes a Sequence Listing.

FIG. 1

A1 = Ara h 1; 190 nucleotide and contains parts of the epitope regions.

A2 = Ara h 2: 120 nucleotides and contains parts of the epitope regions.

A3 = Ara h 3: 100 nucleotides and contains parts of the epitope regions.

A6 = Ara h 6, boxed: 100 nucleotides and contains of the epitope regions.

A7 = Ara h 7, 100 nucleotides and contain parts of the epitope regions.

A8 = Ara h 8, 100 nucleotides and contains parts of the epitope regions.

A14 = Ara h 14, boxed: 150. Epitope region not identified.

A15 = Ara h 15:150 nucleotides. Epitope region not identified.

FIG. 2

Ara h 1- 400 nucleotides. Contains of the epitopes regions.

Ara h 2, boxed: 300 nucleotides, contains parts of the epitope region which is shared with Ara h 6 and Ara h 7.

Ara h 3: 350 nucleotides; Contains parts of the epitope regions.

Ara h 8: 150 nucleotides; Contains the epitope regions.

FIG. 3

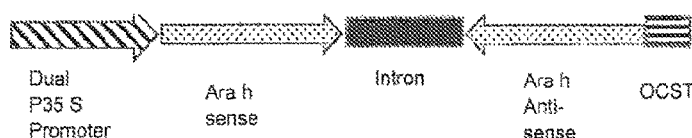

Dual P35 S Promoter    Ara h sense    Intron    Ara h Anti-sense    OCST

Dual P35S promoter aagcttggtccgatgtgagactttttcaacaaagggtaatatccggaaacctcctcggattccattgccagctatct
gtcactttattgtgaagatagtggaaaaggaaggtggctcctacaaatgccatcattgcgataaaggaaaggccatc
gttgaagatgcctctgccgacagtggtcccaaagatggacccccacccacgaggagcatcgtggaaaaagaagacgt
tccaaccacgtcttcaaagcaagtggattgatgtgatggtccgattgagactttttcaacaaagggtaatatccggaa
acctcctcggattccattgccagctatctgtcactttattgtgaagatagtggaaaaggaaggtggctcctacaaa
tgccatcattgcgataaaggaaaggccatcgttgaagatgcctctgccgacagtggtcccaaagatggacccccacc
cacgaggagcatcgtggaaaaagaagacgttccaaccacgtcttcaaagcaagtggattgatgtgatatctccactg
acgtaagggatgacgcacaatcccactatccttcgcaagacccttcctctatataaggaagttcatttcatttgaag
aggacaccggagactacgataatgaccgcgtcaacccgaagagaggaaggaggccgatgggaaccagctgaac Ara h 1 → cgaggagcgtgaaagagaaGCCCAGCATCTGCGAGCCACCACTGGGAACTCCAAGGAGACAGAAGATGCCAGAGCC
Ara h 2 → AGCTCGACAGGGCGAACCTGAGCGCCCTGCGAG*ggttacattgagacttggaacccaaacaaccagggttcgaatgcg*
Ara h 3 → *ccggcgtcgccctctcgcggcttagtcctccgcgcgccacgccct*TTGGTAGCTCTCCTTGCCCTCGTCCTGGTGGCAC
Ara h 6 → ACGCCTCCGCAATGAGGCGCGAGAGGGGGACTCATCAAGCTGCGAGA*tcagcgatcctagtagcatcctggcgcgcct*
Ara h 7 → *tcttgtcgtagcctccgcgacaagatgggatcccgatcgagggtccagagggt*tggagatc*AAGAGTGTTGAATCGTT*
Ara h 8 → *GAGGGAAACGGTGGTCCTGGAACCATCAAAGAAACTCACCATTGTCGAGGAT*Ggtaccccaattggtaaggaaataa

Intron Loop region ttattttattttttcctttagtataaaaatagttaagtgatgttaattagtatgattataataatatagttgttata
attgtgaaaaaataatttatataatatattgtttacataaacaacatagtaatgtaaaaaaatatgacaagtgatgtg
taagacgaagaagataaaagttgagagtaagtatattattttttaatgaatttgatcgaacatgtaagatgatatact
agcattaatatttgttttaatcataatagtaattctagctggtttgatgaattaaatatcaatgataaaatactata
gtaaaataagaataaaataaattaaaataatatattttttatgattaatagttttattatataattaaatatctatacc
attactaaatattttagtttaaaagttaataaatattttgttagaaattccaatctgcttgtaatttatcaataaac
aaaatattaaatacaagctaaagtaacaaataaatatcaaactaatagaaacagtaatctaatgtaacaaaacataa
tctaatgctaatataacaaagcgcaagatctatcattttatatagtattattttcaatcaacattcttattaatttc
taaataatacttgtagtttattaacttctaaatggattgactattaattaaatgaattagtcgaacatgaataaac
aaggtaacatgatagatcatgtcattgtgttatcattgatcttacatttggattgattacagttgggaaattgggtt Ara h 6 → cgaaatcgaTTAGGAGCTGTTACCACTCAAAGAAACTACCAAGGTCCTGGTGGCAAAGGGAGTTGCTAAGTTGTGAG
Ara h 7 → AActagagttgggagacctgggagctagcccctaggtagaacagcgcctcctgcttctttcccgcgcggtcctacga
Ara h 6 → tgatcctacgactAGAGCGTCGAACTACTCAGGGGGAGAGCGCGGAGTAACGCCTCCGCACACGGTGGTCCTGCTCC
Ara h 3 → CGTTCCTCTCGATGGTTtcccgcacgcgcgcctcctgattcgcgctctcccgctgcggccgcgtaagcttgggacca
Ara h 2 → acaaacccaaggttcagagttacattggCAGCGTCCCGGAGTCCAAGCGGGAGAGCTCGACCGAGACCGTAGAAGAC
Ara h 1 → AGAGGAACCTCAAGCGTGACGACGGAGCGTCTACGACCCGaagagaaagtgcgaggggagccaagtcgaccaaggggt
                  agccggaggaaggagagaagcccaactgccgccagtaatagcatcagaggcgcctctagagtcctgctttaatgaga

OCS Terminator catgcgagacgcctatgatcgcatgatatttgcttccaattctgttgtgcacgttgtaaaaacctgagcatgtgta
gctcagatccttaccgccggtttcggttcattctaatgaatatatcaccgcttactatcgtattttatgaataata
ttctccgttcaatttactgattgtacctactactactatatgtacaatattaaaatgaaaacaatatattgtgctgaa
taggtttatagcgacatctatgtatagagcgccacaataacaaacaattggtttttattattacaaatccaattttaa
aaaaagcgcgcagaacggtcaaacctaaagactgattacatataatcttattcaaattttcaaaaggccccaggggct
agtatctacgacaccacgagcggcgaactaataacgttcactgaaggggactccggttcccgccggcgcgcatggg
tgagattccttgaagttgagtattggccgtccgctctaccgaaagttacgggcaaccattcaaccggtccagcacgg
cggccgggtaaccgacttgctgccccgagaattatgcagcatttttttggtgtatgtgggcccaaatgaagtgcag
gtcaaaccttgacagtgacgacaaaatcgttgggcgcgggtccagggcgaattttgcgacaacatgtcgaggctcagcag
gacctgcaggcatgcaagctagcttactagtgatgcatattctatagtgtcacctaaatctgcggccgcgagctctt
t

FIG. 4

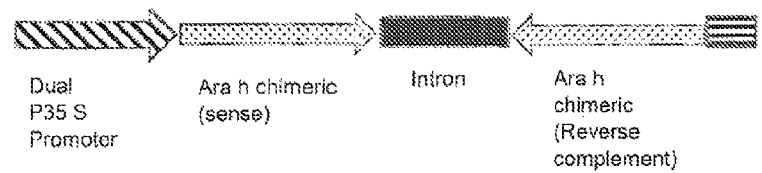

Dual
P35 S
Promoter

Ara h chimeric
(sense)

Intron

Ara h
chimeric
(Reverse
complement)

OCST

Dual P35S promoter aagcttggtccgatgtgagactttttcaacaaagggtaatatccggaaacctcctcggattccattgcccagctatct
gtcactttattgtgaagatagtggaaaaggaaggtggctcctacaaatgccatcattgcgataaaggaaaggccatc
gttgaagatgcctctgccgacagtggtcccaaagatggaccccacccacgaggagcatcgtggaaaaagaagacgt
tccaaccacgtcttcaaagcaagtggattgatgtgatggtccgattgagactttttcaacaaagggtaatatccggaa
acctcctcggattccattgcccagctatctgtcactttattgtgaagatagtggaaaaggaaggtggctcctacaaa
tgccatcattgcgataaaggaaaggccatcgttgaagatgcctctgccgacagtggtcccaaagatggaccccacc
cacgaggagcatcgtggaaaaagaagacgttccaaccacgtcttcaaagcaagtggattgatgtgatatctccactg
acgtaaggatgacgcacaatcccactatccttcgcaagacccttcctctatataaggaagttcatttcatttggag
aggacc

Sense Ara h cccggagactacgataatgacgcgccgtcaacccgaagagaggaaggaggccgatgggaaccagctgaac
cgagggagcgtgaaagagaaGCCCAGCATCTGCCAGGCAGCAGTGGGAACTCCAAGCAGACACGAAGATGCCAGAGCC
AGCTCGAGACGGCCGAACCTGAGGCCCTGCGAG*ggttacattgagacttggaacccaaacaaccagggttcgaatgcg
cggcggtcgccctctcgcgcttagtcctccgccgccacgcgcct*TTGGTAGCTCTCCTTGCCCTCGTCCTGGTGGCAC
ACGCCTCCGCAATGAGGCGCGAGAGGGGACTCATCAAGCTGCGAGA*tcagcatcctagtagcatcctgggcgccct
tcttgtcgtagcctccgcgacaagatgggatcccgatcgagggtccagagggttgagatc*AAGAGTGTTGAATCGTT
GAGGGAAACGGTGGTCCTGGAACCATCAAAGAAACTCACCATTGTCGAGGAT*ggtaccccaattggtaaggaaataa

Intron Loop region

*ttattttcttttttccttttagtatataaaatagttaagtgatgttaattagtatgattataataatatagttgttata
attgtgaaaaaataatttatataatatattgtttcacataaacaacatagtaatgtaaaaaaaatatgacaagtgatgtg
taagacgaagaagataaaagttgagagtaagtatattattttttaatgaatttgatcgaacatgtaagatgatatact
agcattaatatttgttttaatcataatagtaattctagctggtttgatgaattaaatatcaatgataaaatactata
gtaaaataagaataaataaattaaaataatatattttttttatgattaatagtttattatataattaaatatctatacc
attactaaatattttagtttaaaagttaataaatttttgttagaaattccaatctgcttgtaatttatcaataaaac
aaaatattaaataacaagctaaagtaacaaataatatcaaactaatagaaaacagtaatctaatgtaacaaaacataa
tctaatgctaatataacaaagcgcaagatctatcattttatatagtattattttcaatcaacattcttattaatttc
taaataataacttgtagttttattaacttctaaatggattgactattaattaaatgaattagtcgaacatgaataaac
aaggtaacatgatagatcatgtcattgtgttatcattgatcttacatttggattgattacagttgggaaattgggtt*
cgaaatcgat*TAGGAGCTGTTACCACTCAAAGAAACTACCAAGGTCCTGGTGGCAAAGGGAGTTGCTAAGTTGTGAG
AA*ctagagttgggagacctggagctagccctagggtagaacagcgcctcctgctgttcttccgcgcgggtcctacga
tgatcctacgact*AGAGCGTCGAACTACTCAGGGGGAGAGCGCGGAGTAACGCCTCCGCACACGGTGGTCCTGCTCC
CGTTCCTCTCGATGGTT*tcccgcaccgcgccgcctcctgattcgcgtctcccgctgcggcgcgctaagcttgggacca
acaaaccccaaggt*tcagagttacattgg*GAGCGTCCCGGAGTGCCAAGCGGGAGAGCCTCGACCGAGACCGTAGAACAC
AGAGGAACCTCAAGGGTGACGACGGAGCGTCTACGACCCGaagagaaagtgcgagggagcccaagtcgaccaagggt
agccggaggaaggagagaagcccaactgccgccagtaatagcatcagaggccctctagagtcctgctttaatgaga

OCS Terminator tatgcgagacgcctatgatcgcatgatatttgctttcaattctgttgtgcacgttgtaaaaaacctgagcatgtgta
gctcagatccttaccgcggtttcggttcattctaatgaatatatcacccgttactatcgtattttatgaataata
ttctccgttcaatttactgattgtaccctactacttatatgtacaatattaaaatgaaaaccaatatattgtgctgaa
taggtttatagcgacatctatgatagagcgccacaataacaacaattcgtttttattattacaaatccaatttttaa
aaaaagcggcaacaggtcaaacctaaaagactgattacataaatcttattcaaatttcaaaaaggccccagggget
agtatctacgacacccgagcggcgaactaataacgttcactgaagggaactccggttccccgccggtccagcacgg
cggccgggtaaccgacttgctgccccgagaattatgcagcattttttggtgtatgtgggccccaaatgaagtgcag
gtcaaaccttgacagtgacgacaaatcgttgggcgggtccaggcgcgaattttgcgacaacatgtcgaggctcagcag
gacctgcaggcatgcaagctagcttactagtgatgcatattctatagtgtcacctaaatctgcggcgcgagctctt
t

FIG. 5

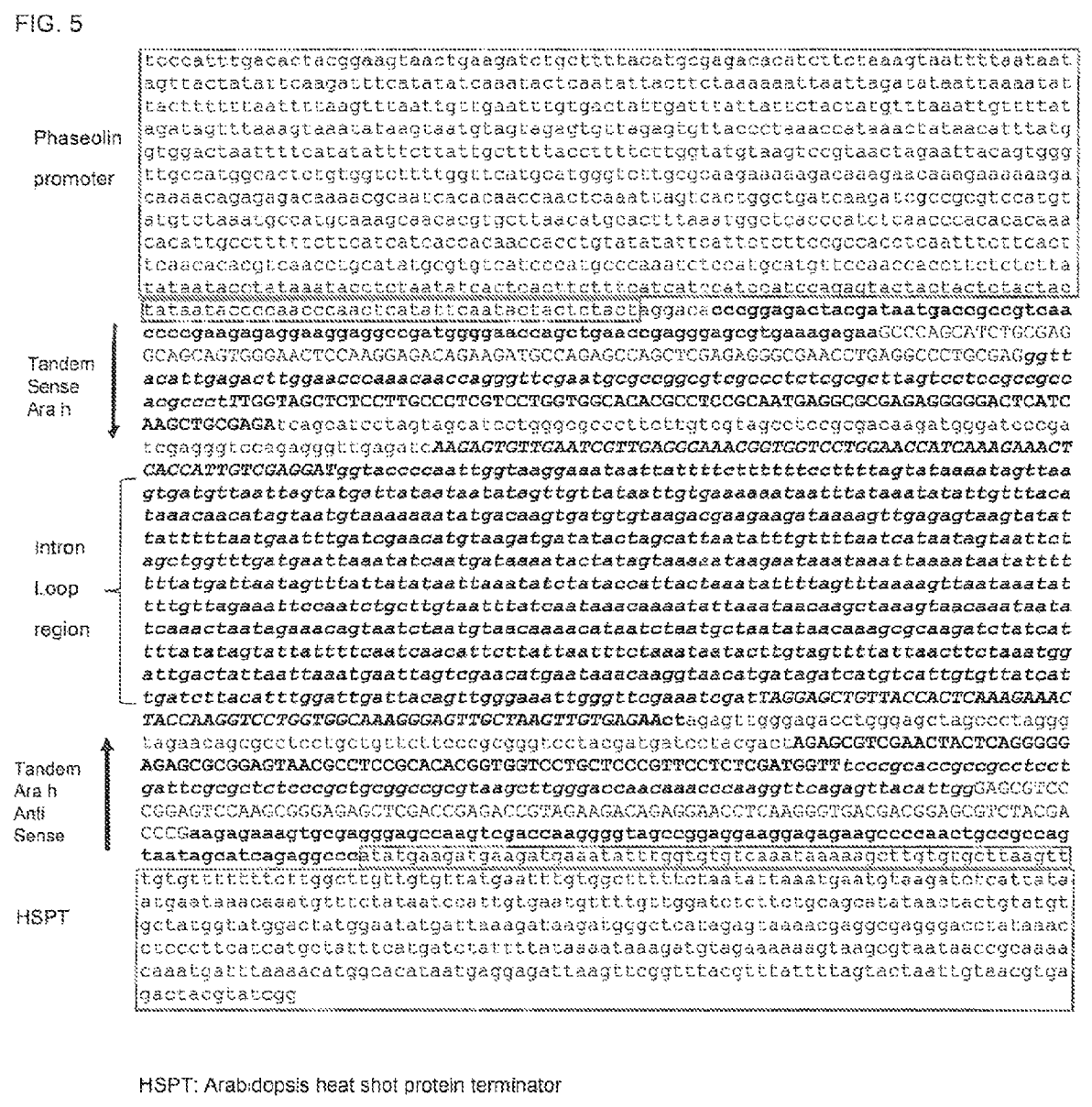

Phaseolin promoter

```
tcccatttgacactacggaagtaactgaagatctgcttttacatgcgagacacatcttctcaaagtaattttaataat
agttactatattcaagatttcatatatcaaatactcaatattacttctaaaaaattaattagatataattaaaatat
tacttttttaattttaagtttaattgttgaattttgtgactattgatttattattctactatgtttaaattgttttat
agatagtttaaagtaaatataagtaatgtagtagagtgttagagtgttaccctcaaccataaactataaacatttatg
gtggactaattttcatatatttcttattgcttttacctttcttggtatgtaagtccgtaactagaattacagtgggg
ttgccatggcactctgtggtcttttggttcatgcatgggtcttgcgcaagaaaaagacaaagaacaaagaaaaaga
caaaacagagagacaaaacgcaatcacacaaccaactcaaattagtcactggctgatcaagatcgccgcgtccatgt
atgtctaaatgccatgcaaagcaacacgtgcttaacatgcactttaaatggctcacccatctcaacccacacacaaa
cacattgcctttttcttcatcatcaccacaaccacctgtatatattcattctcttccgccacctcaatttcttcact
tcaacacagtcaacctgcatatgcgtgtcatcccatgcccaaatctccatgcatgttccaaccaccttctctctta
tataataccctataaatacctctaatatcactcacttcttTcatcatccatccatccagtactactactctactac
```

Tandem Sense Ara h

```
tatataacccaacccaactcatattcaatactactctactgggacaacccggagactacgataatgacgcgtcaa
ccccgaagagaggaaggaggccgatgggaaccagctgaacgagggagcgtgaaagagaaGCCCAGCATCTGCGAG
GCAGCAGTGGGAACTCCAAGGAGACAGAAGATGCCAGAGCCAGCTCGAGAGGGCGAACCTGAGGCCCTGCGAGggtt
acattgagacttggaacccaaacaaccagggttcgaatgcgccggcgtcgccctctcgcgcttagtcctccgcgcc
acgccctTTGGTAGCTCTCCTTGCCCTCGTCCTGGTGGCACACGCCTCCGCAATGAGGCGCGAGAGGGGGACTCATC
AAGCTGCGAGAtcagcatcctagtagcatcctgggcgcccttcttgtcgtagcctccgcgacaagatgggatcccga
tcgagggtccagaggaggttgagatcAAGAGTGTTCAATCCTTGCACGCAAACGGTGGTCCTGGAACCATCAAAGAAACT
CACCATTGTCGAGGATggtaccccaattggtaaggaaataattattttcttttttcctttttagtataaaatagttaa
```

Intron Loop region

```
gtgatgttaattagtagatttataataatatagttgttataattgtgaaaaaataatttataaatatattgtttaca
taaacaacatagtaatgtaaaaaaatatgacaagtgatgtgtaagacgaagaagataaaagttgagagtaagtatat
tattttttaatgaatttgatcgaacatgtaagatgatatactagcattaatatttgttttaatcataatagtaattct
agctggtttgatgaattaaatatcaatgataaaatactatagtaaaaataagaataaataaattaaaataatatttt
tttatgattaatagtttattatataattaaatatctataccattactaaatattttagtttaaaagttaataaatat
tttgttagaaattccaatctgcttgtaattatcaataaacaaaatattaaataacaagctaaagtaacaaataata
tcaaactaatagaaacagtaatctaatgtaacaaaacataatctaatgctaatataacaaagcgcaagatctatcat
tttatatagtattattttcaatcaacattcttattaatttctaaataactacttgtagtttattaacttctaaatgg
attgactattaattaaatgaattagtcgaacatgaataaacaaggtaacatgatagatcatgtcattgtgttatcat
tgatcttacatttggattgattacagttgggaaattgggttcgaaatcgatTAGGAGCTGTTACCACTCAAAGAAAC
TACCAAGGTCCTGGTGGCAAAGGGAGTTGCTAAGTTGTGAGAActagagttgggagacctggagctagcctaggg
```

Tandem Ara h Anti Sense

```
tagaacagcgcctcctgctgttcttccgcgcggtcctacgatgatcctacgactAGAGCGTCGAACTACTCAGGGGG
AGAGCGCGGAGTAACGCCTCCGCACACGGTGGTCCTGCTCCCGTTCCTCTCGATGGTTtcccgcaccgcgcctcct
gattcgcgctctcccgctgcggccgcgtaagcttgggaccaacaaacccaaggttcagagttacattggGAGCGTCC
CGGAGTCCAAGCGGGAGAGCTCGACCGAGACCGTAGAAGACAGAGGAACCTCAAGGGTGACGACGGAGCGTCTACGA
CCCGaagagaaagtgcgagggagccaagtcgaccaaggggtagccggaggaggagagaagccccaactgccgccag
taatagcatcagaggccatatgaagatgaagatgaaatatttgtgtgtcaaataaaaagcttgtgtgcttaagtt
```

HSPT

```
tgtgtttttctttggcttgttgtgtttatgaatttgtggcttttctaatattaaatgaatgtaagatctcattata
atgaataaacaaatgttctataatccattgtgaatgttttgttggatctcttctgcagcatataactactgtatgt
gctatggtatggactatggaatatgattaaagataagatgggctcatagagtaaaacgaggcgagggacctataaac
ctccttcatcatgctatttcatgatctatttatataaaataaagatgtagaaaaaagtaagcgtaataaccgcaaaa
caaatgatttaaaaacatggcacataatgaggagattaagttcggtttacgtttatttttagtactaattgtaacgtga
gactacgtatcgg
```

HSPT: Arabidopsis heat shot protein terminator

FIG. 6

Phaseolin promoter

Tandem Sense Ara h

Intron Loop region

Tandem Ara h Anti parallel

HSPT

```
tcccatttgacactacggaagtasctgaagatctgcttttacatgcgagacacatcttctaaagtaattttaataat
agttactatatccaagatttcatatatcaaatactcaatattacttctaaaaaattaattagatataattaaaatat
tacttttttaattttaagtttaattgttgaatttgtgactattgacttattattctactatgtttaaattgttttat
agatagtttaaagtaaatataagtaatgtagtagagtgttagagtgttaccctaaaccataaactataacattttatg
gtggactaattttcatatatttcttattgcttttacttttctttggtatgtaagtccgtaactagaattacagtggg
ttgccatggcactctgtggtctttggttcatgcatgggtcttgcgcaagaaaaagacaaagaacaaagaaaaaaga
caaaacagagagacaaaacgcaatcacacaaccaactcaaattagtcactggctgatcaagatcgccgcgtccatgt
atgtctaaatgccatgcaaagcaacacgtgcttaacatgcacctttaaatggctcacccatctcaacccacacacaaa
cacattgccttttttcttcatcatcaccacaacoacctgtatatattccttctcttccgccacctcaatttcttcact
tcaacacgtcaacctgcatatgcgtgtctatcccatgcccaaatctccatgcatgttccaaccacottctctctta
tataataccctataaataccctctaatatcactcacttctttcatcatccatccatccagactactactactctactac
```
```
tataataccccaacccaactcatattcaatactcactctactaggacaccggagactacgataatgacccgcgtcaa
ccccgaagagaggaaggaggccgatggggaaccagctgaaccgagggagcgtgaaagagaaGCCCAGCATCTGCGAG
GCAGCAGTCGGAACTCCAAGGAGACAGAAGATGCCAGAGCCAGCTCGAGAGGGCGAACCTGAGGCCCTGCGAGggtt
acattgagacttggaacccaaacaaccagggttcgaatgcgccggcgtcgccctctcgcgcttagtcctccgccgcc
acgcccTTGGTAGCTCTCCTTGCCCTCGTCCTGGTGGCACACGCCTCCGCAATGAGGCGCGAGAGGGGGACTCATC
AAGCTGCGAGAtcagcatcctagtagcatcctgggcgcccttcttgtcgtagcctccgcgacaagatgggatcccga
tcgaggtccagagggttgagatcAAGAGTGTTGAATCGTTGAGGGAAACGGTGGTCCTGGAACCATCAAAGAAACT
CACCATTGTCGAGGATggtaccccaattggtaaggaaataattattttcttttttcctttagtataaaatagttaa
gtgatgttaattagtatgattataataatatagttgttataattgtgaaaaaataatttataaatatattgtttaca
taaacaacatagtaatgtaaaaaaatatgacaagtgatgtgtaagacgaagaagataaaagttgagagtaagtatat
tattttttaatgaatttgatcgaacatgtaagatgatatactagcattaatatttgtttttaatcataatagtaattct
agctggtttgatgaattaaatatcaatgataaaatactatagtaaaataagaataaataaattaaaataatatttt
tttatgattaatagtttattatataattaaatatctataccattactaaatattttagttttaaaagttaataaatat
tttgttagaaattccaatctgcttgtaatttatcaataaacaaaatattaaataacaagctaagtaacaaataata
tcaaactaatagaaacagtaatctaatgtaacaaaacataatctaatgctaatataacaaagcgcaagatctatcat
tttatatagtattcattttcaatcaacattcttattaatttctaaataatacttgtagttttattaacttctaaatgg
attgactattaattaaatgaattagtcgaacatgaataaacaaggtaacatgatagatcatgtcattgtgttatcat
tgatcttacatttggattgattacagttgggaaattgggttcgaaatcgattcctcgacaatggtgagtttctttga
tggttccaggaccaccgtttccctcaacgattcaacactcttgatctcaacccctcggacccctgatcgggatccca
tcttgtcgcgggaggctacgacaagaaggggcgcccaggatgctactaggatgctgatctcgcagcttgatgagtcccc
ctctcgcgcctcattgcggaggcgtgtgccaccaggacagggcaaggagagctaccaaagggcgtgcgcggcggagga
ctaagcggcgagggcgacgcggcggcattggaacctggttgtttgggttccaagtctcaatgtaacccctcgcagg
gcctcaggttcgccctctcgagctggctctgcatcttctgtctccttggagttcccactgctgcctcgcagatgct
aggcttctctttcacgctcctcggttcagctggttccaatcggcctcctcctctctcggggttgacggcggtca
ttatcgtagtctccgctatgaagatgaagatgaaatatttggtgtgtcaaataaaaagcttctgtgcttaagttt
gtgtttttttcttggcttgttgtttatgaatttgtggctttttctaatattaaatgaatgtaagatctcattataa
tgaataaacaaatgtttctataatccattgtgaatgtttgttggatctcttctgcagcatataactactgtatgtg
ctatggtatggactatggaatatgattaaagataagatgggctcataagtaaaaacgaggcgagggacctataaacc
tccccttcatcatgctatttcatgatctatttataaaataaagatgtagaaaaaagtaagcgtaataaccgcaaaac
aaatgatttaaaacatggcacataatgaggagattaagttcggtttcacgtttatttagtactaattgtaacgtgag
actacgtatcgg
```

FIG. 7

Phaseolin promoter

```
tcgcatttgacactacggaagtaactgaagatctgcttttacatgcgagacacatcttctaaagtaattttaataat
agttactatattcaagatttcatatatcaaatactcaatattacttctaaaaaattaattagatataattaaaatat
tactttcttaattttaagtttaattgttgaatttgtgactattgatttattattctactatgtttaaattgttttat
agatagtttaaagtaaatataagtaatgtagtagagtgttagagtgttaccctaaacctaaaactataacatttatg
gtggactaattttcatatatttcttattgcttttacctttttcttggtatgtaagtccgtaactagaattacagtggg
ttgccatggcactctgtggtcttttggttcatgcatgggtcttgcgcaagaaaaagacaaagaacaaagaaaaaaga
caaaacagagagacaaaacgcaatcacacaaccaactcaaattagtcactggctgatcaagatcgccgcgtccatgt
atgtctaaatgccatgcaaagcaacacgtgttaacatgacttttaaatggctcacccatctcaacccacacacaaa
cacattgccttttttcttcatcatcacaacaactgtatatactcattctcttccgcacctcaattcttcact
tcaacacacgtcaacctgcatatgcgtgtcatccatgcccaaatctccatgcatgttccaacacctctctctta
tataataccctataaatacctctaatatcactcacttcttttcatcatccatccatccagagtactactactctactac
```

Ara h 5
Ara h 9
Ara h 10
Ara h 11
Ara h 12
Ara h 13
Ara h 14
Ara h 15
Intron
Loop region

```
tataatacccaacccaactcatattcaatactactctactGCTGTCATTCGAGGGAAGAAGGGTCCTGGTGGTGTT
ACCATTAAGAAGACGAATCAGGCGTTGATCATCGGAATCTACGATGAGCCGATGACTgcctctaaccaaggcaacgc
cgccgccctccctggaagatgcggtgtcagcattccttacaagatcagcacatccaccaacATCGGTGCCGGACCAG
CTGCAATGGCCAAAGCACCCGCATGGCTGACGTGGCCGGTTACGTTGGACAGAAGACCGAACGATGcacttcataattaa
ttaataacatggctgaagcaactctactacggcggcggcgccaacgccaagagcaaccaaggtccaccoTGGTGAAAACA
GAGGCAAAGCTATGCAACCACCTGGCAGATACATACAGAGGACCATGCTTTACCAATGCAAGCTGCCGATGATCATTG
CAtcattctctttcttgctcaggaatatgcgtggagggaaaggagtgttttgaacctaagtgacaaattcaagggac
cgtgtttgggttcaaagaaCGCGTCGACGTTCCACGCCCGCGGCTACGATGTTAGTGGTGGTGGTATTAAGACTCTTC
TCCCCGAGAGAGGTCCGTCCACCTCTCAAATCtaccattatgtctgatcaaacaaggacaggctatggaggaggagg
gtccctatggatcatcctatggtggaggaggcacctatggttcatcggtaccccaattggtaaggaaataattatttt
cttttttccttttagtatataaaatagttaagtgatgttaattagtatgattataataatatagttgttataattgtga
aaaaataattatataaatatattgtttacataaacaacatagtaatgtaaaaaatatgcaagtgatgtgtaagacg
aagaagataaaaagttgagagtaagtatattattttttaatgaatttgatcgaacatgtaagatgatatactagcatta
atatttgtttttaatcataatagtaattctagctggtttgatgaattaaatatcaatgataaaatactatagtaaaa
taagaataaataaattaaaataatatattttttttatgattaatagtttattatataattaaatatctataccattacta
aatattttagttbaaaagttaataaaatattttgttagaaattccaatctgcttgtaatttatcaataaacaaaatat
taaataacaagctaaagtaacaaataatatcaaactaatagaaacagtaatctaatgtaacaaaacataatctaatg
ctaatataacaaagcgcaagatctatcattttatatagtattattttcaatcaacattcttattaatttctaaataa
tacttgtagttttattaacttctaaatggattgactattaattaaatgaattagtcgaacatgaataaaacaaggtaa
catgatagatcatgtcattgtgttatcttcttacattggattgactacagttgggaaattgggttcgaaatc
```

Tandem Ara h Anti parallel

```
gatgatgaaccataggtgcctcctccaccataggatgatccataggaccctcctcctccatagcctgtcctttgattgatcagacat
aatggtagatttgagaggtggagggacctctctcgggagaagagtcttaatacaccaacactaacatcgtagccgcggcgtgga
acgtcgacgcgttcttcgaaccaacacgtccttgaattgtcacttaggttcaaacactcctttccctccacgccatattcct
gagcaagaaagagaatgatgcaatgatcatcgcagcttgcattggtaaagcatggtccttgtatgtatctgccaggtggttgcat
agtttgcctctgtttttcaacagggtggacttggttgctcttggcgttggcggccgcgctagtagagtgcttcagccatgttacta
ttaattatgaagtgcatcctcgtcttctgtccaacgtaaccggccacgtcagccatgcggtgctttggccattccagctgctcggg
cacccgatgttggtggatgtgctgatcttgtaaggaatgctgacaccgcatcttccagcgaggcggcggcgttgccttggttagag
gcagtcatcggctcatcgtagattccgatgatcaacgcctgattcgtcttcttaatggtaaccaccaggacccttcttccctcg
aatgacagtaaccctcgcagggctcaggttcgccctctcgagctggctctggcatcttctgtctccttggagttccc
```

HSPT

```
actgctgcctcgcagatgctgggcttctcttcacgctccctaggttaagctggttccatcggcctcctccctcc
ttcggggttgacggcggtcattatcgtagtctccggatatgaagatgtaagatgaaatattttgytgtgtcaaataaa
aagcttgtgtgcttaagtttgtgttttttctttcttggcttgttgtgttatgaatttgtggcttttttctaatattaaatg
aatgtaagatctcattataatgaataaacaaatgtttctataatccattgtgaatgttttgttggatctcttctgca
gcatataactactgtatgtgctatggtatggactatggaatatgattaaagataagatgggctcatagagtaaaacg
aggcgaggggacctataaacctcccttcatcatgctatttcatgatctatttttataaaataaagatgtagaaaaagt
tagcgtaataaccgcaaaacaaatgatttaaaacatggcacataatgaggagattaagttcggttttacgtttatttt
agtactaattgtaacgtcgagactacgtatcgg
```

FIG. 8

Dual

35 S promoter

Ara h 1

Ara h 2

Ara h 3

Intron

Ara h 3

Ara h 2

Ara h 1

OCST

Sense

Anti Sense

FIG. 9

```
ccaaagcacatacttatcgatttaaatttcatcgaagagagattaatatcgaataatcatatacatactttaaatacat
aacaaatttttaaatacatatatctcggtatataattaattttttaaagtcatgaagtatgtatcaaatacacatatgg
aaaaaattaactattcataatttaaaaaatagaaaagatacatctagtgaaattaggtgcatgtatcaaatacatta
ggaaaaggcatatatcttgatctagataattaacgattttgatttatgtataatttccaaatgaaggtttatatct
acttcagaaataacaatatactttctatcagaacattcaacaaagcaacaaccaactagagtgaaaaatacacattgt
tctctagacatacaaaattgagaaaagaatctcaaaatttagagaaacaaatctgaatttctagaagaaaaaataa
ttatgcactttgctattgctcgaaaaataaatgaaagaaattagacttttttaaaagatgttagactagatatactc
aaaagctattaaaggagtaatattcttcttacattaagtatttagttacagtcctgtaattaaagacacatttttag
attgtatctaaacttaaatgtatctagaatacatatatttgaatgcatcatatacatgtatccgacacaccaattct
cataaaaaacgtaatatcctaaactaatttatccttcaagtcaacttaagcccaatatacattttcatctctaaagg
cccaagtggcacaaaatgtcaggcccaattacgaagaaaagggcttgtaaaaccctaataaagtggcactggcagag
cttacactctcattccatcaacaaagaaaccctaaaagccgcagcgccactgatttctctcctccaggcgaag
```

FIG. 10

```
atatgaagatgaagatgaaatatttggtgtgtcaaataaaaagcttgtgtgcttaagttgtgtttttttcttggct
tgttgtgttatgaatttgtggcttttctaatattaaatgaatgtaagatctcattataatgaataaacaaatgttt
ctataatccattgtgaatgttttgttggatctcttctgcagcatataactactgtatgtgctatggtatggactatg
gaatatgattaaagataagatgggctcatagagtaaaacgaggcgagggacctatataacctcccttcatcatgctat
ttcatgatctattttataaaataaagatgtagaaaaaagtaagcgtaataaccgcaaaacaaatgatttaaaacatg
gcacataatgaggagattaagttcggtttacgtttatttttagtactaattgtaacgtgagctacgtatcgg
```

FIG. 11

```
aagcttcgttgaacaacggaaactcgacttgcttcgcacaatacatcatttcttcttagctcattttcttcttct
tcgttcatacagttttttttctgtttatcagcttacatttcttgaacgtagcttcgtttcttcttttaacttt
ccattcggagttttgtatcttgttcatagttgtccaggattagaatgattaggcatcgaacttcaagaattt
gattgaataaacatcttcattcttagatatgaagataatcttcaaaaggccctggaatctgaaagaagagaag
caggccatttatgggaaagaacaatagtatttcttcatataggcccatttaagttgaaaacaatcttcaaaagtc
ccacatcgcttagataagaaacgaagctgagtttatatcagctagagtcgaagtagtgatt
```

FIG. 12

```
gttttagagctagaaatagcaagttaaaataaggctagtccgttatcaacttgaaaaagtggcaccgagtcggtgct
tttttt
```

Ara h 3 sequence

FIG. 19

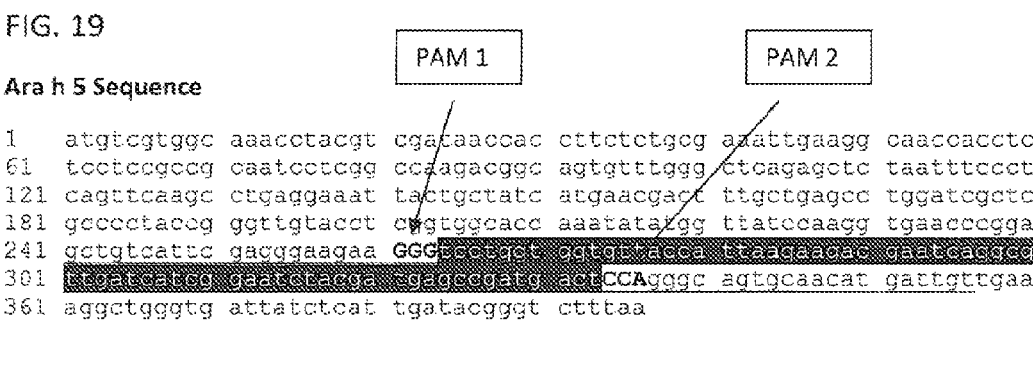

Ara h 5 Sequence

```
1   atgtcgtggc aaacctacgt cgataaccac cttctctgcg agaattgaagg caaccacctc
61  tcctccgccg caatcctcgg ccaagacggc agtgtttggg ctcagagctc taatttccct
121 cagttcaagc ctgaggaaat tactgctatc atgaacgact ttgctgagcc tggatcgctc
181 gccctaccg ggttgtacct cgtggcacc aaatatagg ttatccaagg tgaacccgga
241 gctgtcattc gacggaagaa GGGcccctgct ggtgtacca ttcaagaacac gaatcaacgc
301 tcgatcattcg gaatctacga ctgacccgatg actCCAgggc agtgcaacat gattgttgaa
361 aggctgggtg attatctcat tgatacgggt ctttaa
```

FIG. 20

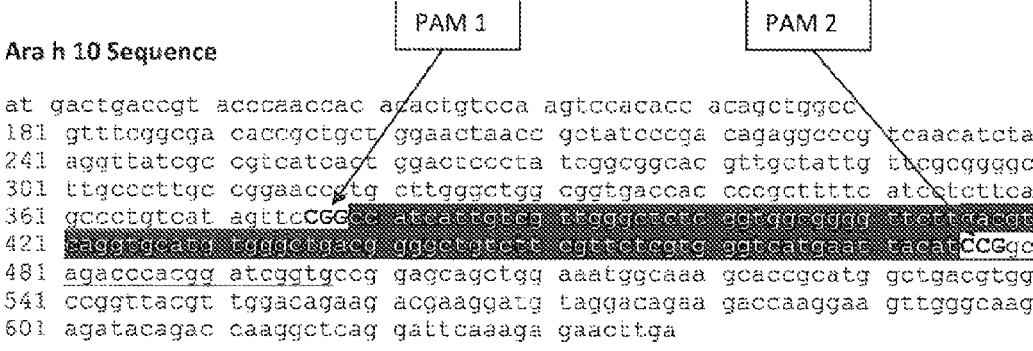

Ara h 9 Sequence

```
1   atggcaagcc tcaagtttgc atttgtgatg cttgtgtgca tggccatggt gggagcacca
61  atggtgaatg ccatatcatg tggccaagtg aacagtgccc tagcaccatg catcccttc
121 ctcacaaagg gtggagctcc ttctccggct tgttgcagcg gagttagagg ccttctcggt
181 gctttaagaa ccacccgcaga cggccaggcc gcctgtaact gcctcaaagc cgctgccggt
241 tcccttcgtg gcctcaacca AGGcaaccacc ggcgccctcc ctggaagatg cggtgtcacc
301 atcctcaca agatctacga ctcaCCAac tgtgctacca ttaagttctg a
```

FIG. 21

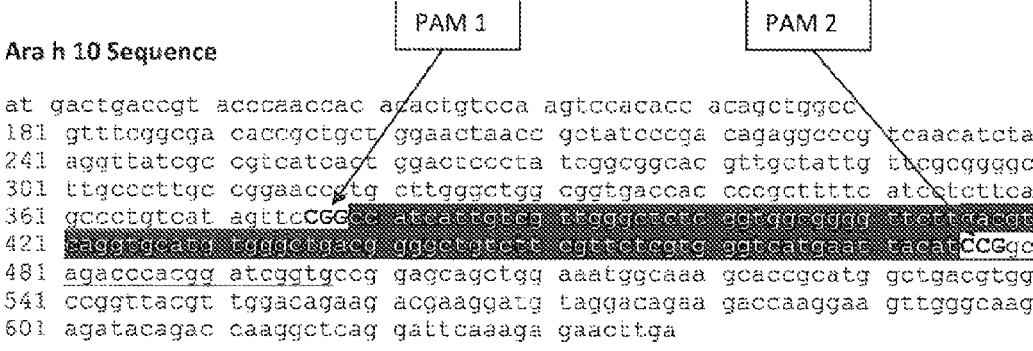

Ara h 10 Sequence

```
at  gactgaccgt acccaaccac agactgtcca agtccacacc acagctggcc
181 gtttcggcga cacegctgct ggaactaacc gctatcccga cagaggcccg tcaacatcta
241 aggttatcgc cgtcatcagt ggactcccta tcggcggcac gttgctattg ttcgcggggc
301 ttgcccttgc cggaaccgtg cttgggctgg cggtgaccac cccgcttttc atcgtcttca
361 gccctgtcat agttCGGcc atcattgtcg ctggcctcat cgtcggcgtgg ctcttcatcgt
421 ctcgtcgcatc tcggctgacg ggctgtctctt cgttctcgtg ggtcatgaac tacatCCGgc
481 agaccacgg atcggtgccg gagcagctgg aaatggcaaa gcaccgcatg gctgacgtgg
541 ccggttacgt tggacagaag acgaaggatg taggacagaa gaccaaggaa gttgggcaag
601 agatacagac caaggctcag gattcaaaga gaacttga
```

FIG. 33

*Ara h 2* taaccaccacaacaacaATGgccaagctcaccatactagtagccctcgcccttttcctcctc
gctgccacgcatctgcgAGGcagcagtgggaactccaaggagacagaagatgccagagcca
gctcgagagggcgaacctgaggc<u>CCTGCGAGCAACATCTCATGCAG</u>aagatccaacg<u>tgacg</u>
<u>aggattcatatgaacGGG</u>acccgtacagccctagtcaggatccgtacagccctagtccatat
gatcggagaggcgctggatcctctcagcaccaagagaggtgttgcaatgagctgaacgagtt
tgagaacaaccaaaggtgcatgtgcgaggcattgcaacagatcatggagaaccagagcgata
ggttgcaggggaggcaacaggagcaacagttcaagagggagctcaggaacttgcctcaacag
tgcggccttagggcaccacagcgttgcgacttggacgtcgaaagtggcggcagagacagata
cTAA*acacctatctcaaaaaaagaaaagaaaagaaaagaaaatagcttatatataagctatt*
*atctatggttatgttagttttggtaataatgaagatcatcactatatgaatgtgttgatcgt*
*gttaactaaggcaagcttaggttatatgagcacctttagagtgcttttatggcgttgtctat*
*gttttgttgctg*
SEQ ID NO:275

Underlined sequences; sgRNA 1 and sgRNA 2 with PAM
Bold ATG and TGA; Start and stop codons respectively
Bold *Italic*; 5`and 3`untranslated regions

SEQUENCE LISTING

```
<160> NUMBER OF SEQ ID NOS: 281

<210> SEQ ID NO 1
<211> LENGTH: 490
<212> TYPE: DNA
<213> ORGANISM: Arachis hypogaea

<400> SEQUENCE: 1
acagaagatg ccagagccag ctcgagaggg cgaacctgag gccctgcgag caacatctca      60
tgcagaagat ccaacgtgac gaggattcat atgaacggga cccgtacagc cctagtcagg     120
atccgtacag ccctagtcca tatgatcgga gaggcgctgg atcctctcag caccaagaga     180
ggtgttgcaa tgagctgaac gagtttgaga acaaccaaag gtgcatgtgc gaggcattgc     240
aacagatcat ggagaaccag agcgataggt tgcagggag gcaacaggag caacagttca     300
agagggagct caggaacttg cctcaacagt gcggccttag ggcaccacag cgttgcgact     360
tggacgtcga aagtggcggc agagacagat actaaacacc tatctcaaaa aagaaaaga     420 aaagaaaaga aaatagctta tatataagct attatctatg gttatgttta gttttggtaa     480
taataaagat                                                             490

<210> SEQ ID NO 2
<211> LENGTH: 2032
<212> TYPE: DNA
<213> ORGANISM: Arachis hypogaea

<400> SEQUENCE: 2
aataatcata tatattcatc aatcatctat ataagtagta gcaggagcaa tgagagggag      60
ggtttctcca ctgatgctgt tgctagggat ccttgtcctg gcttcagttt ctgcaacgca     120
tgccaagtca tcaccttacc agaagaaaac agagaacccc tgcgcccaga ggtgcctcca     180
gagttgtcaa caggaaccgg atgacttgaa gcaaaaggca tgcgagtctc gctgcaccaa     240
gctcgagtat gatcctcgtt gtgtctatga tcctcgagga cacactggca ccaccaacca     300
acgttcccct ccagggggagc ggacacgtgg ccgccaaccc ggagactacg atgatgaccg     360
ccgtcaaccc cgaagagagg aaggaggccg atggggacca gctggaccga gggagcgtga     420
aagagaagaa gactggagac aaccaagaga agattggagg cgaccaagtc atcagcagcc     480
acggaaaata aggcccgaag gaagagaagg agaacaagag tggggaacac caggtagcca     540
tgtgagggaa gaaacatctc ggaacaaccc tttctacttc ccgtcaaggc ggtttagcac     600
ccgctacggg aaccaaaacg gtaggatccg ggtcctgcag aggtttgacc aaaggtcaag     660
gcagtttcag aatctccaga atcaccgtat tgtgcagatc gaggccaaac ctaacactct     720
tgttcttccc aagcacgctg atgctgataa catccttgtt atccagcaag ggcaagccac     780
cgtgaccgta gcaaatggca ataacagaaa gagctttaat cttgacgagg gccatgcact     840
cagaatccca tccggtttca tttcctacat cttgaaccgc catgacaacc agaacctcag     900
agtagctaaa atctccatgc ccgttaacac acccggccag tttgaggatt tcttcccggc     960
gagcagccga gaccaatcat cctacttgca gggcttcagc aggaatacgt tggaggccgc    1020
```

```
cttcaatgcg gaattcaatg agatacggag ggtgctgtta gaagagaatg caggaggtga    1080
gcaagaggag agagggcaga ggcgatggag tactcggagt agtgagaaca atgaaggagt    1140
gatagtcaaa gtgtcaaagg agcacgttga agaacttact aagcacgcta aatccgtctc    1200
aaagaaaggc tccgaagaag agggagatat caccaaccca atcaacttga gagaaggcga    1260
gcccgatctt tctaacaact ttgggaagtt atttgaggtg aagccagaca agaagaaccc    1320
ccagcttcag gacctggaca tgatgctcac ctgtgtagag atcaaagaag gagctttgat    1380
gctcccacac ttcaactcaa aggccatggt tatcgtcgtc gtcaacaaag gaactggaaa    1440
ccttgaactc gtggctgtaa gaaaagagca acaacagagg ggacggcggg aagaagagga    1500
ggacgaagac gaagaagagg agggaagtaa cagagaggtg cgtaggtaca cagcgaggtt    1560
gaaggaaggc gatgtgttca tcatgccagc agctcatcca gtagccatca acgcttcctc    1620
cgaactccat ctgcttggct tcggtatcaa cgctgaaaac aaccacagaa tcttccttgc    1680
aggtgataag gacaatgtga tagaccagat agagaagcaa gcgaaggatt tagcattccc    1740
tgggtcgggt gaacaagttg agaagctcat caaaaaccag aaggaatctc actttgtgag    1800
tgctcgtcct caatctcaat ctcaatctcc gtcgtctcct gagaaagagt ctcctgagaa    1860
agaggatcaa gaggaggaaa accaaggagg gaagggtcca ctcctttcaa tttttgaaggc    1920 ttttaactga gaatggaggc aacttgttat gtatcgataa taagatcacg cttttgtact    1980
ctactatcca aaaacttatc aataaataaa aacgtttgtg cgttgtttct cc            2032
```

```
<210> SEQ ID NO 3
<211> LENGTH: 682
<212> TYPE: DNA
<213> ORGANISM: Arachis hypogaea

<400> SEQUENCE: 3
gacacagacc aactggtaat ggtagcgacc ggcgctcagc tggaattcgc ggccgccaat      60
ggccaagctc accatactag tagccctcgc ccttttcctc ctcgctgccc acgcatctgc     120
gaggcagcag tgggaactcc aaggagacag aagatgccag agccagctcg agagggcgaa     180
cctgaggccc tgcgagcaac atctcatgca gaagatccaa cgtgacgagg attcatatga     240
acgggacccg tacagcccta gtcaggatcc gtacagccct agtccatatg atcggagagg     300
cgctggatcc tctcagcacc aagagaggtg ttgcaatgag ctgaacgagt ttgagaacaa     360
ccaaaggtgc atgtgcgagg cattgcaaca gatcatggag aaccagagcg ataggttgca     420
ggggaggcaa caggagcaac agttcaagag ggagctcagg aacttgcctc aacagtgcgg     480
ccttagggca ccacagcgtt gcgacttgga cgtcgaaagt ggcggcaggc ggccgcgaat     540
tccgccgata ctgacgggct ccaggagtcg tcgccaccaa tccccatatg gaaaccgtcg     600
atattcagcc atgtgccttc ttccgcgtgc agcagatggc gatggctggt ttccatcagt     660
tgctgttgac tgtagcggct ga                                            682
```

```
<210> SEQ ID NO 4
<211> LENGTH: 1853
<212> TYPE: DNA
<213> ORGANISM: Arachis hypogaea

<400> SEQUENCE: 4
atggctaagc ttcttgagct ttcttttttgc ttttgctttc tagttctggg agctagcagc      60
atctccttca ggcagcagcc ggaggagaat gcgtgccagt tccagcgcct caatgcgcag     120
```

-continued

```
agacctgaca accgcattga atcggagggc ggttacattg agacttggaa ccccaacaac    180
caggagttcg aatgcgccgg cgtcgccctc tctcgcttag tcctccgccg caacgccctt    240
cgtaggcctt tctactccaa tgctccccag gagatcttca tccagcaagg aaggggatac    300
tttgggttga tattccctgg ttgtcctagc acatatgaag agcctgcaca acaaggacgc    360
cgatatcagt cccaaagacc accaagacgt ttgcaagaag aagaccaaag ccaacagcaa    420
caagatagtc accagaaggt gcaccgtttc aatgagggtg atctcattgc agttcccacc    480
ggtgttgctt tctggctgta caacgaccac gacactgatg ttgttgctgt ttctcttact    540
gacaccaaca acaacgacaa ccagcttgat cagttcccca ggagattcaa tttggctggg    600
aaccacgagc aagagttctt aaggtaccag caacaaagca gacaaagcag acgaagaagc    660
ttaccatata gcccatacag cccgcatagt cggcctagac gagaagagcg tgaatttcgc    720
cctcgaggac agcacagccg cagagaacga gcaggacaag aagaagaaga cgaaggtgga    780
aacatcttca gcggcttcac gccggagttc ctgaacaag ccttccaggt tgacgacaga     840
cagattgtgc aaaatctgtg gggcgagaac gagagtgaag aagagggagc cattgtgacg    900
gtgaggggag gcctcagaat cttgagccca gatggaacga gaggtgccga cgaagaagag    960
gaatacgatg aagatcaata tgaataccat gaacaggatg gaaggcgtgg caggggaagc   1020
agaggcgggg ggaatggtat tgaagagacg atctgcaccg catgtgttaa aaagaacatt   1080
ggtggaaaca gatcccctca catctacgat cctcagcgct ggttcactca aaactgccac   1140
gatctcaacc ttctaatcct taggtggctt ggacttagtg ctgaatatgg aaatctctac   1200
aggaatgcat tgtttgtccc tcactacaac accaacgcac acagcatcat atatgcattg   1260
aggggacggg ctcacgtgca agtggtggac agcaacggca acagagtgta cgacgaggag   1320
cttcaagagg gtcacgttct tgtggtgcca cagaacttcg ccgtggctgg gaagtcccag   1380
agcgagaact tcgaatacgt ggcattcaag acagattcaa ggcccagcat agccaacttt   1440
gccggtgaaa actccttcat agataacctg ccggaggagg tggttgcaaa ttcatatggc   1500
ctcccaaggg agcaggcaag gcagcttaag aacaacaacc ccttcaagtt cttcgttcca   1560
ccttttcagc agtctccgag ggctgtggct taaaaacgac cagtatcttt tgcaagcgtg   1620
ttatccacta acataacttt ttgccacaaa tgaataatat aataataaga agaataatgt   1680
agttttaatt tttagtatga ataagaatac aaagggcat tgatgccttt ttgtttaaga    1740
tcggaatgta acatatgtgc aatgagcaga tatggagaaa accttttgcg ggaaaaacat   1800
gaataataaa agaagttatg gtctcacgca aaaaaaaaaa aaaaaaaaaa aaa          1853
```

```
<210> SEQ ID NO 5
<211> LENGTH: 743
<212> TYPE: DNA
<213> ORGANISM: Arachis hypogaea

<400> SEQUENCE: 5
agaaagagaa gacaagatgt cgtggcaaac ctacgtcgat aaccaccttc tctgcgaaat      60
tgaaggcgac cacctctcct ccgccgcaat cctcggccaa gacggcggtg tttgggctca     120
gagctctcat ttccctcagt tcaagcctga ggaaattact gctatcatga cgactttgc     180 tgagcctgga tcgctcgccc ctaccgggtt gtacctcggt ggcaccaaat acatggttat    240
ccaaggtgaa cccggagcta tcattccagg gaagaagggt cctggtggtg ttaccattga    300
gaagacgaat caggcgttaa tcatcggaat ctacgataag ccaatgactc cggggcagtg    360
caacatgatt gttgaaaggc tgggtgatta tctcattgat acgggtcttt aagtcctctt    420
```

-continued

```
tgttatttct tgttatctgc ttgcttattt cactggctcc tatacgaggc ttcgcatcga    480
tgtgccaaga gaatgctcga ttgtagtgta ataatattaa ttgatgggta ttcaaaagtc    540
atgggatctg cgtctaggga agaagttatg gtgcttgaga agtgaatgat aactatcatc    600
tctgttgttg tgcttttttag cgggtatctg tatacaattt acaagtggtt ttaatgctgt    660
gggcataaat gggcattaaa aaaaaaaaaa aaaaaaaaaa aaaaaaaaaa aaaaaaaaaa    720
aaaaaaaaaa aaaaaaaaaa aaa                                             743
```

```
<210> SEQ ID NO 6
<211> LENGTH: 438
<212> TYPE: DNA
<213> ORGANISM: Arachis hypogaea

<400> SEQUENCE: 6
atggccaagt ccaccatcct ggtagctctc cttgccctcg tcctggtggc acacgcctcc     60
gcaatgaggc gcgagagggg gagacagggg gactcatcaa gctgcgagag gcaggtagac    120
agggttaacc tcaagccctg cgagcagcac ataatgcaga ggatcatggg cgagcaagag    180
cagtacgact cctacgatat taggagtact cgatcctccg accagcaaca gaggtgctgc    240
gatgagctga cgagatgga gaacacacag agatgcatgt gcgaggcatt gcagcagata    300
atggagaacc agtgcgatag gttgcaggac aggcaaatgg tgcagcagtt caagagagag    360
ctcatgaact tgccccaaca gtgtaacttt agggcaccac agcgttgcga tttggacgtg    420
agtggcggca gatgctag                                                   438
```

```
<210> SEQ ID NO 7
<211> LENGTH: 712
<212> TYPE: DNA
<213> ORGANISM: Arachis hypogaea

<400> SEQUENCE: 7
atgatggtca agctcagcat cctggtagcc ctcctgggcg cccttcttgt cgtagcctcc     60
gcgacaagat gggatcccga tcgagggtcc agagggtcga gatgggacgc accgagcaga    120
ggggatgacc agtgccagag gcagttgcag agggcaaacc tgaggccctg tgaggaacac    180
atgaggcgaa gggtggagca ggagcaagag caagagcaag acgagtaccc gtacagccga    240
cggggatcca gaggacgaca acccggcgaa tctgacgaaa tcaagagca gaggtgctgc    300 aacgagctca accggttcca gaataaccaa aggtgcatgt gccaggcact tcaacagatc    360
ctccagaacc agagctttg ggttccagca ggacaggagc cagttgcatc agatggagag    420
ggagctcagg aacttgcccc agaactgcgg gttcaggtca ccaagccgtt gcgacctttg    480
tagccgcacg ccctactaaa cagacgagca ctttgcgttt taatttgctt accccacaag    540
agaaatccaa tgatgatgat tgattgcttt tttacaagct atttctatgt ctatggtgtt    600
gtggtaacaa taaagatcat caccatttta tgtaatgatg atcgtattgt ccgtggcgaa    660
gttgtatggg gcactttgaa atgtgctttt atggcaaaaa aaaaaaaaaa aa            712
```

```
<210> SEQ ID NO 8
<211> LENGTH: 702
<212> TYPE: DNA
<213> ORGANISM: Arachis hypogaea
```

<400> SEQUENCE: 8

```
attcctctct tcatcaacca cacacacact acaaaactaa tttaacctca cttcttacca        60
tctacttctc attccttccc ttagcttctt aattcacaat catggccgtc ttcactttcg       120
aggatgaaat cacctccacc ctaccccctg ctaagcttta caatgctatg aaggatgccg       180
actccctcac ccctaagatt attgatgacg tcaagagtgt tgaaatcgtc gagggaaacg       240
gtggtcctgg aaccatcaag aaactcacca ttgtcgagga tggagaaacc aagtttatct       300
tacacaaagt ggaggcaata gatgaggcta actatgcata caactacagc gtggttggag       360
gagtggcgct gcctcccacg gcggagaaga taacatttga gacaaagctg gtagaaggac       420
ccaacggagg atccatcggg aagctgagtg tgaagttcca ctcgaaagga gaagcgaagc       480
cagaggagga agacatgaag aagggtaagg ccaagggtga agctctcttc aaggctattg       540
agggttacgt cttggccaac cctgctcaat attagaacac tttgctccat cttgatatgc       600
acttcttctt ttgagcatgt ttgtgtgtgc gtatgcttca agtaattggt ttttttctat       660
gtaataagaa aaataagtgt tgctttttctt tgttttttttg at                       702
```

```
<210> SEQ ID NO 9
<211> LENGTH: 758
<212> TYPE: DNA
<213> ORGANISM: Arachis hypogaea
```

<400> SEQUENCE: 9

```
gaccaaattc aagctttcaa cactccaaaa cacacttagc tttttatttca catacatcac        60 cacttcctct tcttcttctt gttcatatta taactaatgg caggcctcaa gtttgcattt       120
gtgatgcttg tgtgcatggc catggtggga gcaccaatgg tgaatgccct atcatgtggc       180
caagtgaaca gtgccctagc accatgcatc actttcctca caaagggtgg agctccttct       240
ccgccttgtt gtagcggagt tagaggcctt ctcggtgctg caaaaaccac cgcggaccgc       300
caggccgcct gtaactgcct caaagccgct gccggttccg ttcatggcct caaccaaggc       360
aacgccgccg ccctccctgg aagatgcggt gtcagcattc cttacaagat cagcacctcc       420
accaactgtg ctaccattaa gttctgagga gaggaagatg aagaaggtgg ctctagccag       480
cactggacac aacaagtagt tatgtgaaag cagcttatat taattattaa ttaatgagaa       540
taaacatgag ggtgatgatg agggctatat atatacttat atatatatat atgcccctct       600
cctcttgtag tctttgtatg aggtggaaat ggattctctt atttcttttt ttttttgtta       660
tgcatatgga gttgttactt gtttcaactt ccaactacct atagcaatca atgaagctgc       720
ttttatttgg ttaaaaaaaa aaaaaaaaa aaaaaaaa                               758
```

```
<210> SEQ ID NO 10
<211> LENGTH: 954
<212> TYPE: DNA
<213> ORGANISM: Arachis hypogaea
```

<400> SEQUENCE: 10

```
gacgtcacat gcatacacaa accaaattaa atatctttcc ttctctttac ctcttctccc        60
tcaaacctgc ttcattcaga gtaaaacaaa cataaggaag aaaagggagc ttcctgcaac       120
catcagccat gactgaccgt acccaaccac acactgtcca agtccacacc acagctggcc       180
gtttcggcga caccgctgct ggaactaacc gctatcccga cagaggcccg tcaacatcta       240
aggttatcgc cgtcatcact ggactcccta tcggcggcac gttgctattg ttcgcggggc       300
```

-continued

```
ttgcccttgc cggaaccctg cttgggctgg cggtgaccac cccgctttttc atcctcttca      360 gccctgtcat agttccggcc atcattgtcg ttgggctctc ggtggcgggg ttcttgacgt      420
caggtgcatg tgggctgacg gggctgtctt cgttctcgtg ggtcatgaat tacatccggc      480
agacccacgg atcggtgccg gagcagctgg aaatggcaaa gcaccgcatg gctgacgtgg      540
ccggttacgt tggacagaag acgaaggatg taggacagaa gaccaaggaa gttgggcaag      600
agatacagac caaggctcag gattcaaaga gaacttgata gaatagtggt ttaagcttaa      660
ggatgaaagg ggtctatggg ttttgatggt gatacgcaaa taaattatgt tctccttgta      720
gttgaagttg tgagcatttt gtgtcttttct atgatcttgt aggtagcggt ttggtttgtt      780
tatgttcttg ttgatttgct tttttaatga gagaagtgat ttttcttttt ttttggtcag      840
agaagtggtt tgtttgtcat caagaggtgc tgctaccagc tttgtttgtg tgtcagtatg      900
catgtaggtt tggttcactt caattgttta atttcaatgc gagtgttttc tgtt           954
```

```
<210> SEQ ID NO 11
<211> LENGTH: 655
<212> TYPE: DNA
<213> ORGANISM: Arachis hypogaea

<400> SEQUENCE: 11
ttatggccgg ggattcgcat tagcattagc cctttcattt cacttcataa ttaattaata       60
acatggctga agcactctac tacggcggcc gccaacgcca agagcaacca aggtccaccc      120
agcttgtcaa ggccaccacc gctgttgtcg ccggaggctc cctcttgatc ctcgccggcc      180
ttgtgctggc cggcaccgtc attggcctca caacgatcac accgctcttc gtgatcttca      240
gcccggtgct tgtgccagct gtcatcactg tggcactctt aggcttgggg ttcttggcct      300
ctggaggctt cggcgtggcg gcaataacag tgctgacgtg gatctatagg tacgtaacag      360
gtaagcatcc acctggcgcc aaccaattgg acacagcccg ccacaagctg atgggcaagg      420
cgcgtgagat taaggacttt ggtcaacaac aaaccagtgg ggcccaggct tcttgagcat      480
accatcttcg tttgcatctt tgtttgcacg cacgtccacg ccatcattta tcttttttcga      540 attgttatgg tttattttat tttatttaat tttttttatga gtctggggtt tccttgaaat      600
taaccgttgg tttaaaatat tttccctggg ttatccaatc ccattcaaat ttttta         655
```

```
<210> SEQ ID NO 12
<211> LENGTH: 494
<212> TYPE: DNA
<213> ORGANISM: Arachis hypogaea

<400> SEQUENCE: 12 cagcctttttt gttgataaca atctctgcat gcgtccacac tactactagt ctactacact       60
tagatgtaca ttgttgactt ttcttcactt tcaaaataaa ttgacaccca catcatacac      120
tggaattgaa atctcatgcc acgtgtttat ttcttagtat ggcacctacg tacttaaatc      180
tctcttgttc atagtccgaa actgtgtata taaatagatc acacacataa acctcaacga      240
tcggtacaaa tcgaaacagc aataatggag aagaaacag ttgctggatt ctgcatcttc       300
ttcctcgttc tctttcttgc tcaggaggga gtggtgaaaa cagaggcaaa gctatgcaac      360
cacctggcag atacatacag aggaccatgc tttaccaatg caagctgcga tgatcattgc      420
aagaacaaag agcactttgt tagtggaacc tgcatgaaaa tggcgtgttg gtgtgctcac      480
aactgttgat gtaa                                                       494
```

```
<210> SEQ ID NO 13
<211> LENGTH: 370
<212> TYPE: DNA
<213> ORGANISM: Arachis hypogaea

<400> SEQUENCE: 13
cagtacaaaa acgaacgata ataatggaga agaaaatggc tggattctgc atctttttcc        60
tcattctctt tcttgctcag gaatatggcg tggagggaaa ggagtgtttg aacctaagtg       120
acaaattcaa gggaccgtgt ttgggttcaa agaactgcga tcatcactgc agggacatag       180
agcacttgct cagcggagtt tgcagggacg atttccgctg ctggtgcaac agaaagtgtt       240
aaaactactc catcatcatc aaacctctaa aaccatatga tataataata ataataataa       300
tatatgaata ataaatgctt agcttgcatt atattggatc cccacgatgc gttagacgca       360
tgcacctagc                                                             370

<210> SEQ ID NO 14
<211> LENGTH: 531
<212> TYPE: DNA
<213> ORGANISM: Arachis hypogaea

<400> SEQUENCE: 14
atggctactg ctactgatcg tgcacctcac caggttcaag ttcacacccc caccacacaa        60
cgcgtcgacg ttccacgccg cggctacgat gttagtggtg gtggtattaa gactcttctc       120
cccgagagag gtccgtccac ctctcaaatc atcgccgtcc tcgtcggcgt ccccactggg       180
ggcactctgt tgctcctctc cggcctttca cttctcggaa ccataatcgg gctggcaatt       240 gccacccgg tttttacttt cttcagcccg gttatagttc ccgcggtcgt taccattgga       300
cttgcagtca ctggtattct cacggcggga gcatgtggac taaccgggct gatgtctttg       360
tcatggatga ttaacttcat ccgacaggta catgggacga cggtgccgga tcagctggac       420
tcagtgaagc ggcgcatggc ggacatggcg gattacgtgg ggcagaagac aaaggatgct       480
ggccaacaga tacagactaa ggcccaggat gttaagaggt catcatcata a               531

<210> SEQ ID NO 15
<211> LENGTH: 647
<212> TYPE: DNA
<213> ORGANISM: Arachis hypogaea

<400> SEQUENCE: 15
gaaaccccat cacttcttgt ctaaaaattc tcaaaagtca ccagccacca aaaacccatt        60
taccattatg tctgatcaaa caaggacagg ctatggagga ggagggtcct atggatcatc       120
ctatggtgga ggaggcacct atggttcatc ttatggaacc tcctatgacc ccagtactaa       180
ccaacctata cgccaagcca tcaagttcat gacagcatca accattggtg tctcattctt       240
gatcctgtct gggttgatcc tcactggaac tgtcataggt ttgatcattg caacaccact       300
tcttgttatc ttcagtccta tccttgtccc tgctgccata acccttgcac tggctgctgg       360 tggattttttg ttctctggtg ctgtggtgt tgctgccatt gctgcattgt catggttgta       420
cagctatgtc actgggaaac accctgctgg ctctgatagg cttgattatg ctaaaggggt       480
gattgctgat aaggctaggg atgttaagga cagggccaag gattatgctg gtgctggtag       540
ggctcaggag ggcacccag ggtattgatc ctcattgtga tgaaaaaaaa tggaagcttt       600
tgtgtgtaat gtgtgggtga agtgaaggtc tgaaaggtga cacccc                      647

<210> SEQ ID NO 16
```

-continued

```
<211> LENGTH: 30
<212> TYPE: DNA
<213> ORGANISM: Arachis hypogaea

<400> SEQUENCE: 16
gccaagtcat caccttacca gaagaaaaca                                        30

<210> SEQ ID NO 17
<211> LENGTH: 27
<212> TYPE: DNA
<213> ORGANISM: Arachis hypogaea

<400> SEQUENCE: 17
caggaaccgg atgacttgaa gcaaaag                                           27

<210> SEQ ID NO 18
<211> LENGTH: 39
<212> TYPE: DNA
<213> ORGANISM: Arachis hypogaea

<400> SEQUENCE: 18
ctcgagtatg atcctcgttg tgtctatgat cctcgagga                              39

<210> SEQ ID NO 19
<211> LENGTH: 84
<212> TYPE: DNA
<213> ORGANISM: Arachis hypogaea

<400> SEQUENCE: 19
ggggagcgga cacgtggccg ccaacccgga gactacgatg atgaccgccg tcaaccccga       60
agagaggaag gaggccgatg ggga                                              84

<210> SEQ ID NO 20
<211> LENGTH: 35
<212> TYPE: DNA
<213> ORGANISM: Arachis hypogaea

<400> SEQUENCE: 20
gggagcgtga aagagaagaa gactggagac aacca                                  35

<210> SEQ ID NO 21
<211> LENGTH: 57
<212> TYPE: DNA
<213> ORGANISM: Arachis hypogaea

<400> SEQUENCE: 21
gaagattgga ggcgaccaag tcatcagcag ccacggaaaa taaggcccga aggaaga          57

<210> SEQ ID NO 22
<211> LENGTH: 30
<212> TYPE: DNA
<213> ORGANISM: Arachis hypogaea

<400> SEQUENCE: 22
acacccggcc agtttgagga tttcttcccg                                        30

<210> SEQ ID NO 23
<211> LENGTH: 30
<212> TYPE: DNA
<213> ORGANISM: Arachis hypogaea

<400> SEQUENCE: 23
tcctacttgc agggcttcag caggaatacg                                        30
```

<210> SEQ ID NO 24
<211> LENGTH: 30
<212> TYPE: DNA
<213> ORGANISM: Arachis hypogaea

<400> SEQUENCE: 24
ttcaatgcgg aattcaatga gatacggagg                                    30

<210> SEQ ID NO 25
<211> LENGTH: 39
<212> TYPE: DNA
<213> ORGANISM: Arachis hypogaea

<400> SEQUENCE: 25
gagcaagagg agagagggca gaggcgatgg agtactcgg                          39

<210> SEQ ID NO 26
<211> LENGTH: 31
<212> TYPE: DNA
<213> ORGANISM: Arachis hypogaea

<400> SEQUENCE: 26
caaagaaagg ctccgaagaa gagggagata t                                  31

<210> SEQ ID NO 27
<211> LENGTH: 29
<212> TYPE: DNA
<213> ORGANISM: Arachis hypogaea

<400> SEQUENCE: 27
tgggaagtta tttgaggtga agccagaca                                     29

<210> SEQ ID NO 28
<211> LENGTH: 30
<212> TYPE: DNA
<213> ORGANISM: Arachis hypogaea

<400> SEQUENCE: 28
agcttcagga cctggacatg atgctcacct                                    30

<210> SEQ ID NO 29
<211> LENGTH: 52
<212> TYPE: DNA
<213> ORGANISM: Arachis hypogaea

<400> SEQUENCE: 29
agatcaaaga aggagctttg atgctcccac acttcaactc aaaggccatg gt           52

<210> SEQ ID NO 30
<211> LENGTH: 30
<212> TYPE: DNA
<213> ORGANISM: Arachis hypogaea

<400> SEQUENCE: 30
ccttgaactc gtggctgtaa gaaaagagca                                    30

<210> SEQ ID NO 31
<211> LENGTH: 38
<212> TYPE: DNA
<213> ORGANISM: Arachis hypogaea -continued

<400> SEQUENCE: 31
tatcaacgct gaaaacaacc acagaatctt ccttgcag                              38

<210> SEQ ID NO 32
<211> LENGTH: 30
<212> TYPE: DNA
<213> ORGANISM: Arachis hypogaea

<400> SEQUENCE: 32
atgtgataga ccagatagag aagcaagcga                                      30

<210> SEQ ID NO 33
<211> LENGTH: 51
<212> TYPE: DNA
<213> ORGANISM: Arachis hypogaea

<400> SEQUENCE: 33
tagcattccc tgggtcgggt gaacaagttg agaagctcat caaaaaccag a              51

<210> SEQ ID NO 34
<211> LENGTH: 66
<212> TYPE: DNA
<213> ORGANISM: Arachis hypogaea

<400> SEQUENCE: 34
gcatctgcga ggcagcagtg ggaactccaa ggagacagaa gatgccagag ccagctcgag     60
agggcg                                                                66

<210> SEQ ID NO 35
<211> LENGTH: 114
<212> TYPE: DNA
<213> ORGANISM: Arachis hypogaea

<400> SEQUENCE: 35
aggccctgcg agcaacatct catgcagaag atccaacgtg acgaggattc atatgaacgg     60
gacccgtaca gccctagtca ggatccgtac agccctagtc catatgatcg gaga          114

<210> SEQ ID NO 36
<211> LENGTH: 27
<212> TYPE: DNA
<213> ORGANISM: Arachis hypogaea

<400> SEQUENCE: 36
gctggatcct ctcagcacca agagagg                                         27

<210> SEQ ID NO 37
<211> LENGTH: 18
<212> TYPE: DNA
<213> ORGANISM: Arachis hypogaea

<400> SEQUENCE: 37
atggagaacc agagcgat                                                   18

<210> SEQ ID NO 38
<211> LENGTH: 18
<212> TYPE: DNA
<213> ORGANISM: Arachis hypogaea

<400> SEQUENCE: 38
aggcaacagg agcaacag                                                   18

-continued

<210> SEQ ID NO 39
<211> LENGTH: 24
<212> TYPE: DNA
<213> ORGANISM: Arachis hypogaea

<400> SEQUENCE: 39
ggccttaggg caccacagcg ttgc                                                        24

<210> SEQ ID NO 40
<211> LENGTH: 45
<212> TYPE: DNA
<213> ORGANISM: Arachis hypogaea

<400> SEQUENCE: 40
cattgagact tggaacccca acaaccagga gttcgaatgc gccgg                                 45

<210> SEQ ID NO 41
<211> LENGTH: 45
<212> TYPE: DNA
<213> ORGANISM: Arachis hypogaea

<400> SEQUENCE: 41
aacatcttca gcggcttcac gccggagttc ctggaacaag ccttc                                 45

<210> SEQ ID NO 42
<211> LENGTH: 39
<212> TYPE: DNA
<213> ORGANISM: Arachis hypogaea

<400> SEQUENCE: 42
gacggtgagg ggaggcctca gaatcttgag cccagatgg                                        39

<210> SEQ ID NO 43
<211> LENGTH: 36
<212> TYPE: DNA
<213> ORGANISM: Arachis hypogaea

<400> SEQUENCE: 43
atacgatgaa gatcaatatg aataccatga acagga                                          36

<210> SEQ ID NO 44
<211> LENGTH: 60
<212> TYPE: DNA
<213> ORGANISM: Arachis hypogaea

<400> SEQUENCE: 44
cttctctgcg aaattgaagg cgaccacctc tcctccgccg caatcctcgg ccaagacggc                60

<210> SEQ ID NO 45
<211> LENGTH: 60
<212> TYPE: DNA
<213> ORGANISM: Arachis hypogaea

<400> SEQUENCE: 45
cttgccctcg tcctggtggc acacgcctcc gcaatgaggc gcgagagggg gagacagggg                60

<210> SEQ ID NO 46
<211> LENGTH: 60
<212> TYPE: DNA
<213> ORGANISM: Arachis hypogaea

<400> SEQUENCE: 46
ctcctgggcg cccttcttgt cgtagcctcc gcgacaagat gggatcccga tcgagggtcc                60

-continued

```
<210> SEQ ID NO 47
<211> LENGTH: 47
<212> TYPE: DNA
<213> ORGANISM: Arachis hypogaea

<400> SEQUENCE: 47
agtgttgaaa tcgtcgaggg aaacggtggt cctggaacca tcaagaa                    47

<210> SEQ ID NO 48
<211> LENGTH: 90
<212> TYPE: DNA
<213> ORGANISM: Arachis hypogaea

<400> SEQUENCE: 48
aaccaaggca acgccgccgc cctccctgga agatgcggtg tcagcattcc ttacaagatc      60
agcacctcca ccaactgtgc taccattaag                                       90

<210> SEQ ID NO 49
<211> LENGTH: 90
<212> TYPE: DNA
<213> ORGANISM: Arachis hypogaea

<400> SEQUENCE: 49
atcggtgccg gagcagctgg aaatggcaaa gcaccgcatg gctgacgtgg ccggttacgt      60
tggacagaag acgaaggatg taggacagaa                                       90

<210> SEQ ID NO 50
<211> LENGTH: 57
<212> TYPE: DNA
<213> ORGANISM: Arachis hypogaea

<400> SEQUENCE: 50
ccaaggtcca cccagcttgt caaggccacc accgctgttg tcgccggagg ctccctc         57

<210> SEQ ID NO 51
<211> LENGTH: 57
<212> TYPE: DNA
<213> ORGANISM: Arachis hypogaea

<400> SEQUENCE: 51
cctttctact tcccgtcaag gcggtttagc acccgctacg ggaaccaaaa cggtagg         57

<210> SEQ ID NO 52
<211> LENGTH: 58
<212> TYPE: DNA
<213> ORGANISM: Arachis hypogaea

<400> SEQUENCE: 52
ccggcgagca gccgagacca atcatcctac ttgcaccaac gtattcctgc tgaagccc        58

<210> SEQ ID NO 53
<211> LENGTH: 69
<212> TYPE: DNA
<213> ORGANISM: Arachis hypogaea

<400> SEQUENCE: 53
agaggtttga ccaaaggtca aggcagtttc agaatctcca gaatcaccgt attgtgcaga      60
tcgaggcca                                                              69

<210> SEQ ID NO 54
```

<211> LENGTH: 65
<212> TYPE: DNA
<213> ORGANISM: Arachis hypogaea

<400> SEQUENCE: 54
ccgagaccaa tcatcctact tgcagggctt cagcaggaat acccgcattg aaggcggcct      60
ccaac                                                                  65

<210> SEQ ID NO 55
<211> LENGTH: 64
<212> TYPE: DNA
<213> ORGANISM: Arachis hypogaea

<400> SEQUENCE: 55
cctttctact tcccgtcaag gcggtttagc acccgctacg ggaaccaaaa cggtaggatc      60
cggg                                                                   64

<210> SEQ ID NO 56
<211> LENGTH: 61
<212> TYPE: DNA
<213> ORGANISM: Arachis hypogaea

<400> SEQUENCE: 56
ccggccagtt tgaggatttc ttcccggcga gcagccgacc ctgcaagtag gatgattggt      60
c                                                                      61

<210> SEQ ID NO 57
<211> LENGTH: 58
<212> TYPE: DNA
<213> ORGANISM: Arachis hypogaea

<400> SEQUENCE: 57
ccctttctac ttcccgtcaa ggcggtttag cacccgctac gggaaccaaa acgtagg         58

<210> SEQ ID NO 58
<211> LENGTH: 73
<212> TYPE: DNA
<213> ORGANISM: Arachis hypogaea

<400> SEQUENCE: 58
ccatgtgagg gaagaaacat ctcggaacaa ccctttctac ttcccgtcaa ggcggtttag      60
cacccgctac ggg                                                         73

<210> SEQ ID NO 59
<211> LENGTH: 77
<212> TYPE: DNA
<213> ORGANISM: Arachis hypogaea

<400> SEQUENCE: 59
cctcgaggat catagacaca acgacacact ggcaccacca accaacgttc ccctccaggg      60
gagcggacac gtggccg                                                     77

<210> SEQ ID NO 60
<211> LENGTH: 68
<212> TYPE: DNA
<213> ORGANISM: Arachis hypogaea

<400> SEQUENCE: 60
cccggagact acgatgatga ccgccgtcaa ccccgaagag aggaaggagg ccgatgggga      60
ccagctgg                                                               68

<210> SEQ ID NO 61
<211> LENGTH: 62
<212> TYPE: DNA
<213> ORGANISM: Arachis hypogaea

<400> SEQUENCE: 61
cctctttctc aggagactct ttcatcaaga ggaggaaaac caaggaggga agggtccact      60
cc                                                                     62

<210> SEQ ID NO 62
<211> LENGTH: 70
<212> TYPE: DNA
<213> ORGANISM: Arachis hypogaea

<400> SEQUENCE: 62
ccaagcacgc tgatgctgat aacatccttg ttatccagca agggcaagcc accgtgaccg      60
tagcaaatgg                                                             70

<210> SEQ ID NO 63
<211> LENGTH: 58
<212> TYPE: DNA
<213> ORGANISM: Arachis hypogaea

<400> SEQUENCE: 63
agagaaggag aacaagagtg gggaacacca ggtagccatg tgagggaaga aacatctc        58

<210> SEQ ID NO 64
<211> LENGTH: 69
<212> TYPE: DNA
<213> ORGANISM: Arachis hypogaea

<400> SEQUENCE: 64
gaagctcatc aaaaaccaga aggaatctca ctttgtgagt gctcgtcctc aatctcaatc      60
tcaatctcc                                                              69

<210> SEQ ID NO 65
<211> LENGTH: 58
<212> TYPE: DNA
<213> ORGANISM: Arachis hypogaea

<400> SEQUENCE: 65
ccggcgagca gccgagacca atcatcctac ttgcaccaac gtattcctgc tgaagccc        58

<210> SEQ ID NO 66
<211> LENGTH: 65
<212> TYPE: DNA
<213> ORGANISM: Arachis hypogaea

<400> SEQUENCE: 66
ccgagaccaa tcatcctact tgcagggctt cagcaggaat acgttggagg ccgccttcaa      60
tgcgg                                                                  65

<210> SEQ ID NO 67
<211> LENGTH: 60
<212> TYPE: DNA
<213> ORGANISM: Arachis hypogaea

<400> SEQUENCE: 67
ccggccagtt tgaggatttc ttcccggcga gcagccgcct gcaagtagga tgattggtct      60

-continued

<210> SEQ ID NO 68
<211> LENGTH: 70
<212> TYPE: DNA
<213> ORGANISM: Arachis hypogaea

<400> SEQUENCE: 68
gttatcagca tcagcgtgct tggatccttg ttatccagca agggcaacca tttgctacgg    60
tcacggtggc                                                           70

<210> SEQ ID NO 69
<211> LENGTH: 58
<212> TYPE: DNA
<213> ORGANISM: Arachis hypogaea

<400> SEQUENCE: 69
ccccactctt gttctccttc tctaacacca ggtaggagat gtttcttccc tcacatgg      58

<210> SEQ ID NO 70
<211> LENGTH: 57
<212> TYPE: DNA
<213> ORGANISM: Arachis hypogaea

<400> SEQUENCE: 70
cggtcatcat cgtagtctcc gggccgtcaa ccccccatcg gcctccttcc tctcttc       57

<210> SEQ ID NO 71
<211> LENGTH: 69
<212> TYPE: DNA
<213> ORGANISM: Arachis hypogaea

<400> SEQUENCE: 71
ccttctggtt tttgatgagc ttcaatctca ctttgtgagt gctcgtcctc aatctcaatc    60
tcaatctcc                                                            69

<210> SEQ ID NO 72
<211> LENGTH: 58
<212> TYPE: DNA
<213> ORGANISM: Arachis hypogaea

<400> SEQUENCE: 72
cctcaatctc aatctcaatc tccgtcgtct cctgacctct ttctcaggag actctttc      58

<210> SEQ ID NO 73
<211> LENGTH: 77
<212> TYPE: DNA
<213> ORGANISM: Arachis hypogaea

<400> SEQUENCE: 73
tggacgtcga aagtggcggc aggcggccgc gaattccgcc gatactgacg ggctccagga    60
gtcgtcgcca ccaatcc                                                   77

<210> SEQ ID NO 74
<211> LENGTH: 62
<212> TYPE: DNA
<213> ORGANISM: Arachis hypogaea

<400> SEQUENCE: 74
ccgtcagtat cggcggaatt cgcgctccag gagtcgtcgc caccaatccc catatggaaa    60
cc                                                                   62

<210> SEQ ID NO 75
<211> LENGTH: 77
<212> TYPE: DNA
<213> ORGANISM: Arachis hypogaea

<400> SEQUENCE: 75
ccttagggca ccacagcgtt gcgacttgga cgtcgaaagt ggcggcaggc ggccccgtca      60
gtatcggcgg aattcgc                                                       77

<210> SEQ ID NO 76
<211> LENGTH: 61
<212> TYPE: DNA
<213> ORGANISM: Arachis hypogaea

<400> SEQUENCE: 76
cccgtcagta tcggcggaat tcgctccagg agtcgtcgcc accaatcccc atatggaaac      60
c                                                                        61

<210> SEQ ID NO 77
<211> LENGTH: 63
<212> TYPE: DNA
<213> ORGANISM: Arachis hypogaea

<400> SEQUENCE: 77
ccatatgggg attggtggcg acgaaaccgt cgatattcag ccatgtgcct tcttccgcgt      60
gca                                                                      63

<210> SEQ ID NO 78
<211> LENGTH: 64
<212> TYPE: DNA
<213> ORGANISM: Arachis hypogaea

<400> SEQUENCE: 78
cccgtcagta tcggcggaat tcgctccagg agtcgtcgcc accaatcccc atatggaaac      60
cgtc                                                                     64

<210> SEQ ID NO 79
<211> LENGTH: 57
<212> TYPE: DNA
<213> ORGANISM: Arachis hypogaea

<400> SEQUENCE: 79
cctggagccc gtcagtatcg gcgagtcgtc gccaccaatc cccatatgga aaccgtc         57

<210> SEQ ID NO 80
<211> LENGTH: 77
<212> TYPE: DNA
<213> ORGANISM: Arachis hypogaea

<400> SEQUENCE: 80
tggacgtcga aagtggcggc aggcggccgc gaattccgcc gatactgacg ggctccagga      60
gtcgtcgcca ccaatcc                                                       77

<210> SEQ ID NO 81
<211> LENGTH: 62
<212> TYPE: DNA
<213> ORGANISM: Arachis hypogaea -continued

<400> SEQUENCE: 81
ccgtcagtat cggcggaatt cgcgctccag gagtcgtcgc caccaatccc catatggaaa      60
cc                                                                    62

<210> SEQ ID NO 82
<211> LENGTH: 61
<212> TYPE: DNA
<213> ORGANISM: Arachis hypogaea

<400> SEQUENCE: 82
cccgtcagta tcggcggaat tcgctccagg agtcgtcgcc accaatcccc atatggaaac      60
c                                                                     61

<210> SEQ ID NO 83
<211> LENGTH: 63
<212> TYPE: DNA
<213> ORGANISM: Arachis hypogaea

<400> SEQUENCE: 83
ccatatgggg attggtggcg acgaaaccgt cgatattcag ccatgtgcct tcttccgcgt      60
gca                                                                   63

<210> SEQ ID NO 84
<211> LENGTH: 64
<212> TYPE: DNA
<213> ORGANISM: Arachis hypogaea

<400> SEQUENCE: 84
cccgtcagta tcggcggaat tcgctccagg agtcgtcgcc accaatcccc atatggaaac      60
cgtc                                                                  64

<210> SEQ ID NO 85
<211> LENGTH: 57
<212> TYPE: DNA
<213> ORGANISM: Arachis hypogaea

<400> SEQUENCE: 85
cctggagccc gtcagtatcg gcgagtcgtc gccaccaatc cccatatgga aaccgtc         57

<210> SEQ ID NO 86
<211> LENGTH: 63
<212> TYPE: DNA
<213> ORGANISM: Arachis hypogaea

<400> SEQUENCE: 86
cctcaacagt gcggccttag ggcaccacag cgttgcgact tggacgtcga aagtggcggc      60
agg                                                                   63

<210> SEQ ID NO 87
<211> LENGTH: 77
<212> TYPE: DNA
<213> ORGANISM: Arachis hypogaea

<400> SEQUENCE: 87
ccttagggca ccacagcgtt gcgacttgga cgtcgaaagt ggcggcaggc ggcccgtca       60 gtatcggcgg aattcgc                                                    77

<210> SEQ ID NO 88

-continued

```
<211> LENGTH: 71
<212> TYPE: DNA
<213> ORGANISM: Arachis hypogaea

<400> SEQUENCE: 88
ccgtcacaat ggctccctct tcttgagggg aggcctcaga atcttgagcg gcacctctcg      60
ttccatctgg g                                                           71

<210> SEQ ID NO 89
<211> LENGTH: 72
<212> TYPE: DNA
<213> ORGANISM: Arachis hypogaea

<400> SEQUENCE: 89
gcccatacag cccgcatagt cggcctagac gagaagagcg tgaatttcgc cctcgaggac      60
agcacagccg ca                                                          72

<210> SEQ ID NO 90
<211> LENGTH: 68
<212> TYPE: DNA
<213> ORGANISM: Arachis hypogaea

<400> SEQUENCE: 90
gtgcgttggt gttgtagtga gggacagcat catatatgca ttgagccact tgcacgtgag      60
cccgtccc                                                               68

<210> SEQ ID NO 91
<211> LENGTH: 74
<212> TYPE: DNA
<213> ORGANISM: Arachis hypogaea

<400> SEQUENCE: 91
gacagattgt gcaaaatctg tggggcgaga acgagagtga agaagaggga gccattgtga      60
cggtgagggg aggc                                                        74

<210> SEQ ID NO 92
<211> LENGTH: 58
<212> TYPE: DNA
<213> ORGANISM: Arachis hypogaea

<400> SEQUENCE: 92
tggagtagaa aggcctacga aggatgctcc ccaggccttc cttgctggat gaagatct       58

<210> SEQ ID NO 93
<211> LENGTH: 67
<212> TYPE: DNA
<213> ORGANISM: Arachis hypogaea

<400> SEQUENCE: 93
ccagcaacaa agcagacaaa gcagacgaag aagcttacca tatagcccat acagcccgca      60
tagtcgg                                                                67

<210> SEQ ID NO 94
<211> LENGTH: 77
<212> TYPE: DNA
<213> ORGANISM: Arachis hypogaea

<400> SEQUENCE: 94
ccaaattgaa tctcctgggg aacctgggaa ccacgagcaa gagttcttaa ggtaccagca      60
acaaagcaga caaagca                                                     77
```

<210> SEQ ID NO 95
<211> LENGTH: 59
<212> TYPE: DNA
<213> ORGANISM: Arachis hypogaea

<400> SEQUENCE: 95
tggagtagaa aggcctacga aggatgctcc ccaggaccct tccttgctgg atgaagatc          59

<210> SEQ ID NO 96
<211> LENGTH: 76
<212> TYPE: DNA
<213> ORGANISM: Arachis hypogaea

<400> SEQUENCE: 96
ccttccttgc tggatgaaga tctggatact ttgggttgat attccctggt tgtgcaggct          60
cttcatatgt gctagg                                                         76

<210> SEQ ID NO 97
<211> LENGTH: 58
<212> TYPE: DNA
<213> ORGANISM: Arachis hypogaea

<400> SEQUENCE: 97
gcatgtgtta aaagaacat tggtggaaac agatcccctc acatctacga tcctcagc            58

<210> SEQ ID NO 98
<211> LENGTH: 60
<212> TYPE: DNA
<213> ORGANISM: Arachis hypogaea

<400> SEQUENCE: 98
cctttctact ccaatgctcc ccaggagatc ttcatccccc aaagtatccc cttccttgct          60

<210> SEQ ID NO 99
<211> LENGTH: 77
<212> TYPE: DNA
<213> ORGANISM: Arachis hypogaea

<400> SEQUENCE: 99
tggacgtcga aagtggcggc aggcggccgc gaattccgcc gatactgacg ggctccagga          60
gtcgtcgcca ccaatcc                                                        77

<210> SEQ ID NO 100
<211> LENGTH: 62
<212> TYPE: DNA
<213> ORGANISM: Arachis hypogaea

<400> SEQUENCE: 100
ccgtcagtat cggcggaatt cgcgctccag gagtcgtcgc caccaatccc catatggaaa          60
cc                                                                        62

<210> SEQ ID NO 101
<211> LENGTH: 77
<212> TYPE: DNA
<213> ORGANISM: Arachis hypogaea

<400> SEQUENCE: 101
ccttagggca ccacagcgtt gcgacttgga cgtcgaaagt ggcggcaggc ggccccgtca          60
gtatcggcgg aattcgc                                                        77

-continued

```
<210> SEQ ID NO 102
<211> LENGTH: 61
<212> TYPE: DNA
<213> ORGANISM: Arachis hypogaea

<400> SEQUENCE: 102
cccgtcagta tcggcggaat tcgctccagg agtcgtcgcc accaatcccc atatggaaac      60
c                                                                       61

<210> SEQ ID NO 103
<211> LENGTH: 63
<212> TYPE: DNA
<213> ORGANISM: Arachis hypogaea

<400> SEQUENCE: 103
ccatatgggg attggtggcg acgaaaccgt cgatattcag ccatgtgcct tcttccgcgt      60
gca                                                                     63

<210> SEQ ID NO 104
<211> LENGTH: 64
<212> TYPE: DNA
<213> ORGANISM: Arachis hypogaea

<400> SEQUENCE: 104
cccgtcagta tcggcggaat tcgctccagg agtcgtcgcc accaatcccc atatggaaac      60
cgtc                                                                    64

<210> SEQ ID NO 105
<211> LENGTH: 57
<212> TYPE: DNA
<213> ORGANISM: Arachis hypogaea

<400> SEQUENCE: 105
cctggagccc gtcagtatcg gcgagtcgtc gccaccaatc cccatatgga aaccgtc         57

<210> SEQ ID NO 106
<211> LENGTH: 76
<212> TYPE: DNA
<213> ORGANISM: Arachis hypogaea

<400> SEQUENCE: 106
ggtgccaccg aggtacaacc cggaaataca tggttatcca aggtgaaccc ggagctatca      60
ttccagggaa gaaggg                                                       76

<210> SEQ ID NO 107
<211> LENGTH: 63
<212> TYPE: DNA
<213> ORGANISM: Arachis hypogaea

<400> SEQUENCE: 107
cgccttcaat ttcgcagaga aggaccacct ctcctccgcc gcaatcctcg gccaagacgg      60
cgg                                                                     63

<210> SEQ ID NO 108
<211> LENGTH: 60
<212> TYPE: DNA
<213> ORGANISM: Arachis hypogaea

<400> SEQUENCE: 108
gctatcattc cagggaagaa gggtcctggt ggtgttacca ttgagaagac gaatcaggcg      60
```

```
<210> SEQ ID NO 109
<211> LENGTH: 69
<212> TYPE: DNA
<213> ORGANISM: Arachis hypogaea

<400> SEQUENCE: 109
gaacccggag ctatcattcc agggaagaag ggtcctggtg gtgttaccat tgagaagacg      60
aatcaggcg                                                              69

<210> SEQ ID NO 110
<211> LENGTH: 63
<212> TYPE: DNA
<213> ORGANISM: Arachis hypogaea

<400> SEQUENCE: 110
cgccttcaat ttcgcagaga aggaccacct ctcctccgcc ccgccgtctt ggccgaggat      60
tgc                                                                    63

<210> SEQ ID NO 111
<211> LENGTH: 60
<212> TYPE: DNA
<213> ORGANISM: Arachis hypogaea

<400> SEQUENCE: 111
cccttcttcc ctggaatgat agctcctggt ggtgttacca ttgagaagac gaatcaggcg      60

<210> SEQ ID NO 112
<211> LENGTH: 76
<212> TYPE: DNA
<213> ORGANISM: Arachis hypogaea

<400> SEQUENCE: 112
ggtgccaccg aggtacaacc cggaaataca tggttatcca aggtgaaccc ggacccttct      60
tccctggaat gatagc                                                      76

<210> SEQ ID NO 113
<211> LENGTH: 69
<212> TYPE: DNA
<213> ORGANISM: Arachis hypogaea

<400> SEQUENCE: 113
cctggaatga tagctccggg ttcgaagaag ggtcctggtg gtgttaccat tgagaagacg      60
aatcaggcg                                                              69

<210> SEQ ID NO 114
<211> LENGTH: 60
<212> TYPE: DNA
<213> ORGANISM: Arachis hypogaea

<400> SEQUENCE: 114
ccttgccctc gtcctggtgg cacacgcctc cgcaatgagg cgcgagaggg ggagacaggg      60

<210> SEQ ID NO 115
<211> LENGTH: 76
<212> TYPE: DNA
<213> ORGANISM: Arachis hypogaea
```

-continued

<400> SEQUENCE: 115
ccatcctggt agctctcctt gccctcgtcc tggtggcaca cgcctccgca atgaggcgcg      60 agaggggag acaggg                                                      76

<210> SEQ ID NO 116
<211> LENGTH: 72
<212> TYPE: DNA
<213> ORGANISM: Arachis hypogaea

<400> SEQUENCE: 116
cctggtagct ctccttgccc tcgtcctggt ggcacacgcc tccgcaatga ggcgcgagag      60
ggggagacag gg                                                         72

<210> SEQ ID NO 117
<211> LENGTH: 66
<212> TYPE: DNA
<213> ORGANISM: Arachis hypogaea

<400> SEQUENCE: 117
cctcctgggc gcccttcttg tcgtagcctc cgcgacaaga tgggatcccg atcgagggtc      60
cagagg                                                                66

<210> SEQ ID NO 118
<211> LENGTH: 67
<212> TYPE: DNA
<213> ORGANISM: Arachis hypogaea

<400> SEQUENCE: 118
ccctcctggg cgcccttctt gtcgtagcct ccgcgacaag atgggatccc gatcgagggt      60
ccagagg                                                               67

<210> SEQ ID NO 119
<211> LENGTH: 76
<212> TYPE: DNA
<213> ORGANISM: Arachis hypogaea

<400> SEQUENCE: 119
gatggtcaag ctcagcatcc tggtagccct cctgggcgcc cttcttgtcg tagcctccgc      60
gacaagatgg gatccc                                                     76

<210> SEQ ID NO 120
<211> LENGTH: 76
<212> TYPE: DNA
<213> ORGANISM: Arachis hypogaea

<400> SEQUENCE: 120
gatggtcaag ctcagcatcc tggtagccct cctgggcgcc cttcttgtcg tagcctccgc      60
gacaagatgg gatccc                                                     76

<210> SEQ ID NO 121
<211> LENGTH: 63
<212> TYPE: DNA
<213> ORGANISM: Arachis hypogaea

<400> SEQUENCE: 121
gtcgagggaa acggtggtcc tggaaccatc aagaaactca ccattgtcga ggatggagaa      60
acc                                                                   63

-continued

```
<210> SEQ ID NO 122
<211> LENGTH: 72
<212> TYPE: DNA
<213> ORGANISM: Arachis hypogaea

<400> SEQUENCE: 122
ccgtttccct cgacgatttc aactggtcct ggaaccatca agaaactcac cattgtcgag      60
gatggagaaa cc                                                          72

<210> SEQ ID NO 123
<211> LENGTH: 70
<212> TYPE: DNA
<213> ORGANISM: Arachis hypogaea

<400> SEQUENCE: 123
cctggaacca tcaagaaact caccattgtc gaggatggag aaaccaagtt tatcttacac      60
aaagtggagg                                                             70

<210> SEQ ID NO 124
<211> LENGTH: 58
<212> TYPE: DNA
<213> ORGANISM: Arachis hypogaea

<400> SEQUENCE: 124
cctcaatagc cttgaagaga gctgttacgt cttgggttct aatattgagc agggttgg       58

<210> SEQ ID NO 125
<211> LENGTH: 63
<212> TYPE: DNA
<213> ORGANISM: Arachis hypogaea

<400> SEQUENCE: 125
gtcgagggaa acggtggtcc tggaaccatc aagaaactca ccattgtcga ggatggagaa      60
acc                                                                    63

<210> SEQ ID NO 126
<211> LENGTH: 72
<212> TYPE: DNA
<213> ORGANISM: Arachis hypogaea

<400> SEQUENCE: 126
ccgtttccct cgacgatttc aactggtcct ggaaccatca agaaactcac cattgtcgag      60
gatggagaaa cc                                                          72

<210> SEQ ID NO 127
<211> LENGTH: 70
<212> TYPE: DNA
<213> ORGANISM: Arachis hypogaea

<400> SEQUENCE: 127
cctggaacca tcaagaaact caccattgtc gaggatggag aaaccaagtt tatcttacac      60
aaagtggagg                                                             70

<210> SEQ ID NO 128
<211> LENGTH: 58
<212> TYPE: DNA
<213> ORGANISM: Arachis hypogaea

<400> SEQUENCE: 128
cctcaatagc cttgaagaga gctgttacgt cttggccaac cctgctcaat attagaac       58
```

```
<210> SEQ ID NO 129
<211> LENGTH: 75
<212> TYPE: DNA
<213> ORGANISM: Arachis hypogaea

<400> SEQUENCE: 129
ccctggaaga tgcggtgtca gcattcctta caagatcagc acctccacca accctcagaa      60
cttaatggta gcaca                                                       75

<210> SEQ ID NO 130
<211> LENGTH: 58
<212> TYPE: DNA
<213> ORGANISM: Arachis hypogaea

<400> SEQUENCE: 130
ccgcggtggt ttttgcagca ccgaccgcca ggccgagcgg ctttgaggca gttacagg       58

<210> SEQ ID NO 131
<211> LENGTH: 64
<212> TYPE: DNA
<213> ORGANISM: Arachis hypogaea

<400> SEQUENCE: 131
ccaccatggc catgcacaca agcgagcacc aatggtgaat ggttcacttg gccacatgat      60
aggg                                                                   64

<210> SEQ ID NO 132
<211> LENGTH: 67
<212> TYPE: DNA
<213> ORGANISM: Arachis hypogaea

<400> SEQUENCE: 132
ccatggccat gcacacaagc atctgggagc accaatggtg aatggttcac ttggccacat      60 gatOggg                                                                67

<210> SEQ ID NO 133
<211> LENGTH: 75
<212> TYPE: DNA
<213> ORGANISM: Arachis hypogaea

<400> SEQUENCE: 133
tgctgacacc gcatcttcca gggttcctta caagatcagc acctccacca actgtgctac      60
cattaagttc tgagg                                                       75

<210> SEQ ID NO 134
<211> LENGTH: 76
<212> TYPE: DNA
<213> ORGANISM: Arachis hypogaea

<400> SEQUENCE: 134
ccgcggtggt ttttgcagca ccgaccgcca ggccgcctgt aactgcctca aaggccatga      60
acggaaccgg cagcgg                                                      76

<210> SEQ ID NO 135
<211> LENGTH: 61
<212> TYPE: DNA
<213> ORGANISM: Arachis hypogaea
```

-continued

<400> SEQUENCE: 135
gttcacttgg ccacatgata gggagtgccc tagcaccacc ctttgtgagg aaagtgatgc      60
a                                                                      61

<210> SEQ ID NO 136
<211> LENGTH: 71
<212> TYPE: DNA
<213> ORGANISM: Arachis hypogaea

<400> SEQUENCE: 136
gtggaggtgc tgatcttgta aggcaactgt gctaccatta agttctgacc accttcttca      60
tcttcctctc c                                                           71

<210> SEQ ID NO 137
<211> LENGTH: 76
<212> TYPE: DNA
<213> ORGANISM: Arachis hypogaea

<400> SEQUENCE: 137
ccatgactga ccgtacccaa ccacacactg tccaagtcca caccacagct ggccgtttcg      60
gcgacaccgc tgctgg                                                      76

<210> SEQ ID NO 138
<211> LENGTH: 67
<212> TYPE: DNA
<213> ORGANISM: Arachis hypogaea

<400> SEQUENCE: 138
ccggccatca ttgtcgttgg gctctcggtg gcggggttct tgacgtcagg tgcatgtggg      60
ctgacgg                                                                67

<210> SEQ ID NO 139
<211> LENGTH: 70
<212> TYPE: DNA
<213> ORGANISM: Arachis hypogaea

<400> SEQUENCE: 139
cgtttcggcg acaccgctgc tggaactaac cgctatcccg acagaggccc gtcaacatct      60
aaggttatcg                                                             70

<210> SEQ ID NO 140
<211> LENGTH: 60
<212> TYPE: DNA
<213> ORGANISM: Arachis hypogaea

<400> SEQUENCE: 140
ccaaccacac actgtccaag tccacaccac agctggccgt ttcggcgaca ccgctgctgg      60

<210> SEQ ID NO 141
<211> LENGTH: 61
<212> TYPE: DNA
<213> ORGANISM: Arachis hypogaea

<400> SEQUENCE: 141
cccaaccaca cactgtccaa gtccacacca cagctggccg tttcggcgac accgctgctg      60
g                                                                      61

<210> SEQ ID NO 142

-continued

```
<211> LENGTH: 60
<212> TYPE: DNA
<213> ORGANISM: Arachis hypogaea

<400> SEQUENCE: 142
cgtttcggcg acaccgctgc tggaactaac cgctatcccg acagaggccc gtcaacatct      60

<210> SEQ ID NO 143
<211> LENGTH: 68
<212> TYPE: DNA
<213> ORGANISM: Arachis hypogaea

<400> SEQUENCE: 143
cctcacaacg atcacaccgc tcttcgtgat cttcagcccg gtgcttgtgc cagctgtcat      60
cactgtgg                                                             68

<210> SEQ ID NO 144
<211> LENGTH: 63
<212> TYPE: DNA
<213> ORGANISM: Arachis hypogaea

<400> SEQUENCE: 144
cccggtgctt gtgccagctg tcatcactgt ggcactctta ccagaggcca agaaccccaa      60
gcc                                                                  63

<210> SEQ ID NO 145
<211> LENGTH: 57
<212> TYPE: DNA
<213> ORGANISM: Arachis hypogaea

<400> SEQUENCE: 145
tgtgaggcca atgacggtgc cggacgatca caccgctctt cgtgatcttc agcccgg        57

<210> SEQ ID NO 146
<211> LENGTH: 59
<212> TYPE: DNA
<213> ORGANISM: Arachis hypogaea

<400> SEQUENCE: 146
gtttccttga aattaaccgt tggtttaaaa tattttgaat gggattggat aacccaggg      59

<210> SEQ ID NO 147
<211> LENGTH: 70
<212> TYPE: DNA
<213> ORGANISM: Arachis hypogaea

<400> SEQUENCE: 147
tgtgccagct gtcatcactg tggcactctt aggcttgggg ttcttggcct ctggaggctt      60
cggcgtggcg                                                           70

<210> SEQ ID NO 148
<211> LENGTH: 60
<212> TYPE: DNA
<213> ORGANISM: Arachis hypogaea

<400> SEQUENCE: 148
cctaagagtg ccacagtgat gaccttgggg ttcttggcct ctggaggctt cggcgtggcg      60

<210> SEQ ID NO 149
<211> LENGTH: 57
<212> TYPE: DNA
<213> ORGANISM: Arachis hypogaea
```

-continued

<400> SEQUENCE: 149
ccggcgagga tcaagaggga gccccttgtg ctggtgtgag gccaatgacg gtgccgg          57

<210> SEQ ID NO 150
<211> LENGTH: 62
<212> TYPE: DNA
<213> ORGANISM: Arachis hypogaea

<400> SEQUENCE: 150
ccagcacaag gccggcgagg atcccggcac cgtcattggc ctcacaacga tcacaccgct          60
ct                                                                          62

<210> SEQ ID NO 151
<211> LENGTH: 73
<212> TYPE: DNA
<213> ORGANISM: Arachis hypogaea

<400> SEQUENCE: 151
ccggcgagga tcaagaggga gccccttgtg ctggccggca ccgtcattgg cctcacaacg          60
atcacaccgc tct                                                              73

<210> SEQ ID NO 152
<211> LENGTH: 64
<212> TYPE: DNA
<213> ORGANISM: Arachis hypogaea

<400> SEQUENCE: 152
cctctggagg cttcggcgtg gcggcaataa cagtgctgac gcctgttacg tacctataga          60
tcca                                                                        64

<210> SEQ ID NO 153
<211> LENGTH: 68
<212> TYPE: DNA
<213> ORGANISM: Arachis hypogaea

<400> SEQUENCE: 153
tgacggtgcc ggccagcaca aggttggcct cacaacgatc acaccgctct tcgtgatctt          60
cagcccgg                                                                    68

<210> SEQ ID NO 154
<211> LENGTH: 68
<212> TYPE: DNA
<213> ORGANISM: Arachis hypogaea

<400> SEQUENCE: 154
cctcacaacg atcacaccgc tcttcgtgat cttcagcccg gtgcttgtgc cagctgtcat          60
cactgtgg                                                                    68

<210> SEQ ID NO 155
<211> LENGTH: 57
<212> TYPE: DNA
<213> ORGANISM: Arachis hypogaea

<400> SEQUENCE: 155
ccggcaccgt cattggcctc acaacgatca caccccgggc tgaagatcac gaagagc          57

<210> SEQ ID NO 156
<211> LENGTH: 57
<212> TYPE: DNA

-continued

<213> ORGANISM: Arachis hypogaea

<400> SEQUENCE: 156
ccggcgagga tcaagaggga gccccttgtg ctggccggca ccgtcattgg cctcaca          57

<210> SEQ ID NO 157
<211> LENGTH: 62
<212> TYPE: DNA
<213> ORGANISM: Arachis hypogaea

<400> SEQUENCE: 157
ccagcacaag gccggcgagg atcccggcac cgtcattggc ctcacaacga tcacaccgct          60
ct          62

<210> SEQ ID NO 158
<211> LENGTH: 68
<212> TYPE: DNA
<213> ORGANISM: Arachis hypogaea

<400> SEQUENCE: 158
ccttgtgctg gccggcaccg tcattggcct cacaacgatc acaccccggg ctgaagatca          60
cgaagagc          68

<210> SEQ ID NO 159
<211> LENGTH: 75
<212> TYPE: DNA
<213> ORGANISM: Arachis hypogaea

<400> SEQUENCE: 159
ggtggccttg acaagctggg tggaccgctg ttgtcgccgg aggctccctc ttccagcaca          60
aggccggcga ggatc          75

<210> SEQ ID NO 160
<211> LENGTH: 63
<212> TYPE: DNA
<213> ORGANISM: Arachis hypogaea

<400> SEQUENCE: 160
ccggcgagga tcaagaggga gccccttgtg ctggccggca ccgtcattgg cctcacaacg          60
atc          63

<210> SEQ ID NO 161
<211> LENGTH: 71
<212> TYPE: DNA
<213> ORGANISM: Arachis hypogaea

<400> SEQUENCE: 161
cggtggtggc cttgacaagc tggctgttgt cgccggaggc tccctcttcc agcacaaggc          60
cggcgaggat c          71

<210> SEQ ID NO 162
<211> LENGTH: 63
<212> TYPE: DNA
<213> ORGANISM: Arachis hypogaea

<400> SEQUENCE: 162
cccggtgctt gtgccagctg tcatcactgt ggcactctta ccagaggcca agaaccccaa          60
gcc          63

-continued

```
<210> SEQ ID NO 163
<211> LENGTH: 72
<212> TYPE: DNA
<213> ORGANISM: Arachis hypogaea

<400> SEQUENCE: 163
ggtggtggcc ttgacaagct ggggctgttg tcgccggagg ctccctcttc cagcacaagg      60
ccggcgagga tc                                                          72

<210> SEQ ID NO 164
<211> LENGTH: 70
<212> TYPE: DNA
<213> ORGANISM: Arachis hypogaea

<400> SEQUENCE: 164
tgtgccagct gtcatcactg tggcactctt aggcttgggg ttcttggcct ctggaggctt      60
cggcgtggcg                                                             70

<210> SEQ ID NO 165
<211> LENGTH: 64
<212> TYPE: DNA
<213> ORGANISM: Arachis hypogaea

<400> SEQUENCE: 165
cctctggagg cttcggcgtg gcggcaataa cagtgctgac gcctgttacg tacctataga      60
tcca                                                                   64

<210> SEQ ID NO 166
<211> LENGTH: 60
<212> TYPE: DNA
<213> ORGANISM: Arachis hypogaea

<400> SEQUENCE: 166
cctaagagtg ccacagtgat gaccttgggg ttcttggcct ctggaggctt cggcgtggcg      60

<210> SEQ ID NO 167
<211> LENGTH: 70
<212> TYPE: DNA
<213> ORGANISM: Arachis hypogaea

<400> SEQUENCE: 167
ccggcgacaa cagcggtggt ggcaggctcc ctcttgatcc tcgccggcct tgtgctggcc      60
ggcaccgtca                                                             70

<210> SEQ ID NO 168
<211> LENGTH: 66
<212> TYPE: DNA
<213> ORGANISM: Arachis hypogaea

<400> SEQUENCE: 168
ccggcgacaa cagcggtggt ggcaggctcc ctcttgatcc tcgccggcct tgtgctggcc      60
ggcacc                                                                 66

<210> SEQ ID NO 169
<211> LENGTH: 59
<212> TYPE: DNA
<213> ORGANISM: Arachis hypogaea

<400> SEQUENCE: 169
gtttccttga aattaaccgt tggtttaaaa tattttgaat gggattggat aacccaggg       59
```

-continued

```
<210> SEQ ID NO 170
<211> LENGTH: 59
<212> TYPE: DNA
<213> ORGANISM: Arachis hypogaea

<400> SEQUENCE: 170
cgaccgcggg aactataacc gggttaccat tggactccgt gagaatacca gtgactgca          59

<210> SEQ ID NO 171
<211> LENGTH: 67
<212> TYPE: DNA
<213> ORGANISM: Arachis hypogaea

<400> SEQUENCE: 171
gacggcgatg atttgagagg tggctcgtcg gcgtccccac tgggccggag aggagcaaca          60
gagtgcc                                                                   67

<210> SEQ ID NO 172
<211> LENGTH: 66
<212> TYPE: DNA
<213> ORGANISM: Arachis hypogaea

<400> SEQUENCE: 172
ccagccacca aaaacccatt taccattatg tctgatcaaa caaccctcct cctccatagc          60
ctgtcc                                                                    66

<210> SEQ ID NO 173
<211> LENGTH: 66
<212> TYPE: DNA
<213> ORGANISM: Arachis hypogaea

<400> SEQUENCE: 173
ccagccacca aaaacccatt taccattatg tctgatcaaa caaccctcct cctccatagc          60
ctgtcc                                                                    66

<210> SEQ ID NO 174
<211> LENGTH: 190
<212> TYPE: DNA
<213> ORGANISM: Arachis hypogaea

<400> SEQUENCE: 174
gaaaacaacc acagaatctt ccttgcaggt gataaggaca atgtgataga ccagatagag          60
aagcaagcga aggatttagc attccctggt tcgggtgaac aagttgagaa gctcatcaaa         120
aaccagaggg agtctcactt tgtgagtgct ctgcctcaat ctcaatctcc gtcgtctcct         180
gaaaaagagg                                                                190

<210> SEQ ID NO 175
<211> LENGTH: 28
<212> TYPE: DNA
<213> ORGANISM: Arachis hypogaea

<400> SEQUENCE: 175
gaaaacaacc acagaatctt ccttgcag                                            28

<210> SEQ ID NO 176
<211> LENGTH: 30
<212> TYPE: DNA
<213> ORGANISM: Arachis hypogaea
```

-continued

<400> SEQUENCE: 176
atgtgataga ccagatagag aagcaagcga                                                          30

<210> SEQ ID NO 177
<211> LENGTH: 54
<212> TYPE: DNA
<213> ORGANISM: Arachis hypogaea

<400> SEQUENCE: 177
tagcattccc tggttcgggt gaacaagttg agaagctcat caaaaaccag aggg          54

<210> SEQ ID NO 178
<211> LENGTH: 30
<212> TYPE: DNA
<213> ORGANISM: Arachis hypogaea

<400> SEQUENCE: 178
aatctcaatc tccgtcgtct cctgaaaaag                                                          30

<210> SEQ ID NO 179
<211> LENGTH: 120
<212> TYPE: DNA
<213> ORGANISM: Arachis hypogaea

<400> SEQUENCE: 179
caatggccaa gctcaccata ctagtagccc tcgccctttt cctcctcgct gcccacgcat          60
ctgcgaggca gcagtgggaa ctccaaggag acagaagatg ccagagccag ctcgagaggg          120

<210> SEQ ID NO 180
<211> LENGTH: 67
<212> TYPE: DNA
<213> ORGANISM: Arachis hypogaea

<400> SEQUENCE: 180
cacgcatctg cgaggcagca gtgggaactc caaggagaca gaagatgcca gagccagctc          60
gagaggg                                                                                              67

<210> SEQ ID NO 181
<211> LENGTH: 110
<212> TYPE: DNA
<213> ORGANISM: Arachis hypogaea

<400> SEQUENCE: 181
tccagcgcct gaatgcgcaa aggcctgaca accgcattga atcggagggc ggttacattg          60
agacttggaa cccaaacaac caggagttag aatgcgccgg cgtcgccctc          110

<210> SEQ ID NO 182
<211> LENGTH: 110
<212> TYPE: DNA
<213> ORGANISM: Arachis hypogaea

<400> SEQUENCE: 182
tccagcgcct gaatgcgcaa aggcctgaca accgcattga atcggagggc ggttacattg          60
agacttggaa cccaaacaac caggagttag aatgcgccgg cgtcgccctc          110

<210> SEQ ID NO 183
<211> LENGTH: 100
<212> TYPE: DNA
<213> ORGANISM: Arachis hypogaea -continued

<400> SEQUENCE: 183
tggtagctct ccttgccctc gtcctggtgg cacacgcctc cgcaatgagg cgcgagaggg     60
ggagacaggg ggactcatca agctgcgaga ggcaggtaga                          100

<210> SEQ ID NO 184
<211> LENGTH: 60
<212> TYPE: DNA
<213> ORGANISM: Arachis hypogaea

<400> SEQUENCE: 184
ccttgccctc gtcctggtgg cacacgcctc cgcaatgagg cgcgagaggg ggagacaggg     60

<210> SEQ ID NO 185
<211> LENGTH: 101
<212> TYPE: DNA
<213> ORGANISM: Arachis hypogaea

<400> SEQUENCE: 185
tcagcatcct agtagccctc ctgggcgccc ttcttgtcgt gagcctccgc gacaagatgg     60
gatcccgatc gagggtccag agggttgaga tgggacgcac c                        101

<210> SEQ ID NO 186
<211> LENGTH: 48
<212> TYPE: DNA
<213> ORGANISM: Arachis hypogaea

<400> SEQUENCE: 186
aagagtgttg aaatcgttga gggaaagggt ggtcctggaa ccatcaag                  48

<210> SEQ ID NO 187
<211> LENGTH: 100
<212> TYPE: DNA
<213> ORGANISM: Arachis hypogaea

<400> SEQUENCE: 187
ttgatgacgt caagagtgtt gaaatcgttg agggaaaggg tggtcctgga accatcaaga     60
aactcaccat tgtcgaggat ggagaaacca agtttatctt                          100

<210> SEQ ID NO 188
<211> LENGTH: 48
<212> TYPE: DNA
<213> ORGANISM: Arachis hypogaea

<400> SEQUENCE: 188
aagagtgttg aaatcgttga gggaaagggt ggtcctggaa ccatcaag                  48

<210> SEQ ID NO 189
<211> LENGTH: 150
<212> TYPE: DNA
<213> ORGANISM: Arachis hypogaea

<400> SEQUENCE: 189
cccgagagag gtccgtccac ctctcaaatc atcgccgtcc tcgtcggcgt ccccactggg     60
ggcactctgt tgctcctctc cggcctttca cttctcggaa ccataatcgg gctggcaatt    120 gccacccccgg tttttacttt cttcagcccg                                    150

<210> SEQ ID NO 190
<211> LENGTH: 150
<212> TYPE: DNA
<213> ORGANISM: Arachis hypogaea

<400> SEQUENCE: 190
gaaaccccat cacttcttgt ctaaaaattc tcaaaagtca ccagccacca aaaacccatt      60
taccattatg tctgatcaaa caaggacagg ctatggagga ggagggtcct atggatcatc     120
ctatggtgga ggaggcacct atggttcatc                                     150

<210> SEQ ID NO 191
<211> LENGTH: 402
<212> TYPE: DNA
<213> ORGANISM: Arachis hypogaea

<400> SEQUENCE: 191
tttctgcaac gcaggccaag tcaccttacc ggaaaacaga gaacccctgc gcccagaggt      60
gcctccagag ttgtcaacag gaaccggacg acttgaagca aaaggcatgc gagtctcgct     120
gcaccaagct cgagtatgat cctcgttgtg tctatgacac tggcgccacc aaccaacgtc     180
accctccagg ggagcggaca cgtggccgcc aacccggaga ctacgatgat gaccgccgtc     240
aaccccgaag agaggaagga ggccgatggg gaccagctga accgagggag cgtgaaagag     300
aagaagactg gagacaacca agagaagatt ggaggcgacc aagtcatcag cagccacgga     360
aaataaggcc cgaaggaaga gaaggagaac aagagtgggg aa                       402

<210> SEQ ID NO 192
<211> LENGTH: 29
<212> TYPE: DNA
<213> ORGANISM: Arachis hypogaea

<400> SEQUENCE: 192
ccaagtcacc ttaccggaaa acagagaac                                       29

<210> SEQ ID NO 193
<211> LENGTH: 30
<212> TYPE: DNA
<213> ORGANISM: Arachis hypogaea

<400> SEQUENCE: 193
accggacgac ttgaagcaaa aggcatgcga                                      30

<210> SEQ ID NO 194
<211> LENGTH: 29
<212> TYPE: DNA
<213> ORGANISM: Arachis hypogaea

<400> SEQUENCE: 194
tcctcgttgt gtctatgaca ctggcgcca                                       29

<210> SEQ ID NO 195
<211> LENGTH: 84
<212> TYPE: DNA
<213> ORGANISM: Arachis hypogaea

<400> SEQUENCE: 195
acccggagac tacgatgatg accgccgtca accccgaaga gaggaaggag gccgatgggg      60
accagctgaa ccgagggagc gtga                                            84

<210> SEQ ID NO 196
<211> LENGTH: 30
<212> TYPE: DNA
<213> ORGANISM: Arachis hypogaea -continued

```
<400> SEQUENCE: 196
acaaccaaga gaagattgga ggcgaccaag                                               30

<210> SEQ ID NO 197
<211> LENGTH: 56
<212> TYPE: DNA
<213> ORGANISM: Arachis hypogaea

<400> SEQUENCE: 197
tcagcagcca cggaaaataa ggcccgaagg aagagaagga gaacaagagt ggggaa           56

<210> SEQ ID NO 198
<211> LENGTH: 300
<212> TYPE: DNA
<213> ORGANISM: Arachis hypogaea

<400> SEQUENCE: 198
ctccaaggag acagaagatg ccagagccag ctcgagaggg cgaacctgag gccctgcgag           60
caacatctca tgcagaagat ccaacgtgac gaggattcat atgaacggga cccgtacagc          120
cctagtcagg atccgtacag ccctagtcca tatgatcgga gaggcgctgg atcctctcag          180
caccaagaga ggtgttgcaa tgagctgaac gagtttgaga acaaccaaag gtgcatgtgc          240
gaggcattgc aacagatcat ggagaaccag agcgataggt tgcaggggag gcaacaggag          300

<210> SEQ ID NO 199
<211> LENGTH: 299
<212> TYPE: DNA
<213> ORGANISM: Arachis hypogaea

<400> SEQUENCE: 199
tccaaggaga cagaagatgc cagagccagc tcgagagggc gaacctgagg ccctgcgagc           60
aacatctcat gcagaagatc caacgtgacg aggattcata tgaacgggac ccgtacagcc          120
ctagtcagga tccgtacagc cctagtccat atgatcggag aggcgctgga tcctctcagc          180
accaagagag gtgttgcaat gagctgaacg agtttgagaa caaccaaagg tgcatgtgcg          240
aggcattgca acagatcatg gagaaccaga gcgataggtt gcaggggagg caacaggag           299

<210> SEQ ID NO 200
<211> LENGTH: 367
<212> TYPE: DNA
<213> ORGANISM: Arachis hypogaea

<400> SEQUENCE: 200
aggggaggca acaggagaag aagaccgtga atttagccct cgaggacagc acggccgcag           60
agaacgagca ggacaagaac aagaaaacga aggtggaaac atcttcagcg gcttcacgcc          120
ggagttcctg gcacaagcct tccaggttga cgacagacag atattgcaaa acctaagagg          180
cgagaacgag agtgacgaac agggagccat tgtgacagtg aggggaggcc tcagaatctt          240
gagcccagat agaaagagaa ggcagcagta tgaacgtccc gacgaagaag aggaatacga          300
tgaagatgaa tatgaatatg atgaagagga gaggcaacaa gatagaaggc gtggcagggg          360
aagcaga                                                                    367

<210> SEQ ID NO 201
<211> LENGTH: 35
<212> TYPE: DNA
<213> ORGANISM: Arachis hypogaea
```

-continued

<400> SEQUENCE: 201
gaaacatctt cagcggcttc acgccggagt tcctg                           35

<210> SEQ ID NO 202
<211> LENGTH: 26
<212> TYPE: DNA
<213> ORGANISM: Arachis hypogaea

<400> SEQUENCE: 202
cagaatcttg agcccagata gaaaga                                     26

<210> SEQ ID NO 203
<211> LENGTH: 30
<212> TYPE: DNA
<213> ORGANISM: Arachis hypogaea

<400> SEQUENCE: 203
atgaagatga atatgaatat gatgaagagg                                 30

<210> SEQ ID NO 204
<211> LENGTH: 150
<212> TYPE: DNA
<213> ORGANISM: Arachis hypogaea

<400> SEQUENCE: 204
acctccaccc tgccccctgc taagctttac aacgctctga aggatgccga taccatcacc    60
cctaagatta ttgatgacgt caagagtgtt gaaatcgttg agggaaacgg tggtcctgga   120
accatcaaga aactcaccat tgtcgaggat                                150

<210> SEQ ID NO 205
<211> LENGTH: 49
<212> TYPE: DNA
<213> ORGANISM: Arachis hypogaea

<400> SEQUENCE: 205
aagagtgttg aaatcgttga gggaaacggt ggtcctggaa ccatcaaga              49

<210> SEQ ID NO 206
<211> LENGTH: 23
<212> TYPE: DNA
<213> ORGANISM: Arachis hypogaea

<400> SEQUENCE: 206
cggacacgtg gccgccaacc cgg                                        23

<210> SEQ ID NO 207
<211> LENGTH: 23
<212> TYPE: DNA
<213> ORGANISM: Arachis hypogaea

<400> SEQUENCE: 207
ccaagagaag attggaggcg acc                                        23

<210> SEQ ID NO 208
<211> LENGTH: 23
<212> TYPE: DNA
<213> ORGANISM: Arachis hypogaea

<400> SEQUENCE: 208
ggtcgcctcc aatcttctct tgg                                        23

-continued

<210> SEQ ID NO 209
<211> LENGTH: 23
<212> TYPE: DNA
<213> ORGANISM: Arachis hypogaea

<400> SEQUENCE: 209
tcgctgccca cgcatctgcg agg                                              23

<210> SEQ ID NO 210
<211> LENGTH: 23
<212> TYPE: DNA
<213> ORGANISM: Arachis hypogaea

<400> SEQUENCE: 210
cctgcgagca acatctcatg cag                                              23

<210> SEQ ID NO 211
<211> LENGTH: 23
<212> TYPE: DNA
<213> ORGANISM: Arachis hypogaea

<400> SEQUENCE: 211
ctgcatgaga tgttgctcgc agg                                              23

<210> SEQ ID NO 212
<211> LENGTH: 23
<212> TYPE: DNA
<213> ORGANISM: Arachis hypogaea

<400> SEQUENCE: 212
aaccgcattg aatcggaggg cgg                                              23

<210> SEQ ID NO 213
<211> LENGTH: 23
<212> TYPE: DNA
<213> ORGANISM: Arachis hypogaea

<400> SEQUENCE: 213
ccttcggagg cctttctact cca                                              23

<210> SEQ ID NO 214
<211> LENGTH: 23
<212> TYPE: DNA
<213> ORGANISM: Arachis hypogaea

<400> SEQUENCE: 214
tggagtagaa aggcctccga agg                                              23

<210> SEQ ID NO 215
<211> LENGTH: 23
<212> TYPE: DNA
<213> ORGANISM: Arachis hypogaea

<400> SEQUENCE: 215
agccctcctt gccctcgtcc tgg                                              23

<210> SEQ ID NO 216
<211> LENGTH: 23
<212> TYPE: DNA
<213> ORGANISM: Arachis hypogaea

<400> SEQUENCE: 216
cctcaagccc tgcgagcagc aca                                              23

<210> SEQ ID NO 217
<211> LENGTH: 23
<212> TYPE: DNA
<213> ORGANISM: Arachis hypogaea

<400> SEQUENCE: 217
tgtgctgctc gcagggcttg agg                                              23

<210> SEQ ID NO 218
<211> LENGTH: 23
<212> TYPE: DNA
<213> ORGANISM: Arachis hypogaea

<400> SEQUENCE: 218
gatggtcaag ctcagcatcc tgg                                              23

<210> SEQ ID NO 219
<211> LENGTH: 23
<212> TYPE: DNA
<213> ORGANISM: Arachis hypogaea

<400> SEQUENCE: 219
ccagagggtc gagatgggac gca                                              23

<210> SEQ ID NO 220
<211> LENGTH: 23
<212> TYPE: DNA
<213> ORGANISM: Arachis hypogaea

<400> SEQUENCE: 220
tgcgtcccat ctcgaccctc tgg                                              23

<210> SEQ ID NO 221
<211> LENGTH: 23
<212> TYPE: DNA
<213> ORGANISM: Arachis hypogaea

<400> SEQUENCE: 221
caagagtgtt gaaatcgttg agg                                              23

<210> SEQ ID NO 222
<211> LENGTH: 23
<212> TYPE: DNA
<213> ORGANISM: Arachis hypogaea

<400> SEQUENCE: 222
ccaagtttat cttacacaaa gtg                                              23

<210> SEQ ID NO 223
<211> LENGTH: 23
<212> TYPE: DNA
<213> ORGANISM: Arachis hypogaea

<400> SEQUENCE: 223
cactttgtgt aagataaact tgg                                              23

<210> SEQ ID NO 224
<211> LENGTH: 23
<212> TYPE: DNA
<213> ORGANISM: Arachis hypogaea

<400> SEQUENCE: 224
gctgtcattc gagggaagaa ggg                                                23

<210> SEQ ID NO 225
<211> LENGTH: 23
<212> TYPE: DNA
<213> ORGANISM: Arachis hypogaea

<400> SEQUENCE: 225
ccagggcagt gcaacatgat tgt                                                23

<210> SEQ ID NO 226
<211> LENGTH: 23
<212> TYPE: DNA
<213> ORGANISM: Arachis hypogaea

<400> SEQUENCE: 226
acaatcatgt tgcactgccc tgg                                                23

<210> SEQ ID NO 227
<211> LENGTH: 23
<212> TYPE: DNA
<213> ORGANISM: Arachis hypogaea

<400> SEQUENCE: 227
tcccttcgtg gcctcaacca agg                                                23

<210> SEQ ID NO 228
<211> LENGTH: 23
<212> TYPE: DNA
<213> ORGANISM: Arachis hypogaea

<400> SEQUENCE: 228
ccaactgtgc taccattaag ttc                                                23

<210> SEQ ID NO 229
<211> LENGTH: 23
<212> TYPE: DNA
<213> ORGANISM: Arachis hypogaea

<400> SEQUENCE: 229
gaacttaatg gtagcacagt tgg                                                23

<210> SEQ ID NO 230
<211> LENGTH: 23
<212> TYPE: DNA
<213> ORGANISM: Arachis hypogaea

<400> SEQUENCE: 230
cttcagccct gtcatagttc cgg                                                23

<210> SEQ ID NO 231
<211> LENGTH: 22
<212> TYPE: DNA
<213> ORGANISM: Arachis hypogaea

<400> SEQUENCE: 231
ccggcagacc cacggatcgg tg                                                 22

<210> SEQ ID NO 232
<211> LENGTH: 22
<212> TYPE: DNA

<213> ORGANISM: Arachis hypogaea

<400> SEQUENCE: 232
caccgatccg tgggtctgcc gg                                        22

<210> SEQ ID NO 233
<211> LENGTH: 23
<212> TYPE: DNA
<213> ORGANISM: Arachis hypogaea

<400> SEQUENCE: 233
gccaacgcca agagcaacca agg                                       23

<210> SEQ ID NO 234
<211> LENGTH: 26
<212> TYPE: DNA
<213> ORGANISM: Arachis hypogaea

<400> SEQUENCE: 234
ccgtcattgg cctcacaacg atcaca                                    26

<210> SEQ ID NO 235
<211> LENGTH: 26
<212> TYPE: DNA
<213> ORGANISM: Arachis hypogaea

<400> SEQUENCE: 235
tgtgatcgtt gtgaggccaa tgacgg                                    26

<210> SEQ ID NO 236
<211> LENGTH: 23
<212> TYPE: DNA
<213> ORGANISM: Arachis hypogaea

<400> SEQUENCE: 236
cctcgttctc tttcttgctc agg                                       23

<210> SEQ ID NO 237
<211> LENGTH: 23
<212> TYPE: DNA
<213> ORGANISM: Arachis hypogaea

<400> SEQUENCE: 237
ccaatgcaag ctgcgatgat cat                                       23

<210> SEQ ID NO 238
<211> LENGTH: 23
<212> TYPE: DNA
<213> ORGANISM: Arachis hypogaea

<400> SEQUENCE: 238
atgatcatcg cagcttgcat tgg                                       23

<210> SEQ ID NO 239
<211> LENGTH: 23
<212> TYPE: DNA
<213> ORGANISM: Arachis hypogaea

<400> SEQUENCE: 239
cctcattctc tttcttgctc agg                                       23

<210> SEQ ID NO 240
<211> LENGTH: 23

```
<212> TYPE: DNA
<213> ORGANISM: Arachis hypogaea

<400> SEQUENCE: 240
ccgctgctgg tgcaacagaa agt                                              23

<210> SEQ ID NO 241
<211> LENGTH: 23
<212> TYPE: DNA
<213> ORGANISM: Arachis hypogaea

<400> SEQUENCE: 241
actttctgtt gcaccagcag cgg                                              23

<210> SEQ ID NO 242
<211> LENGTH: 23
<212> TYPE: DNA
<213> ORGANISM: Arachis hypogaea

<400> SEQUENCE: 242
cgcgtcgacg ttccacgccg cgg                                              23

<210> SEQ ID NO 243
<211> LENGTH: 23
<212> TYPE: DNA
<213> ORGANISM: Arachis hypogaea

<400> SEQUENCE: 243
cctcgtcggc gtccccactg ggg                                              23

<210> SEQ ID NO 244
<211> LENGTH: 23
<212> TYPE: DNA
<213> ORGANISM: Arachis hypogaea

<400> SEQUENCE: 244
ccccagtggg gacgccgacg agg                                              23

<210> SEQ ID NO 245
<211> LENGTH: 23
<212> TYPE: DNA
<213> ORGANISM: Arachis hypogaea

<400> SEQUENCE: 245
caaacaagga caggctatgg agg                                              23

<210> SEQ ID NO 246
<211> LENGTH: 20
<212> TYPE: DNA
<213> ORGANISM: Arachis hypogaea

<400> SEQUENCE: 246
cctatgaccc cagtactaac                                                  20

<210> SEQ ID NO 247
<211> LENGTH: 20
<212> TYPE: DNA
<213> ORGANISM: Arachis hypogaea

<400> SEQUENCE: 247
gttagtactg gggtcatagg                                                  20

<210> SEQ ID NO 248
```

```
<211> LENGTH: 4201
<212> TYPE: DNA
<213> ORGANISM: Arachis hypogaea

<400> SEQUENCE: 248
atggctccta agaagaagcg gaaggttggt attcacgggg tgcctgcggc tgacaagaag      60
tactccatcg gcctcgacat cggcaccaac agcgtcggct gggcggtgat caccgacgag     120
tacaaggtcc cgtccaagaa gttcaaggtc ctgggcaaca ccgaccgcca ctccatcaag     180
aagaacctca tcggcgccct cctcttcgac tccggcgaga cggcggaggc gacccgcctc     240
aagcgcaccg cccgccgccg ctacacccgc cgcaagaacc gcatctgcta cctccaggag     300
atcttctcca acgagatggc gaaggtcgac gactccttct tccaccgcct cgaggagtcc     360
ttcctcgtgg aggaggacaa gaagcacgag gccaccccat cttcggcaac atcgtcgacg     420
aggtcgccta ccacgagaag tacccccacta tctaccacct tcgtaagaag cttgttgact     480
ctactgataa ggctgatctt cgtctcatct accttgctct cgctcacatg atcaagttcc     540
gtggtcactt ccttatcgag ggtgacctta accctgataa ctccgacgtg gacaagctct     600
tcatccagct cgtccagacc tacaaccagc tcttcgagga gaaccctatc aacgcttccg     660
gtgtcgacgc taaggcgatc ctttccgcta ggctctccaa gtccaggcgt ctcgagaacc     720
tcatcgccca gctccctggt gagaagaaga cggtctttt cggtaacctc atcgctctct     780
ccctcggtct gaccccctaac ttcaagtcca acttcgacct cgctgaggac gctaagcttc     840
agctctccaa ggatacctac gacgatgatc tcgacaacct cctcgctcag attggagatc     900
agtacgctga tctcttcctt gctgctaaga acctctccga tgctatcctc ctttcggata     960
tccttagggt taacactgag atcactaagg ctcctctttc tgcttccatg atcaagcgct    1020
acgacgagca ccaccaggac ctcacccctcc tcaaggctct tgttcgtcag cagctccccg    1080
agaagtacaa ggagatcttc ttcgaccagt ccaagaacgg ctacgccggt tacattgacg    1140
gtggagctag ccaggaggag ttctacaagt tcatcaagcc aatccttgag aagatggatg    1200
gtactgagga gcttctcgtt aagcttaacc gtgaggacct ccttaggaag cagaggactt    1260
tcgataacgg ctctatccct caccagatcc accttggtga gcttcacgcc atccttcgta    1320
ggcaggagga cttctacccct ttcctcaagg acaaccgtga gaagatcgag aagatcctta    1380
ctttccgtat tccttactac gttggtcctc ttgctcgtgg taactcccgt ttcgcttgga    1440
tgactaggaa gtccgaggag actatcaccc cttggaactt cgaggaggtt gttgacaagg    1500
gtgcttccgc ccagtccttc atcgagcgca tgaccaactt cgacaagaac ctccccaacg    1560
agaaggtcct ccccaagcac tccctcctct acgagtactt cacggtctac aacgagctca    1620
ccaaggtcaa gtacgtcacc gagggtatgc gcaagcctgc cttcctctcc ggcgagcaga    1680
agaaggctat cgttgacctc ctcttcaaga ccaaccgcaa ggtcaccgtc aagcagctca    1740
aggaggacta cttcaagaag atcgagtgct tcgactccgt cgagatcagc ggcgttgagg    1800
accgtttcaa cgcttctctc ggtacctacc acgatctcct caagatcatc aaggacaagg    1860
acttcctcga caacgaggag aacgaggaca tcctcgagga catcgtcctc actcttactc    1920
tcttcgagga tagggagatg atcgaggaga ggctcaagac ttacgctcat ctcttcgatg    1980
acaaggtttg aagcagctca agcgtcgccg ttacaccggt tggggtaggc tctcccgcaa    2040
gctcatcaac ggtatcaggg ataagcagag cggcaagact atcctcgact tcctcaagtc    2100
tgatggtttc gctaacagga acttcatgca gctcatccac gatgactctc ttaccttcaa    2160
ggaggatatt cagaaggctc aggtgtccgg tcagggcgac tctctccacg agcacattgc    2220
```

```
taaccttgct ggttcccctg ctatcaagaa gggcatcctt cagactgtta aggttgtcga        2280
tgagcttgtc aaggttatgg gtcgtcacaa gcctgagaac atcgtcatcg agatggctcg        2340
tgagaaccag actacccaga agggtcagaa gaactcgagg gagcgcatga agaggattga        2400
ggagggtatc aaggagcttg gttctcagat ccttaaggag caccctgtcg agaacaccca        2460
gctccagaac gagaagctct acctctacta cctccagaac ggtagggata tgtacgttga        2520
ccaggagctc gacatcaaca ggctttctga ctacgacgtc gaccacattg ttcctcagtc        2580
tttccttaag gatgactcca tcgacaacaa ggtcctcacg aggtccgaca agaacagggg        2640
taagtcggac aacgtccctt ccgaggaggt gtgtcaagaag atgaagaact actggaggca        2700
gcttctcaac gctaagctca ttacccagag gaagttcgac aacctcacga aggctgagag        2760
gggtggcctt tccgagcttg acaaggctgg tttcatcaag aggcagcttg ttgagacgag        2820
gcagattacc aagcacgttg ctcagatcct cgattctagg atgaacacca agtacgacga        2880
gaacgacaag ctcatccgcg aggtcaaggt gatcaccctc aagtccaagc tcgtctccga        2940
cttccgcaag gacttccagt ctacaaggt ccgcgagatc aacaactacc accacgctca        3000
cgatgcttac cttaacgctg tcgttggtac cgctcttatc aagaagtacc ctaagcttga        3060
gtccgagttc gtctacggtg actacaaggt ctacgacgtt cgtaagatga tcgccaagtc        3120
cgagcaggag atcggcaagg ccaccgccaa gtacttcttc tactccaaca tcatgaactt        3180
cttcaagacc gagatcaccc tcgccaacgg cgagatccgc aagcgccctc ttatcgagac        3240
gaacggtgag actggtgaga tcgtttggga caagggtcgc gacttcgcta ctgttcgcaa        3300
ggtcctttct atgcctcagg ttaacatcgt caagaagacc gaggtccaga ccggtggctt        3360
ctccaaggag tctatccttc caaagagaaa ctcggacaag ctcatcgcta ggaagaagga        3420
ttgggaccct aagaagtacg gtggtttcga ctcccctact gtcgcctact ccgtcctcgt        3480
ggtcgccaag gtggagaagg gtaagtcgaa gaagctcaag tccgtcaagg agctcctcgg        3540
catcaccatc atggagcgct cctccttcga gaagaacccg atcgacttcc tcgaggccaa        3600
gggctacaag gaggtcaaga aggacctcat catcaagctc cccaagtact ctcttttcga        3660
gctcgagaac ggtcgtaaga ggatgctggc ttccgctggt gagctccaga agggtaacga        3720
gcttgctctt ccttccaagt acgtgaactt cctctacctc gcctcccact acgagaagct        3780
caagggttcc cctgaggata cgagcagaa gcagctcttc gtggagcagc acaagcacta        3840
cctcgacgag atcatcgagc agatctccga gttctccaag cgcgtcatcc tcgctgacgc        3900
taacctcgac aaggtcctct ccgcctacaa caagcaccgc gacaagccca tccgcgagca        3960
ggccgagaac atcatccacc tcttcacgct cacgaacctc ggcgcccctg ctgctttcaa        4020
gtacttcgac accaccatcg acaggaagcg ttacacgtcc accaaggagg ttctcgacgc        4080
tactctcatc caccagtcca tcaccggtct ttacgagact cgtatcgacc tttcccagct        4140
tggtggtgat aagcgtcctg ctgccaccaa aaaggccgga caggctaaga aaaagaagta        4200
g                                                                                        4201
```

<210> SEQ ID NO 249
<211> LENGTH: 1021
<212> TYPE: DNA
<213> ORGANISM: Artificial
<220> FEATURE:
<223> OTHER INFORMATION: Chimeric cDNA -continued

```
<400> SEQUENCE: 249
gaaaacaacc acagaatctt ccttgcaggt gataaggaca atgtgataga ccagatagag      60
aagcaagcga aggatttagc attccctggt tcgggtgaac aagttgagaa gctcatcaaa     120
aaccagaggg agtctcactt tgtgagtgct ctgcctcaat ctcaatctcc gtcgtctcct     180
gaaaaagagg caatggccaa gctcaccata ctagtagccc tcgccctttt cctcctcgct     240
gcccacgcat ctgcgaggca gcagtgggaa ctccaaggag acagaagatg ccagagccag     300
ctcgagaggg tccagcgcct gaatgcgcaa aggcctgaca accgcattga atcggagggc     360
ggttacattg agacttggaa cccaaacaac caggagttag aatgcgccgg cgtcgccctc     420
tggtagctct ccttgccctc gtcctggtgg cacacgcctc cgcaatgagg cgcgagaggg     480
ggagacaggg ggactcatca agctgcgaga ggcaggtaga tcagcatcct agtagccctc     540
ctgggcgccc ttcttgtcgt gagcctccgc gacaagatgg gatcccgatc gagggtccag     600
agggttgaga tgggacgcac cttgatgacg tcaagagtgt tgaaatcgtt gagggaaagg     660
gtggtcctgg aaccatcaag aaactcacca ttgtcgagga tggagaaacc aagtttatct     720
tcccgagaga ggtccgtcca cctctcaaat catcgccgtc ctcgtcggcg tccccactgg     780
gggcactctg ttgctcctct ccggcctttc acttctcgga accataatcg ggctggcaat     840
tgccaccccg gttttactt tcttcagccc ggaaacccca tcacttcttg tctaaaaatt     900
ctcaaaagtc accagccacc aaaaacccat ttaccattat gtctgatcaa acaaggacag     960
gctatggagg aggagggtcc tatggatcat cctatggtgg aggaggcacc tatggttcat    1020
c                                                                   1021

<210> SEQ ID NO 250
<211> LENGTH: 1210
<212> TYPE: DNA
<213> ORGANISM: Artificial
<220> FEATURE:
<223> OTHER INFORMATION: Chimeric cDNA

<400> SEQUENCE: 250
ggctcgagtt tctgcaacgc aggccaagtc accttaccgg aaaacagaga acccctgcgc      60
ccagaggtgc ctccagagtt gtcaacagga accggacgac ttgaagcaaa aggcatgcga     120
gtctcgctgc accaagctcg agtatgatcc tcgttgtgtc tatgacactg cgccaccaa     180 ccaacgtcac cctccagggg agcggacacg tggccgccaa cccggagact acgatgatga     240
ccgccgtcaa ccccgaagag aggaaggagg ccgatgggga ccagctgaac cgagggagcg     300
tgaaagagaa gaagactgga gacaaccaag agaagattgg aggcgaccaa gtcatcagca     360
gccacggaaa ataaggcccg aaggaagaga aggagaacaa gagtggggaa ctccaaggag     420
acagaagatg ccagagccag ctcgagaggg cgaacctgag gccctgcgag caacatctca     480
tgcagaagat ccaacgtgac gaggattcat atgaacggga cccgtacagc cctagtcagg     540
atccgtacag ccctagtcca tatgatcgga gaggcgctgg atcctctcag caccaagaga     600
ggtgttgcaa tgagctgaac gagtttgaga caaccaaag gtgcatgtgc gaggcattgc     660
aacagatcat ggagaaccag agcgataggt tgcagggggg gcaacaggag aagaagaccg     720
tgaatttagc cctcgaggac agcacggccg cagagaacga gcaggacaag aacaagaaaa     780
cgaaggtgga aacatcttca gcggcttcac gccggagttc ctggcacaag ccttccaggt     840
tgacgacaga cagatattgc aaaacctaag aggcgagaac gagagtgacg aacagggagc     900
```

-continued

```
cattgtgaca gtgaggggag gcctcagaat cttgagccca gatagaaaga gaaggcagca        960
gtatgaacgt cccgacgaag aagaggaata cgatgaagat gaatatgaat atgatgaaga       1020
ggagaggcaa caagatagaa ggcgtggcag gggaagcaga acctccaccc tgcccctgc        1080 taagctttac aacgctctga aggatgccga taccatcacc cctaagatta ttgatgacgt       1140
caagagtgtt gaaatcgttg agggaaacgg tggtcctgga accatcaaga aactcaccat       1200
tgtcgaggat                                                              1210

<210> SEQ ID NO 251
<211> LENGTH: 3235
<212> TYPE: DNA
<213> ORGANISM: Artificial
<220> FEATURE:
<223> OTHER INFORMATION: Chimeric cDNA

<400> SEQUENCE: 251
aagcttggtc cgatgtgaga cttttcaaca aagggtaata tccggaaacc tcctcggatt         60
ccattgccca gctatctgtc actttattgt gaagatagtg gaaaggaag gtggctccta         120 caaatgccat cattgcgata aaggaaaggc catcgttgaa gatgcctctg ccgacagtgg         180
tcccaaagat ggaccccac ccacgaggag catcgtggaa aaagaagacg ttccaaccac         240
gtcttcaaag caagtggatt gatgtgatgg tccgattgag acttttcaac aaagggtaat         300
atccggaaac ctcctcggat tccattgccc agctatctgt cactttattg tgaagatagt        360
ggaaaaggaa ggtggctcct acaaatgcca tcattgcgat aaaggaaagg ccatcgttga        420
agatgcctct gccgacagtg gtcccaaaga tggaccccca cccacgagga gcatcgtgga        480
aaaagaagac gttccaacca cgtcttcaaa gcaagtggat tgatgtgata tctccactga        540 cgtaaggat gacgcacaat cccactatcc ttcgcaagac ccttcctcta tataaggaag        600
ttcatttcat ttggagagga cacccggaga ctacgataat gaccgccgtc aaccccgaag        660
agaggaagga ggccgatggg gaaccagctg aaccgaggga gcgtgaaaga gaagcccagc        720
atctgcgagg cagcagtggg aactccaagg agacagaaga tgccagagcc agctcgagag        780
ggcgaacctg aggccctgcg agggttacat tgagacttgg aacccaaaca accagggttc        840
gaatgcgccg gcgtcgccct ctcgcgctta gtcctccgcc gccacgccct ttggtagctc        900
tccttgccct cgtcctggtg gcacacgcct ccgcaatgag gcgcgagagg gggactcatc        960
aagctgcgag atcagcatcc tagtagcatc ctgggcgccc ttcttgtcgt agcctccgcg       1020
acaagatggg atcccgatcg agggtccaga gggttgagat caagagtgtt gaatcgttga       1080
gggaaacggt ggtcctggaa ccatcaaaga aactcaccat tgtcgaggat ggtaccccaa       1140
ttggtaagga ataattatt ttctttttttc ctttttagtat aaaatagtta agtgatgtta       1200
attagtatga ttataataat atagttgtta taattgtgaa aaaataattt ataaatatat       1260
tgtttacata aacaacatag taatgtaaaa aaatatgaca agtgatgtgt aagacgaaga       1320
agataaaagt tgagagtaag tatattattt ttaatgaatt tgatcgaaca tgtaagatga       1380
tatactagca ttaatatttg ttttaatcat aatagtaatt ctagctggtt tgatgaatta       1440
aatatcaatg ataaaatact atagtaaaaa taagaataaa taaattaaaa taatattttt       1500
ttatgattaa tagtttatta tataattaaa tatctatacc attactaaat attttagttt       1560
aaaagttaat aaatattttg ttagaaattc caatctgctt gtaatttatc aataaacaaa       1620
atattaaata acaagctaaa gtaacaaata atatcaaact aatagaaaca gtaatctaat       1680
gtaacaaaac ataatctaat gctaatataa caaagcgcaa gatctatcat tttatatagt       1740
```

-continued

```
attattttca atcaacattc ttattaattt ctaaataata cttgtagttt tattaacttc       1800
taaatggatt gactattaat taaatgaatt agtcgaacat gaataaacaa ggtaacatga       1860
tagatcatgt cattgtgtta tcattgatct tacatttgga ttgattacag ttgggaaatt       1920
gggttcgaaa tcgattagga gctgttacca ctcaaagaaa ctaccaaggt cctggtggca       1980
aagggagttg ctaagttgtg agaactagag ttgggagacc tgggagctag ccctagggta       2040
gaacagcgcc tcctgctgtt cttcccgcgg gtcctacgat gatcctacga ctagagcgtc       2100
gaactactca gggggagagc gcggagtaac gcctccgcac acggtggtcc tgctcccgtt       2160
cctctcgatg gtttcccgca ccgccgcctc ctgattcgcg ctctcccgct gcggccgcgt       2220
aagcttggga ccaacaaacc caaggttcag agttacattg ggagcgtccc ggagtccaag       2280
cgggagagct cgaccgagac cgtagaagac agaggaacct caagggtgac gacgagcgt       2340 ctacgacccg aagagaaagt gcgagggagc caagtcgacc aaggggtagc cggaggaagg       2400
agagaagccc caactgccgc cagtaatagc atcagaggcc ctctagagtc ctgctttaat       2460
gagatatgcg agacgcctat gatcgcatga tatttgcttt caattctgtt gtgcacgttg       2520
taaaaaacct gagcatgtgt agctcagatc cttaccgccg gtttcggttc attctaatga       2580
atatatcacc cgttactatc gtatttttat gaataatatt ctccgttcaa tttactgatt       2640
gtaccctact acttatatgt acaatattaa aatgaaaaca atatattgtg ctgaataggt       2700
ttatagcgac atctatgata gagcgccaca ataacaaaca attgcgtttt attattacaa       2760
atccaatttt aaaaaaagcg gcagaaccgg tcaaacctaa aagactgatt acataaatct       2820
tattcaaatt tcaaaaggcc ccaggggcta gtatctacga cacaccgagc ggcgaactaa       2880
taacgttcac tgaagggaac tccggttccc cgccggcgcg catgggtgag attccttgaa       2940
gttgagtatt ggccgtccgc tctaccgaaa gttacgggca ccattcaacc cggtccagca       3000
cggcggccgg gtaaccgact tgctgccccg agaattatgc agcattttt tggtgtatgt       3060 gggccccaaa tgaagtgcag gtcaaacctt gacagtgacg acaaatcgtt gggcgggtcc       3120
agggcgaatt ttgcgacaac atgtcgaggc tcagcaggac ctgcaggcat gcaagctagc       3180
ttactagtga tgcatattct atagtgtcac ctaaatctgc ggccgcgagc tcttt          3235
```

<210> SEQ ID NO 252
<211> LENGTH: 3235
<212> TYPE: DNA
<213> ORGANISM: Artificial
<220> FEATURE:
<223> OTHER INFORMATION: Chimeric cDNA

<400> SEQUENCE: 252

```
aagcttggtc cgatgtgaga cttttcaaca aagggtaata tccggaaacc tcctcggatt        60
ccattgccca gctatctgtc actttattgt gaagatagtg gaaaaggaag gtggctccta       120
caaatgccat cattgcgata aaggaaaggc catcgttgaa gatgcctctg ccgacagtgg       180
tcccaaagat ggacccccac ccacgaggag catcgtggaa aaagaagacg ttccaaccac       240
gtcttcaaag caagtggatt gatgtgatgg tccgattgag acttttcaac aaagggtaat       300
atccggaaac ctcctcggat tccattgccc agctatctgt cactttattg tgaagatagt       360
ggaaaaggaa ggtggctcct acaaatgcca tcattgcgat aaaggaaagg ccatcgttga       420
agatgcctct gccgacagtg gtcccaaaga tggaccccca cccacgagga gcatcgtgga       480
aaaagaagac gttccaacca cgtcttcaaa gcaagtggat tgatgtgata tctccactga       540
```

```
cgtaagggat gacgcacaat cccactatcc ttcgcaagac ccttcctcta tataaggaag    600
ttcatttcat ttggagagga cacccggaga ctacgataat gaccgccgtc aaccccgaag    660
agaggaagga ggccgatggg gaaccagctg aaccgaggga gcgtgaaaga gaagcccagc    720
atctgcgagg cagcagtggg aactccaagg agacagaaga tgccagagcc agctcgagag    780
ggcgaacctg aggccctgcg agggttacat tgagacttgg aacccaaaca accagggttc    840
gaatgcgccg gcgtcgccct ctcgcgctta gtcctccgcc gccacgccct ttggtagctc    900
tccttgccct cgtcctggtg gcacacgcct ccgcaatgag gcgcgagagg gggactcatc    960
aagctgcgag atcagcatcc tagtagcatc ctgggcgccc ttcttgtcgt agcctccgcg   1020
acaagatggg atcccgatcg agggtccaga gggttgagat caagagtgtt gaatcgttga   1080
gggaaacggt ggtcctggaa ccatcaaaga aactcaccat tgtcgaggat ggtaccccaa   1140
ttggtaagga aataattatt ttctttttttc cttttagtat aaaatagtta agtgatgtta   1200
attagtatga ttataataat atagttgtta taattgtgaa aaaataattt ataaatatat   1260
tgtttacata aacaacatag taatgtaaaa aaatatgaca agtgatgtgt aagacgaaga   1320
agataaaagt tgagagtaag tatattattt ttaatgaatt tgatcgaaca tgtaagatga   1380
tatactagca ttaatatttg ttttaatcat aatagtaatt ctagctggtt tgatgaatta   1440
aatatcaatg ataaaatact atagtaaaaa taagaataaa taaattaaaa taatattttt   1500
ttatgattaa tagtttatta tataattaaa tatctatacc attactaaat attttagttt   1560
aaaagttaat aaatattttg ttagaaattc caatctgctt gtaatttatc aataaacaaa   1620
atattaaata acaagctaaa gtaacaaata atatcaaact aatagaaaca gtaatctaat   1680
gtaacaaaac ataatctaat gctaatataa caaagcgcaa gatctatcat tttatatagt   1740
attattttca atcaacattc ttattaattt ctaaataata cttgtagttt tattaacttc   1800
taaatggatt gactattaat taaatgaatt agtcgaacat gaataaacaa ggtaacatga   1860
tagatcatgt cattgtgtta tcattgatct tacatttgga ttgattacag ttgggaaatt   1920
gggttcgaaa tcgattagga gctgttacca ctcaaagaaa ctaccaaggt cctggtggca   1980
aagggagttg ctaagttgtg agaactagag ttgggagacc tgggagctag ccctagggta   2040
gaacagcgcc tcctgctgtt cttcccgcgg gtcctacgat gatcctacga ctagagcgtc   2100
gaactactca gggggagagc gcggagtaac gcctccgcac acggtggtcc tgctcccgtt   2160
cctctcgatg gtttcccgca ccgccgcctc ctgattcgcg ctctcccgct gcggccgcgt   2220
aagcttggga ccaacaaacc caaggttcag agttacattg ggagcgtccc ggagtccaag   2280
cgggagagct cgaccgagac cgtagaagac agaggaacct caagggtgac gacggagcgt   2340
ctacgacccg aagagaaagt gcgagggagc caagtcgacc aaggggtagc cggaggaagg   2400
agagaagccc caactgccgc cagtaatagc atcagaggcc ctctagagtc ctgctttaat   2460
gagatatgcg agacgcctat gatcgcatga tatttgcttt caattctgtt gtgcacgttg   2520
taaaaaacct gagcatgtgt agctcagatc cttaccgccg gtttcggttc attctaatga   2580
atatatcacc cgttactatc gtatttttat gaataatatt ctccgttcaa tttactgatt   2640
gtaccctact acttatatgt acaatattaa aatgaaaaca atatattgtg ctgaataggt   2700
ttatagcgac atctatgata gagcgccaca ataacaaaca attgcgtttt attattacaa   2760
atccaatttt aaaaaaagcg gcagaaccgg tcaaacctaa aagactgatt acataaatct   2820
tattcaaatt tcaaaaggcc ccaggggcta gtatctacga cacaccgagc ggcgaactaa   2880
taacgttcac tgaagggaac tccggttccc cgccggcgcg catgggtgag attccttgaa   2940
```

-continued gttgagtatt ggccgtccgc tctaccgaaa gttacgggca ccattcaacc cggtccagca    3000
cggcggccgg gtaaccgact tgctgccccg agaattatgc agcattttt tggtgtatgt    3060 gggcccaaa tgaagtgcag gtcaaacctt gacagtgacg acaaatcgtt gggcgggtcc    3120
agggcgaatt ttgcgacaac atgtcgaggc tcagcaggac ctgcaggcat gcaagctagc    3180
ttactagtga tgcatattct atagtgtcac ctaaatctgc ggccgcgagc tcttt    3235

<210> SEQ ID NO 253
<211> LENGTH: 3170
<212> TYPE: DNA
<213> ORGANISM: Artificial
<220> FEATURE:
<223> OTHER INFORMATION: Chimeric cDNA

<400> SEQUENCE: 253
tcccatttga cactacggaa gtaactgaag atctgctttt acatgcgaga cacatcttct      60
aaagtaattt taataatagt tactatattc aagatttcat atatcaaata ctcaatatta     120
cttctaaaaa attaattaga tataattaaa atattacttt tttaatttta agtttaattg     180
ttgaatttgt gactattgat ttattattct actatgttta aattgtttta tagatagttt     240
aaagtaaata taagtaatgt agtagagtgt tagagtgtta ccctaaacca taaactataa     300
catttatggt ggactaattt tcatatattt cttattgctt ttacctttt ttggtatgta     360 agtccgtaac tagaattaca gtgggttgcc atggcactct gtggtctttt ggttcatgca     420
tgggtcttgc gcaagaaaaa gacaaagaac aaagaaaaaa gacaaacag agagacaaaa     480 cgcaatcaca caaccaactc aaattagtca ctggctgatc aagatcgccg cgtccatgta     540
tgtctaaatg ccatgcaaag caacacgtgc ttaacatgca cttaaatgg ctcacccatc     600 tcaacccaca cacaaacaca ttgcctttt cttcatcatc accacaacca cctgtatata     660
ttcattctct tccgccacct caatttcttc acttcaacac acgtcaacct gcatatgcgt     720
gtcatcccat gcccaaatct ccatgcatgt tccaaccacc ttctctctta tataatacct     780
ataaatacct ctaatatcac tcacttcttt catcatccat ccatccagag tactactact     840
ctactactat aataccccaa cccaactcat attcaatact actctactag gacacccgga     900
gactacgata atgaccgccg tcaaccccga agagaggaag gaggccgatg gggaaccagc     960
tgaaccgagg gagcgtgaaa gagaagccca gcatctgcga ggcagcagtg gaactccaa    1020 ggagacagaa gatgccagag ccagctcgag agggcgaacc tgaggccctg cgagggttac    1080
attgagactt ggaacccaaa caaccagggt tcgaatgcgc cggcgtcgcc ctctcgcgct    1140
tagtcctccg ccgccacgcc ctttggtagc tctccttgcc ctcgtcctgg tggcacacgc    1200
ctccgcaatg aggcgcgaga gggggactca tcaagctgcg agatcagcat cctagtagca    1260
tcctgggcgc ccttcttgtc gtagcctccg cgacaagatg ggatcccgat cgagggtcca    1320
gagggttgag atcaagagtg ttgaatcgtt gagggaaacg gtggtcctgg aaccatcaaa    1380
gaaactcacc attgtcgagg atggtacccc aattggtaag gaaataatta ttttctttt    1440 tccttttagt ataaaatagt taagtgatgt taattagtat gattataata atatagttgt    1500
tataattgtg aaaaaataat ttataaatat attgtttaca taaacaacat agtaatgtaa    1560
aaaaatatga caagtgatgt gtaagacgaa gaagataaaa gttgagagta agtatattat    1620
ttttaatgaa tttgatcgaa catgtaagat gatatactag cattaatatt tgttttaatc    1680
ataatagtaa ttctagctgg tttgatgaat taaatatcaa tgataaaata ctatagtaaa    1740

-continued

```
aataagaata aataaattaa aataatattt ttttatgatt aatagtttat tatataatta      1800
aatatctata ccattactaa atattttagt ttaaaagtta ataaatattt tgttagaaat      1860
tccaatctgc ttgtaattta tcaataaaca aaatattaaa taacaagcta aagtaacaaa      1920
taatatcaaa ctaatagaaa cagtaatcta atgtaacaaa acataatcta atgctaatat      1980
aacaaagcgc aagatctatc attttatata gtattatttt caatcaacat tcttattaat      2040
ttctaaataa tacttgtagt tttattaact tctaaatgga ttgactatta attaaatgaa      2100
ttagtcgaac atgaataaac aaggtaacat gatagatcat gtcattgtgt tatcattgat      2160
cttacatttg gattgattac agttgggaaa ttgggttcga aatcgattag gagctgttac      2220
cactcaaaga aactaccaag gtcctggtgg caaagggagt tgctaagttg tgagaactag      2280
agttgggaga cctgggagct agccctaggg tagaacagcg cctcctgctg ttcttcccgc      2340
gggtcctacg atgatcctac gactagagcg tcgaactact caggggagag gcgcggagta      2400
acgcctccgc acacggtggt cctgctcccg ttcctctcga tggtttcccg caccgccgcc      2460
tcctgattcg cgctctcccg ctgcggccgc gtaagcttgg gaccaacaaa cccaaggttc      2520
agagttacat tgggagcgtc ccggagtcca agcgggagag ctcgaccgag accgtagaag      2580
acagaggaac ctcaagggtg acgacggagc gtctacgacc cgaagagaaa gtgcgaggga      2640
gccaagtcga ccaaggggta gccggaggaa ggagagaagc cccaactgcc gccagtaata      2700
gcatcagagg cccatatgaa gatgaagatg aaatatttgg tgtgtcaaat aaaaagcttg      2760
tgtgcttaag tttgtgtttt tttcttggct tgttgtgtta tgaatttgtg gctttttcta      2820
atattaaatg aatgtaagat ctcattataa tgaataaaca aatgtttcta taatccattg      2880
tgaatgtttt gttggatctc ttctgcagca tataactact gtatgtgcta tggtatggac      2940
tatggaatat gattaaagat aagatgggct catagagtaa aacgaggcga gggacctata      3000
aacctccctt catcatgcta tttcatgatc tattttataa aataaagatg tagaaaaaag      3060
taagcgtaat aaccgcaaaa caaatgattt aaaacatggc acataatgag gagattaagt      3120
tcggtttacg tttattttag tactaattgt aacgtgagac tacgtatcgg                 3170
```

<210> SEQ ID NO 254
<211> LENGTH: 3169
<212> TYPE: DNA
<213> ORGANISM: Artificial
<220> FEATURE:
<223> OTHER INFORMATION: Chimeric cDNA

<400> SEQUENCE: 254

```
tcccatttga cactacggaa gtaactgaag atctgctttt acatgcgaga cacatcttct        60
aaagtaattt taataatagt tactatattc aagatttcat atatcaaata ctcaatatta       120
cttctaaaaa attaattaga tataattaaa atattacttt tttaatttta agtttaattg       180
ttgaatttgt gactattgat ttattattct actatgttta aattgtttta tagatagttt       240
aaagtaaata taagtaatgt agtagagtgt tagagtgtta ccctaaacca taaactataa       300
catttatggt ggactaattt tcatatattt cttattgctt ttaccttttc ttggtatgta       360
agtccgtaac tagaattaca gtgggttgcc atggcactct gtggtctttt ggttcatgca       420
tgggtcttgc gcaagaaaaa gacaaagaac aaagaaaaaa gacaaaacag agagacaaaa       480
cgcaatcaca caaccaactc aaattagtca ctggctgatc aagatcgccg cgtccatgta       540
tgtctaaatg ccatgcaaag caacacgtgc ttaacatgca ctttaaatgg ctcacccatc       600
tcaacccaca cacaaacaca ttgccttttt cttcatcatc accacaacca cctgtatata       660
```

-continued

```
ttcattctct tccgccacct caatttcttc acttcaacac acgtcaacct gcatatgcgt      720
gtcatcccat gcccaaatct ccatgcatgt tccaaccacc ttctctctta tataatacct      780
ataaatacct ctaatatcac tcacttcttt catcatccat ccatccagag tactactact      840
ctactactat aataccccaa cccaactcat attcaatact actctactag gacacccgga      900
gactacgata atgaccgccg tcaaccccga agagaggaag gaggccgatg gggaaccagc      960
tgaaccgagg gagcgtgaaa gagaagccca gcatctgcga ggcagcagtg ggaactccaa     1020
ggagacagaa gatgccagag ccagctcgag agggcgaacc tgaggccctg cgagggttac     1080
attgagactt ggaacccaaa caaccagggt tcgaatgcgc cggcgtcgcc ctctcgcgct     1140
tagtcctccg ccgccacgcc ctttggtagc tctccttgcc ctcgtcctgg tggcacacgc     1200
ctccgcaatg aggcgcgaga gggggactca tcaagctgcg agatcagcat cctagtagca     1260
tcctgggcgc ccttcttgtc gtagcctccg cgacaagatg ggatcccgat cgagggtcca     1320
gagggttgag atcaagagtg ttgaatcgtt gagggaaacg gtggtcctgg aaccatcaaa     1380
gaaactcacc attgtcgagg atggtacccc aattggtaag gaaataatta ttttcttttt     1440
tccttttagt ataaaatagt taagtgatgt taattagtat gattataata atatagttgt     1500
tataattgtg aaaaaataat ttataaatat attgtttaca taaacaacat agtaatgtaa     1560
aaaaatatga caagtgatgt gtaagacgaa gaagataaaa gttgagagta agtatattat     1620
ttttaatgaa tttgatcgaa catgtaagat gatatactag cattaatatt tgttttaatc     1680
ataatagtaa ttctagctgg tttgatgaat aaaatatcaa tgataaaata ctatagtaaa     1740
aataagaata aataaattaa aataatattt ttttatgatt aatagtttat tatataatta     1800
aatatctata ccattactaa atattttagt ttaaaagtta ataaatattt tgttagaaat     1860
tccaatctgc ttgtaattta tcaataaaca aaatattaaa taacaagcta aagtaacaaa     1920
taatatcaaa ctaatagaaa cagtaatcta atgtaacaaa acataatcta atgctaatat     1980
aacaaagcgc aagatctatc attttatata gtattatttt caatcaacat tcttattaat     2040
ttctaaataa tacttgtagt tttattaact tctaaatgga ttgactatta attaaatgaa     2100
ttagtcgaac atgaataaac aaggtaacat gatagatcat gtcattgtgt tatcattgat     2160
cttacatttg gattgattac agttgggaaa ttgggttcga aatcgattcc tcgacaatgg     2220
tgagtttctt tgatggttcc aggaccaccg tttccctcaa cgattcaaca ctcttgatct     2280
caaccctctg gaccctcgat cgggatccca tcttgtcgcg gaggctacga caagaagggc     2340
gcccaggatg ctactaggat gctgatctcg cagcttgatg agtccccctc tcgcgcctca     2400
ttgcggaggc gtgtgccacc aggacagggc aaggagagct accaaagggc gtggcggcgg     2460
aggactaagc gcgagagggc gacgccggcg cattcgaacc ctggttgttt gggttccaag     2520
tctcaatgta accctcgcag ggcctcaggt tcgccctctc gagctggctc tggcatcttc     2580
tgtctccttg gagttccac tgctgcctcg cagatgctgg gcttctcttt cacgctccct     2640
cggttcagct ggttcccatc ggcctccttc ctctcttcgg ggttgacggc ggtcattatc     2700
gtagtctccg ggatatgaag atgaagatga aatatttggt gtgtcaaata aaaagcttgt     2760
gtgcttaagt ttgtgttttt ttcttggctt gttgtgttat gaatttgtgg cttttttctaa    2820 tattaaatga atgtaagatc tcattataat gaataaacaa atgtttctat aatccattgt     2880
gaatgttttg ttggatctct tctgcagcat ataactactg tatgtgctat ggtatggact     2940
atggaatatg attaaagata agatgggctc atagagtaaa acgaggcgag ggacctataa     3000
```

-continued

```
acctcccttc atcatgctat ttcatgatct attttataaa ataaagatgt agaaaaaagt      3060
aagcgtaata accgcaaaac aaatgattta aaacatggca cataatgagg agattaagtt      3120
cggtttacgt ttattttagt actaattgta acgtgagact acgtatcgg                 3169

<210> SEQ ID NO 255
<211> LENGTH: 3724
<212> TYPE: DNA
<213> ORGANISM: Artificial
<220> FEATURE:
<223> OTHER INFORMATION: Chimeric cDNA

<400> SEQUENCE: 255
tcccatttga cactacggaa gtaactgaag atctgctttt acatgcgaga cacatcttct        60
aaagtaattt taataatagt tactatattc aagatttcat atatcaaata ctcaatatta       120
cttctaaaaa attaattaga tataattaaa atattacttt tttaatttta agtttaattg       180
ttgaatttgt gactattgat ttattattct actatgttta aattgtttta tagatagttt       240
aaagtaaata taagtaatgt agtagagtgt tagagtgtta ccctaaacca taaactataa       300
catttatggt ggactaattt tcatatattt cttattgctt ttaccttttc ttggtatgta       360
agtccgtaac tagaattaca gtgggttgcc atggcactct gtggtctttt ggttcatgca       420
tgggtcttgc gcaagaaaaa gacaagaac aaagaaaaaa gacaaacag agagacaaaa        480 cgcaatcaca caaccaactc aaattagtca ctggctgatc aagatcgccg cgtccatgta       540
tgtctaaatg ccatgcaaag caacacgtgc ttaacatgca ctttaaatgg ctcacccatc       600
tcaacccaca cacaaacaca ttgccttttt cttcatcatc accacaacca cctgtatata       660
ttcattctct tccgccacct caatttcttc acttcaacac acgtcaacct gcatatgcgt       720
gtcatcccat gcccaaatct ccatgcatgt tccaaccacc ttctctctta tataatacct       780
ataaatacct ctaatatcac tcacttcttt catcatccat ccatccagag tactactact       840
ctactactat aataccccaa cccaactcat attcaatact actctactgc tgtcattcga       900
gggaagaagg gtcctggtgg tgttaccatt aagaagacga atcaggcgtt gatcatcgga       960
atctacgatg agccgatgac tgcctctaac caaggcaacg ccgccgccct ccctggaaga      1020
tgcggtgtca gcattcctta caagatcagc acatccacca acatcggtgc cggagcagct      1080
ggaatggcaa agcaccgcat ggctgacgtg gccggttacg ttggacagaa gacgaaggat      1140
gcacttcata attaattaat aacatggctg aagcactcta ctacggcggc cgccaacgcc      1200
aagagcaacc aaggtccacc ctggtgaaaa cagaggcaaa gctatgcaac cacctggcag      1260
atacatacag aggaccatgc tttaccaatg caagctgcga tgatcattgc atcattctct      1320
ttcttgctca ggaatatggc gtggaggaa aggagtgttt gaacctaagt gacaaattca       1380
agggaccgtg tttgggttca aagaacgcgt cgacgttcca cgccgcggct acgatgttag      1440
tggtggtggt attaagactc ttctccccga gagaggtccg tccacctctc aaatctacca      1500
ttatgtctga tcaaacaagg acaggctatg gaggaggagg gtcctatgga tcatcctatg      1560
gtggaggagg cacctatggt tcatcggtac cccaattggt aaggaaataa ttattttctt      1620
ttttcctttt agtataaaat agttaagtga tgttaattag tatgattata ataatatagt      1680
tgttataatt gtgaaaaaat aatttataaa tatattgttt acataaacaa catagtaatg      1740
taaaaaaata tgacaagtga tgtgtaagac gaagaagata aaagttgaga gtaagtatat      1800 tattttttaat gaatttgatc gaacatgtaa gatgatatac tagcattaat atttgtttta      1860
atcataatag taattctagc tggtttgatg aattaaatat caatgataaa atactatagt      1920
```

```
aaaaataaga ataaataaat taaaataata tttttttatg attaatagtt tattatataa     1980
ttaaatatct ataccattac taaatatttt agtttaaaag ttaataaata ttttgttaga     2040
aattccaatc tgcttgtaat ttatcaataa acaaaatatt aaataacaag ctaaagtaac     2100
aaataatatc aaactaatag aaacagtaat ctaatgtaac aaaacataat ctaatgctaa     2160
tataacaaag cgcaagatct atcattttat atagtattat tttcaatcaa cattcttatt     2220
aatttctaaa taatacttgt agtttttatta acttctaaat ggattgacta ttaattaaat    2280
gaattagtcg aacatgaata aacaaggtaa catgatagat catgtcattg tgttatcatt     2340
gatcttacat ttggattgat tacagttggg aaattgggtt cgaaatcgat gatgaaccat     2400
aggtgcctcc tccaccatag gatgatccat aggaccctcc tcctccatag cctgtccttg     2460
tttgatcaga cataatggta gatttgagag gtggacggac ctctctcggg gagaagagtc     2520
ttaataccac caccactaac atcgtagccg cggcgtggaa cgtcgacgcg ttctttgaac     2580
ccaaacacgg tcccttgaat tgtcacttag gttcaaacac tcctttccct ccacgccata     2640
ttcctgagca agaaagagaa tgatgcaatg atcatcgcag cttgcattgg taaagcatgg     2700
tcctctgtat gtatctgcca ggtggttgca tagtttgcct ctgtttttcac cagggtggac    2760 cttggttgct cttggcgttg gcggccgccg tagtagagtg cttcagccat gttattatta     2820
attatgaagt gcatccttcg tcttctgtcc aacgtaaccg gccacgtcag ccatgcggtg     2880
ctttgccatt ccagctgctc cggcaccgat gttggtggat gtgctgatct tgtaaggaat     2940
gctgacaccg catcttccag ggagggcggc ggcgttgcct tggttagagg cagtcatcgg     3000
ctcatcgtag attccgatga tcaacgcctg attcgtcttc ttaatggtaa caccaccagg     3060
acccttcttc cctcgaatga cagcaacccct cgcagggcct caggttcgcc ctctcgagct     3120
ggctctggca tcttctgtct ccttggagtt cccactgctg cctcgcagat gctgggcttc     3180
tctttcacgc tccctcggtt cagctggttc ccatcggcct ccttcctctc ttcggggttg     3240
acggcggtca ttatcgtagt ctccgggata tgaagatgaa gatgaaatat ttggtgtgtc     3300
aaataaaaag cttgtgtgct taagtttgtg ttttttttctt ggcttgttgt gttatgaatt     3360
tgtggctttt tctaatatta aatgaatgta agatctcatt ataatgaata aacaaatgtt     3420
tctataatcc attgtgaatg ttttgttgga tctcttctgc agcatataac tactgtatgt     3480
gctatggtat ggactatgga atatgattaa agataagatg ggctcataga gtaaaacgag     3540
gcgagggacc tataaacctc ccttcatcat gctatttcat gatctatttt ataaaataaa     3600
gatgtagaaa aaagtaagcg taataaccgc aaaacaaatg atttaaaaca tggcacataa     3660
tgaggagatt aagttcggtt tacgtttatt ttagtactaa ttgtaacgtg agactacgta     3720
tcgg                                                                 3724
```

<210> SEQ ID NO 256
<211> LENGTH: 3581
<212> TYPE: DNA
<213> ORGANISM: Artificial
<220> FEATURE:
<223> OTHER INFORMATION: Chimeric cDNA
<220> FEATURE:
<221> NAME/KEY: misc_feature
<222> LOCATION: (1250)..(1250)
<223> OTHER INFORMATION: n is a, c, g, or t
<220> FEATURE:
<221> NAME/KEY: misc_feature
<222> LOCATION: (1255)..(1255)
<223> OTHER INFORMATION: n is a, c, g, or t
<220> FEATURE:

<221> NAME/KEY: misc_feature
<222> LOCATION: (2165)..(2165)
<223> OTHER INFORMATION: n is a, c, g, or t
<220> FEATURE:
<221> NAME/KEY: misc_feature
<222> LOCATION: (2170)..(2170)
<223> OTHER INFORMATION: n is a, c, g, or t

<400> SEQUENCE: 256

```
ggtccgatgt gagacttttc aacaaagggt aatatccgga aacctcctcg gattccattg    60
cccagctatc tgtcactta ttgtgaagat agtggaaaag gaaggtggct cctacaaatg   120
ccatcattgc gataaaggaa aggccatcgt tgaagatgcc tctgccgaca gtggtcccaa   180
agatggaccc ccacccacga ggagcatcgt ggaaaaagaa gacgttccaa ccacgtcttc   240
aaagcaagtg gattgatgtg atggtccgat tgagactttt caacaaaggg taatatccgg   300
aaacctcctc ggattccatt gcccagctat ctgtcacttt attgtgaaga gagtggaaaa   360
ggaaggtggc tcctacaaat gccatcattg cgataaagga aaggccatcg ttgaagatgc   420
ctctgccgac agtggtccca agatggaccc ccacccacg aggagcatcg tggaaaaaga   480
agacgttcca accacgtctt caaagcaagt ggattgatgt gatatctcca ctgacgtaag   540
ggatgacgca caatcccact atccttcgca agacccttcc tctatataag gaagttcatt   600
tcatttggag aggacactcc ttgtcctggc ttcagtttct gcaacgcatg ccaagtcatc   660
accttaccag aagaaaacag agaaccctg cgcccagagg tgcctccaga gttgtcaaca   720
ggaaccggat gacttgaagc aaaaggcatg cgagtctcgc tgcaccaagc tcgagtatga   780
tcctcgttgt gtctatgatc ctcgagacac actggcacca ccaaccaacg ttcccctcca   840
ggggagcggc cgcgcgagca acatctcatg cagaaggtcc aacgtgacga ggattcatat   900
gaacgggacc cgtacagccc tagtcaggat ccgtacagcc ctagtccata tgatcggaga   960
ggcgctggat cctctcagca ccaagagagg tgttgcaatg agctgaacga gtttgagaac  1020
aaccaaaggt gcatgtgcga ggcattgcaa cagatcatgg agaaccagag cgataggttg  1080
caggggaggc aacaggagca acagttcaag agggagctct agaacagcac ggccgcagag  1140
aacgagcagg acaagaacaa gaaaacgaag gtggaaacat cttcagcggc ttcacgccgg  1200
agttcctggc acaaagcctt ccaggttgac gacagacaga tattgcaaan cctangaggc  1260
gaggaacgag agtgacgaac agggagccat tgtgacagtg aagggaagct tggccaattg  1320
gtaaggaaat aattattttc tttttccctt ttagtataaa atagttaagt gatgttaatt  1380
agtatgatta taataatata gttgttataa ttgtgaaaaa ataatttata aatatattgt  1440
ttacataaac aacatagtaa tgtaaaaaaa tatgacaagt gatgtgtaag acgaagaaga  1500
taaaagttga gagtaagtat attatttta atgaatttga tcgaacatgt aagatgatat  1560
actagcatta atatttgttt taatcataat agtaattcta gctggtttga tgaattaaat  1620
atcaatgata aaatactata gtaaaaataa gaataaataa attaaaataa tattttttta  1680
tgattaatag tttattatat aattaaatat ctataccatt actaaatatt ttagtttaaa  1740
agttaataaa tattttgtta gaaattccaa tctgcttgta atttatcaat aaacaaaata  1800
ttaaataaca agctaaagta acaaataata tcaaactaat agaaacagta atctaatgta  1860
acaaaacata atctaatgct aatataacaa agcgcaagat ctatcatttt atatagtatt  1920
attttcaatc aacattctta ttaatttcta ataatactt gtagttttat taacttctaa  1980
atggattgac tattaattaa atgaattagt cgaacatgaa taaacaaggt aacatgatag  2040
atcatgtcat tgtgttatca ttgatcttac atttggattg attacagttg ggaaattggg  2100
```

-continued

```
ttcgaaggtt cgaagggaag tgacagtgtt accgagggac aagcagtgag agcaaggagc   2160
ggagnatccn aaacgttata gacagacagc agttggacct tccgaaacac ggtccttgag   2220
gccgcacttc ggcgacttct acaaaggtgg aagcaaaaga acaagaacag gacgagcaag   2280
agacgccggc acgacaagat ctcgagggag aacttgacaa cgaggacaac ggaggggacg   2340
ttggatagcg agaccaagag gtactagaca acgttacgga gcgtgtacgt ggaaaccaac   2400
aagagtttga gcaagtcgag taacgttgtg gagagaacca cgactctcct aggtcgcgga   2460
gaggctagta tacctgatcc cgacatgcct aggactgatc ccgacatgcc cagggcaagt   2520
atacttagga gcagtgcaac ctggaagacg tactctacaa cgagcgcgcc ggcgagggga   2580
cctccccttg caaccaacca ccacggtcac acagagctcc tagtatctgt gttgctccta   2640
gtatgagctc gaaccacgtc gctctgagcg tacggaaaac gaagttcagt aggccaagga   2700
caactgttga gacctccgtg gagacccgcg tccccaagag acaaagaag accattccac    2760 tactgaaccg tacgcaacgt ctttgacttc ggtcctgttc ctgtcctgct ttaatgagat   2820
atgcgagacg cctatgatcg catgatattt gctttcaatt ctgttgtgca cgttgtaaaa   2880
aacctgagca tgtgtagctc agatccttac cgccggtttc ggttcattct aatgaatata   2940
tcacccgtta ctatcgtatt tttatgaata atattctccg ttcaatttac tgattgtacc   3000
ctactactta tatgtacaat attaaaatga aaacaatata ttgtgctgaa taggtttata   3060
gcgacatcta tgatagagcg ccacaataac aaacaattgc gttttattat tacaaatcca   3120
attttaaaaa aagcggcaga accggtcaaa cctaaaagac tgattacata aatcttattc   3180
aaatttcaaa aggccccagg ggctagtatc tacgacacac cgagcggcga actaataacg   3240
ttcactgaag ggaactccgg ttccccgccg gcgcgcatgg gtgagattcc ttgaagttga   3300
gtattggccg tccgctctac cgaaagttac gggcaccatt caacccggtc cagcacggcg   3360
gccgggtaac cgacttgctg ccccgagaat tatgcagcat ttttttggtg tatgtgggcc   3420
ccaaatgaag tgcaggtcaa accttgacag tgacgacaaa tcgttgggcg ggtccagggc   3480
gaattttgcg acaacatgtc gaggctcagc aggacctgca ggcatgcaag ctagcttact   3540
agtgatgcat attctatagt gtcacctaaa tctgcggccg c                       3581
```

<210> SEQ ID NO 257
<211> LENGTH: 920
<212> TYPE: DNA
<213> ORGANISM: Arachis hypogaea

<400> SEQUENCE: 257

```
ccaaagcaca tacttatcga tttaaatttc atcgaagaga ttaatatcga ataatcatat     60
acatacttta aatacataac aaattttaaa tacatatatc tggtatataa ttaattttt     120 aaagtcatga agtatgtatc aaatacacat atggaaaaaa ttaactattc ataatttaaa    180
aaatagaaaa gatacatcta gtgaaattag gtgcatgtat caaatacatt aggaaaaggg    240
catatatctt gatctagata attaacgatt ttgatttatg tataatttcc aaatgaaggt    300
ttatatctac ttcagaaata acaatatact tttatcagaa cattcaacaa agcaacaacc    360
aactagagtg aaaaatacac attgttctct agacatacaa aattgagaaa agaatctcaa    420
aatttagaga aacaaatctg aatttctaga agaaaaaaat aattatgcac tttgctattg    480
ctcgaaaaat aaatgaaaga aattagactt ttttaaaaga tgttagacta gatatactca    540
aaagctatta aaggagtaat attcttctta cattaagtat tttagttaca gtcctgtaat    600
```

```
taaagacaca ttttagattg tatctaaact taaatgtatc tagaatacat atatttgaat        660
gcatcatata catgtatccg acacaccaat tctcataaaa aacgtaatat cctaaactaa        720
tttatccttc aagtcaactt aagcccaata tacattttca tctctaaagg cccaagtggc        780
acaaaatgtc aggcccaatt acgaagaaaa gggcttgtaa aaccctaata aagtggcact        840
ggcagagctt acactctcat tccatcaaca aagaaaccct aaaagccgca gcgccactga        900
tttctctcct ccaggcgaag                                                    920
```

```
<210> SEQ ID NO 258
<211> LENGTH: 457
<212> TYPE: DNA
<213> ORGANISM: Arachis hypogaea

<400> SEQUENCE: 258
atatgaagat gaagatgaaa tatttggtgt gtcaaataaa aagcttgtgt gcttaagttt         60 gtgtttttt cttggcttgt tgtgttatga atttgtggct ttttctaata ttaaatgaat        120
gtaagatctc attataatga ataaacaaat gtttctataa tccattgtga atgtttgtt         180 ggatctcttc tgcagcatat aactactgta tgtgctatgg tatggactat ggaatatgat        240
taaagataag atgggctcat agagtaaaac gaggcgaggg acctataaac ctcccttcat        300
catgctattt catgatctat tttataaaat aaagatgtag aaaaaagtaa gcgtaataac        360
cgcaaaacaa atgatttaaa acatggcaca taatgaggag attaagttcg gtttacgttt        420
attttagtac taattgtaac gtgagactac gtatcgg                                 457
```

```
<210> SEQ ID NO 259
<211> LENGTH: 448
<212> TYPE: DNA
<213> ORGANISM: Arachis hypogaea

<400> SEQUENCE: 259
aagcttcgtt gaacaacgga aactcgactt gccttccgca caatacatca tttcttctta         60
gctttttttc ttcttcttcg ttcatacagt ttttttttgt ttatcagctt acattttctt        120
gaaccgtagc tttcgttttc ttctttttaa ctttccattc ggagtttttg tatcttgttt        180
catagtttgt cccaggatta gaatgattag gcatcgaacc ttcaagaatt tgattgaata        240
aaacatcttc attcttaaga tatgaagata atcttcaaaa ggccctggg aatctgaaag         300 aagagaagca ggcccattta tatgggaaag aacaatagta tttcttatat aggcccattt        360
aagttgaaaa caatcttcaa aagtcccaca tcgcttagat aagaaaacga agctgagttt        420
atatacagct agagtcgaag tagtgatt                                           448
```

```
<210> SEQ ID NO 260
<211> LENGTH: 83
<212> TYPE: DNA
<213> ORGANISM: Arachis hypogaea

<400> SEQUENCE: 260
gttttagagc tagaaatagc aagttaaaat aaggctagtc cgttatcaac ttgaaaaagt         60
ggcaccgagt cggtgctttt ttt                                                 83
```

```
<210> SEQ ID NO 261
<211> LENGTH: 2670
<212> TYPE: DNA
<213> ORGANISM: Arachis hypogaea
```

<400> SEQUENCE: 261

```
taccactcac ctccctccat catttcacca tccacactca taataatcat atatattcat        60
caatcatcta tataagtagt agcaggagca atgagaggga gggtttctcc actgatgctg       120
ttgctaggga tccttgtcct ggcttcagtt tctgcaacgc atgccaagtc atcaccttac       180
cagaagaaaa cagagaaccc ctgcgcccag aggtgcctcc agagttgtca acaggaaccg       240
gatgacttga agcaaaaggc atgcgagtct cgctgcacca agctcgagta tgatcctcgt       300
tgtgtctatg atcctcgagg acacactggc accaccaacc aacgttcccc tccaggggag       360
cggacacgtg gccgccaacc agactacgat gatgaccgcc gtcaaccccg aagagaggaa       420
ggaggccgat ggggaccagc tggaccgagg gagcgtgaaa gagaagaaga ctggagacaa       480
ccaagagaag attggaggcg accaagtcat cagcagccac ggaaaataag gcccgaagga       540
agagaaggag aacaagagtg gggaacacca ggtagccatg tgagggaaga aacatctcgg       600
aacaaccctt tctacttccc gtcaaggcgg tttagcaccc gctacgggaa ccaaaacggt       660
aggatccggg tcctgcagag gtttgaccaa aggtcaaggc agtttcagaa tctccagaat       720
caccgtattg tgcagatcga ggccaaacct aacactcttg ttcttcccaa gcacgctgat       780
gctgataaca tccttgttat ccagcaaggt atcaaatcta attctattct aaactacata       840
tattttgttg cttgatacat atgattcatt ggattgcagg gcaagccacc gtgaccgtag       900
caaatggcaa taacagaaag agctttaatc ttgacgaggg ccatgcactc agaatcccat       960
ccggtttcat ttcctacatc ttgaaccgcc atgacaacca gaacctcaga gtagctaaaa      1020
tctccatgcc cgttaacaca cccggccagt ttgaggtacc tctttctttt cacatatata      1080
ttcaagagga atgttaggag gccagcaact tttgtaattt gtagttatca aatagtcatt      1140
agtgatgata ttaatgttat taataatgat tttaatggtg taaaatttta tctaatggtt      1200
catttttttt ttttgataca tgttggtcag aatttaacaa attactggtc ctagattttt      1260
cttatattca attctcaatt atcatcttac atgttgcttc acaggatttc ttcccggcga      1320
gcagccgaga ccaatcatcc tacttgcagg gcttcagcag gaatacgttg gaggccgcct      1380
tcaatgtaag caaatgtatc ataattagga attaaaataa cgtatcatgt tataataaac      1440
ttataatata tatacatagg cggaattcaa tgagatacgg agggtgctgt tagaagagaa      1500
tgcaggaggt gagcaagagg agagagggca gaggcgatgg agtactcgga gtagtgagaa      1560
caatgaagga gtgatagtca aagtgtcaaa ggagcacgtt gaagaactta ctaagcacgc      1620
taaatccgtc tcaaagaaag gctccgaaga agagggagat atcaccaacc caatcaactt      1680
gagagaaggc gagcccgatc tttctaacaa ctttgggaag ttatttgagg tgaagcagac      1740
aagaagaacc cccagcttca ggacctggac atgatgctca cctgtgtaga gatcaaagaa      1800
ggagctttga tgctcccaca cttcaactca aaggccatgg ttatcgtcgt cgtcaacaaa      1860
ggaactggaa accttgaact cgtggctgta agaaaagagc aacaacagag gggacgcgg      1920 gaagaagagg aggacgaaga cgaagaagag gagggaagta acagagaggt gcgtaggtac      1980
acagcgaggt tgaaggaagg cgatgtgttc atcatgccag cagctcatcc agtagccatc      2040
aacgcttcct ccgaactcca tctgcttggc ttcggtatca acgctgaaaa caaccacaga      2100
atcttccttg caggtgataa ggacaatgtg atagaccaga tagagaagca agcgaaggat      2160
ttagcattcc ctgggtcggg tgaacaagtt gagaagctca tcaaaaacca gaaggaatct      2220
cactttgtga gtgctcgtcc tcaatctcaa tctcaatctc cgtcgtctcc tgagaaagag      2280
```

```
tctcctgaga aagaggatca agaggaggaa aaccaaggag ggaagggtcc actcctttca    2340
attttgaagg cttttaactg agaatggagg caacttgtta tgtatcgata ataagatcac    2400
gcttttgtac tctactatcc aaaaacttat caataaataa aaacgtttgt gcgttgtttc    2460
tccaagaaag gtgtggcgct tatggttttt atttatacga aactaattaa atacatcata    2520
acggcaaaga cctcttatta tgtaattttc ttttaaaaaa tatagactgc caaaatatat    2580
atgaatattt acatgaacaa gtcaaatgga atacttgttg agacatatct catcgatcct    2640
atctactaat tagtagatac aaacatattt                                      2670

<210> SEQ ID NO 262
<211> LENGTH: 472
<212> TYPE: DNA
<213> ORGANISM: Arachis hypogaea

<400> SEQUENCE: 262
caatggccaa gctcaccata ctagtagccc tcgccctttt cctcctcgct gcccacgcat      60
ctgcgaggca gcagtgggaa ctccaaggag acagaagatg ccagagccag ctcgagaggg     120
cgaacctgag gccctgcgag caacatctca tgcagaagat ccaacgtgac gaggattcat     180
atgaacggga cccgtacagc cctagtcagg atccgtacag ccctagtcca tatgatcgga     240
gaggcgctgg atcctctcag caccaagaga ggtgttgcaa tgagctgaac gagtttgaga     300
acaaccaaag gtgcatgtgc gaggcattgc aacagatcat ggagaaccag agcgataggt     360
tgcaggggag gcaacaggag caacagttca agagggagct caggaacttg cctcaacagt     420
gcggccttag ggcaccacag cgttgcgact tggacgtcga aagtggcggc ag             472

<210> SEQ ID NO 263
<211> LENGTH: 3825
<212> TYPE: DNA
<213> ORGANISM: Arachis hypogaea

<400> SEQUENCE: 263
taataatttt gtataattca aactctttct ttctttcttg cattataaaa gtaaattta      60 ttgagttata attaacttat ataaacttgt atgccaaaaa aaacttgtat gtgtagcagg     120
tctctaatat ttataagatt aaaaatttat aaaatctaaa ataaataaaa taattttaaa     180
aaattaatta atattaatta aaaaaattaa ttatctaaca ttattcatgt ttaaattact     240
caactattct agtactctaa tgattcatat cgttgtgtgg tgttcccaaa ttcaatttgc     300
attctttcta ctcaaactat tagtaacgcg ccccatcagg tgctgcagaa aaacagagta     360
ttccattgca ttaaacaatg catctaaccg gaaaattagg catcagcaag aaaagaaaag     420
aactgaagcc gtgcatgcgt ggtccccttt gtgcagaaat cctcagatgc atgcttatga     480
tgatcttata gagatgcttt gtgaggtgta acgcaggaag ggtgccatag ccatgcatgc     540
tgaagagtgt cacaaatgct ctcctacgtg tcccttcctt caccccctct cgcccctata     600
aatcacttgc ttctcattct tctcttcatc acaaccacag caataacaat aatagcagcc     660
atgggtaagc tgcttgcgct ttctgtttgc ttttgctttc tagtcctggg agctagcagc     720
atctccttca ggcagcagcc ggaggaaaat gcgtgccagt tccagcgcct caatgcgcaa     780
aggcctgaca accgcattga tcggagggc ggttacattg agacttggaa cccaaacaac     840
caggagttcg aatgcgccgg cgtcgccctc tcgcgcttag tcctccgccg caacgccctt     900
cggaggcctt tctactccaa tgctccccag gagatcttca tccagcaagg ttattactac     960
tttttcgtat tattattgtc aattattctt tattctccct caaatgattg aatttaatta    1020
```

```
ttaatttgta cactcactaa acttactaag attttataag aatttccgtt tgacatgaaa    1080
aaaacaacta tgttaagtca tgtattttta tatcaaaatt atcgaaaatg agtaaaataa    1140
cacgtgcatt tgtacaaaaa taatatgata taaaaataat attatatcaa aaatatgtta    1200
aataacacat gcattcgtac aaaaataata ttatagctaa tttggtgaat ttaatttata    1260
catataaaat atatatgatg acatacagga aggggatact ttggtttgat attccctggt    1320
tgtcctagca catatgaaga gcctgcacaa caaggacgcc gacatcagtc ccaaagacca    1380
ccaagacgtt ttcaaggaca agaccaaagc caacagcaac aggatagtca ccagaaggtg    1440
caccgtttcg atgagggtga tctcattgca gttcccaccg gtgttgcttt ctggatgtac    1500
aacgaccatg acactgatgt tgttgctgtt tctcttactg acaccaacaa caacgacaac    1560
cagcttgatc agttccccag ggtatatata tgtttcaatc tcattcgtta tttttggcat    1620
gtgcatatat atcatgaagg aatggtgaca attaataata cataacagag attcaatttg    1680
gctgggaacc acgagcaaga gttcttaaga taccagcaac aaagcagacg aagaagctta    1740
ccatatagcc catacagccc gcaaactcag cctaaacaag aagaccgtga atttagccct    1800
cgaggacagc acggccgcag agaacgagca ggacaagaac aagaaaacga aggtggaaac    1860
atcttcagcg gcttcacgcc ggagttcctg gcacaagcct tccaggttga cgacagacag    1920
atattgcaaa acctaagagg cgagaacgag agtgacgaac agggagccat tgtgacagtg    1980
aggggaggcc tcagaatctt gagcccagat agaaagagaa ggcagcagta tgaacgtccc    2040
gacgaagaag aggaatacga tgaagatgaa tatgaatatg atgaagagga gaggcaacaa    2100
gatagaaggc gtggcagggg aagcagaggc agcggcaatg gcattgagga gaccatctgc    2160
accgcaagtt ttaaaaagaa cattggtaga aacagatccc ctgacatcta caaccctcaa    2220
gctggttcac tcaaaactgc caacgagctc cagcttaacc ttctaatcct taggtggctt    2280
ggacttagtg ctgaatatgg aaatctctac agggtttgta ctttctcttt ttctatgttt    2340
ttttagcaat atatactatc attttttaagt attaaatttt aaatactaat gctataagaa    2400
taaaatgtta actactgttg attaatatcg ataaaaagga ttacattaga catttattta    2460
catattgaaa tgtgattgca gaatgcattg tttgtccctc actacaacac gaacgcacac    2520
agcatcatat atgcattgag gggacgggct cacgtgcaag tggtggacag caacggcgac    2580
agagtgttcg acgaggagct tcaagaaggt cacgtgcttg tggtgccaca gaacttcgcc    2640
gtggctggaa agtcccagag cgagaacttt gaatacgtgg cattcaagac agactcaagg    2700
cccagcatag ccaacctagc cggagaaaac tccttcatag ataacttgcc ggaggaggtg    2760
gttgcaaatt catatggcct cccaagggag caggcaaggc agcttaagaa caacaacccc    2820
ttcaagttct tcgttccacc gtctgaacag tctctgaggg ctgtggctta aaaacaagcg    2880
tgacatgtat gtgtgttatc cactacatac atactttttg ccacaactga ataatacata    2940
ataataacga gaataatgta gttttatttt tgtagtgtga ataagaatac aaaggggcat    3000
tgatgccttt ttgtttaagc tataagatcg gaatgtaatg tatgtgcaat gagcagcatc    3060
gatctggaga aaacctttg cgggaaaaac ttgaataaaa gaagggatgg tttaacgcag    3120
ccagatttgt ctttgtttcc tccttctttc ttttttcttt tttctttttt cttttttga    3180 taaaacaaac ttgaaaagaa tatcaacaac acaatatgct cacattttca tttaggaaac    3240
tccgaaagtc catttgctag gatttctagt caagcacgca ctataaaatc gcgacaattc    3300
aattttaaca tgcatgcatg gtacatatag ccttgcttat ggtcattgat gacttaccaa    3360
```

```
cataaatcca attttttacat ttaagatgtc aagtttttggg tgtagagatc gattctcgca         3420
tcgcctgaat aaaagatttc aggtgggtct ttttttttttt tttttttttt tgggttaaaa         3480
gagtaatcct aaagaatcaa acggtcaacc tttcgcgaat attataacaa gttgtcaaat         3540
aaatcaaata taaaatctaa taaaaataat tttttatgaa tttgatttga aagattcttt         3600
taattaaatt ttaaatattt ttatttttaa cagtttttat cttttttttt tcttatatta         3660
agggttgctg caatgttggt actttctctc ttcaaaaaga aaaatatcca atccattcat         3720
taatggcctg aaaaatgaat acaatggtcc aatttcaaga caaaaaagca ttcttaagtg         3780
tgaagttgat gagtaatatt attttatggg aaagtataat gatcc                         3825

<210> SEQ ID NO 264
<211> LENGTH: 438
<212> TYPE: DNA
<213> ORGANISM: Arachis hypogaea

<400> SEQUENCE: 264
atggccaagt ccaccatcct ggtagccctc cttgccctcg tcctggtggc acacgcctcc         60
gcgatgaggc gcgagagggg gcgacaaggg gactcatcaa gctgcgagag gcaggtagac        120
agggtgaacc tcaagccctg cgagcagcac ataatgcaga ggataatggg cgagcaagag        180
cagtacgact cctacgatat taggagtact cgatcctccg accagcaaca gaggtgctgc        240
gatgagctga cgagatgga gaacacacag agatgcatgt gcgaggcatt gcagcagata        300
atggagaacc agtgcgatag gttgcaggac aggcaaatgg tgcagcagtt caagagagag        360
ctcatgaact tgccccaaca gtgtaacttt agggcaccac agcgttgcga tttggacgtg        420
agtggcggca gatgctag                                                        438

<210> SEQ ID NO 265
<211> LENGTH: 712
<212> TYPE: DNA
<213> ORGANISM: Arachis hypogaea

<400> SEQUENCE: 265
atgatggtca agctcagcat cctggtagcc ctcctgggcg cccttcttgt cgtagcctcc         60
gcgacaagat gggatcccga tcgagggtcc agagggtcga gatgggacgc accgagcaga        120
ggggatgacc agtgccagag gcagttgcag agggcaaacc tgaggccctg tgaggaacac        180
atgaggcgaa gggtggagca ggagcaagag caagagcaag acgagtaccc gtacagccga        240
cggggatcca gaggacgaca acccggcgaa tctgacgaaa tcaagagca gaggtgctgc         300 aacgagctca accggttcca gaataaccaa aggtgcatgt gccaggcact tcaacagatc        360
ctccagaacc agagcttttg ggttccagca ggacaggagc cagttgcatc agatggagag        420
ggagctcagg aacttgcccc agaactgcgg gttcaggtca ccaagccgtt gcgacctttg        480
tagccgcacg ccctactaaa cagacgagca ctttgcgttt taatttgctt accccacaag        540
agaaatccaa tgatgatgat tgattgcttt tttacaagct atttctatgt ctatggtgtt        600
gtggtaacaa taaagatcat caccatttta tgtaatgatg atcgtattgt ccgtggcgaa        660
gttgtatggg gcactttgaa atgtgctttt atggcaaaaa aaaaaaaaaa aa                 712

<210> SEQ ID NO 266
<211> LENGTH: 565
<212> TYPE: DNA
<213> ORGANISM: Arachis hypogaea
```

```
<400> SEQUENCE: 266
atgggcgtct tcactttcga ggatgaaatc acctccaccc tgccccctgc caagctttac      60
aatgctatga aggatgccga ttccatcacc cctaagatta ttgatgacgt caagagtgtt     120
gaaatcgttg agggaaacgg tggtcctgga accatcaaga aactcaccat tgtcgagggt     180
cagtaactat tcaattcagt atacatacat actatatgtg tgataattat gtgttgtaaa     240
ttgtaataat aataatgata tatatgcaga tggagaaacc aagtttatct tacacaaagt     300
ggaggcaata gatgaggcta actatgcata caactacagc gtggttggag gagtggcgct     360
gcctcccacg gcggagaaga taacatttga gacgaagctg gtagaaggac ccaacgagg      420 atccatcggg aagctgagtg tgaagttcca ctcgaaagga gaagcgaagc cagaggagga     480
agacatgaag aagggtaagg ccaagggcga agctctcttc aaggctattg agggttacgt     540
tttggccaac cctactcaat attag                                           565

<210> SEQ ID NO 267
<211> LENGTH: 396
<212> TYPE: DNA
<213> ORGANISM: Arachis hypogaea

<400> SEQUENCE: 267
atgtcgtggc aaacctacgt cgataaccac cttctctgcg aaattgaagg caaccacctc      60
tcctccgccg caatcctcgg ccaagacggc agtgtttggg ctcagagctc taatttccct     120
cagttcaagc ctgaggaaat tactgctatc atgaacgact ttgctgagcc tggatcgctc     180
gcccctaccg ggttgtacct cggtggcacc aaatatatgg ttatccaagg tgaacccgga     240
gctgtcattc gagggaagaa gggtcctggt ggtgttacca ttaagaagac gaatcaggcg     300
ttgatcatcg gaatctacga tgagccgatg actccagggc agtgcaacat gattgttgaa     360
aggctgggtg attatctcat tgatacgggt ctttaa                              396

<210> SEQ ID NO 268
<211> LENGTH: 351
<212> TYPE: DNA
<213> ORGANISM: Arachis hypogaea

<400> SEQUENCE: 268
atggcaagcc tcaagtttgc atttgtgatg cttgtgtgca tggccatggt gggagcacca      60
atggtgaatg ccatatcatg tggccaagtg aacagtgccc tagcaccatg catccctttc     120
ctcacaaagg gtggagctcc tcctccggct tgttgcagcg gagttagagg ccttctcggt     180
gctttaagaa ccaccgcaga ccgccaggcc gcctgtaact gcctcaaagc cgctgccggt     240
tcccttcgtg gcctcaacca aggcaacgcc gccgccctcc ctggaagatg cggtgtcagc     300
attccttaca agatcagcac ctccaccaac tgtgctacca ttaagttctg a              351

<210> SEQ ID NO 269
<211> LENGTH: 510
<212> TYPE: DNA
<213> ORGANISM: Arachis hypogaea

<400> SEQUENCE: 269
atgactgacc gtacccaacc acacactgtc caagtccaca ccacagctgg ccgtttcggc      60
gacaccgctg ctggaactaa ccgctatccc gacagaggcc cgtcaacatc taaggttatc     120
gccgtcatca ctggactccc tatcggcggc acgttgctat tgttcgcggg gcttgccctt     180
```

```
gccggaaccc tgcttgggct ggcggtgacc accccgcttt tcatcctctt cagccctgtc        240
atagttccgg ccatcattgt cgttgggctc tcggtggcgg ggttcttgac gtcaggtgca        300
tgtgggctga cggggctgtc ttcgttctcg tgggtcatga attacatccg gcagacccac        360
ggatcggtgc cggagcagct ggaaatggca aagcaccgca tggctgacgt ggccggttac        420
gttggacaga agacgaagga tgtaggacag aagaccaagg aagttgggca agagatacag        480
accaaggctc aggattcaaa gagaacttga                                          510
```

```
<210> SEQ ID NO 270
<211> LENGTH: 414
<212> TYPE: DNA
<213> ORGANISM: Arachis hypogaea

<400> SEQUENCE: 270
atggctgaag cactctacta cggcggccgc caacgccaag agcaaccaag gtccacccag         60
cttgtcaagg ccaccaccgc tgttgtcgcc ggaggctccc tcttgatcct cgccggcctt        120
gtgctggccg gcaccgtcat tggcctcaca acgatcacac cgctcttcgt gatcttcagc        180
ccggtgcttg tgccagctgt catcactgtg gcactcttag gcttggggtt cttggcctct        240
ggaggcttcg gcgtggcggc aataacagtg ctgacgtgga tctataggta cgtaacaggt        300
aagcatccac ctggcgccaa ccaattggac acagcccgcc acaagctgat gggcaaggcg        360
cgtgagatta aggactttgg tcaacaacaa accagtgggg cccaggcttc ttga              414
```

```
<210> SEQ ID NO 271
<211> LENGTH: 305
<212> TYPE: DNA
<213> ORGANISM: Arachis hypogaea

<400> SEQUENCE: 271
agaaaacagt tgctggattc tgcatcttct tcctcgttct ctttcttgct caggagggag         60
tggtgaaaac agaggcaaag ctatgcaacc acctggcaga tacatacaga ggaccatgct        120
ttaccaatgc aagctgcgat gatcattgca agaacaaaga gcactttgtt agtggaacct        180
gcatgaaaat ggcgtgttgg tgtgctcaca actgttgatg taataatata cttagtaatt        240
aaataatgat atgaatgata ctctgtatgt tgtcatcata tctatccctt ataattaata        300
atatg                                                                     305
```

```
<210> SEQ ID NO 272
<211> LENGTH: 370
<212> TYPE: DNA
<213> ORGANISM: Arachis hypogaea

<400> SEQUENCE: 272
cagtacaaaa acgaacgata ataatggaga agaaaatggc tggattctgc atctttttcc         60
tcattctctt tcttgctcag gaatatggcg tggagggaaa ggagtgtttg aacctaagtg        120
acaaattcaa gggaccgtgt ttgggttcaa agaactgcga tcatcactgc agggacatag        180
agcacttgct cagcggagtt tgcagggacg atttccgctg ctggtgcaac agaaagtgtt        240
aaaactactc catcatcatc aaacctctaa aaccatatga tataataata ataataataa        300
tatatgaata ataaatgctt agcttgcatt atattggatc cccacgatgc gttagacgca        360
tgcacctagc                                                                370
```

```
<210> SEQ ID NO 273
<211> LENGTH: 531
```

```
<212> TYPE: DNA
<213> ORGANISM: Arachis hypogaea

<400> SEQUENCE: 273
atggctactg ctactgatcg tgcacctcac caggttcaag ttcacacccc caccacacaa         60
cgcgtcgacg ttccacgccg cggctacgat gttagtggtg gtggtattaa gactcttctc        120
cccgagagag gtccgtccac ctctcaaatc atcgccgtcc tcgtcggcgt ccccactggg        180
ggcactctgt tgctcctctc cggcctttca cttctcggaa ccataatcgg ctggcaatt         240 gccacccccgg tttttacttt cttcagcccg gttatagttc ccgcggtcgt taccattgga        300
cttgcagtca ctggtattct cacggcggga gcatgtggac taaccgggct gatgtctttg        360
tcatggatga ttaacttcat ccgacaggta catgggacga cggtgccgga tcagctggac        420
tcagtgaagc ggcgcatggc ggacatggcg gattacgtgg ggcagaagac aaaggatgct        480
ggccaacaga tacagactaa ggcccaggat gttaagaggt catcatcata a                 531

<210> SEQ ID NO 274
<211> LENGTH: 501
<212> TYPE: DNA
<213> ORGANISM: Arachis hypogaea

<400> SEQUENCE: 274
atgtctgatc aaacaaggac aggctatgga ggaggagggt cctatggatc atcctatggt         60
ggaggaggca cctatggttc atcttatgga acctcctatg accccagtac taaccaacct        120
atacgccaag ccatcaagtt catgacagca tcaaccattg gtgtctcatt cttgatcctg        180
tctgggttga tcctcactgg aactgtcata ggtttgatca ttgcaacacc acttcttgtt        240
atcttcagtc ctatccttgt ccctgctgcc ataacccttg cactggctgc tggtggattt        300
ttgttctctg gtggctgtgg tgttgctgcc attgctgcat tgtcatggtt gtacagctat        360
gtcactggga aacaccctgc tggctctgat aggcttgatt atgctaaagg ggtgattgct        420
gataaggcta gggatgttaa ggacagggcc aaggattatg ctggtgctgg tagggctcag        480
gagggcaccc cagggtattg a                                                   501

<210> SEQ ID NO 275
<211> LENGTH: 694
<212> TYPE: DNA
<213> ORGANISM: Arachis hypogaea

<400> SEQUENCE: 275
taaccaccac aacaacaatg gccaagctca ccatactagt agccctcgcc cttttcctcc         60
tcgctgccca cgcatctgcg aggcagcagt gggaactcca aggagacaga agatgccaga        120
gccagctcga gagggcgaac ctgaggccct gcgagcaaca tctcatgcag aagatccaac        180
gtgacgagga ttcatatgaa cgggacccgt acagccctag tcaggatccg tacagcccta        240
gtccatatga tcggagaggc gctggatcct ctcagcacca agagaggtgt tgcaatgagc        300
tgaacgagtt tgagaacaac caaaggtgca tgtgcgaggc attgcaacag atcatggaga        360
accagagcga taggttgcag gggaggcaac aggagcaaca gttcaagagg gagctcagga        420
acttgcctca acagtgcggc cttagggcac cacagcgttg cgacttggac gtcgaaagtg        480
gcggcagaga cagatactaa acacctatct caaaaaaaga aagaaaaga aaagaaaata         540 gcttatatat aagctattat ctatggttat gttagttttg gtaataatga agatcatcac        600
```

-continued

```
tatatgaatg tgttgatcgt gttaactaag gcaagcttag gttatatgag cacctttaga      660 gtgctttat ggcgttgtct atgttttgtt gctg                                   694

<210> SEQ ID NO 276
<211> LENGTH: 21
<212> TYPE: DNA
<213> ORGANISM: Arachis hypogaea

<400> SEQUENCE: 276
cctcgaggac acactggcac c                                                 21

<210> SEQ ID NO 277
<211> LENGTH: 23
<212> TYPE: DNA
<213> ORGANISM: Arachis hypogaea

<400> SEQUENCE: 277
cggacacgtg gccgccaacc cgg                                               23

<210> SEQ ID NO 278
<211> LENGTH: 23
<212> TYPE: DNA
<213> ORGANISM: Arachis hypogaea

<400> SEQUENCE: 278
caggagatct tcatccagca agg                                               23

<210> SEQ ID NO 279
<211> LENGTH: 23
<212> TYPE: DNA
<213> ORGANISM: Arachis hypogaea

<400> SEQUENCE: 279
cctcgaggac agcacggccg cag                                               23

<210> SEQ ID NO 280
<211> LENGTH: 4201
<212> TYPE: DNA
<213> ORGANISM: Artificial
<220> FEATURE:
<223> OTHER INFORMATION: Mutated Cas9

<400> SEQUENCE: 280
atggctccta agaagaagcg gaaggttggt attcacgggg tgcctgcggc tgacaagaag      60
tactccatcg gcctcgccat cggcaccaac agcgtcggct gggcggtgat caccgacgag      120
tacaaggtcc cgtccaagaa gttcaaggtc ctgggcaaca ccgaccgcca ctccatcaag      180
aagaacctca tcggcgccct cctcttcgac tccggcgaga cggcggaggc gacccgcctc      240
aagcgcaccg cccgccgccg ctacacccgc cgcaagaacc gcatctgcta cctccaggag      300
atcttctcca cgagatggc gaaggtcgac gactccttct tccaccgcct cgaggagtcc      360
ttcctcgtgg aggaggacaa gaagcacgag gccacccccat cttcggcaac atcgtcgacg      420
aggtcgccta ccacgagaag taccccacta tctaccacct tcgtaagaag cttgttgact      480
ctactgataa ggctgatctt cgtctcatct accttgctct cgctcacatg atcaagttcc      540
gtggtcactt ccttatcgag ggtgacctta accctgataa ctccgacgtg gacaagctct      600
tcatccagct cgtccagacc tacaaccagc tcttcgagga gaaccctatc aacgcttccg      660
gtgtcgacgc taaggcgatc ctttccgcta ggctctccaa gtccaggcgt ctcgagaacc      720
```

```
tcatcgccca gctccctggt gagaagaaga acggtctttt cggtaacctc atcgctctct     780
ccctcggtct gacccctaac ttcaagtcca acttcgacct cgctgaggac gctaagcttc     840
agctctccaa ggatacctac gacgatgatc tcgacaacct cctcgctcag attggagatc     900
agtacgctga tctcttcctt gctgctaaga acctctccga tgctatcctc ctttcggata     960
tccttagggt taacactgag atcactaagg ctcctctttc tgcttccatg atcaagcgct    1020
acgacgagca ccaccaggac ctcaccctcc tcaaggctct tgttcgtcag cagctccccg    1080
agaagtacaa ggagatcttc ttcgaccagt ccaagaacgg ctacgccggt tacattgacg    1140
gtggagctag ccaggaggag ttctacaagt tcatcaagcc aatccttgag aagatggatg    1200
gtactgagga gcttctcgtt aagcttaacc gtgaggaccc ccttaggaag cagaggactt    1260
tcgataacgg ctctatccct caccagatcc accttggtga gcttcacgcc atccttcgta    1320
ggcaggagga cttctaccct ttcctcaagg acaaccgtga gaagatcgag aagatcctta    1380
ctttccgtat tccttactac gttggtcctc ttgctcgtgg taactcccgt ttcgcttgga    1440
tgactaggaa gtccgaggag actatcaccc cttggaactt cgaggaggtt gttgacaagg    1500
gtgcttccgc ccagtccttc atcgagcgca tgaccaactt cgacaagaac ctccccaacg    1560
agaaggtcct ccccaagcac tccctcctct acgagtactc cacggtctac aacgagctca    1620
ccaaggtcaa gtacgtcacc gagggtatgc gcaagcctgc cttcctctcc ggcgagcaga    1680
agaaggctat cgttgacctc ctcttcaaga ccaaccgcaa ggtcaccgtc aagcagctca    1740
aggaggacta cttcaagaag atcgagtgct cgactccgt cgagatcagc ggcgttgagg    1800
accgtttcaa cgcttctctc ggtacctacc acgatctcct caagatcatc aaggacaagg    1860
acttcctcga caacgaggag aacgaggaca tcctcgagga catcgtcctc actcttactc    1920
tcttcgagga tagggagatg atcgaggaga ggctcaagac ttacgctcat ctcttcgatg    1980
acaaggtttg aagcagctca agcgtcgccg ttacaccggt tggggtaggc tctcccgcaa    2040
gctcatcaac ggtatcaggg ataagcagag cggcaagact atcctcgact tcctcaagtc    2100
tgatggtttc gctaacagga acttcatgca gctcatccac gatgactctc ttaccttcaa    2160
ggaggatatt cagaaggctc aggtgtccgg tcagggcgac tctctccacg agcacattgc    2220
taaccttgct ggttcccctg ctatcaagaa gggcatcctt cagactgtta aggttgtcga    2280
tgagcttgtc aaggttatgg gtcgtcacaa gcctgagaac atcgtcatcg agatggctcg    2340
tgagaaccag actacccaga agggtcagaa gaactcgagg gagcgcatga gagaggattga    2400 ggagggtatc aaggagcttg gttctcgat ccttaaggag caccctgtcg agaacaccca    2460
gctccagaac gagaagctct acctctacta cctccagaac ggtagggata tgtacgttga    2520
ccaggagctc gacatcaaca ggctttctga ctacgacgtc gaccacattg ttcctcagtc    2580
tttccttaag gatgactcca tcgacaacaa ggtcctcacg aggtccgaca agaacagggg    2640
taagtcggac aacgtccctt ccgaggaggt tgtcaagaag atgaagaact actggaggca    2700
gcttctcaac gctaagctca ttacccagag gaagttcgac aacctcacga aggctgagag    2760
gggtggcctt tccgagcttg acaaggctgg tttcatcaag aggcagcttg ttgagacgag    2820
gcagattacc aagcacgttg ctcagatcct cgattctagg atgaacacca agtacgacga    2880
gaacgacaag ctcatccgcg aggtcaaggt gatcaccctc aagtccaagc tcgtctccga    2940
cttccgcaag gacttccagt ctctacaaggt ccgcgagatc aacaactacc accacgctca    3000
cgatgcttac cttaacgctg tcgttggtac cgctctttatc aagaagtacc ctaagcttga    3060
gtccgagttc gtctacggtg actacaaggt ctacgacgtt cgtaagatga tcgccaagtc    3120
```

```
cgagcaggag atcggcaagg ccaccgccaa gtacttcttc tactccaaca tcatgaactt      3180
cttcaagacc gagatcaccc tcgccaacgg cgagatccgc aagcgccctc ttatcgagac      3240
gaacggtgag actggtgaga tcgtttggga caagggtcgc gacttcgcta ctgttcgcaa      3300
ggtcctttct atgcctcagg ttaacatcgt caagaagacc gaggtccaga ccggtggctt      3360
ctccaaggag tctatccttc caaagagaaa ctcggacaag ctcatcgcta ggaagaagga      3420
ttgggaccct aagaagtacg gtggtttcga ctcccctact gtcgcctact ccgtcctcgt      3480
ggtcgccaag gtggagaagg gtaagtcgaa gaagctcaag tccgtcaagg agctcctcgg      3540
catcaccatc atggagcgct cctccttcga gaagaacccg atcgacttcc tcgaggccaa      3600
gggctacaag gaggtcaaga aggacctcat catcaagctc cccaagtact ctcttttcga      3660
gctcgagaac ggtcgtaaga ggatgctggc ttccgctggt gagctccaga agggtaacga      3720
gcttgctctt ccttccaagt acgtgaactt cctctacctc gcctcccact acgagaagct      3780
caagggttcc cctgaggata cgagcagaa gcagctcttc gtggagcagc acaagcacta      3840
cctcgacgag atcatcgagc agatctccga gttctccaag cgcgtcatcc tcgctgacgc      3900
taacctcgac aaggtcctct ccgcctacaa caagcaccgc gacaagccca tccgcgagca      3960
ggccgagaac atcatccacc tcttcacgct cacgaacctc ggcgcccctg ctgctttcaa      4020
gtacttcgac accaccatcg acaggaagcg ttacacgtcc accaaggagg ttctcgacgc      4080
tactctcatc caccagtcca tcaccggtct ttacgagact cgtatcgacc tttcccagct      4140
tggtggtgat aagcgtcctg ctgccaccaa aaaggccgga caggctaaga aaaagaagta      4200
g                                                                     4201
```

<210> SEQ ID NO 281
<211> LENGTH: 3825
<212> TYPE: DNA
<213> ORGANISM: Arachis hypogaea

<400> SEQUENCE: 281

```
taataatttt gtataattca aactctttct ttctttcttg cattataaaa gtaaatttta       60
ttgagttata attaacttat ataaacttgt atgccaaaaa aaacttgtat gtgtagcagg      120
tctctaatat ttataagatt aaaaatttat aaaatctaaa ataaataaaa taattttaaa      180
aaattaatta atattaatta aaaaaattaa ttatctaaca ttattcatgt ttaaattact      240
caactattct agtactctaa tgattcatat cgttgtgtgg tgttcccaaa ttcaatttgc      300
attctttcta ctcaaactat tagtaacgcg ccccatcagg tgctgcagaa aaacagagta      360
ttccattgca ttaaacaatg catctaaccg gaaaattagg catcagcaag aaaagaaaag      420
aactgaagcc gtgcatgcgt ggtccccttt gtgcagaaat cctcagatgc atgcttatga      480
tgatcttata gagatgcttt gtgaggtgta acgcaggaag ggtgccatag ccatgcatgc      540
tgaagagtgt cacaaatgct ctcctacgtg tcccttcctt caccccctct cgcccctata      600
aatcacttgc ttctcattct tctcttcatc acaaccacag caataacaat aatagcagcc      660
atgggtaagc tgcttgcgct ttctgtttgc ttttgctttc tagtcctggg agctagcagc      720
atctccttca ggcagcagcc ggaggaaaat gcgtgccagt tccagcgcct caatgcgcaa      780
aggcctgaca accgcattga atcggagggc ggttacattg agacttggaa cccaaacaac      840
caggagttcg aatgcgccgg cgtcgccctc tcgcgcttag tcctccgccg caacgccctt      900
cggaggcctt tctactccaa tgctccccag gagatcttca tccagcaagg ttattactac      960
```

-continued

```
ttttttcgtat tattattgtc aattattctt tattctccct caaatgattg aatttaatta     1020
ttaatttgta cactcactaa acttactaag attttataag aatttccgtt tgacatgaaa     1080
aaaacaacta tgttaagtca tgtattttta tatcaaaatt atcgaaaatg agtaaaataa     1140
cacgtgcatt tgtacaaaaa taatatgata taaaaataat attatatcaa aaatatgtta     1200
aataacacat gcattcgtac aaaaataata ttatagctaa tttggtgaat ttaatttata     1260
catataaaat atatatgatg acatacagga aggggatact ttggtttgat attccctggt     1320
tgtcctagca catatgaaga gcctgcacaa caaggacgcc gacatcagtc ccaaagacca     1380
ccaagacgtt ttcaaggaca agaccaaagc caacagcaac aggatagtca ccagaaggtg     1440
caccgtttcg atgagggtga tctcattgca gttcccaccg gtgttgcttt ctggatgtac     1500
aacgaccatg acactgatgt tgttgctgtt tctcttactg acaccaacaa caacgacaac     1560
cagcttgatc agttccccag ggtatatata tgtttcaatc tcattcgtta ttttttggcat     1620 gtgcatatat atcatgaagg aatggtgaca attaataata cataacagag attcaatttg     1680
gctgggaacc acgagcaaga gttcttaaga taccagcaac aaagcagacg aagaagctta     1740
ccatatagcc catacagccc gcaaactcag cctaaacaag aagaccgtga atttagccct     1800
cgaggacagc acggccgcag agaacgagca ggacaagaac aagaaaacga aggtggaaac     1860
atcttcagcg gcttcacgcc ggagttcctg gcacaagcct tccaggttga cgacagacag     1920
atattgcaaa acctaagagg cgagaacgag agtgacgaac agggagccat tgtgacagtg     1980
aggggaggcc tcagaatctt gagcccagat agaaagagaa ggcagcagta tgaacgtccc     2040
gacgaagaag aggaatacga tgaagatgaa tatgaatatg atgaagagga gaggcaacaa     2100
gatagaaggc gtggcagggg aagcagaggc agcggcaatg gcattgagga gaccatctgc     2160
accgcaagtt ttaaaaagaa cattggtaga aacagatccc ctgacatcta caaccctcaa     2220
gctggttcac tcaaaactgc caacgagctc cagcttaacc ttctaatcct taggtggctt     2280
ggacttagtc ctgaatatgg aaatctctac agggtttgta ctttctcttt ttctatgttt     2340
ttttagcaat atatactatc atttttaagt attaaatttt aaatactaat gctataagaa     2400
taaaatgtta actactgttg attaatatcg ataaaaagga ttacattaga catttattta     2460
catattgaaa tgtgattgca gaatgcattg tttgtccctc actacaacac gaacgcacac     2520
agcatcatat atgcattgag gggacgggct cacgtgcaag tggtggacag caacggcgac     2580
agagtgttcg acgaggagct tcaagaaggt cacgtgcttg tggtgccaca gaacttcgcc     2640
gtggctggaa agtcccagag cgagaacttt gaatacgtgg cattcaagac agactcaagg     2700
cccagcatag ccaacctagc cggagaaaac tccttcatag ataacttgcc ggaggaggtg     2760
gttgcaaatt catatggcct cccaagggag caggcaaggc agcttaagaa caacaacccc     2820
ttcaagttct tcgttccacc gtctgaacag tctctgaggg ctgtggctta aaaacaagcg     2880
tgacatgtat gtgtgttatc cactacatac atacttttg ccacaactga ataatacata     2940
ataataacga gaataatgta gttttatttt tgtagtgtga ataagaatac aaaggggcat     3000
tgatgccttt ttgtttaagc tataagatcg gaatgtaatg tatgtgcaat gagcagcatc     3060
gatctggaga aaacctttg cgggaaaaac ttgaataaaa gaagggatgg tttaacgcag     3120
ccagatttgt ctttgtttcc tccttctttc ttttttcttt tttctttttt cttttttga     3180 taaaacaaac ttgaaaagaa tatcaacaac acaatatgct cacattttca tttaggaaac     3240
tccgaaagtc catttgctag gatttctagt caagcacgca ctataaaatc gcgacaattc     3300
aattttaaca tgcatgcatg gtacatatag ccttgcttat ggtcattgat gacttaccaa     3360
```

```
cataaatcca attttttacat ttaagatgtc aagttttggg tgtagagatc gattctcgca   3420
tcgcctgaat aaaagatttc aggtgggtct ttttttttttt tttttttttt tgggttaaaa   3480
gagtaatcct aaagaatcaa acggtcaacc tttcgcgaat attataacaa gttgtcaaat   3540
aaatcaaata taaaatctaa taaaaataat tttttatgaa tttgatttga aagattcttt   3600
taattaaatt ttaaatattt ttatttttaa cagtttttat ctttttttttt tcttatatta   3660 agggttgctg caatgttggt actttctctc ttcaaaaaga aaaatatcca atccattcat   3720
taatggcctg aaaaatgaat acaatggtcc aatttcaaga caaaaaagca ttcttaagtg   3780
tgaagttgat gagtaatatt attttatggg aaagtataat gatcc                   3825
```

PEANUT WITH REDUCED ALLERGEN LEVELS

STATEMENT OF PRIORITY

This application is a 35 U.S.C. § 371 national phase application of International Application Serial No. PCT/US2018/044312, filed Jul. 30, 2018, which claims the benefit, under 35 U.S.C. § 119 (e), of U.S. Provisional Application No. 62/539,308 filed on Jul. 31, 2017, the entire contents of each of which is incorporated by reference herein.

STATEMENT OF GOVERNMENT SUPPORT

This invention was made with government support under grant numbers 2001-38814-11389, 2003-388814-14048, and 2006-38814-17424 awarded by the United States Department of Agriculture/Cooperative State Research, Education, and Extension Service (CSREES) and under grant numbers 141590 and 1620897 awarded by the National Science Foundation. The government has certain rights to this invention.

STATEMENT REGARDING ELECTRONIC FILING OF A SEQUENCE LISTING

A Sequence Listing in ASCII text format, submitted under 37 C.F.R. § 1.821, entitled 1496-2WO_ST25.txt, 132,019 bytes in size, generated on Jul. 30, 2018 and filed via EFS-Web, is provided in lieu of a paper copy. This Sequence Listing is hereby incorporated herein by reference into the specification for its disclosures.

FIELD OF THE INVENTION

This disclosure relates to artificial nucleic acid constructs useful in the genetic modification of peanut plants to reduce or eliminate allergens. Such constructs are described, as well as numerous beneficial uses thereof.

BACKGROUND

Food allergy is a serious health problem, and can be life threatening. Public awareness of food allergies is at an all-time high, in part, due to the fact that allergic reactions to foods are being reported more frequently. Up to 160 foods have been found to cause allergic reactions.

The most common allergen-containing foods are peanuts, soybeans, tree nuts, cow's milk, eggs, crustaceans, and fish. The frequency of food allergy is highest in infancy and early childhood, and decreases with increasing age. About 5% of children younger than three and 1.5% of the general population experience food allergy disorders, or about 4 million Americans suffer from food allergies.

Peanut is one of the most allergenic food products. It is estimated that over 600,000 children in the United States have peanut allergies. While childhood allergies to egg and cow's milk may disappear with age, allergies to nuts, peanuts, soybeans, fish and shellfish tend to persist for the lifetime of the individual.

Hypersensitive responses to peanut allergens can be fatal. Contact with the slightest amount of peanut protein can be life threatening to particularly sensitive individuals. The allergy can show up at the first exposure to peanuts, often before the age of three. Most people develop peanut allergies early in life, and few ever grow out of peanut allergies, even in adulthood. Allergic reactions to peanuts are often acute and severe. The most common manifestation of peanut allergy is acute hives (or urticaria) following exposure. However, some patients may rapidly develop severe angiodema, swelling of the face, bronchospasm and ana-phylaxis, following exposure. Some individuals are so sensitive that they will develop symptoms if they kiss someone who has eaten peanuts or if they eat out of a food utensil that has been in contact with peanuts.

The peanut plant (*Arachis hypogaea*) is an annual plant belonging to the family Leguminosae, originally native to South America. The commercially grown peanut is the result of a natural cross between two wild species, *Arachis duranensis* and *Arachis ipaensis*, which occurred about 4,000 to 6,000 years ago. As a results, today's commercial peanut is a polyploid, meaning the species can carry two separate genomes, designated A and B subgenomes. The two ancestor wild species have been collected in nature, conserved in germplasm banks and used to study and better understand the peanut genome. The genomes of the two ancestor species provide excellent models for the genome of the cultivated peanut. *A. duranenis* serves as a model for the A subgenome of the cultivated peanut while *A. ipaensis* represents the B subgenome. The genomes of the two ancestral parents have been sequenced and together they represent 96 percent of all peanut genes. The sequences from these progenitor plants provide a molecular map allows quicker and more efficient breeding of new varieties of peanuts having such characteristics as drought-resistance, disease-resistance, lower-input and higher-yield.

The peanut plant is commercially grown in the Southeastern regions of the United States, specifically in Alabama, Florida, Georgia, North Carolina, and Virginia, and in many other countries of the world. In the United States, several types of peanut are grown, although the four most popular peanut types are the Virginia, Spanish, Valencia, and runner varieties. Virginia peanuts are used primarily for whole kernel consumption and confections. Runner types are used most frequently for oil production and peanut butter. Most of the peanut crop in the United States is used for the production of peanut butter. The most widely cultivated peanut cultivars in the USA are 'Florunner', 'New Mexico Valencia', 'Georgia Green', and 'Georgia Red'.

Several allergenic peanut proteins have been isolated, identified, characterized and classified as minor or major allergens. These proteins include glycoproteins, arachin, conarachin, peanut agglutinin and peanut phospholipase. Of these peanut protein allergens, six were classified as major allergens, with estimated molecular weights of 44, 40, 33, 21, 20, and 18 kDa.

Burks et al. 1992 identified two major peanut allergens, designated Ara h 1 and Ara h 2, which are glycoproteins with isoelectric points and molecular weights of 4.55 and 63,500 Daltons and 5.2 and 17,000 Daltons, respectively. These peanut allergens are stable at a temperature of up to 100° C., at pH conditions between pH 2.8 and pH 10, and resistant to digestion by acid and digestive enzymes. Peanut, peanut butter, and peanut flour retain their allergenicity through processing, and crude peanut oil may also be contaminated with these proteins.

The allergens Ara h1 and Ara h2 are found in the cotyledon of peanut, and both are recognized by more than 90% of peanut-sensitive patients, establishing them as major allergens.

Currently, no cure exists for food allergies. Administration of epinephrine and antihistamines is used to reverse the symptoms of food-allergic reactions. Thus, the most effective management strategy in the prevention of peanut allergies is complete avoidance of peanut-containing foods. However, this is a difficult course of action, as it requires diligent reading of labels and ingredient listings and avoidance of food prepared outside of the home. Unfortunately, there is a social stigma associated with refraining from taking part in restaurant or other communal meals by allergic individuals, and makes the strict avoidance of peanut unlikely and unrealistic.

Despite their allergenic hazards, peanuts are an excellent source of human nutrition. Peanuts provide niacin, magnesium, Vitamin C, manganese and chromium in significant amounts and smaller amounts of potassium, Vitamin B6, folic acid, phosphorus, copper and biotin. Furthermore, peanut is widely used in cuisine all over the world, and is added to a variety of foods such as pastries, sandwiches, egg rolls, chili, syrups, flours, sauces, and confections.

An investigation of a wide variety of commercially grown peanuts showed no naturally occurring allergen-free peanut lines.

Therefore, there is a need for an alternative solution for the allergic individual. Specifically, there is a need for reduced allergen peanut plants, peanuts, and peanut products.

SUMMARY

The present disclosure describes nucleic acid constructs that address the problems described above by reducing the allergen content of the seeds of a genetically modified peanut plant.

In a first aspect, a nucleic acid construct for the suppression of multiple Ara h proteins in a peanut is provided, said construct comprising: a sense region comprising a first sense sequence (i.e., sense fragment) of at least one Ara h protein, optionally an epitope region of the at least one Ara h protein; and an antisense region comprising a first antisense sequence (i.e., antisense fragment) of the first sense sequence.

In a second aspect, a nucleic acid encoding a small guide RNA (gRNA) for use in generating a deletion when used in combination with a CRISPR/Cas9 protein is provided, the nucleic acid comprising a guide sequence (e.g., spacer) and a gRNA scaffold, wherein the guide sequence is antiparallel to a target sequence that encodes a region of at least one Ara h protein (e.g., any part of the coding region as well as the 5' and 3' untranscribed regions), optionally an epitope region of the at least one Ara h protein.

In a third aspect, a genetically modified peanut cell is provided, comprising the nucleic acid construct of the first and/or second aspect.

In a fourth aspect, a genetically modified peanut cell is provided, comprising a deletion in a sequence that encodes at least one Ara h protein (e.g., any part of the coding region as well as the 5' and 3' untranscribed regions), optionally an epitope region of the at least one Ara h protein.

In a fifth aspect, a genetically modified peanut plant is provided, comprising the cell of at least one of the third or fourth aspects.

In a sixth aspect, an expression cassette and/or vector is provided comprising the nucleic acid construct of the first and/or second aspect.

In a seventh aspect, a method of producing a genetically modified peanut plant with reduced allergen content in the seed is provided, the method comprising: transfecting a recipient peanut plant cell with at least one construct of the first and/or second aspect; generating a peanut plant from the recipient cell which has been transformed with the at least one construct; and identifying a fertile transgenic plant that produces seeds having reduced allergen content.

In an eighth aspect, a kit for making a genetically modified plant with reduced allergen content is provided, the kit comprising the nucleic acid construct of the first and/or second aspect. In some embodiments, an expression cassette and/or vector for delivering CRISPR associated protein 9 (Cas9) to a cell may be provided.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 1. An exemplary chimeric cDNA sequence of an RNAi construct (SEQ ID NO:249).

FIG. 2. An alternative exemplary chimeric cDNA sequence of an RNAi construct (SEQ ID NO:250).

FIG. 3. A second alternative exemplary chimeric cDNA sequence of an RNAi construct (SEQ ID NO:251).

FIG. 4. A third alternative exemplary chimeric cDNA sequence of an RNAi construct (SEQ ID NO:252).

FIG. 5. A fourth alternative exemplary chimeric cDNA sequence of an RNAi construct (SEQ ID NO:253).

FIG. 6. A fifth alternative exemplary chimeric cDNA sequence of an RNAi construct (SEQ ID NO:254).

FIG. 7. A sixth alternative exemplary chimeric cDNA sequence of an RNAi construct (SEQ ID NO:255).

FIG. 8 A seventh alternative exemplary chimeric cDNA sequence of an RNAi construct (SEQ ID NO:256).

FIG. 9. The canonical sequence of the potato ubiquitin 3 promoter (SEQ ID NO:257).

FIG. 10. The canonical sequence of the *Arabidopsis* heat shock storage protein terminator (SEQ ID NO:258).

FIG. 11. The canonical sequence of the *Arabidopsis* AtU6-26 promoter (Pol III promoter) (SEQ ID NO:259).

FIG. 12. An exemplary DNA sequence encoding a gRNA scaffold region (SEQ ID NO:260).

FIG. 19. A canonical Ara h5 sequence, showing an example of a deletion target in the epitope region, examples of gRNA targets to create such a deletion, and the PAMs in the gRNA targets (SEQ ID NO:267).

FIG. 20. A canonical Ara h9 sequence, showing an example of a deletion target in the epitope region, examples of gRNA targets to create such a deletion, and the PAMs in the gRNA targets (SEQ ID NO:268).

FIG. 21. A canonical Ara h10 sequence, showing an example of a deletion target in the epitope region, examples of gRNA targets to create such a deletion, and the PAMs in the gRNA targets (SEQ ID NO:269).

FIG. 33. Nucleotide sequence of Ara h 2 including untranscribed regions (italics) with possible sgRNAs identified by underlining (SEQ ID NO:275)

DETAILED DESCRIPTION

Figure 13:
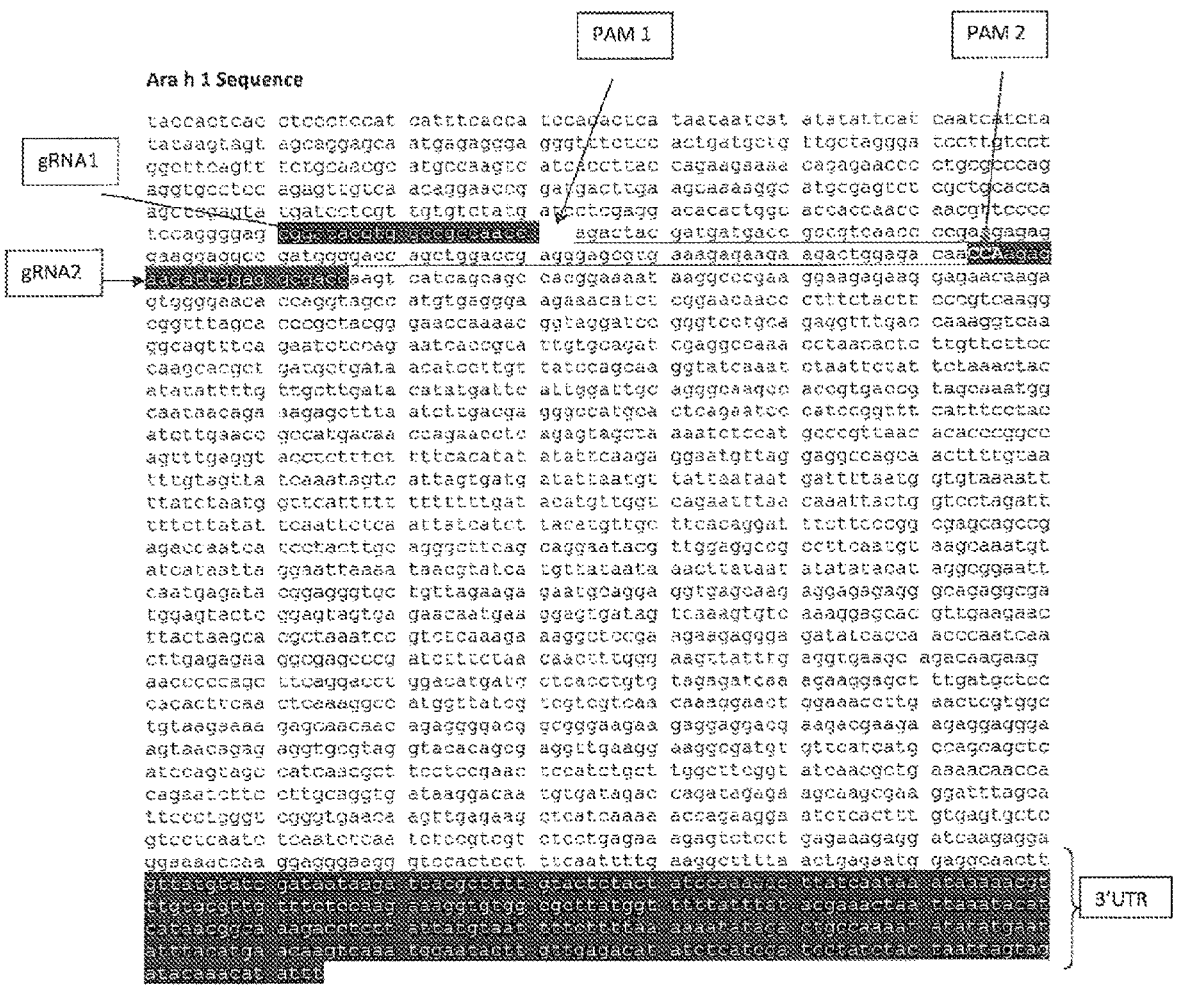
FIG. 13. A canonical Ara h1 sequence, showing an example of a deletion target in the epitope region, examples of gRNA targets to create such a deletion, and the PAMs in the gRNA targets (SEQ ID NO:261).
Figure 14:
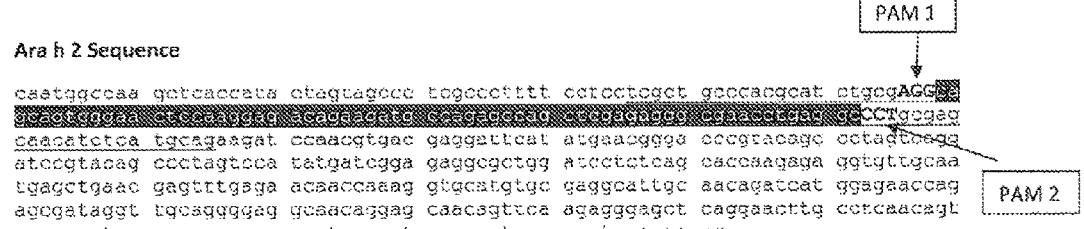
FIG. 14. A canonical Ara h2 sequence, showing an example of a deletion target in the epitope region, examples of gRNA targets to create such a deletion, and the protospacer motifs (PAMs) in the gRNA targets (SEQ ID NO:262).
Figure 15:
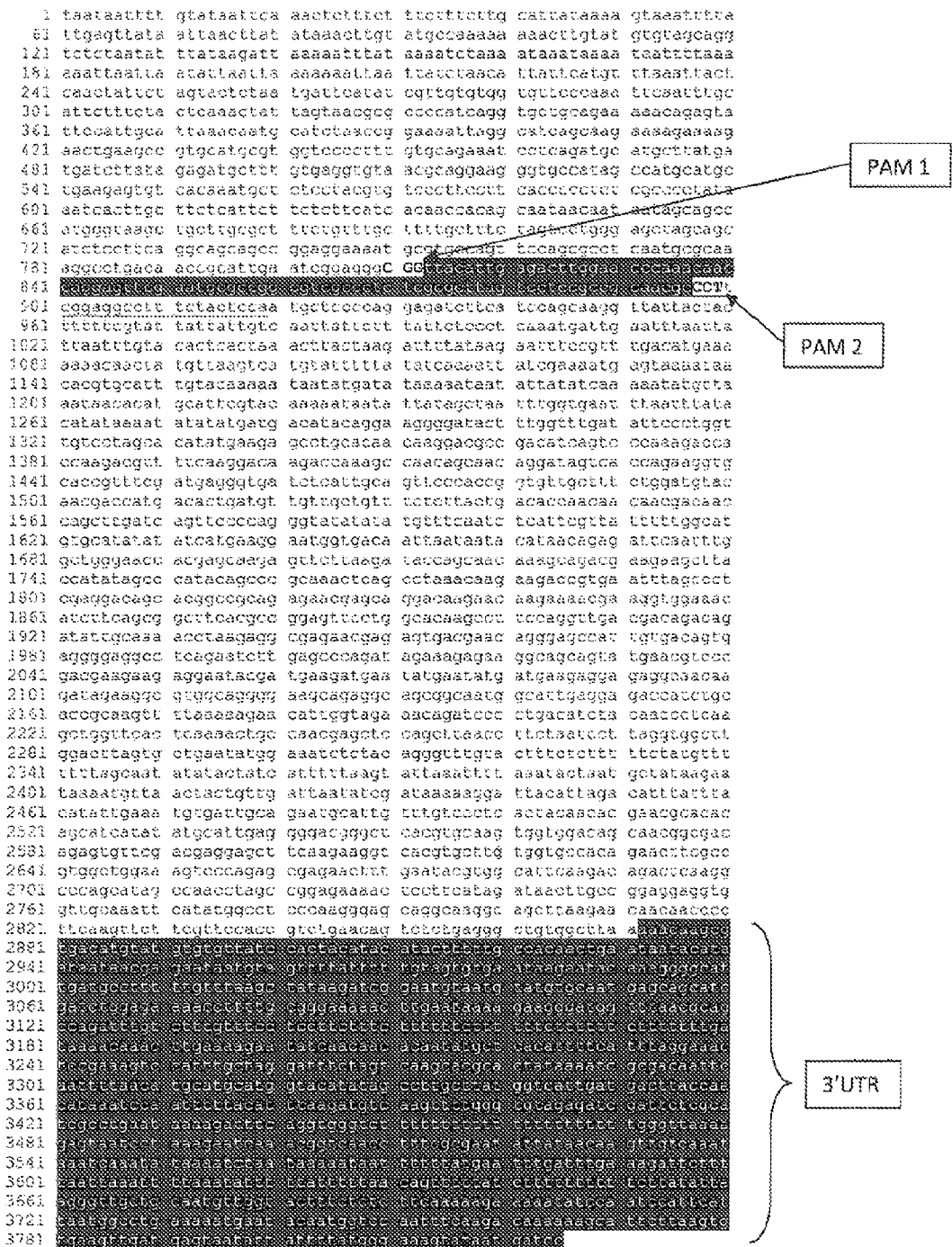
FIG. 15. A canonical Ara h3 sequence, showing an example of a deletion target in the epitope region, examples of gRNA targets to create such a deletion, and the PAMs in the gRNA targets (SEQ ID NO:263).
Figure 16:
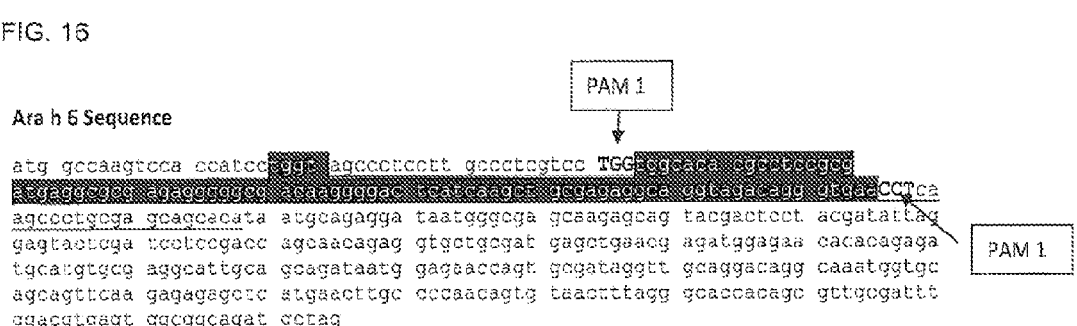
FIG. 16. A canonical Ara h6 sequence, showing an example of a deletion target in the epitope region, examples of gRNA targets to create such a deletion, and the PAMs in the gRNA targets (SEQ ID NO:264).
Figure 17:
FIG. 17. A canonical Ara h7 sequence, showing an example of a deletion target in the epitope region, examples of gRNA targets to create such a deletion, and the PAMs in the gRNA targets (SEQ ID NO:265).
Figure 18:
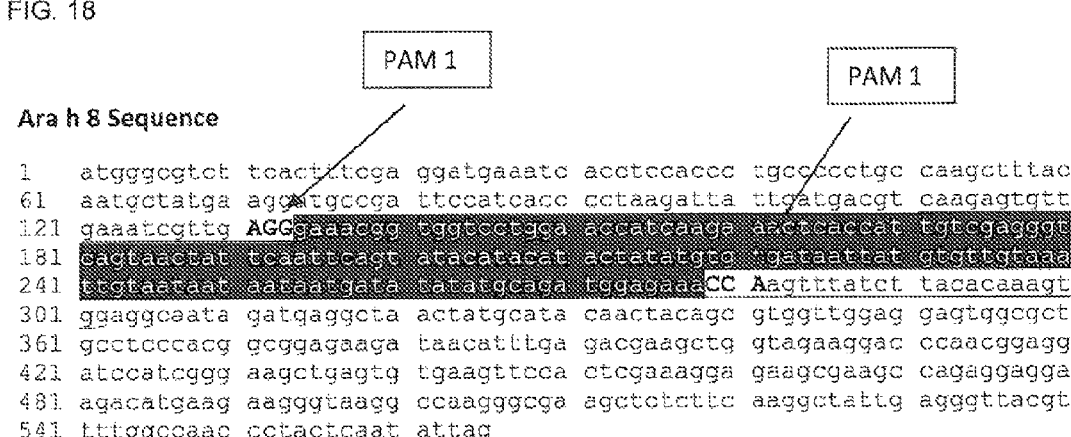
FIG. 18. A canonical Ara h8 sequence, showing an example of a deletion target in the epitope region, examples of gRNA targets to create such a deletion, and the PAMs in the gRNA targets (SEQ ID NO:266).
Figures 22, 23, 24, 25:
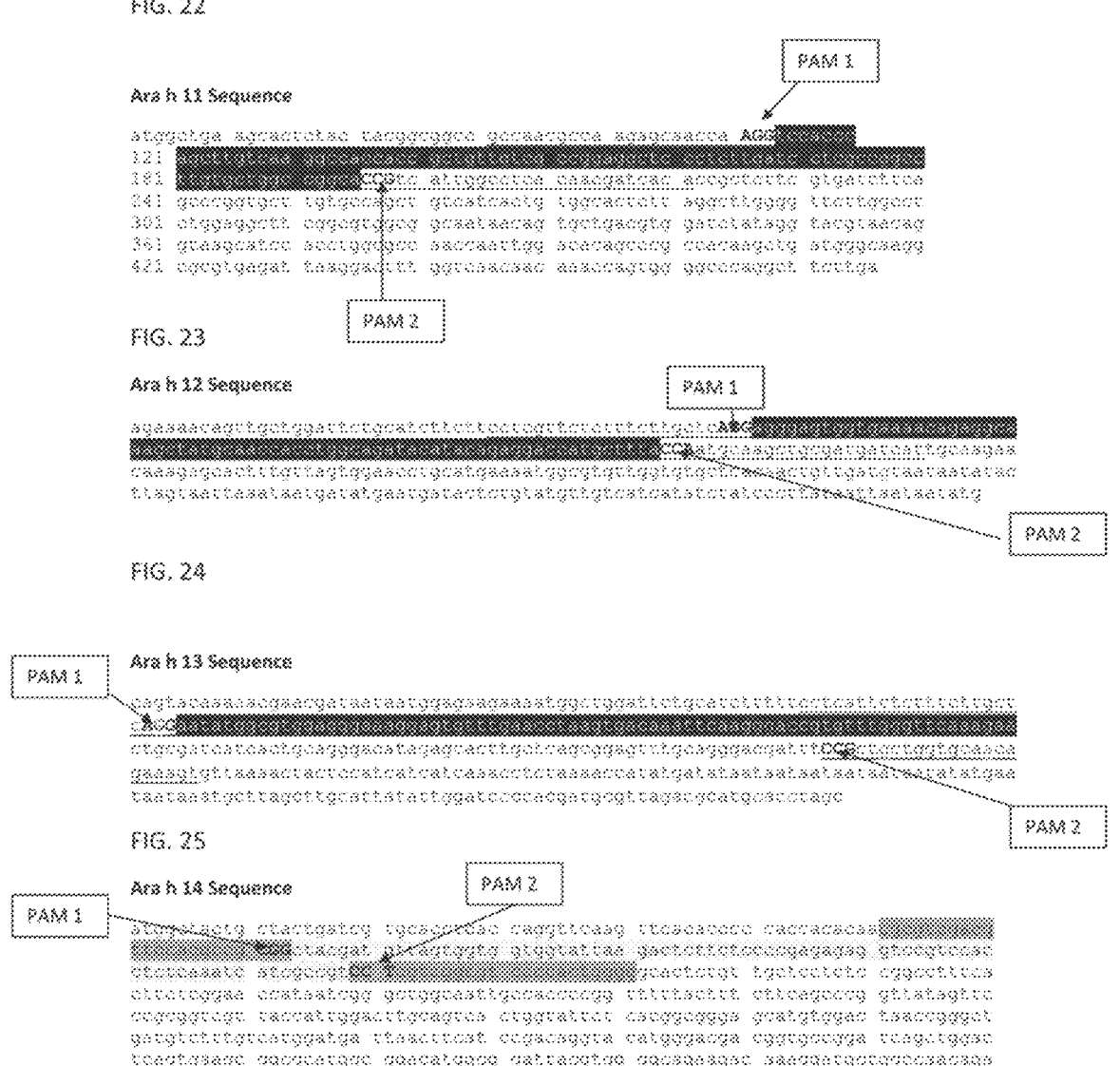
FIG. 22. A canonical Ara h11 sequence, showing an example of a deletion target in the epitope region, examples of gRNA targets to create such a deletion, and the PAMs in the gRNA targets (SEQ ID NO:270).
FIG. 23. A canonical Ara h12 sequence, showing an example of a deletion target in the epitope region, examples of gRNA targets to create such a deletion, and the PAMs in the gRNA targets (SEQ ID NO:271).
FIG. 24. A canonical Ara h13 sequence, showing an example of a deletion target in the epitope region, examples of gRNA targets to create such a deletion, and the PAMs in the gRNA targets (SEQ ID NO:272).
FIG. 25. A canonical Ara h14 sequence, showing an example of a deletion target in the epitope region, examples of gRNA targets to create such a deletion, and the PAMs in the gRNA targets (SEQ ID NO:273).
Figures 26, 27:
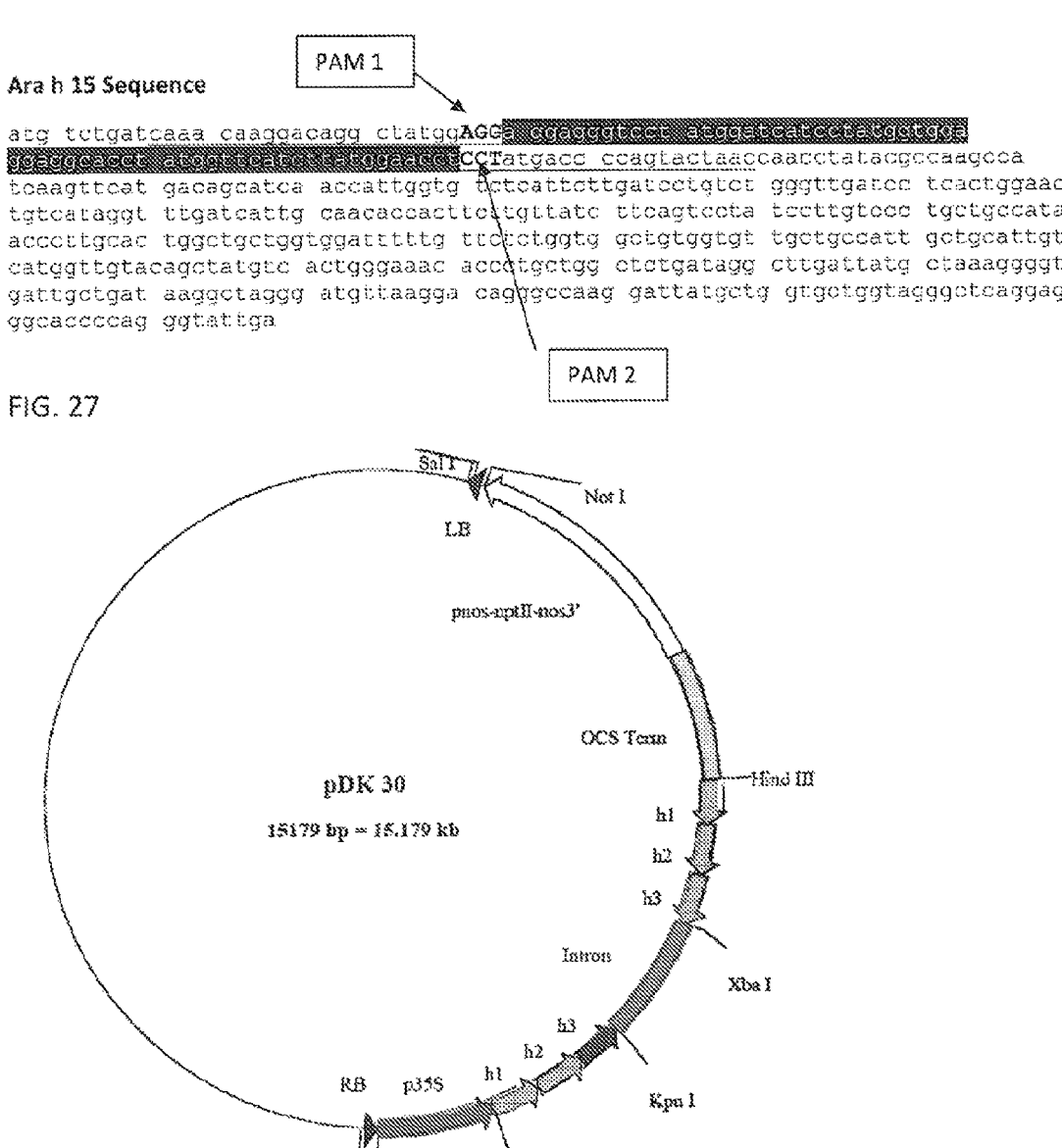
FIG. 26. A canonical Ara h15 sequence, showing an example of a deletion target in the epitope region, examples of gRNA targets to create such a deletion, and the PAMs in the gRNA targets (SEQ ID NO:274).
FIG. 27. A schematic diagram of plasmid pDK 30.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. The terminology used in the description of the invention herein is for the purpose of describing particular embodiments only and is not intended to be limiting of the invention. Well known functions or constructions may not be described in detail for brevity or clarity.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

In some places reference is made to standard methods, such as but not limited to methods of measurement, and biochemical database record numbers. It is to be understood that such standards and database records are revised from time to time, and unless explicitly stated otherwise reference to such standard or record in this disclosure must be interpreted to refer to the most recent published standard or version of the record as of the time of filing.

The terms "about" and "approximately" shall generally mean an acceptable degree of error or variation for the quantity measured given the nature or precision of the measurements Typical, exemplary degrees of error or variation are meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, the singular forms "a", "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount. Thus, for example, reduced transcription of a target DNA or reduced translation of a target polynucleotide can mean a 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% as compared to a control (e.g., a plant not comprising the modification of the invention (e.g., siRNA or CRISPR of the invention).

As used herein, "modify," "modifying" or "modification" (and grammatical variations thereof) of a polynucleotide or polypeptide means any alteration of a polynucleotide and/or a polypeptide of interest (e.g., an Ara h polynucleotide or an Ara h polypeptide) or other polypeptide or polynucleotide that results in the reduction or elimination of the expression of the polynucleotides and/or the production and/or activity of the polypeptides. Such modifications can include, but are not limited to, deleting or inserting one or more nucleotides or an entire nucleic acid region (transcribed and untranscribed regions) (indel), and/or introducing one or more point mutations, which reduce or eliminate the expression of the nucleic acids and/or the production and/or activity of the polypeptides.

As used herein, the terms "modulate," "modulates," modulated" or "modulation" refer to inhibition (e.g., a reduction) in a specified activity or content (e.g., modulated Ara h polypeptide production/content). In some embodiments, expression level or activity/content may be reduced by about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% as compared to a control.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a polynucleotide may express, for example, a polypeptide of interest or a functional untranslated RNA.

As used herein, "chimeric" refers to a nucleic acid molecule or a polypeptide in which at least two components are derived from different sources (e.g., different organisms, different coding regions).

The term "nucleotide" as used herein refers to any nucleotide, natural or synthetic. It includes conventional DNA or RNA bases (A, G, C, T, U), base analogs, e.g., inosine, 5-nitroindazole and others, imidazole-4-carboxamide, pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine, N-4-methyl deoxyguanosine, 4-ethyl-2'-deoxycytidine, 4,6-difluorobenzimidazole and 2,4-difluorobenzene nucleoside analogues, pyrene-functionalized LNA nucleoside analogues, deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, O-4-alkyl-pyrimidines and hydrophobic nucleobases that form duplex DNA without hydrogen bonding. Nucleobases can be joined together by a variety of linkages or conformations, including phosphodiester, phosphorothioate or methylphosphonate linkages, peptide-nucleic acid linkages.

As used herein, the terms "nucleic acid," "nucleic acid molecule," "nucleic acid construct," "nucleotide sequence" and "polynucleotide" can be used interchangeably and encompass both RNA and DNA, including cDNA, genomic DNA, mRNA, synthetic (e.g., chemically synthesized) DNA or RNA and chimeras of RNA and DNA (i.e., multimeric compounds comprising nucleotides linked together to form a polymer, including conventional RNA, DNA, LNA, BNA, copolymers of any of the foregoing, and analogs thereof). The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

The term "peptide" or polypeptide refers to a polymer of two or more amino acids. The constituent amino acids may include the 20 "standard" amino acids but are not limited to them, and may include nonstandard or modified amino acids.

A "native" or "wild type" nucleic acid, polynucleotide, polypeptide or amino acid sequence refers to a naturally occurring or endogenous nucleic acid, polynucleotide, polypeptide or amino acid sequence. Thus, for example, a "wild type mRNA" is a mRNA that is naturally occurring in or endogenous to the organism. A "homologous" nucleic acid sequence is a polynucleotide naturally associated with a host cell into which it is introduced.

In some embodiments, polypeptides and fragments of the invention can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. For example, one or more non-naturally occurring amino acids, such as D-alanine, can be added to the termini. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Additionally, the peptide terminus can be modified, e.g., by acetylation of the N-terminus and/or amidation of the C-terminus. Likewise, the peptides can be covalently or noncovalently coupled to pharmaceutically acceptable "carrier" proteins prior to administration.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," or "substantial identity" in the context of at least two nucleic acid molecules, nucleotide sequences or protein sequences, refers to two or more sequences or subsequences that have at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 99.5% or more nucleotide or amino acid residue identity, when compared and aligned for maximum correspondence, as measured using one of the following sequence comparison algorithms or by visual inspection.

Nucleic acids are "complementary" to each other, as used herein, when a nucleotide sequence in one strand of a nucleic acid, due to orientation of its nucleotide hydrogen atoms, hydrogen bonds to another sequence on an opposing nucleic acid strand (of course, a strand of a nucleic acid may be self-complementary as well). The complementary bases typically are, in DNA, A with T, and C with G, and, in RNA, C with G, and U with A. Complementarity can be perfect or partial/substantial/sufficient. Perfect complementarity between two nucleic acids means that the two nucleic acids can form a duplex in which every base in the duplex is bonded to a complementary base by Watson-Crick pairing (100% complementarity). "Substantial," "partial," or "sufficient" complementary means that a sequence in one strand is not perfectly complementary to a sequence in an opposing strand, but that sufficient bonding occurs between bases on the two strands to form a stable hybrid complex at a given set of hybridization conditions (e.g., salt concentration and temperature). Such conditions can be predicted by using the sequences and standard models to predict the $T_m$ of hybridized strands, or by empirical determination of $T_m$ by using established methods. $T_m$ refers to the temperature at which a population of hybridization complexes formed between two nucleic acid strands are 50% denatured. At a temperature below the $T_m$, formation of a hybridization complex is favored, whereas at a temperature above the $T_m$, melting or separation of the strands in the hybridization complex is favored. Such stringency is based on the melting temperature ($T_m$) of the nucleic acid binding complex, as taught in Berger and Kimmel (1987, Guide to Molecular Cloning Techniques, *Methods in Enzymology,* 152, Academic Press, San Diego CA). The $T_m$ of an annealed duplex depends on the base composition of the duplex, the frequency of base mismatches, and the ionic strength of the reaction medium. The $T_m$ of a duplex can be calculated by those of ordinary skill in the art based on these two factors using accepted algorithms. Maximum stringency typically occurs at about 5° C. below $T_m$; high stringency at about 5-10° C. below $T_m$; intermediate stringency at about 10-20° C. below $T_m$; and low stringency at about 20-25° C. below $T_m$. As will be understood by those of skill in the art, a maximum stringency hybridization can be used to identify or detect identical nucleotide sequences while an intermediate (or low) stringency hybridization can be used to identify or detect similar or related sequences. Terms such as maximally stringent, highly stringent, and poorly stringent, refer to conditions of maximal stringency, high stringency, and low stringency respectively.

An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

As used herein, the term "gene" refers to a nucleic acid molecule capable of being used to produce mRNA, antisense RNA, RNAi (miRNA, siRNA, shRNA), anti-microRNA antisense oligodeoxyribonucleotide (AMO), and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "fragment" or "portion" of a nucleotide sequence or polypeptide sequence will be understood to mean a nucleotide sequence or polypeptide of reduced length relative (e.g., reduced by 1, 2, 3, 4, 5, 6, 7, 8, 9, 10, 11, 12, 13, 14, 15, 16, 17, 18, 19, 20 or more nucleotides or amino acids) to a reference nucleotide sequence or amino acid and comprising, consisting essentially of and/or consisting of a nucleotide sequence of contiguous nucleotides/amino acids identical (100% identical) or substantially identical (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleotide sequence or amino acid sequence. Such a nucleic acid or amino acid "fragment" or "portion" according to the invention may be, where appropriate, included in a larger polynucleotide or amino acid of which it is a constituent.

A "heterologous" or a "recombinant" nucleic acid is a nucleotide sequence not naturally associated with a host cell into which it is introduced, including non-naturally occurring multiple copies of a naturally occurring nucleotide sequence. Alternatively, a heterologous nucleotide sequence can be one that does not naturally occur with another nucleotide sequence to which it is associated. For example, a nucleic acid construct comprising a "heterologous promoter" operably associated with a nucleic acid molecule is a promoter that does not naturally occur with said nucleic acid molecule to which it is associated.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to a nucleotide sequence of the invention.

As used herein a "genetically engineered" or "genetically modified" plant, plant part, plant cell, or seed refers to a plant, plant part, plant cell or seed having a modified genome such that the plant, plant part, plant cell, or seed has reduced transcription or translation of an *Arachis hypogaea* allergen (Ara h) gene or polypeptide. In some embodiments, the genetically engineered plant or seed may comprise the nucleic acid construct of the invention in its genome (e.g., RNAi). In some embodiments, the genetically engineered plant, plant part, plant cell, or seed comprises a modified genome (e.g., at least one modified Ara h gene) but does not comprise a nucleic acid construct of the invention in its genome (e.g., CRISPR).

The term "plant part," as used herein, includes but is not limited to reproductive tissues (e.g., petals, sepals, stamens, pistils, receptacles, anthers, pollen, flowers, fruits, flower bud, ovules, peg, seeds, embryos, nuts); vegetative tissues (e.g., petioles, stems, roots, root hairs, root tips, pith, coleoptiles, stalks, shoots, branches, bark, apical meristem, axillary bud, cotyledon, hypocotyls, trichomes, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

siRNA Nucleic Acid Constructs

A nucleic acid construct for the suppression of one or more Ara h proteins in a peanut is provided. In some embodiments, the construct may encode an RNAi (e.g., siRNA) molecule that targets one or more Ara mRNAs (e.g., any part of the coding region as well as the 5' and 3' untranscribed regions, optionally an epitope encoding region). In some embodiments, a construct may encode a small guide RNA (gRNA) that targets one or more regions of an Ara h gene (e.g., any part of the coding region as well as the 5' and 3' untranslated regions, optionally an epitope encoding region) for, for example, deletion. Both types of constructs may be introduced into and expressed in a plant cell.

In some embodiments, an RNAi construct may comprise a sense fragment and an antisense fragment, and optionally a loop region. In some embodiments, an RNAi construct comprises a sense fragment and an antisense fragment of any part of the coding region as well as the 5' and 3' untranscribed regions, optionally a region encoding an epitope region of the encoded Ara h polypeptide. The sense and antisense fragments each contain a sense and respective antisense sequence of an Ara h gene, optionally an epitope region of the Ara h gene. The sense and antisense fragments may contain sense and respective antisense sequences of more than one Ara h gene, which allows the simultaneous silencing of one or more genes encoding one or more allergens using a single construct. Of course, multiple constructs may be used to silence multiple Ara h genes. The sense and antisense fragments are complementary and self-anneal under, for example, stringent conditions. The construct may be configured so that the sense and antisense are co-transcribed. In some embodiments, an RNAi construct may also comprise a promoter that is operatively linked to the sense fragment and antisense fragment, and, when present, the loop. In some embodiments, the sense and antisense fragments may be operably linked to separate promoters (e.g., pol III). Some embodiments of an RNAi construct may comprise a chimeric sequence that encodes parts of two or more epitope regions of Ara h proteins, as explained in greater detail below.

The peanut allergen may be any known in the art, including but not limited to the known Ara h peptides. The Ara h peptide may be selected from the group consisting of: Ara h1, Ara h2, Ara h3, Ara h3.02 (originally Ara h4), Ara h5, Ara h6, Ara h7, Ara h8, Ara h9, Ara h10, Ara h11, Ara h12, Ara h13, Ara h14, Ara h15, Ara h16 and Ara h17. The Ara h peptide may have a canonical sequence, such as one shown below in Table 1, or it may be a variant of a canonical sequence.

TABLE 1

| Canonical cDNA Sequences of Peanut Allergens | |
|---|---|
| Protein ID | Database Accession No. |
| Ara h 1 | AF432231 |
| Ara h 2 | AY117434 |
| Ara h 3/Ara 4 (now Ara h 3.02) | AF510854 |
| Ara h 5 | GU354312* |
| Ara h 6 | AF092846 |
| Ara h 7 | AY722691* |
| Ara h 8 | EU661964* |
| Ara h 9 | EU159429* |
| Ara h 10 | AY722694* |
| Ara h 11 | DQ097716* |
| Ara h 12 | EY396089.1 |
| Ara h 13 | EY396019.1 |
| Ara h 14 | AF325917.1* |
| Ara h 15 | AY722696.1* |
| Ara h 16 | Not Available |
| Ara h 17 | Not Available |

Each sequence in the database records specified by each accession number is incorporated herein by reference in its entirety. Accession numbers marked with * are from the European Nucleotide Archive, and the remainder are from GenBank.

In some embodiments, a sense and antisense sequence may be at least about 15-25 nucleotides in length up to about 1000 nucleotides in length having substantial or full complementarity to a consecutive nucleotides of an Ara h gene (optionally an epitope encoding region of an Ara h gene). As is known in the art, the RNA interference pathway in plants digests double stranded RNA into about 20-25 base pair fragments (e.g., about 20, 21, 22, 23, 24, 25 bp fragments) using the Dicer endonuclease. Non-limiting examples of sense sequences and epitope sequences for Ara h peptides are provided in Table 2 below. The siRNA nucleic acid construct may include any of these sequences, alone or in any combination.

TABLE 2

| | Exemplary Epitope Regions | |
|---|---|---|
| SEQ ID NO | DESCRIPTION | SEQUENCE |
| 174 | Exemplary Ara h 1 sense cDNA | gaaaacaaccacagaatcttccttgcaggtgataagg acaatgtgatagaccagatagagaagcaagcgaagga tttagcattccctggttcgggtgaacaagttgagaag ctcatcaaaaaccagagggagtctcactttgtgagtg ctctgcctcaatctcaatctccgtcgtctcctgaaaa agagg |
| 175 | First epitopic region of Ara h 1 | gaaaacaaccacagaatcttccttgcag |
| 176 | Second epitopic region Ara h1 1 | atgtgatagaccagatagagaagcaagcga |
| 177 | Third epitopic region of Ara h 1 | tagcattccctggttcgggtgaacaagttgagaagct catcaaaaaccagaggg |
| 178 | Fourth epitopic region of Ara h 1 | aatctcaatctccgtcgtctcctgaaaaag |
| 179 | Exemplary Ara h 2 sense cDNA | caatggccaagctcaccatactagtagccctcgccct tttcctcctcgctgcccacgcatctgcgaggcagcag tgggaactccaaggagacagaagatgccagagccagc tcgagaggg |
| 180 | Epitopic region of Ara h 2 | cacgcatctgcgaggcagcagtgggaactccaaggag acagaagatgccagagccagctcgagaggg |
| 181 | Exemplary Ara h 3 sense cDNA | tccagcgcctgaatgcgcaaaggcctgacaaccgcat tgaatcggagggcggttacattgagacttggaaccca aacaaccaggagttagaatgcgccggcgtcgccctc |

TABLE 2 -continued

| SEQ ID NO | DESCRIPTION | SEQUENCE |
|---|---|---|
| 182 | Epitopic region of Ara h 3 | tccagcgcctgaatgcgcaaaggcctgacaaccgcat gtaatcggagggcggttacattgagacttggaaccca aacaaccaggagttagaatgcgccggcgtcgccctc |
| 183 | Exemplary Ara h 6 sense cDNA | tggtagctctccttgccctcgtcctggtggcacacgc ctccgcaatgaggcgcgagaggggggagacaggggggac tcatcaagctgcgagaggcaggtaga |
| 184 | Epitopic region of Ara h 6 | ccttgccctcgtcctggtggcacacgcctccgcaatg aggcgcgagaggggggagacaggg |
| 185 | Exemplary Ara h 7 sense cDNA | tcagcatcctagtagccctcctgggcgcccttcttgt cgtgagcctccgcgacaagatgggatcccgatcgagg gtccagagggttgagatgggacgcacc |
| 186 | Epitopic region of Ara h 7 | aagagtgttgaaatcgttgagggaaagggtggtcctg gaaccatcaag |
| 187 | Exemplary Ara h 8 sense cDNA | ttgatgacgtcaagagtgttgaaatcgttgagggaaa gggtggtcctggaaccatcaagaaactcaccattgtc gaggatggagaaaccaagtttatctt |
| 188 | Epitopic region of Ara h 8 | aagagtgttgaaatcgttgagggaaagggtggtcctg gaaccatcaag |
| 189 | Exemplary Ara h 14 sense cDNA | cccgagagaggtccgtccacctctcaaatcatcgccg tcctcgtcggcgtcccccactgggggcactctgttgct ccctctcggcctttcacttctcggaaccataatcggg ctggcaattgccaccccggttttttactttcttcagcc cg |
| 190 | Exemplary Ara h 15 sense cDNA | gaaaccccatcacttcttgtctaaaaattctcaaaag tcaccagccaccaaaaacccatttaccattatgtctg atcaaacaaggacaggctatggaggaggagggtccta ttggacatcctatggtggaggaggcacctatggttca tc |
| 191 | Alternative exemplary Ara h 1 cDNA | tttctgcaacgcaggccaagtcaccttaccggaaaac agagaaccctgcgcccagaggtgcctccagagttgt caacaggaaccggacgacttgaagcaaaaggcatgcg agtctcgctgcaccaagctcgagtatgatcctcgttg tgtctatgacactggcgccaccaaccaacgtcaccct ccaggggagcggacacgtggccgccaacccggagact acgatgatgaccgccgtcaaccccgaagagaggaagg aggccgatggggaccagctgaaccgagggagcgtgaa agagaagaagactggagacaaccaagagaagattgga ggcgaccaagtcatcagcagccacggaaaataaggcc cgaaggaagagaaggagaacaagagtggggaa |
| 192 | First epitopic region of Ara h 1 | ccaagtcaccttaccggaaaacagagaac |
| 193 | Second epitopic region Ara h 1 | accggacgacttgaagcaaaaggcatgcga |
| 194 | Third epitopic region of Ara h 1 | tcctcgttgtgtctatgacactggcgcca |
| 195 | Fourth epitopic region of Ara h 1 | acccggagactacgatgatgaccgccgtcaaccccga agagaggaaggaggccgatggggaccagctgaaccga gggagcgtga |
| 196 | Fifth epitopic region of Ara h 1 | acaaccaagagaagattggaggcgaccaag |
| 197 | Sixth epitopic region of Ara h 1 | tcagcagccacggaaaataaggcccgaaggaagaga aggagaacaagagtggggaa |
| 198 | Alternative exemplary Ara h 2 cDNA | ctccaaggagacagaagatgccagagccagctcgaga gggcgaacctgaggccctgcgagcaacatctcatgca gaagatccaacgtgacgaggattcatatgaacgggac ccgtacagccctagtcaggatccgtacagccctagtc catatgatcggagaggcgctggatcctctcagcacca agagaggtgttgcaatgagctgaacgagtttgagaac aaccaaaggtgcatgtgcgaggcattgcaacagatca tggagaaccagagcgataggttgcaggggaggcaaca ggag |

TABLE 2 -continued

_Exemplary Epitope Regions_

| SEQ ID NO | DESCRIPTION | SEQUENCE |
|---|---|---|
| 199 | Epitopic region of Ara h 2 | tccaaggagacagaagatgccagagccagctcgagag<br>ggcgaacctgaggccctgcgagcaacatctcatgcag<br>aagatccaacgtgacgaggattcatatgaacgggacc<br>cgtacagccctagtcaggatccgtacagccctagtcc<br>atatgatcggagaggcgctggatcctctcagcaccaa<br>gagaggtgttgcaatgagctgaacgagtttgagaaca<br>accaaaggtgcatgtgcgaggcattgcaacagatcat<br>ggagaaccagagcgataggttgcaggggaggcaacag<br>gag |
| 200 | Alternative exemplary Ara h 3 cDNA | aggggaggcaacaggagaagaagaccgtgaatttagc<br>cctcgaggacagcacggccgcagagaacgagcaggac<br>aagaacaagaaaacgaaggtggaaacatcttcagcgg<br>cttcacgccggagttcctggcacaagccttccaggtt<br>gacgacagacagatattgcaaaacctaagaggcgaga<br>acgagagtgacgaacagggagccattgtgacagtgag<br>gggaggcctcagaatcttgagcccagatagaaagaga<br>aggcagcagtatgaacgtcccgacgaagaagaggaat<br>acgatgaagatgaatatgaatatgatgaagaggagag<br>gcaacaagatagaaggcgtggcaggggaagcaga |
| 201 | First epitopic region of Ara h 3 | gaaacatcttcagcggcttcacgccggagttcctg |
| 202 | Second epitopic region of Ara h 3 | cagaatcttgagcccagatagaaaga |
| 203 | Third epitopic region of Ara h 3 | atgaagatgaatatgaatatgatgaagagg |
| 204 | Alternative exemplary Ara h 8 cDNA | acctccaccctgccccctgctaagctttacaacgctc<br>tgaaggatgccgataccatcacccctaagattattga<br>tgacgtcaagagtgttgaaatcgttgagggaaacggt<br>ggtcctggaaccatcaagaaactcaccattgtcgagg<br>at |
| 205 | Epitopic region of Ara h 8 | aagagtgttgaaatcgttgagggaaacggtggtcctg<br>gaaccatcaaga |

In some embodiments, the sense fragment of a RNAi construct of this invention may comprise any combination of sequences from any region (for example, an epitope region) of one or more Ara h1-h17 polynucleotides. The cDNA sequences of allergen peptides Ara h3 and Ara h3.02 have 95-96% homology. Therefore, sequences from the Ara h3 and Ara h3.02 homologous regions may be used for allergen gene control. In some embodiments, an RNAi construct may comprise sense and antisense sequences for Ara h1, h2, Ara h3, Ara h3.02, Ara h5, Ara h6, Ara h7, Ara h8, Ara h9, Ara h10, Ara h11, Ara h12, Ara h13, Ara h14, Ara h15, Ara h16, Ara h17, or any combination thereof. In some embodiments, an RNAi construct may comprise sense and antisense sequences for Ara h1, h2, h3, h6, h7, h8, h14, and h15, in any combination. In some embodiments, an siRNA construct may comprise sense and antisense sequences for Ara h1, Ara h2, Ara h3, Ara h6, Ara h7, Ara h8, Ara h14, and Ara h15, in any combination, Ara h1, Ara h2, Ara h3, Ara h6, and Arah7 in any combination or an siRNA construct may comprise sense and antisense sequences for Ara h2, Ara h6, and Arah7, in any combination.

FIG. 1 provides one embodiment of an siRNA construct of the invention, which comprises a sense fragment comprising, consisting essentially of, or consisting of nucleotide sequences from Ara h1, h2, h3, h6, h8, h7, h14 and h15 (in that order) (SEQ ID NO:249), followed by a loop, and then an antisense fragment that hybridizes with the sense fragment. In some embodiments a siRNA construct may comprise sense and antisense sequences for Ara h1, h2, h3, and h8. FIG. 2 provides a further embodiment of an siRNA construct, which comprises a sense fragment comprising, consisting essentially of, or consisting of nucleotide sequences of Ara h1, h2, h3, and h8, (in that order) (SEQ ID NO:250), followed by a loop, and then an antisense fragment that hybridizes with the sense fragment. Further examples of RNAi constructs are provided in FIGS. 3-8 (SEQ ID NOs:251-256).

The sense fragment of an RNAi construct may encode a variant of a canonical polypeptide sequence of an Ara h peptide, optionally a variant of an Ara h epitope region. These may find use in controlling allergen expression and content in strains of peanut with mutant variants of ara h genes. Variants of the peptide will have some degree of (e.g., substantial) identity with the canonical or wild type peptide (e.g., polypeptides encoded by SEQ ID NOs:2-15 (Ara h 1-15). For example, those skilled in the art would expect that an siRNA construct comprising a sense fragment (and corresponding antisense fragment) encoding a variant peptide (or portion thereof) having from about 75-85% to 85-100% identity (e.g., about 75, 76, 77, 78, 79, 80, 81, 82, 83, 84, 85, 86, 87, 88, 89, 90, 91, 92, 93, 94, 95, 96, 97, 98, 99, 99.5, 100% identity) with the native peptide would retain some function (e.g., ability to repress expression by antisense). It is contemplated that the nucleic acid constructs disclosed herein may comprise sense sequence(s) having at least substantial identity with an Ara h polynucleotide encoding an Ara h polypeptide.

Some embodiments of the siRNA nucleic acid construct are RNA. The construct may be directly introduced into a cell in the form of RNA to temporarily silence one or more Ara h genes. Permanent silencing may be achieved by introducing into a plant cell a DNA construct, in which the sense fragment, loop, and antisense fragment are together operatively linked to one promoter. In some embodiments, a construct comprising a sense fragment and an antisense fragment which are each operably linked to a separate promoter may be introduced into a plant cell.

A promoter useful with the siRNA constructs of the invention may be any promoter functional in a plant. In some embodiments, a promoter can be used that is suitable for use in a peanut cell (e.g., a cell in an edible peanut seed). It will be appreciated that the promoter employed in the present invention should be strong enough to control the transcription of a sufficient amount of an antisense RNA molecule to cause an inhibition of expression of a peanut allergen in transformed cells. A promoter is not limited and may be, for example, a constitutive promoter, an inducible promoter, or a repressible promoter. A constitutive promoter has the advantage of producing high levels of expression of the construct thereby constantly silencing the Ara h gene (or genes).

Examples of suitable constitutive promoters include, but are not limited to, CaMV 35S promoter, CaMV 19S promoter, plant ubiquitin promoter, plant RNA polymerase III promoter (e.g., *Arabidospsis* RNA pol III AtU6-26 promoter, H1 promoter), an opine promoter, rice actin 1 promoter, maize alcohol dehydrogenase 1 promoter, nopaline synthase promoter, octopine synthase promoter, and heat shock 80 (hsp 80) promoter, and the like.

Examples of suitable inducible or developmentally regulated promoters include, but are not limited to, the promoter from the napin storage protein gene (induced during seed development), the malate synthase gene (induced during seedling germination), the small sub-unit RUBISCO gene (induced in photosynthetic tissue in response to light), the patatin gene (highly expressed in potato tubers) and the like.

Some embodiments of an siRNA construct of the invention may comprise a tissue-preferred promoter. A tissue-preferred/tissue specific promoter is a promoter that, when operably linked to a gene, directs a higher level of transcription of that gene in a specific tissue of an organism. For example, a seed-preferred promoter is a promoter that directs a higher level of transcription of an associated gene in plant seeds. Examples of seed-preferred promoters include, but are not limited to, the seed specific promoter of the USP gene of *Vicia faba* (U.S. Pat. No. 5,917,127); the 7S protein promoter of soybean (Bray et al., 1987, *Planta* 172:364-370) and the 2S promoter (Krebbers et al., 1988, *Plant Physiol.* 87:859-866). Additional tissue specific or tissue preferred promoters include, but are not limited to, the AdoMet-synthetase stem-specific promoter (Peleman et al., 1989, *The Plant Cell* 1:81-93), and a tuber-specific promoter (Rocha-Sosa et al., 1989, *EMBO J.* 8:23-29).

A full length promoter or alternatively, a "core promoter" may be used with the nucleic acid constructs of the invention. The core promoter is a region of a promoter that is located most proximally and contains the RNA polymerase binding site, TATA box, and transcription start site (TSS).

In some embodiments, an siRNA construct of the invention comprises a terminator downstream of the antisense region. Examples of terminators suitable for use in nucleic acid constructs include the nopaline synthase polyadenylation signal of *Agrobacterium tumefaciens*, the 35S polyadenylation signal of CaMV, octopine synthase polyadenylation signal, a heat shock storage protein terminator, the *Arabidopsis* heat shock storage protein terminator, and the zein polyadenylation signal from *Zea mays*.

Accordingly, in some embodiments, a nucleic acid construct encoding at least one (e.g., about 1, 2, 3, 4, 5, 6, 7, 8, 9, 10, 11, 12, 13, 14, 15, 16, 17, 18, 19, 20, or more) RNAi molecule effective for silencing an *Arachis hypogaea* allergen (Ara h) gene is provided, comprising: an antisense fragment that is about 15 to about 1000 nucleotides (nt) in length and about 75% to 100% (e.g., about 75, 76, 77, 78, 79, 80, 81, 82, 83, 84, 85, 86, 87, 88, 89, 90, 91, 92, 93, 94, 95, 96, 97, 98, 99, 100%) complementary to a target region of the Ara h gene; and a sense fragment that is substantially complementary to the antisense fragment.

An RNAi molecule of a nucleic acid construct of the invention may comprise an antisense fragment that is complementary to a target region of any Ara h gene. An Ara h gene includes, but is not limited to, Ara h1, Ara h2, Ara h3/Ara h3.02, Ara h5, Ara h6, Ara h7, Ara h8, Ara h9, Ara h10, Ara h11, Ara h12, Ara h13, Ara h14, Ara h15, Ara h16, Ara h17, and any combination thereof. In some embodiments, the at least one Ara h gene may be Ara h1, Ara h2, Ara h3, Ara h6, Arah7, and any combination thereof. In some embodiments, the at least one Ara h gene may be Ara h2, Ara h6, Arah7, and any combination thereof. Some Ara h genes share homologous regions, wherein an RNAi molecule may be designed to comprise these homologous regions, thereby the RNAi molecule may be useful for silencing each of the genes sharing the homologous region.

In some embodiments, the Ara h1 gene comprises the nucleotide sequence of SEQ ID NO:2; the Ara h2 gene comprises the nucleotide sequence of SEQ ID NO:3 and SEQ ID NO:275 (including untranslated regions); the Ara h3/Ara h3.02 gene comprises the nucleotide sequence of SEQ ID NO:4 and SEQ ID NO:281 (including untranslated regions); the Ara h5 gene comprises the nucleotide sequence of SEQ ID NO:5; the Ara h6 gene comprises the nucleotide sequence of SEQ ID NO:6; the Ara h7 gene comprises the nucleotide sequence of SEQ ID NO:7; the Ara h8 gene comprises the nucleotide sequence of SEQ ID NO:8; the Ara h9 gene comprises the nucleotide sequence of SEQ ID NO:9; the Ara h10 gene comprises the nucleotide sequence of SEQ ID NO:10; the Ara h11 gene comprises the nucleotide sequence of SEQ ID NO:11; the Ara h12 gene comprises the nucleotide sequence of SEQ ID NO:12; the Ara h13 gene comprises the nucleotide sequence of SEQ ID NO:13; the Ara h14 gene comprises the nucleotide sequence of SEQ ID NO:14; and the Ara h15 gene comprises the nucleotide sequence of SEQ ID NO:15.

In some embodiments, an antisense fragment useful with this invention may have a length in a range from about 15 to about 1000, about 15 to about 800, about 15 to about 700, about 15 to about 600, about 15 to about 500, about 15 to about 400, about 15 to about 300, about 15 to about 250, about 15 to about 200, about 15 to about 100, about 15 to about 90, about 15 to about 80, about 15 to about 75, about 15 to about 70, about 15 to about 60, about 15 to about 50, about 15 to about 40, about 15 to about 45, about 15 to about 35, about 19 to about 50, about 19 to about 40, about 19 to about 30, about 20 to about 600, about 20 to about 500, about 20 to about 400, about 20 to about 300, about 20 to about 250, about 20 to about 200, about 20 to about 100, about 20 to about 90, about 20 to about 80, about 20 to about 75, about 20 to about 70, about 20 to about 60, about 20 to about 50, about 20 to about 40, about 50 to about 600, about 50 to about 500, about 50 to about 400, about 50 to about 300, about 50 to about 250, about 50 to about 200, about 50 to about 100, about 50 to about 90, about 50 to about 80, about 50 to about 75, about 50 to about 70, about 20 to about 60 nucleotides (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 625, 650, 675, 700, 750, 750, 775, 800, 850, 850, 875, 900, 950, 950, 975, 1000 nt, and any range or value therein). In some embodiments, the antisense fragment may have a length of about 15 nt to about 35 nt, about 19 nt to about 30 nt, about 19 nt to about 25 nt, about 19 nt to about 21 nt, and/or about 20 nt to about 21 nt.

In some embodiments, a nucleic acid construct of the invention may comprise a sense fragment that is the same length or substantially the same length as the antisense fragment (e.g., about 15 nt to about 1000 nt). In some embodiments, the sense fragment and the antisense fragment of a nucleic acid construct of the invention may be substantially complementary (e.g., at least 75% complementary to one another (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more complementary) or fully (100%) complementary to one another.

Various types of RNAi molecules are useful with the present invention for triggering gene silencing of Ara h genes in peanut. For example a construct may be made of short (about 10 nt to about 100 nt, about 15 nt to about 60 nt, about 20 nt to about 60 nt) sense and antisense sequences separated by a short loop (short hairpin RNA (shRNA)). An RNAi construct may comprise a long hairpin RNA (lhRNA). In some embodiments, long (50-600 nt to 1000-1500 nt) sequences may be selected for a long hairpin (lhRNA) RNA that the enzyme DICER may cleave into one or more siRNAs during RNAi processing. In some embodiments, an RNAi construct of the invention may encode a portion or the entire length of an epitope region of an Ara h polypeptide. Exemplary, Ara h epitope regions are provided in Tables 2 and 4-13 (e.g., SEQ ID NOs: 16-50, and 174-205), and indicated in SEQ ID NOs:2-11.

RNAi design tools are available for designing specific siRNAs that provide efficient silencing for selected genes. An entire target gene sequence may be analyzed and the shortest region identified that produces efficient RNAi molecules useful with this invention.

In some aspects, an RNAi molecule may be a single strand that is capable of folding back on itself to form a hairpin RNA (hpRNA) or stem-loop structure. In the case of a hpRNA, the double-stranded region or 'stem' is formed from two regions or segments of the RNA that are essentially inverted complements of one another and possess sufficient complementarity to allow the formation of a double-stranded region. At least one functional silencing element (e.g., antisense fragment) is present in a double-stranded region or 'stem' of an RNAi molecule. The stem-forming single-stranded regions may be separated by a region or segment of the RNA known as the "loop." Thus, in some embodiments, a sense fragment and an antisense fragment of the invention may be linked via a loop (spacer) sequence. In general, the loop is a substantially single-stranded sequence that acts to separate the inverted complements (e.g., sense and antisense sequences) and may comprise any nucleotide sequence conferring enough flexibility to allow self-pairing to occur between the flanking complementary regions of the RNA. In some embodiments, a loop (or spacer) sequence may link the 3' end of the sense fragment to the 5' end of the antisense fragment, which upon hybridization between the sense and antisense sequences forms a double stranded RNAi hairpin.

A loop (or spacer) sequence may comprise a length in a range of about 2 nucleotides to about 1000 nucleotides, about 2 nucleotides to about 100 nucleotides, about 2 nucleotides to about 50 nucleotides, about 6 nucleotides to about 500 nucleotides, about 6 nucleotides to about 100 nucleotides, about 6 nucleotides to about 50 nucleotides, about 6 nucleotides to about 25 nucleotides, about 10 nucleotides to about 500 nucleotides, about 10 nucleotides to about 100 nucleotides, about 10 nucleotides to about 50 nucleotides, or about 10 nucleotides to about 25 nucleotides (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 625, 650, 675, 700, 750, 750, 775, 800, 850, 850, 875, 900, 950, 950, 975, 1000 nt, and any range or value therein).

A loop may comprise any sequence of nucleotides that provides enough flexibility to allow self-pairing to occur between the flanking complementary regions of the RNA and which may increase the proportion and the efficiency of gene silencing. For example, a loop may comprise a functional intron sequence. Any intron sequence may be used. A non-limiting example of an intron useful with this invention is an intron from the pyruvate dehydrogenase kinase gene (pdk), which is 742 nts long.

In some embodiments, an antisense fragment, sense fragment and loop sequence of an RNAi molecule may be operably linked to a single promoter, wherein the 3' end of the sense fragment is linked to the 5' end of the loop sequence and the 5' end of the antisense fragment is linked to the 3' end of the loop sequence and a promoter is operably linked to the 5' end of the sense fragment.

Any promoter that results in transcription of the nucleic acid construct to produce a silencing RNA may be used. In some embodiments, the promoter may be a RNA polymerase III (pol III) promoter (e.g., U6, H1), CaMV promoter or an actin promoter. A full length promoter or a "core promoter" may be used with the nucleic acid constructs of the invention.

In some embodiments, an antisense fragment and a sense fragment may be operably linked to separate RNA polymerase III (pol III) promoters. Opposing polymerase III promoters may be used to independently drive expression of the sense and antisense strands of the siRNA duplex from the same template (see, e.g., Nassania et al. *PLoS One* 2(8): e767.doi:10.1371/journal.pone.0000767). In some embodiments, no loop sequence is required when a pol III promoter is operably linked to the antisense fragment of an RNAi molecule and another pol III promoter is operably linked to the sense fragment. Thus in some embodiments of the invention, a pol III promoter may be operably linked to the 5' end of a sense fragment and another pol III promoter may be operably linked to the 3' end of an antisense fragment, wherein the pol III promoter transcribes both the sense and the antisense fragments, which hybridize to form an RNAi molecule.

The nucleic acid constructs of the present invention are designed to silence one or more genes encoding *Arachis hypogaea* allergen (Ara h) polypeptides to reduce the allergen content of a peanut plant and the seeds produced from the peanut plant. Any region of an Ara h gene may be used in designing nucleic acid construct/siRNA of the invention. In some embodiments, the target region of the Ara h gene may encode at least a portion of an Ara h polypeptide epitope region. In some embodiments, "at least a portion of an Ara h polypeptide epitope region" may comprise part of an Ara h epitope region or an entire Ara h epitope region. Thus, "at least a portion of an Ara h polypeptide epitope region" may comprise about 5 to about 200 consecutive nucleotides (e.g., about 5 to about 150, about 5 to about 100, about 5 to about 50, about 5 to about 25, about 10 to about 200, about 10 to about 150, about 10 to about 100, about 10 to about 50, about 10 to about 25, about 20 to about 200, about 20 to about 150, about 20 to about 100, about 20 to about 50, about 20 to about 30, about 40 to about 200, about 40 to about 150, about 40 to about 100, about 40 to about 50 nucleotides (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200 nucleotides) that encode an epitope of an Ara h polypeptide. Exemplary Ara h polypeptide epitope regions include, but are not limited to, those set forth in Tables 2 and 4-13 and SEQ ID NOs: 16-50 and 174-205, and indicated in SEQ ID NOs:2-11.

The present invention includes nucleic acid constructs designed to silence one or more than one Ara h gene. This may be accomplished through the use of a single nucleic construct of the invention which comprise RNAi molecules designed to target more than one Ara h gene and/or by using more than one nucleic acid construct comprising one or more RNAi molecules that are designed to target more than one Ara h gene.

Thus, in some embodiments, an RNAi molecule of a nucleic acid construct of the invention may comprise an antisense fragment that is about 75% to 100% (e.g., about 75, 76, 77, 78, 79, 80, 81, 82, 83, 84, 85, 86, 87, 88, 89, 90, 91, 92, 93, 94, 95, 96, 97, 98, 99, 100%) complementary to a target region of at least two different Ara h genes (e.g., 2, 3, 4, 5, 6, 7, 8, 9, 10, 11, 12, 13, 14, 15, 16, 17 or more Ara h genes) and is effective for silencing the at least two different Ara h genes.

In some embodiments, a nucleic acid construct of the invention may comprise two or more RNAi molecules (e.g., 2, 3, 4, 5, 6, 7, or more) each of which comprises an antisense fragment that is about 75% to 100% (e.g., about 75, 76, 77, 78, 79, 80, 81, 82, 83, 84, 85, 86, 87, 88, 89, 90, 91, 92, 93, 94, 95, 96, 97, 98, 99, 100%) complementary to a target region of a different Ara h gene. Thus, for example a nucleic acid construct of the invention may comprise two RNAi molecules that are effective for silencing two different Ara h genes or a nucleic acid construct of the invention may comprise three RNAi molecules that are effective for silencing three different Ara h, and so on.

Further provided are expression cassettes comprising a nucleic acid construct of the present invention comprising an RNAi molecule and/or vector comprising the expression cassettes of the invention.

In some embodiments, a nucleic acid construct of the invention comprising/encoding at least one an RNAi molecule effective for silencing an *Arachis hypogaea* allergen (Ara h) gene may be used in combination with a nucleic acid construct of the invention encoding at least one CRISPR guide nucleic acid (gRNA, gDNA) as described herein to reduce the allergenicity of a peanut plant and/or part thereof and/or seed.

Small Guide RNA Encoding Constructs

Repressing allergens as described herein may also be carried out using a clustered regularly interspaced short palindromic repeats (CRISPR) approach. A CRISPR nucleic acid construct (guide RNA); gRNA) may be useful for producing targeted deletions and other gene knockouts in genes encoding peanut allergen proteins, as described herein. Thus, in some embodiments, a CRISPR nucleic acid construct may be used to target one or more Ara h genes for deletion (e.g., any part of the coding region as well as the 5' and 3' untranscribed regions, optionally an epitope encoding region). In some embodiments, a CRISPR nucleic acid construct may be used to target an epitope-encoding region of an Ara h gene, thereby generating a deletion in the Ara h gene. CRISPR utilizes a DNA endonuclease CRISPR associated endonuclease such as Cas9 to make double stranded breaks in genomic DNA. The endonucleases are guided to the target site for deletion by the CRISPR nucleic acid construct (e.g., guide nucleic acid, e.g., gRNA) via "spacer" sequence.

Thus, in some embodiments, Cas9 may be used to modify the Ara h genes (e.g., generate deletions) in a peanut plant (and its seed), thereby reducing the allergenicity of the peanut plant and its seeds that comprise the modification(s). Cas9 is conjugated with a guide RNA (gRNA), which targets the Cas9 to a specific DNA sequence (e.g., target DNA sequence) that then becomes the site for the endonuclease activity. The gRNA comprises a "scaffold" sequence that binds the Cas9 and at least one "spacer" sequence that defines the genomic target for editing and guides the bound Cas9 to the site(s) targeted for deletion. The scaffold sequences are defined by the Cas9 to be used. The at least one spacer sequence comprises a sequence of at least about 15 nucleotides (e.g., about 15 to about 25 nucleotides) in length and has substantial homology to the genomic sequence targeted for deletion (e.g., the Ara h gene). This approach can produce deletions of any length. In some embodiments, the length of a deleted region may be from about 50 base pairs to the full length of the targeted gene. In some embodiments, the length of a deleted region of the targeted gene may be from about 50 to about 500 base pairs, or about 60 to about 140 base pairs.

In some embodiments, a spacer sequence of a gRNA may be substantially complementary to fully complementary (e.g., about 75%-100%) to a consecutive nucleotides sequence encoding any region of an Ara h polypeptide (e.g., any region of Ara h1-Ara h17; see e.g., SEQ ID NOs 2-15 and SEQ ID NO:275; e.g., any part of the coding region as well as the 5' and 3' untranscribed regions, optionally an epitope encoding region). In some embodiments, a spacer sequence of a gRNA may be substantially complementary to fully complementary (e.g., about 75%-100%) to a sequence that encodes an epitope region of an Ara h polypeptide (e.g., an epitope coding region of Ara h1-Ara h17 (Ara h genes, see, e.g., SEQ ID NOs 2-15, 275 and 281); e.g., an epitope region such as that set forth in Tables 2 and 4-13 and encoded by SEQ ID NOs: 16-50, and 174-205) or any combination of epitope regions from one or more Ara h polypeptides. The epitope region may be any epitope region of an Ara h peptide disclosed above as suitable for targeting by the RNAi approach. In some embodiments, a CRISPR nucleic acid construct may include a gRNA scaffold sequence immediately downstream of the spacer sequence, a terminator sequence immediately downstream of the gRNA scaffold sequence; and a promoter operatively linked to the spacer sequence, scaffold sequence, and terminator sequence.

Any promoter functional in a plant cell may be used in with the guide nucleic acid constructs of the present invention. In some embodiments, the promoter is functional in a peanut cell (e.g., in an edible peanut seed). A promoter may include, but is not limited to, a constitutive promoter, an inducible promoter, or a repressible promoter. A constitutive promoter has the advantage of constantly silencing the Ara h gene (or genes) and producing high levels of expression of the construct. Any promoter that is disclosed above as suitable for use with the RNAi construct may be used in a gRNA construct.

Any terminator disclosed above as suitable for use in the RNAi construct may be used in the gRNA construct. In some embodiments, the terminator of a gRNA construct is a poly-T region (e.g., a poly-T hexanucleotide).

In some embodiments, more than one gRNA construct may be used. Use of more than one gRNA construct may enhance specificity. For example, two gRNA encoding sequences may be used. The two gRNA encoding sequences may complement targets on opposite strands of the target region of the gene to be deleted. A protospacer adjacent motif (PAM) is present on the target DNA assisting with the targeting of the gRNA and Cas9. For Cas9, a PAM may be about a 2-6 bp motif located immediately following the DNA sequence targeted by the Cas9 nuclease (protospacer sequence) (e.g., 3' end of targeted (protospacer) sequence). In the case of Cas9, a canonical PAM includes, but is not limited to, the sequence 5'-NGG-3'. Other Cas9 PAM sequences have been engineered and include, but are not limited to YG, TTTN, and YTN.

Examples of suitable guide sequences are provided below in Table 3.

TABLE 3

EXEMPLARY GUIDE SEQEUNCES

| GenBank accession number of targeted peanut Ara h genes | Name of gRNA | gRNA guide sequence (underlined) and deletion targets in peanut Ara h genes. | SEQ ID NO |
|---|---|---|---|
| AF432231 (A1) Deletion length = 100 bp | gRNA/A1-1 gRNA/A1-2 | 5'-cggacacgtggccgccaaccCGG-3' *** 5'-CCAagagaagattggaggcgacc-3 ** 5'-ggtcgcctccaatcttctctTGG-3' Antiparallel* | 206 207 208 |
| AV007229 (A2) Deletion length = 64 bp | gRNA/A2-1 gRNA/A2-2 | 5'-tcgctgcccacgcatctgcgAGG-3' *** 5-CCTgcgagcaacatctcatgcag-3' ** 5'-ctgcatgagatgttgctcgcAGG-3' Antiparallel* | 209 210 211 |
| AF510854 (A3) Deletion length = 91 bp | gRNA/A3-1 gRNA/A3-2 | 5'-aaccgcattgaatcggagggCGG-3' *** 5'-CCTtcggaggcctttctactcca-3' ** 5'-tggagtagaaaggcctccgaagg-3' Antiparallel* | 212 213 214 |
| EF609644 (A6) Deletion length = 82 bp | gRNA/A6-1 gRNA/A6-2 | 5'-agccctccttgccctcgtccTGG-3' *** 5'-CCTcaagccctgcgagcagcaca-3' ** 5'-tgtgctgctcgcagggcttgAGG-3' Antiparallel* | 215 216 217 |
| AF091737 (A7) Deletion length = 60 bp | gRNA/A7-1 gRNA/A7-2 | 5'-gatggtcaagctcagcatccTGG-3' *** 5'-CCAgagggtcgagatgggacgca-3' ** 5'-tgcgtcccatctcgaccctctgg-3' Antiparallel* | 218 219 220 |
| EU514465 (A8) Deletion length = 140 bp | gRNA/A8-1 gRNA/A8-2 | 5'-caagagtgttgaaatcgttcAGG-3 *** 5'-CCAagtttatcttacacaaagtg-3' ** 5'-cactttgtgtaagataaactTGG-3' Antiparallel* | 221 222 223 |
| GU354312 (Ara h 5) Deletion length = 70 bp | gRNA/A5-1 gRNA/A5-2 | 5'-gctgtcattcgagggaacaaGGG-3' *** 5'-CCAgggcagtgcaacatgattgt-3' ** 5'-acaatcatgttgcactgcccTGG-3' Antiparallel* | 224 225 226 |
| EU159429 (Ara h 9) Deletion length = 62 bp | gRNA/A9-1 gRNA/A9-2 | 5'-tcccttcgtggcctcaaccaAGG-3' *** 5'-CCAactgtgctaccattaagttc-3' ** 5'-gaacttaatggtagcacagtTGG-3' Antiparallel* | 227 228 229 |
| AY722694 (Ara h 10) Deletion length = 90 bp | gRNA/A10-1 gRNA/A10-2 | 5'-cttcagccctgtcatagttcCGG-3' *** 5'-CCGgcagacccacggatcggtg-3' ** 5'-caccgatccgtgggtctgcCGG-3' Antiparallel* | 230 231 232 |

TABLE 3 -continued

EXEMPLARY GUIDE SEQEUNCES

| GenBank accession number of targeted peanut Ara h genes | Name of gRNA | gRNA guide sequence (underlined) and deletion targets in peanut Ara h genes. | SEQ ID NO |
|---|---|---|---|
| DQ097716 (Ara h 11) Deletion length = 75 bp | gRNA/A11-1 gRNA/A11-2 | 5' -gccaacgccaagagcaaccaAGG-3' *** 5' -CCGtcattggcctcacaacgatcaca-3' ** 5' -ttgtgatcgttgtgaggccaatgaCGG-3 Antiparallel* | 233 234 235 |
| EY396089.1 (Ara h 12) Deletion length = 72 bp | gRNA/A12-1 gRNA/A12-2 | 5' -cctcgttctctttcttgctcAGG-3 *** 5' -CCAatgcaagctgcgatgatcat-3' ** 5 -atgatcatcgcagcttgcatTGG-3' Antiparallel* | 236 237 238 |
| EY396019.1 (Ara h 13) Deletion length = 70 bp | gRNA/A13-1 gRNA/A13-2 | 5' -cctcattctctttcttgctcAGG-3 *** 5' -CCGctgctggtgcaacagaaagt-3' ** 5' -actttctgttgcaccagcagCGG-3' Antiparallel* | 239 240 241 |
| AF325917.1 (Ara h 14) Deletion length = 75 bp | gRNA/A14-1 gRNA/A14-2 | 5' -cgcgtcgacgttccacgccgCGG-3 *** 5' -CCTcgtcggcgtccccactgggg-3' ** 5' -ccccagtggggacgccgacgAGG-3' Antiparallel* | 242 243 244 |
| AY722696.1 (Ara h 15) Deletion length = 70 bp | gRNA/A15-1 gRNA/A15-2 | 5' -caaacaaggacaggctatggAGG-3' *** 5' -CCTatgaccccagtactaac-3' ** 5' -gttagtactggggtcatAGG-3' Antiparallel* | 245 246 247 |

*The underlined sequence labelled "antiparallel" is the "spacer" sequence that is used to guide the Cas9 to the target site on the gene.
** The sequences that are not underlined are the region on the gene that is targeted.
*** The other underlined sequence provides the Pam (NGG) location on the target gene (opposite strand).

Additional examples of possible target sequences (for sgRNAs) for Ara h1 and Ara h3 genes include, but are not limited to, 5'-3', Ara h1: CCTCGAGGACACACTGGCACC (SEQ ID NO:276) and cggacacgtggccgccaaccCGG (SEQ ID NO:277); Ara h3: caggagatcttcatccagcaAGG (SEQ ID NO:278) and CCTCGAGGACACAGCACGGCCGCAG (SEQ ID NO:279), as well as those provided in FIG. 33 for Ara h2.

In addition to a construct encoding a gRNA, a nucleic acid construct encoding an endonuclease may be introduced into a plant (e.g., a nucleic acid construct encoding Cas9). Cas9 and the gRNA may be introduced on different or on the same nucleic acid construct. In some embodiments, a gRNA encoding construct may be used in concert with a second construct that encodes Cas9. Any suitable Cas9 as known in the art may be used with the nucleic acid constructs of this invention, including wild-type and nickase Cas9. In some embodiments, at least one wild-type Cas9 may be introduced into a plant. In some embodiments, at least one mutant Cas9 (e.g., nickase Cas9) may be introduced into a plant. In some embodiments, the Cas9 may be a plant-codon optimized version of Cas9, such as for example, a peanut-optimized Cas9.

"Wild-type Cas9" comprises two active catalytic sites (HNH and RuVC1). In addition, various mutant Cas9 nickases are known in the art in which one or the other catalytic site is mutated to be inactive, including Cas9 D10A (RuVC1 site mutated and non-active) and the mutant Cas9H840A (HNH site mutated and non-active). Use of a nickase mutant Cas9 may reduce off-target double stranded breaks observed with wild type Cas9. Thus, in some embodiments, use of a nickase variant (e.g., Cas9 D10A and/or Cas9H840A) may provide improved specificity when used in combination with the nucleic acid constructs of the invention encoding gRNAs. Thus, in some embodiments, a paired nicking strategy may be used to improve specificity, the method comprising introducing two single guide nucleic acids (DNA/RNA)(sgDNA/sgRNA)) (on one or more nucleic acid constructs) targeting adjacent sites on opposite DNA strands of a target site, each sgDNA/sgRNA recruiting a Cas9 mutant (such as Cas9-D10A) that nicks each strand of the target DNA, thereby generating a deletion. Any Cas9 nickase mutant may be used with this invention. It is noted that off-target single stranded breaks may be generated with a Cas9 nickase mutant; however, the nickase mutants have less damaging consequences because the single stranded breaks (SSB) may be repaired by hi-fidelity base excision repair mechanism. Thus, off target events may still occur but generally do not result in a mutation.

A Cas9 encoding sequence may also be operatively linked to a promoter, which may be the same promoter that is linked to the gRNA encoding sequence, or it may be operably linked to a separate promoter from the promoter for the gRNA nucleic acid construct. The separate promoter may be any that is disclosed above to be suitable for use with an RNAi construct in plant. In some embodiments, a Cas9-encoding nucleic acid may be operatively linked to a plant ubiquitin promoter (pUbi). The separate promoter may be any that is disclosed below as suitable to be linked to the gRNA encoding sequence as well. A terminator may also be present, including but not limited to any terminator disclosed above as suitable for use in the RNAi construct.

In some embodiments, a construct encoding an endonuclease (e.g., Cas9) may be introduced into a plant. A construct encoding Cas9 may also encode one or more nuclear localization signals (NLS). An NLS is an amino acid sequence that tags a protein for import into the cell nucleus by nuclear transport. Typically, this signal consists of one or more short sequences of positively charged lysine residues or arginine residues exposed on the protein surface. The NLS may be either monopartite or bipartite. Monopartite NLSs have a single cluster of basic amino acid residues. There are two classes of monopartite NLS: 1.) Class has at least four consecutive basic amino acids and 2.) Class 2 has three basic amino acids and is represented by K(K/R)X(K/R) as a putative consensus sequence where K=Lysine, R=Arginine and X=any amino acid. A putative consensus sequence of the bipartite NLS has been defined as (K/R)(K/R)X$_{10-12}$(K/R)$_{3/5}$, where (K/R)$_{3/5}$ represents at least three of either lysine or arginine of five consecutive amino acid, in which the linker region has been found to be tolerant to amino acid conversion. Although the consensus sequences of NLSs have been defined, there are still many NLSs that do not match the consensus rule and many nonfunctional sequences that match the consensus (Shunichi Kosugi et al. 2009, attached).

Any appropriate Cas9 endonuclease, including a nickase, may be used with this invention. An exemplary embodiment of a Cas9 encoding nucleotide sequence with flanking nuclear localization signals is shown below SEQ ID NO:248, which is a plant codon optimized wild type Cas9. The NLS sequences are highlighted.

(SEQ ID NO 248)

```
atggctcctaagaagaagcggaaggttggtattcacggggtgcctgcggctgacaagaagtactccatcggcctc gacatcggcaccaacagcgtcggctgggcggtgatcaccgacgagtacaaggtcccgtccaagaagttcaaggtc ctgggcaacaccgaccgccactccatcaagaagaacctcatcggcgccctcctcttcgactccggcgagacggcg gaggcgacccgcctcaagcgcaccgcccgccgccgctacacccgccgcaagaaccgcatctgctacctccaggag atcttctccaacgagatggcgaaggtcgacgactccttcttccaccgcctcgaggagtccttcctcgtggaggag gacaagaagcacgaggccaccccatcttcggcaacatcgtcgacgaggtcgcctaccacgagaagtaccccacta tctaccaccttcgtaagaagcttgttgactctactgataaggctgatcttcgtctcatctaccttgctctcgctc acatgatcaagttccgtggtcacttccttatcgagggtgaccttaaccctgataactccgacgtggacaagctct tcatccagctcgtccagacctacaaccagctcttcgaggagaaccctatcaacgcttccggtgtcgacgctaagg cgatcctttccgctaggctctccaagtccaggcgtctcgagaacctcatcgcccagctccctggtgagaagaaga acggtctttcggtaacctcatcgctctctccctcggtctgacccctaacttcaagtccaacttcgacctcgctg aggacgctaagcttcagctctccaaggatacctacgacgatgatctcgacaacctcctcgctcagattggagatc agtacgctgatctcttccttgctgctaagaacctctccgatgctatcctcctttcggatatccttagggttaaca ctgagatcactaaggctcctctcttctgcttccatgatcaagcgctacgacgagcaccaccaggacctcacccctcc tcaaggctcttgttcgtcagcagctccccgagaagtacaaggagatcttcttcgaccagtccaagaacggctacg ccggttacattgacggtggagctagccaggaggagttctacaagttcatcaagccaatccttgagaagatggatg gtactgaggagcttctcgttaagcttaaccgtgaggacctccttaggaagcagaggactttcgataacggctcta tccctcaccagatccaccttggtgagcttcacgccatccttcgtaggcaggaggacttctacccttccctcaagg acaaccgtgagaagatcgagaagatccttactttccgtattccttactacgttggtcctcttgctcgtggtaact cccgtttcgcttggatgactaggaagtccgaggagactatcaccccttggaacttcgaggaggttgttgacaagg gtgcttccgcccagtccttcatcgagcgcatgaccaacttcgacaagaacctccccaacgagaaggtcctcccca agcactcctcctctacgagtacttcacggtctacaacgagctcaccaaggtcaagtacgtcaccgagggtatgc gcaagcctgccttcctctccggcgagcagaagaaggctatcgttgacctcctcttcaagaccaaccgcaaggtca ccgtcaagcagctcaaggaggactacttcaagaagatcgagtgcttcgactccgtcgagatcagcggcgttgagg accgtttcaacgcttctctcggtacctaccacgatctcctcaagatcatcaaggacaaggacttcctcgacaacg aggagaacgaggacatcctcgaggacatcgtcctcactcttactctcttcgaggatagggagatgatcgaggaga ggctcaagacttacgctcatctcttcgatgacaaggtttgaagcagctcaagcgtcgccgttacaccggttgggg taggctctcccgcaagctcatcaacggtatcagggataagcagagcggcaagactatcctcgacttcctcaagtc tgatggtttcgctaacaggaacttcatgcagctcatccacgatgactctcttacctttcaaggaggatattcagaa ggctcaggtgtccggtcagggcgactctctccacgagcacattgctaaccttgctggttcccctgctatcaagaa gggcatccttcagactgttaaggttgtcgatgagcttgtcaaggttatgggtcgtcacaagcctgagaacatcgt catcgagatggctcgtgagaaccagactacccagaagggtcagaagaactcgagggagcgcatgaagaggattga ggagggtatcaaggagcttggttctcagatccttaaggagcaccctgtcgagaacacccagctccagaacgagaa
```

-continued
```
gctctacctctactacctccagaacggtagggatatgtacgttgaccaggagctcgacatcaacaggctttctga ctacgacgtcgaccacattgttcctcagtctttccttaaggatgactccatcgacaacaaggtcctcacgaggtc cgacaagaacaggggtaagtcggacaacgtcccttccgaggaggttgtcaagaagatgaagaactactggaggca gcttctcaacgctaagctcattacccagaggaagttcgacaacctcacgaaggctgagaggggtggcctttccga gcttgacaaggctggtttcatcaagaggcagcttgttgagacgaggcagattaccaagcacgttgctcagatcct cgattctaggatgaacaccaagtacgacgagaacgacaagctcatccgcgaggtcaaggtgatcaccctcaagtc caagctcgtctccgacttccgcaaggacttccagttctacaaggtccgcgagatcaacaactaccaccacgctca cgatgcttaccttaacgctgtcgttggtaccgctcttatcaagaagtaccctaagcttgagtccgagttcgtcta cggtgactacaaggtctacgacgttcgtaagatgatcgccaagtccgagcaggagatcggcaaggccaccgccaa gtacttcttctactccaacatcatgaacttcttcaagaccgagatcacccctcgccaacggcgagatccgcaagcg ccctcttatcgagacgaacggtgagactggtgagatcgtttgggacaagggtcgcgacttcgctactgttcgcaa ggtcctttctatgcctcaggttaacatcgtcaagaagaccgaggtccagaccggtggcttctccaaggagtctat ccttccaaagagaaactcggacaagctcatcgctaggaagaaggattgggaccctaagaagtacggtggtttcga ctcccctactgtcgcctactccgtcctcgtggtcgccaaggtggagaagggtaagtcgaagaagctcaagtccgt caaggagctcctcggcatcaccatcatggagcgctcctccttcgagaagaacccgatcgacttcctcgaggccaa gggctacaaggaggtcaagaaggacctcatcatcaagctccccaagtactctcttttcgagctcgagaacggtcg taagaggatgctggcttccgctggtgagctccagaaggggtaacgagcttgctcttccttccaagtacgtgaactt cctctacctcgcctcccactacgagaagctcaagggttcccctgaggataacgagcagaagcagctcttcgtgga gcagcacaagcactacctcgacgagatcatcgagcagatctccgagttctccaagcgcgtcatcctcgctgacgc taacctcgacaaggtcctctccgcctacaacaagcaccgcgacaagcccatccgcgagcaggccgagaacatcat ccacctcttcacgctcacgaacctcggcgcgccctgctgctttcaagtacttcgacaccaccatcgacaggaagcg ttacacgtccaccaaggaggttctcgacgctactctcatccaccagtccatcaccggtctttacgagactcgtat cgacctttcccagttggtggtgat*aagcgtcctgctgccaccaaaaaggccggacaggctaagaaaaagaagta*
```
*g*

40

In some embodiments, a Cas9 variant of the nucleotide sequence shown above may be useful with the invention. In some embodiments, a Cas9 variant of SEQ ID NO:248 comprising a mutation in the HNH or RuVC1 site (i.e., a Cas 9 nickase) may be used with the present invention (e.g., introduced into a plant). Thus, for example, a plant codon optimized Cas9 sequence with a mutation in the RuvC domain (D10A) such as the nucleotide sequence of SEQ ID NO:280 may be useful with the present invention.

Nucleotide sequences of a first exemplary promoter (potato Ubiquitin 3 promoter), terminator (*Arabidopsis* heat shock storage protein terminator), a second exemplary promoter (*Arabidopsis* AtU6-26 promoter), and an exemplary gRNA scaffold are shown in FIGS. 9-12, respectively.

Several examples of possible deletion targets in Ara h genes are shown in FIGS. 13-26 and 33.

A kit for making a genetically modified plant with reduced allergen content is provided, the kit comprising any nucleic acid construct expressing a gRNA disclosed above, and a nucleic acid construct encoding a CRISPR associated protein 9 (Cas9) for delivery to a cell.

In some embodiments, a nucleic acid construct encoding at least one CRISPR guide nucleic acid (gRNA, gDNA) is provided, comprising at least one spacer sequence (e.g., 2, 3, 4, 5, 6, 7, 8, 9, 10, 11, 12, 13, 14, 15, 16, 17, 18, 19, 20, or more spacer sequences) having substantial complementarity to a target region of at least one *Arachis hypogaea* allergen (Ara h) gene; and a scaffold sequence for binding a CRISPR Cas endonuclease.

In some embodiments, the at least one spacer sequence may be about 15 nucleotides to about 75 nucleotides in length having about 75% to 100% complementarity to consecutive nucleotides of the target region of the at least one Ara h gene.

Thus, a spacer sequence useful with this invention may comprise a length of about 15 to about 75 nucleotides (e.g., about 15 to about 70, about 15 to about 65, about 15 to about 60, about 15 to about 55, about 15 to about 50, about 15 to about 45, about 15 to about 40, about 15 to about 35, about 15 to about 30, about 15 to about 25, about 15 to about 22, about 18 to 22 or about 19 to 21 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 nucleotides in length, and any range therein). In some embodiments, a spacer may be about 20 nucleotides in length.

In some embodiments, a spacer sequence may be substantially complementary (e.g., about 75, 76, 77, 78, 79, 80, 81, 82, 83, 84, 85, 86, 87, 88, 89, 90, 91, 92, 93, 94, 95, 96, 97, 98, 99, 99.5% complementarity) to consecutive nucleotides of an Ara h gene from peanut (*Arachis hypogaea*) or it may be fully complementary (100% complementary) to consecutive nucleotides of an Ara h gene from peanut.

The complementarity of the 3' region of a spacer sequence to a target DNA may be 100% complementary to the target region while the 5' region of the spacer may be less than 100% complementary. Therefore, the overall complementarity of the spacer sequence to the target DNA may be less than 100%. Thus, for example, the first 7, 8, 9, 10, 11, 12, 13, 14, 15, 16, and the like, nucleotides in the 3' region of a 20 nucleotide spacer sequence (seed sequence) can be 100% complementary to the target DNA, while the remaining nucleotides in the 5' region of the spacer sequence are substantially complementary (e.g., at least about 75% complementary) to the target DNA. Thus, in some embodiments, at least the first 7-10 nucleotides at the 3' end of the spacer are 100% complementary to the target region.

In some embodiments, a CRISPR guide nucleic acid of the invention may comprises a "repeat sequence" flanking the 5' end or the 5' end and the 3' end of the spacer sequence. When a CRISPR guide nucleic acid comprises more than one spacer sequence, the spacer sequences may be separated by a repeat sequence. A "repeat sequence" as used herein may be any repeat sequence of a wild-type CRISPR locus or may be a repeat sequence of a synthetic CRISPR array. In some embodiments, the repeat sequence is from a Type II wild-type CRISPR locus and is compatible with the selected Cas9 endonuclease.

As used herein, a "target DNA," or a "target region" refers to a region of an organism's genome that is fully complementary or substantially complementary (e.g., at least 75% complementary (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more) to a spacer sequence.

In some embodiments, a target region may be about 15 to about 75 consecutive nucleotides in length (e.g., about 15 to about 70, about 15 to about 65, about 15 to about 60, about 15 to about 55, about 15 to about 50, about 15 to about 45, about 15 to about 40, about 15 to about 35, about 15 to about 30, about 15 to about 25, about 15 to about 22, about 18 to 22 or about 19 to 21 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 nucleotides in length, and any range therein) that are located immediately adjacent to a PAM sequence (PAM sequence located immediately 3' of the target region in the case of Type II CRISPR systems (e.g., Cas9)) in the genome of the organism (e.g., peanut, *Arachis hypogaea*).

Guide structures (e.g., spacers sequences, repeat sequences and scaffold sequences) and PAMs are well known (see, e.g., Barrangou Genome Biol. 16:247 (2015)) and design of guide RNAs is well understood, in particular for Type II CRISPR (Cas9) systems. Software is available to assist in the selection of the most efficient gRNAs for a given target site. Such gRNA design software tools include, but are not limited to, the following Cas-OFFinder (rgenome.net/cas-offinder), CRISPR Design (crispr.mit.edu); E-CRISP (e-crisp.org/E-CRISP/), CRISPR MultiTargeter (multicrispr.net/basic_input.html), sgRNA Designer: CRISPRko (portals.broadinstitute.org/gpp/public/analysis-tools/sgrna-design), Off-Spoter (cm.jefferson.edu/Off-Spotter/), CCTop (crispr.cos.uni-heidelberg.de/index.html), CHOPCHOP (chopchop.cbu.uib.no/index.php).

In some embodiments, nucleic acid construct of the invention may encode a CRISPR guide nucleic acid that may comprise two or more spacers, each spacer having at least about 75% to 100% complementarity to a target region of a different Ara h gene, or having at least about 75% to 100% complementarity to a different target region of the same Ara h gene, or any combination thereof. Thus, for example, a CRISPR guide nucleic acid may comprise two different spacers that guide a Cas endonuclease to at least two different target sites on the same Ara h gene (thereby generating a deletion in that gene). As a further non-limiting example of the flexibility of this system, a nucleic acid construct of the invention may encode a CRISPR guide nucleic acid that comprises four different spacers that guide a Cas endonuclease to at least two different Ara h genes (thereby generating a deletion in each of the two different Ara h genes). In a further non-limiting example a nucleic acid construct of the invention may encode a CRISPR guide nucleic acid that may comprise six different spacers targeting three different genes (thereby generating a deletion in each gene) or, alternatively, the six different spacers may target six different sites in the same gene (thereby generating three deletions in the same gene), or further, a nucleic acid construct of the invention may encode a CRISPR guide nucleic acid that targets multiple different genes and multiple sites within a single gene at the same time, thereby generating deletions in multiple genes and multiple deletions in single genes. Thus, this design allows the targeting of one or more than one gene to achieve one or more than one deletion in each targeted gene, thereby knocking out one or more than one Ara h gene and reducing the production of the corresponding allergen polypeptides encoded by the one or more than one Ara h gene.

In some embodiments, the at least one spacer may have about 75% to 100% complementarity to at least about 15 consecutive nucleotides of a target region shared between at least two different Ara h genes. Thus, when regions of sufficient homology are present between to two or more Ara h genes, the two or more Ara h genes may be targeted by a single guide. As an example, homology regions are shared between the Ara h genes Ara h2, Ara h6, Arah7.

In some embodiments, the Ara h gene that may be targeted for reducing expression (e.g., a reduction in expression and production of the allergen polypeptide of 10, 20, 30, 40, 50, 60, 70, 80, 90, 100%) may be Ara h1, Ara h2, Ara h3/Ara h3.02, Ara h5, Ara h6, Ara h7, Ara h8, Ara h9, Ara h10, Ara h11, Ara h12, Ara h13, Ara h14, Ara h15, Ara h16, Ara h17, and any combination thereof. In some embodiments, the Ara h gene may be Ara h1, Ara h2, Ara h3, Ara h6, Arah7, and any combination thereof. In some embodiments, the Ara h gene may be Ara h2, Ara h6, Arah7, and any combination thereof.

In some embodiments, the Ara h1 gene comprises the nucleotide sequence of SEQ ID NO:2; the Ara h2 gene comprises the nucleotide sequence of SEQ ID NO:3 and SEQ ID NO:275 (including untranslated regions); the Ara h3/Ara h3.02 gene comprises the nucleotide sequence of SEQ ID NO:4 and SEQ ID NO:281 (including untranslated regions); the Ara h5 gene comprises the nucleotide sequence of SEQ ID NO:5; the Ara h6 gene comprises the nucleotide sequence of SEQ ID NO:6; the Ara h7 gene comprises the nucleotide sequence of SEQ ID NO:7; the Ara h8 gene comprises the nucleotide sequence of SEQ ID NO:8; the Ara h9 gene comprises the nucleotide sequence of SEQ ID NO:9; the Ara h10 gene comprises the nucleotide sequence of SEQ ID NO:10; the Ara h11 gene comprises the nucleotide sequence of SEQ ID NO:11; the Ara h12 gene comprises the nucleotide sequence of SEQ ID NO:12; the Ara h13 gene comprises the nucleotide sequence of SEQ ID NO:13; the Ara h14 gene comprises the nucleotide sequence of SEQ ID NO:14; and the Ara h15 gene comprises the nucleotide sequence of SEQ ID NO:15.

In some embodiments, a nucleic acid construct of the invention may further comprise a polynucleotide encoding a CRISPR Cas endonuclease. In some embodiments, the CRISPR Cas endonuclease may be a Cas9 endonuclease (see, e.g., SEQ ID NO:248 or SEQ ID NO:280).

In some embodiments, a polynucleotide encoding a CRISPR Cas endonuclease may be operably linked to a promoter. In some embodiments, a polynucleotide encoding the CRISPR Cas endonuclease and the at least one CRISPR guide nucleic acid may be operably linked to a single promoter. In some embodiments, a polynucleotide encoding the CRISPR Cas endonuclease and the at least one CRISPR guide nucleic acid may be operably linked to separate promoters that may be the same promoter or may be different promoters. Any promoter useful with a plant may be used with the nucleic acid construct of the invention encoding a CRISPR guide nucleic acid and/or encoding a Cas9 polypeptide including, but not limited to CaMV 35S promoter, CaMV 19S promoter, plant ubiquitin promoter, plant RNA polymerase III promoter (e.g., *Arabidospsis* RNA pol III AtU6-26 promoter, H1 promoter), an opine promoter, rice actin 1 promoter, maize alcohol dehydrogenase 1 promoter, nopaline synthase promoter, octopine synthase promoter, and heat shock 80 (hsp 80) promoter, and others described above.

Further provided are expression cassettes comprising the nucleic acid constructs of the invention encoding a CRISPR guide nucleic acid and/or vectors comprising expression cassettes of the invention.

In some embodiments, a nucleic acid construct of the invention comprising at least one CRISPR guide nucleic acid (gRNA, gDNA) may be used in combination with aa nucleic acid construct of the invention comprising at least one an RNAi molecule effective for silencing an *Arachis hypogaea* allergen (Ara h) gene as described herein to reduce the allergenicity of a peanut plant and/or part thereof and/or seed.

Genetically Modified Organisms

A genetically modified peanut cell is provided comprising one or more of the nucleic acid constructs of the invention comprising at least one RNAi molecule targeting an Ara h mRNA and/or one or more of the nucleic acid constructs of the invention comprising at least one gRNA targeting an Ara h gene.

In some embodiments, a genetically modified peanut cell is provided, comprising one or more RNAi nucleic acid constructs as described above. In some embodiments, a genetically modified peanut cell of the present invention has reduced (e.g. about 10% to about 100%; e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% and any range or value therein) and/or undetectable levels (100% undetectable) of at least one allergen protein (and therefore, reduced allergenicity) compared to wild-type. Thus in some embodiments, the amount of at least one allergen protein in a genetically modified peanut cell of the present invention may be reduced by about 10% to about 99%, about 10% to about 90%, about 10% to about 80%, about 10% to about 70%, about 10% to about 60%, about 10% to about 50%, about 25% to about 100%, about 25% to about 99%, about 25% to about 90%, about 25% to about 80%, about 25% to about 70%, about 25% to about 60%, about 25% to about 50%, about 40% to about 100%, about 40% to about 99%, about 40% to about 95%, about 40% to about 90%, about 40% to about 85%, about 40% to about 80%, about 40% to about 75%, about 40% to about 70%, about 40% to about 60%, about 50% to about 100%, about 50% to about 99%, about 50% to about 95%, about 50% to about 90%, about 50% to about 85%, about 50% to about 80%, about 50% to about 75%, about 50% to about 70%, about 50% to about 60%, about 60% to about 100%, about 60% to about 95%, about 60% to about 90%, about 6% to about 85%, about 60% to about 80%, about 60% to about 75%, about 60% to about 70%, about 75% to about 100%, about 75% to about 99%, about 75% to about 95%, about 75% to about 90%, about 75% to about 85%, about 75% to about 80%, about 80% to about 100%, about 80% to about 99%, about 80% to about 95%, about 80% to about 90%, about 85% to about 100%, about 85% to about 99%, about 85% to about 95%, about 90% to about 100%, about 90% to about 99%, about 90% to about 95%, about 95% to about 100%, about 95% to about 99%, about 98% to about 100%, about 99% to about 100%, and any range or value therein.

The allergen protein may include but is not limited to Ara h1, h2, h3/3.02, h5, h6, h7, h8, h9, h10, h11, h12, h13, h14, h15, h16 and h17. In some embodiments, a cell of a peanut plant, plant part or seed may have reduced or undetectable levels of more than one allergen protein (e.g., 1, 2, 3, 4, 5, 6, 7, 8, 9, 10, 11, 12, 13, 14, 15, 16, 17 allergen proteins or more) compared to wild-type. For example, a peanut cell comprising the construct of FIG. 1 may have reduced or undetectable levels of Ara h1, h2, h3, h6, h7, h8, h14, and 15 proteins compared to wild-type. As another example, a peanut cell comprising the construct of FIG. 2 may have reduced or undetectable levels of Ara h1, h2, h3, and h8 proteins compared to wild-type. As another example, a peanut cell comprising the construct of FIGS. 3-6 may have reduced or undetectable levels of Ara h1, h2, h3, h6, h7, and h8 proteins compared to wild-type. As another example, a peanut cell comprising the construct of FIG. 7 may have reduced or undetectable levels of Ara h5 and h9-h15 proteins compared to wild-type. As another example, a peanut cell comprising the construct of FIG. 8 may have reduced or undetectable levels of Ara h1-h3 proteins compared to wild-type.

A peanut cell may of course comprise more than one RNAi and/or CRISPR construct of the invention to reduce or eliminate the expression of one or more of the Ara h proteins.

In some embodiments, a genetically modified peanut cell is provided, comprising a deletion in a sequence that may encode at least one Ara h protein, for example, an epitope region. Deletions may also include non-epitope regions of an Ara h gene. Such deletion may be achieved by various means in the art, including the use of Cas9 in conjunction with any nucleic acid of the invention encoding at least one CRISPR guide nucleic acid as described herein.

A cell comprising a deletion in an Ara h gene may have reduced or undetectable (e.g., about 10% to about 100% reduced) allergenicity of at least one allergen protein compared to wild-type. Deletions to knockout Ara h genes can be made anywhere in the gene sequence including coding regions and noncoding regions.

A genetically modified peanut cell is provided comprising one or more of the nucleic acid constructs of the invention comprising a RNAi and/or gRNA targeting an Ara h gene. The genetically modified peanut cell may also comprise a nucleic acid sequence encoding a Cas9 protein. A Cas9 polypeptide may be any disclosed as being suitable for use with the nucleic acid constructs of the invention. In some embodiments, a cell may only temporarily (transiently) comprise the gRNA construct and/or the nucleic acid construct encoding an endonuclease (e.g, Cas9), which in combination generate a deletion in an Ara h gene. In some embodiments, either or both the gRNA or Cas9-encoding sequence may be present on extra-chromosomal genetic material, such as a plasmid, viral DNA, viral RNA, or other episome.

A genetically engineered peanut plant is provided, comprising any cell disclosed above. In some embodiments, a genetically engineered peanut plant is regenerated from a genetically modified peanut cell of the present invention and comprises in its genome the modification of the one or more target Ara h gene(s) (e.g., deletion in one or more target Ara h genes). The present invention further provides a seed produced from the genetically engineered peanut plant, which comprises in its genome the modification of the one or more target Ara h gene(s).

Vectors

A genetic vector is provided comprising any nucleic acid construct disclosed above. Many types of suitable vectors may be used, such as viruses, plasmids, cosmids, fosmids, phagmids, artificial chromosomes, yeast artificial chromosomes, human artificial chromosomes, plant transformation vectors, and liposomes. A vector may be a strain of *Agrobacterium* carrying the nucleic acid construct. In some embodiments, a vector may be the Ti plasmid of *Agrobacterium*. A Ti plasmid may be include but is not limited to *A. tumefaciens* or *A. rhizogenes*. A non-oncogenic strain of the *Agrobacterium* may be used as the vector carrier so that normal non-oncogenic differentiation of the transformed tissues is possible. The *Agrobacterium* may harbor a binary Ti plasmid system. Such a binary system may comprise 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, Biotechnol., 1:262, 1983; Hoekema et al., 1983, *Nature* 303:179.) Such a binary system is effective because it does not require integration into Ti plasmid in *Agrobacterium*.

Other suitable plasmids include root-inducing (Ri) plasmids and plant virus vectors. For reviews of such techniques see, for example, Weissbach & Weissbach, 1988, *Methods for Plant Molecular Biology*, Academic Press, N.Y., Section VIII, pp. 421-463; and Grierson & Corey, 1988, *Plant Molecular Biology,* 2d Ed., Blackie, London, Ch. 7-9, and Florsch et al., *Science* 227:1229 (1985).

Other plant-specific suitable transformation vectors include pUC18, pCB13, pBI434 and versions of pBI426 can be used for carrying out, for example, biolistic transformation. Cauliflower mosaic virus (CaMV) may also be used as a vector for introducing heterologous nucleic acid into plant cells (U.S. Pat. No. 4,407,956). The vector may be a microprojectile comprising one or more nucleic acid constructs of the present invention. Versions of pBI434, a binary vector for transformation using *A. tumefaciens* (FIG. 6), may also be used.

In some embodiments, a cell comprising any said vector is also provided.

Methods

Methods for producing a genetically modified peanut plant with reduced allergen content in the seed are provided. In some embodiments, the method comprises: transfecting a recipient peanut plant cell with any nucleic acid construct of the invention; generating a peanut plant from the recipient cell which has been transformed with one or more nucleic acid constructs of the invention (RNAi and/or CRISPR); and identifying a fertile transgenic plant that produces seeds having reduced allergen content. In some embodiments, a plant is provided comprising one or more of the nucleic acid constructs of the invention.

Transfection may be accomplished using any suitable vector, or by other methods known in the art. Seeds having reduced allergen content may be identified by any suitable method known in the art. Such methods include immunoassays for detecting the presence of a given Ara h protein; mass spectrometry for detecting the presence of a given Ara h protein; electrospray ionization; single or multidirectional electrophoresis; chromatographic methods (such as reverse phase chromatography), microarray technology, and reverse transcription PCR to detect the expression of a target gene mRNA (e.g., Ara h mRNA). Based on such tests plants may be selected for further sexual and asexual propagation.

Methods involving the use of *Agrobacterium* for plant transformation include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*. In addition, gene transfer can be accomplished by in situ transformation by *Agrobacterium*, as described by Bechtold et al., 1993, C. R. Acad. Sci. Paris 316:1194. This approach is based on the vacuum infiltration of a suspension of *Agrobacterium* cells.

Alternatively, a nucleic acid construct described herein may be introduced into a plant cell by contacting the plant cell using mechanical or chemical means. For example, a nucleic acid construct may be mechanically transferred by direct microinjection into plant cells utilizing micropipettes. Moreover, nucleic acid constructs may be transferred into plant cells using polyethylene glycol which forms a precipitation complex with genetic material that is taken up by the cell.

A nucleic acid construct may also be introduced into plant cells by electroporation (Fromm et al., *Proc. Natl. Acad. Sci., U.S.A.* 82:5824 (1985), which is incorporated herein by reference). In this technique, plant protoplasts are electroplated in the presence of vectors or nucleic acids containing the relevant nucleic acid sequences. Electrical impulses of high field strength reversibly permeabilize plant membranes allowing the introduction of nucleic acids. Electroporated plant protoplasts may then reform the cell wall, divide and form a plant callus. Selection of the transformed plant cells with the transformed gene can be accomplished using methods known in the art for detecting modification or alterations in a genome, including but not limited to, Southern, Western and Northernhybridizations and sequencing.

Another method for introducing nucleic acids into a plant cell is high velocity biolistic penetration by small particles with the nucleic acid to be introduced contained either within the matrix of small beads or particles, or on the surface thereof (Klein et al., 1987, Nature 327:70). Although, typically only a single introduction of a new nucleic acid sequence is required, this method particularly provides for multiple introductions.

Cauliflower mosaic virus (CaMV) may also be used as a vector for introducing nucleic acid constructs into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid may be re-cloned and further modified by introduction of a desired nucleic acid sequence. The modified viral portion of the recombinant plasmid is then excised from the parent bacterial plasmid, and used to inoculate the plant cells or plants. Plasmids pCB13, pBI426, and pBI434 may also be used as vectors for introducing heterologous nucleic acids into plants. Peanut allergen genes, or portions/fragments thereof, may be cloned into a vector in sense or antisense orientation for single transformations or multiple transformations (co-bombardments). (Chen et al., 1998 *Nature Biotechnology* 16: 1060-1064; Pawloski, Somers et al., 1996 *Mol Biotechnol* 6:17-30). Using *Agrobacterium* Ti vector-mediated plant transformation methodology, all nucleic acid constructs described herein may be inserted into peanut genomes after the polynucleotide molecules have been placed between the T-DNA border repeats of suitable disarmed Ti-plasmid vectors (Deblaere, R. et al., 1987, *Methods in Enzymology* 153 277-292). This transformation can be carried out in a conventional manner, for example as described in EP 0116718, PCT publication WO 84/02913 and EPA 87400544.0. The nucleic acid construct of the invention may also be in non-specific plasmid vectors which can be used for direct gene transfer (e.g. de la Pena, A., 1987, *Nature,* 325:274-276).

Genetically modified germplasm may be utilized in traditional breeding programs for incorporation of this novel trait into desirable peanut genotypes. Methods for producing genetically modified peanut hybrids are known in the art. See, e.g., Moore, 1989, K. M. et al., J. *Heredity* 80(3): 252; Norden, A. J., *Peanuts, Culture and Uses*. Am. Peanut Res. and Educ. Soc., Stillwater, Okla. (C. T. Wilson ed. 1973); Norden, A. J. in *Hybridization of Crop Plants* (H. H. Hadley ed. 1980); Norden, A. J., et al., Breeding of the cultivated peanut in *Peanut Science and Technology*, (H. E. Pattee ed. 1992); and Norden, A. J. et al. *Florida Agr. Res.* 3:16-18 (1984).

Initially, a homozygous line containing the nucleic acid construct may be obtained, following conventional peanut breeding by self-pollination for a number of generations. This homozygous line may be introgressed into diverse peanut backgrounds in the same or in different market classes by breeding methods known in the art, such as successive selection and inbreeding.

The genetically modified germplasm of the present invention may be introgressed into diverse peanut backgrounds in the same or in different market classes, for example, the runner-type market class as well as the Virginia, Peruvian, Valencia and Spanish market classes. Peanuts in the runner-type market class are the most commonly used varieties and are found in diverse products such as peanut butter, salted nuts and confectionery products. On the other hand, peanut varieties in the Virginia market class are largely used as salted nuts and in-shell market. The Valencia type is largely used in peanut butter while the Spanish type is used in certain niche markets where small round peanuts are needed such as confectionery products and red skin peanuts. Finally, the Peruvian runner market class is grown in certain regions of Mexico.

The genetically modified germplasm of the present invention may be introgressed into different peanut backgrounds by conventional methods known in the art. In some examples, crosses may be made according to methods described by Norden, A. J., *Peanuts, Culture and Uses,* supra. Am. Peanut Res. and Educ. Soc., Stillwater, Okla. (C. T. Wilson ed. 1973); Norden, A. J. in *Hybridization of Crop Plants* (H. H. Hadley ed. 1980); Norden, A. J., et al., Breeding of the cultivated peanut in *Peanut Science and Technology*, (H. E. Pattee ed. 1992); and Norden, A. J. et al. *Florida Agr. Res.* 3:16-18 (1984). Introgression may be performed via the traditional plant breeding cross pollination techniques.

Reduced or allergen-free peanut plants may be propagated by planting homozygous seeds and harvesting the crop.

A plant, plant part or seed that is the product of any of the above processes is provided, having reduced or eliminated expression of at least one peanut allergen protein. In some embodiments, a food product may be provided from the seeds of any genetically modified plant described herein. Peanut seeds described herein may be processed and manufactured into food products using methods well known to a skilled artisan. The same standard food processing methods, processing equipment and sanitation practices, may be used as those used in the production of their non-genetically modified counterparts. Such food products include but are not limited to: salted peanuts, roast peanuts, boiled peanuts, candied ("honey roasted") peanuts, peanut meal, peanut butter, peanut milk, butter from peanut milk, peanut flour, peanuts coated with chocolate or other confections, peanut brittle, peanut oil, peanut margarine, peanut protein hydrolysate, nougat, sauces, pesto, mole sauce, marzipan, cookies, pies, chikki, peanut hearts, food bars, granola, brownies, animal feed, and groundnut cake. An industrial product is also provided that is manufactured from any of the genetically modified plants described herein. Such industrial products include, but are not limited to, paint, varnish, lubricating oil, leather dressings, furniture polish, insecticides, nitroglycerin, soap, textile fibers, plastic, wallboard, abrasives, fuel, cellulose, and mucilage.

In some embodiments, the invention provides a method of reducing the production of at least one *Arachis hypogaea* allergen (Ara h) polypeptide in a peanut plant, plant part and/or cell, comprising: introducing into the peanut plant, plant part and/or cell at least one nucleic acid construct of the invention encoding at least one RNAi molecule, at least one expression cassette comprising the nucleic acid construct, and/or at least one vector comprising the expression cassette to produce a genetically engineered peanut plant, plant part and/or cell in which the Ara h gene encoding the at least one Ara h polypeptide is silenced, thereby reducing production of the at least one Ara h polypeptide in the peanut plant, plant part and/or cell.

In some embodiments, the invention provides a method of reducing the allergen content in a peanut seed, comprising: introducing into a peanut plant cell at least one nucleic acid construct of the invention encoding at least one RNAi molecule, at least one expression cassette comprising the nucleic acid construct, and/or at least one vector comprising the expression cassette to produce a genetically engineered peanut plant cell; regenerating a peanut plant from the genetically engineered peanut plant cell; and producing seed from the regenerated peanut plant, wherein the production of at least one *Arachis hypogaea* allergen (Ara h) polypeptide in the peanut seed is reduced, thereby reducing allergen content in the peanut seed.

In some embodiments, the invention provides a method of reducing the production of at least one *Arachis hypogaea* allergen (Ara h) polypeptide in a peanut seed is provided, comprising: introducing into a peanut plant cell at least one nucleic acid construct of the invention encoding at least one RNAi molecule, at least one expression cassette comprising the nucleic acid construct, and/or at least one vector comprising the expression cassette to produce a genetically engineered peanut plant cell; regenerating a peanut plant from the genetically engineered peanut plant cell; and producing seed from the regenerated peanut plant, wherein the production of the at least one Ara h polypeptide in the peanut seed is reduced.

In some embodiments, a method of making a peanut plant that produces seed with reduced allergen content is provided, comprising: introducing into a peanut plant cell at least one nucleic acid construct of the invention encoding at least one RNAi molecule, at least one expression cassette comprising the nucleic acid construct, and/or at least one vector comprising the expression cassette to produce a genetically engineered peanut plant cell; regenerating a peanut plant from the genetically engineered peanut plant cell; and producing seed from the regenerated peanut plant, wherein the production of at least one *Arachis hypogaea* allergen (Ara h) polypeptide in the peanut seed is reduced, thereby making the peanut plant that produces seed with reducing allergen content.

In some embodiments, a method of producing a peanut seed with reduced allergen content is provided, comprising introducing into a peanut plant cell at least one nucleic acid construct of the invention encoding at least one RNAi molecule, at least one expression cassette comprising the nucleic acid construct, and/or at least one vector comprising the expression cassette to produce a genetically engineered peanut plant cell; regenerating a peanut plant from the genetically engineered peanut plant cell; and producing seed from the regenerated peanut plant, wherein the production of at least one *Arachis hypogaea* allergen (Ara h) polypeptide in the peanut seed is reduced, thereby producing a peanut seed with reducing allergen content.

In some embodiments, the genome of the peanut plant, peanut seed, and/or peanut plant cell comprises the at least one nucleic acid construct of the invention encoding at least one RNAi molecule, the at least one expression cassette or the at least one vector. In some embodiments, the at least one Ara h polypeptide includes, but is not limited to, Ara h1, Ara h2, Ara h3/Ara h3.02, Ara h5, Ara h6, Ara h7, Ara h8, Ara h9, Ara h10, Ara h11, Ara h12, Ara h13, Ara h14, Ara h15, Ara h16, Ara h17, and any combination thereof.

In some embodiments, a method of reducing the production of at least one *Arachis hypogaea* allergen (Ara h) polypeptide in a peanut plant, plant part and/or cell is provided, comprising introducing into the peanut plant, plant part and/or cell at least one nucleic acid construct encoding at least one CRISPR guide nucleic acid, at least one expression cassette of comprising the nucleic acid construct, and/or at least one vector comprising the expression vector, wherein the at least one nucleic acid construct comprises at least two spacers, each spacer having at least about 75% to 100% complementarity to a different target region of an Ara h gene encoding an Ara h polypeptide to produce a genetically engineered peanut plant, plant part and/or cell comprising a deletion in the at least one Ara h gene, thereby reducing production in the peanut plant, plant part and/or cell of the Ara h polypeptide encoded by the Ara h gene.

In some embodiments, the present invention provides a method of reducing the allergen content in a peanut seed, comprising introducing into a peanut plant cell at least one nucleic acid construct encoding at least one CRISPR guide nucleic acid, at least one expression cassette of comprising the nucleic acid construct, and/or at least one vector comprising the expression vector, wherein the at least one nucleic acid construct comprises at least two spacers, each spacer having at least about 75% to 100% complementarity to a different target region of an Ara h gene encoding an *Arachis hypogaea* allergen (Ara h) polypeptide to produce a genetically engineered peanut plant cell comprising a deletion in the Ara h gene, thereby reducing production in the peanut plant cell of the Ara h polypeptide encoded by the Ara h gene; regenerating a peanut plant from the genetically engineered peanut plant cell; and producing seed from the regenerated peanut plant, wherein the seed comprises in its genome the deletion in the Ara h gene, thereby reducing the production of at least one Ara h polypeptide in the peanut seed and reducing allergen content in the peanut seed.

In some embodiments, a method of reducing the production of at least one *Arachis hypogaea* allergen (Ara h) polypeptide in a peanut seed is provided, comprising introducing into a peanut plant cell at least one nucleic acid construct encoding at least one CRISPR guide nucleic acid, at least one expression cassette of comprising the nucleic acid construct, and/or at least one vector comprising the expression vector, wherein the nucleic acid construct comprises at least two spacers, each spacer having at least about 70% to 100% complementarity to a different target region of an Ara h gene encoding the at least one *Arachis hypogaea* allergen (Ara h) polypeptide to produce a genetically engineered peanut plant cell comprising a deletion in the Ara h gene; regenerating a peanut plant from the genetically engineered peanut plant cell; and producing seed from the regenerated peanut plant, wherein the production of the at least one Ara h polypeptide in the peanut seed is reduced.

In some embodiments, a method of a making a peanut plant that produces seed with reduced allergen content is provided, comprising: introducing into a peanut plant cell at least one nucleic acid construct encoding at least one CRISPR guide nucleic acid, at least one expression cassette of comprising the nucleic acid construct, and/or at least one vector comprising the expression vector, wherein the nucleic acid construct comprises at least two spacers, each spacer having at least about 70% to 100% complementarity to a different target region of an Ara h gene encoding an *Arachis hypogaea* allergen (Ara h) polypeptide to produce a genetically engineered peanut plant cell comprising a deletion in the Ara h gene; regenerating a peanut plant from the genetically engineered peanut plant cell; and producing seed from the regenerated peanut plant, wherein the production of the Ara h polypeptide in the peanut seed is reduced, thereby making the peanut plant that produces seed with reducing allergen content.

In some embodiments, the present invention provides a method of producing a peanut seed with reduced allergen content, comprising introducing into a peanut plant cell at least one nucleic acid construct encoding at least one CRISPR guide nucleic acid, at least one expression cassette of comprising the nucleic acid construct, and/or at least one vector comprising the expression vector, wherein the nucleic acid construct comprises at least two spacers, each spacer having at least about 75% to 100% complementarity to a different target region of an Ara h gene encoding an *Arachis hypogaea* allergen (Ara h) polypeptide to produce a genetically engineered peanut plant cell comprising a deletion in the Ara h gene; regenerating a peanut plant from the genetically engineered peanut plant cell; and producing seed from the regenerated peanut plant, wherein the production of the Ara h polypeptide in the peanut seed is reduced, thereby producing peanut seed with reducing allergen content.

To generate a deletion in a gene, generally two regions of the gene are targeted. Thus, a CRISPR guide nucleic acid encoded on a nucleic acid construct of the invention may comprises at least two spacers having substantial complementarity to two different regions of a target gene Ara h gene to generate a deletion. The two target sites may be encoded on the same nucleic acid construct (e.g., the same guide construct) or they may be encoded on different constructs, both of which are introduced. In some embodiments, a single CRISPR guide molecule comprising two or more spacers targeting one or more Ara h genes may be utilized to generate a genetically modified peanut plant, plant part, plant cell, or seed of the invention. In some embodiments, two or more CRISPR guide molecules comprising one or more spacers targeting one or more Ara h genes may be utilized to generate a genetically modified peanut plant, plant part, plant cell, or seed of the invention.

The two target sites of the target gene may be about 10 to about 50 nucleotides or more apart. In some embodiments, for generating a deletion, the distance between two target sites may be about 10 to about 5000, about 10 to about 4500, about 10 to about 4000, about 10 to about 3500, about 10 to about 3000, about 10 to about 2500, about 10 to about 2000, about 10 to about 1500, about 10 to about 1000, about 10 to about 900, about 10 to about 800, about 10 to about 700, about 10 to about 600, about 10 to about 500, about 10 to about 400, about 10 to about 300, about 10 to about 200, about 10 to about 100, about 10 to about 90, about 10 to about 80, about 10 to about 70, about 10 to about 50, about 10 to about 45, about 10 to about 40, about 10 to about 39, about 10 to about 38, about 10 to about 37, about 10 to about 36, about 10 to about 35, about 10 to about 34, about 10 to about 33, about 10 to about 32, about 10 to about 31, about 10 to about 30, about 10 to about 29, about 10 to about 28, about 10 to about 27, about 10 to about 26, about 10 to about 25, about 10 to about 24, about 10 to about 23, about 10 to about 22, about 10 to about 21, about 10 to about 20 nucleotides apart (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 550, 600, 550, 700, 750, 800, 850, 900, 950, 1000, 1500, 2000, 2500, 3000, 3500, 4000, 4500, 5000 nucleotides apart and any value or range therein).

Exemplary nucleotide sequences useful for generating deletions are provided in Table 3, Tables 14-34 and FIGS. 13-26 and 33. These exemplary sequences were generated using the CHOCHOP Online Tool and should generate deletions without off-target effects. As can be seen, in these exemplary sequences for CRISPR guides, the distance between two Cas9 nickases may range from about 10 to about 5000 base pairs as set forth above. There are many online tools available to assist in designing CRIPSR guide molecules useful with this invention.

In some embodiments, a deletion that is generated using the methods of the invention may be about 1 nucleotide to about the full length of the gene in length (e.g., about 1 to about 2000, about 5 to about 2000, about 10 to about 2000, about 20 to about 2000, about 30 to about 2000, about 40 to about 2000, about 50 to about 2000, about 1 to about 1500, about 5 to about 1500, about 10 to about 1500, about 20 to about 1500, about 30 to about 1500, about 40 to about 1500, about 50 to about 1500, about 1 to about 1000, about 5 to about 1000, about 10 to about 1000, about 20 to about 1000, about 30 to about 1000, about 40 to about 1000, about 50 to about 1000, about 1 to about 500, about 5 to about 500, about 10 to about 500, about 20 to about 500, about 30 to about 500, about 40 to about 500, about 50 to about 500, about 1 to about 250, about 5 to about 250, about 10 to about 250, about 20 to about 250, about 30 to about 250, about 40 to about 250, about 50 to about 250, about 1 to about 100, about 5 to about 100, about 10 to about 100, about 20 to about 100, about 30 to about 100, about 40 to about 100, about 50 to about 100, about 1 to about 50, about 10 to about 50, about 20 to about 50, about 25 to about 50, about 20 to about 50, about 30 to about 50 nucleotides in length; e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 60, 650, 700, 750, 800, 850, 900, 950, 1000, 1100, 1200, 1300, 1400, 1500, 1600, 1700, 1800, 1900, 2000 nucleotides or more, and any value or range therein).

In some embodiments, a Cas9 endonuclease or a polynucleotide encoding a Cas9 endonuclease may be introduced into the peanut plant, peanut plant part, or peanut plant cell. The Cas9 endonuclease may be encoded on the same nucleic acid construct as the encoded CRISPR guide molecule, or it may be encoded on a separate nucleic acid construct. In some embodiments, the Cas9 nuclease may be introduced on the same expression cassette and/or vector with the nucleic acid construct encoding the CRISPR guide molecule. In some embodiments, a Cas9 polypeptide may be introduced into the peanut plant, peanut plant part, or peanut plant cell.

Any method of delivering/introducing a nucleic acid construct of the invention (RNAi or CRISPR) and/or Cas9 endonuclease to a plant, plant part, or plant cell may be used. These methods are well known as described herein.

Also provided herein are peanut plants, peanut plant cells and peanut seeds produced by the methods of the invention (e.g., RNAi and/or CRISPR).

Sequences

---

Nucleotide sequence of the homology region between Ara h2, Ara h6 and Ara h7

SEQ ID NO 1;

ACAGAAGATGCCAGAGCCAGCTCGAGAGGGCGAACCTGAGGCCCTGCGAGCAACATCTCATGCAGAAGATCCAAC

GTGACGAGGATTCATATGAACGGGACCCGTACAGCCCTAGTCAGGATCCGTACAGCCCTAGTCCATATGATCGGA

GAGGCGCTGGATCCTCTCAGCACCAAGAGAGGTGTTGCAATGAGCTGAACGAGTTTGAGAACAACCAAAGGTGCA

TGTGCGAGGCATTGCAACAGATCATGGAGAACCAGAGCGATAGGTTGCAGGGGAGGCAACAGGAGCAACAGTTCA

AGAGGGAGCTCAGGAACTTGCCTCAACAGTGCGGCCTTAGGGCACCACAGCGTTGCGACTTGGACGTCGAAAGTG

-continued

GCGGCAGAGACAGATACTAAACACCTATCTCAAAAAAAGAAAGAAAAGAAAGAAAATAGCTTATATATAAGCT

ATTATCTATGGTTATGTTTAGTTTTGGTAATAATAAAGAT

Bold: Homology between Ara h 2 Ara h 6; Underlined: Homology between Ara h 2
and Ara h 7
Bold italic: Start and stop sequences (atg and aataaa)
Nucleotide sequence (cDNA) of peanut allergen protein Ara h 1. IgE epitopes
are in bold and underlined. The boxed areas indicate regions that may be used in
the Ara hRNA constructs. Start codon (ATG) and stop codon (TGA) in bold italic.

SEQ ID NO: 2

AATAATCATA TATATTCATC AATCATCTAT ATAAGTAGTA GCAGGAGCAA TGAGAGGGAG    60

GGTTTCTCCA CTGATGCTST TGCTAGGGAT CCTTGTCCTG GCTTCAGTTT CTGCAACGCA   120

TGCCAAGTCA TCACCTTACC AGAAGAAAAC AGAGAACCCC TGCGCCCAGA GGTGCCTCCA   180

GAGTTGTCAA CAGGAACCGG ATGACTTGAA GCAAAAGGCA TGCGAGTCTC GCTGCACCAA   240

GCTCGAGTAT GATCCTCGTT GTGTCTATGA TCCTCGAGGA CACACTGGCA CCACCAACCA   300

ACGTTCCCCT CCA**GGGGAGC GGACACGTGG CCGCCAACCC GGAGACTACG ATGATGACCG   360

CCGTCAACCC CGAAGAGAGG AAGGAGGCCG ATGGGACCA GCTGGACCGA GGGAGCGTGA   420

AAGAGAAGAA GACTGGAGAC AACCA**AGAGA AGATTGGAGG CGACCAAGTC ATCAGCAGCC   480

ACGGAAAATA AGGCCCGAAG AAGA**GAAGG AGAACAAGAG TGGGGAACAC CAGGTAGCCA   540

TGTGAGGGAA GAAACATCTC GGAACAACCC TTTCTACTTC CCGTCAAGGC GGTTTAGCAC   600

CCGCTACGGG AACCAAAACG GTAGGATCCG GGTCCTGCAG AGGTTTGACC AAAGGTCAAG   660

GCAGTTTCAG AATCTCCAGA ATCACCGTAT TGTGCAGATC GAGGCCAAAC CTAACACTCT   720

TGTTCTTCCC AAGCACGCTG ATGCTGATAA CATCCTTGTT ATCCAGCAAG GGCAAGCCAC   780

CGTGACCGTA GCAAATGGCA ATAACAGAAA GAGCTTTAAT CTTGACGAGG GCCATGCACT   840

CAGAATCCCA TCCGGTTTCA TTTCCTACAT CTTGAACCGC CATGACAACC AGAACCTCAG   900

AGTAGCTAAA ATCTCCATGC CCGTTAACAC ACCCGGCCAG TTTGAGGATT TCTTCCCGGC   960

GAGCAGCCGA GACCAATCAT CCTACTTGCA GGGCTTCAGC AGGAATACGT TGGAGGCCGC  1020

CTTCAATGCG GAATTCAATG AGATACGGAG GGTGCTGTTA AAGAGAATG CAGGAGGT**GA  1080

GCAAGAGGAG AGAGGGCAGA GGCGATGGA TACTCGGAGT AGTGAGAACA ATGAAGGAGT  1140

GATAGTCAAA GTGTCAAAGG AGCACGTTGA AGAACTTACT AAGCACGCTA AATCCGTCTC  1200

AAAGAAAGGC TCCGAAGAAG AGGGAGATAT CACCAACCCA ATCAACTTGA GAGAAGGCGA  1260

GCCCGATCTT TCTAACAACT TTGGGAAGTT ATTTGAGGTG AAGCCAGACA AGAAGAACCC  1320

CCAGCTTCAG GACCTGGACA TGATGCTCAC CTGTGTAGAG ATCAAAGAAG GAGCTTTGAT  1380

GCTCCCACAC TTCAACTCAA AGGCCATGGT TATCGTCGTC GTCAACAAAG GAACTGGAAA  1440

CCTTGAACTC GTGGCTGTAA GAAAAGAGCA ACCACAGAGG GGACGGCGGG AAGAAGAGGA  1500

GGACGAAGAC GAAGAAGAGG AGGGAAGTAA CAGAGAGGTG CGTAGGTACA CAGCGAGGTT  1560

GAAGGAAGGC GATGTGTTCA TCATGCCAGC AGCTCATCCA GTAGCCATCA ACGCTTCCTC  1620

CGAACTCCAT CTGCTTGGCT TCGGTATCAA CGCTGAAAAC AACCACAGAA TCTTCCTTGC  1680

AGGTGATAAG GACAATGTGA TAGACCAGAT AGAGAAGCAA GCGAGGATT TAGCATTCCC  1740

TGGGTCGGGT GAACAAGTTG AGAAGCTCAT CAAAAACCAG AAGGAATCTC ACTTTGTGAG  1800

TGCTCGTCCT CAATCTCAAT CTCAATCTCC GTCGTCTCCT GAGAAAGAGT CTCCTGAGAA  1860

AGAGGATCAA GAGGAGGAAA ACCAAGGAGG GAAGGGTCCA CTCCTTTCAA TTTTGAAGGC  1920

-continued

```
TTTTAACTGA GAATGGAGGC AACTTGTTAT GTATCGATAA TAAGATCACG CTTTTGTACT 1980

CTACTATCCA AAAACTTATC AATAAATAAA AACGTTTGTG CGTTGTTTCT CC       2032
```

TABLE 4

Nucleic acid sequences in the Epitope regions of SEQ ID NO: 2

| Epitope NO | Position | Nucleotide sequence (5'-3') | SEQ ID NO |
|---|---|---|---|
| 1 | 122-151 | GCCAAGTCATCACCT TACCAGAAGAAAACA | 16 |
| 2 | 191-217 | CAGGAACCGGATGAC TTGAAGCAAAAG | 17 |
| 3 | 242-280 | CTCGAGTATGATCCT CGTTGTGTCTATGAT CCTCGAGGA | 18 |
| 4 | 313-397 | GGGGAGCGGACACGT GGCCGCCAACCCGGA GACTACGATGATGAC CGCCGTCAACCCCGA AGAGAGGAAGGAGGC CGATGGGA | 19 |
| 5 | 415-445 | GGGAGCGTGAAAGAG AAGAAGACTGGAGAC AACCA | 20 |
| 6 | 448-507 | GAAGATTGGAGGCGA CCAAGTCATCAGCAG CCACGGAAAATAAGG CCCGAAGGAAGA | 21 |
| 7 | 928-958 | ACACCCGGCCAGTTT GAGGATTTCTTCCCG | 22 |
| 8 | 979-1019 | TCCTACTTGCAGGGC TTCAGCAGGAATACG | 23 |
| 9 | 1022-1051 | TTCAATGCGGAATTC AATGAGATACGGAGG | 24 |

TABLE 4 -continued

Nucleic acid sequences in the Epitope regions of SEQ ID NO: 2

| Epitope NO | Position | Nucleotide sequence (5'-3') | SEQ ID NO |
|---|---|---|---|
| 10 | 1078-1117 | GAGCAAGAGGAGAGA GGGCAGAGGCGATGG AGTACTCGG | 25 |
| 11 | 1199-1230 | CAAAGAAAGGCTCCG AAGAAGAGGGAGATA T | 26 |
| 12 | 1282-1310 | TGGGAAGTTATTTGA GGTGAAGCCAGACA | 27 |
| 13 | 1323-1352 | AGCTTCAGGACCTGG ACATGATGCTCACCT | 28 |
| 14 | 1358-1410 | AGATCAAAGAAGGAG CTTTGATGCTCCCAC ACTTCAACTCAAAGG CCATGGT | 29 |
| 15 | 1441-1470 | CCTTGAACTCGTGGC TGTAAGAAAAGAGCA | 30 |
| 16 | 1645-1682 | TATCAACGCTGAAAA CAACCACAGAATCTT CCTTGCAG | 31 |
| 17 | 1694-1724 | ATGTGATAGACCAGA TAGAGAAGCAAGCGA | 32 |
| 18 | 1731-1781 | TAGCATTCCCTGGGT CGGGTGAACAAGTTG AGAAGCTCATCAAAA ACCAGA | 33 |

Nucleotide sequence (cDNA) of peanut allergen protein Ara h 2. IgE epitopes are in bold and underlined. The boxed area indicates a region that may be used in the Ara hRNA constructs. Start codon (ATG) and stop codon (CAG) in bold italic.

SEQ ID NO: 3

```
GACACAGACC AACTGGTAAT GGTAGCGACC GGCGCTCAGC TGGAATTCGC GGCCGCCAAT   60

GGCCAAGCTC ACCATACTAG TAGCCCTCGC CCTTTTCCTC CTCGCTGCCC ACGCATCTGC   120

GAGGCAGCAG TGGGAACTCC AAGGAGACAG AAGATGCCAG AGCCAGCTCG AGAGGGCGAA   180

CCTGAGGCCC TGCGAGCAAC ATCTCATGCA GAAGATCCAA CGTGACGAGG ATTCATATGA   240

ACGGGACCCG TACAGCCCTA GTCAGGATCC GTACAGCCCT AGTCCATATG ATCGGAGAGG   300

CGCTGGATCC TCTCAGCACC AAGAGAGGTG TTGCAATGAG CTGAACGAGT TTGAGAACAA   360

CCAAAGGTGC ATGTGCGAGG CATTGCAACA GATCATGGAG AACCAGAGCG ATAGGTTGCA   420

GGGGAGGCAA CAGGAGCAAC AGTTCAAGAG GGAGCTCAGG AACTTGCCTC AACAGTGCGG   480

CCTTAGGGCA CCACAGCGTT GCGACTTGGA CGTCGAAAGT GGCGGCAGGC GGCCGCGAAT   540

TCCGCCGATA CTGACGGGCT CCAGGAGTCG TCGCCACCAA TCCCCATATG GAAACCGTCG   600

ATATTCAGCC ATGTGCCTTC TTCCGCGTGC AGCAGATGGC GATGGCTGGT TTCCATCAGT   660

TGCTGTTGAC TGTAGCGGCT GA
```

TABLE 5

Nucleic acid sequences in the Epitope
regions of SEQ ID NO: 3

| Epitope NO | Position | Nucleotide sequence (5'-3') | SEQ ID NO |
|---|---|---|---|
| 1 | 113-178 | GCATCTGCGAGGCAGCAGTGG GAACTCCAAGGAGACAGAAGA TGCCAG AGCCAGCTCG AGAGGGCG | 34 |
| 2 | 184-298 | AGGCCCTGCGAGCAACATCTC ATGCAGAAGATCCAACGTGAC GAGGATTCATATGAACGGGAC CCGTACAGCCCTAGTCAGGAT CCGTACAGCCCTAGTCCATAT G ATCGGAGA | 35 |

TABLE 5-continued

Nucleic acid sequences in the Epitope
regions of SEQ ID NO: 3

| Epitope NO | Position | Nucleotide sequence (5'-3') | SEQ ID NO |
|---|---|---|---|
| 3 | 301-328 | GCTGGATCCTCTCAGCACCAA GAGAGG | 36 |
| 4 | 394-412 | ATGGAGAACCAGAGCGAT | 37 |
| 5 | 424-442 | AGGCAACAGGAGCAACAG | 38 |
| 6 | 478-502 | GGCCTTAGGGCACCACAGCGT TGC | 39 |

Nucleotide sequence (cDNA) of peanut allergen protein Ara h 3/3.02. IgE
epitopes are in bold and underlined. The boxed areas indicate regions that may be used
in the Ara hRNA constructs. Start codon (ATG) and stop codon (TAA) in bold italic.

SEQ ID NO: 4

```
   1 ATGGCTAAGC TTCTTGAGCT TTCTTTTTGC TTTTGCTTTC TAGTTCTGGG AGCTCGCAGC

61 ATCTCCTTCA GGCAGCAGCC GGAGGAGAAT GCGTGCCAGT TCCAGCGCCT CAATGCGCAG

121 AGACCTGACA ACCGCATTGA ATCGGAGGGC GGTTACATTG AGACTTGGAA CCCCAACAAC

181 CAGGAGTTCG AATGCGCCGG CGTCGCCCTC CGTCGCCCTC TCTCGCTTAG CAACGCCCTT

241 CGTAGGCCTT TCTACTCCAA TGCTCCCCAG GAGATCTTCA TCCAGCAAGG AAGGGGATAC

301 TTTGGGTTGA TATTCCCTGG TTGTCCTAGC ACATATGAAG AGCCTGCACA CAAGGACGC

361 CGATATCAGT CCCAAAGACC ACCAAGACGT TTGCAAGAAG AAGACCAAAG CCAACAGCAA

421 CAAGATAGTC ACCAGAAGGT GCACCGTTTC AATGAGGGTG ATCTCATTGC AGTTCCCACC

481 GGTGTTGCTT CTGGCTGTA CAACGACCAC GACACTGATG TTGTTGCTGT TTCTCTTACT

541 GACACCAACA ACAACGACAA CCAGCTTGAT CAGTTCCCCA GGAGATTCAA TTTGGCTGGG

601 AACCACGAGC AAGAGTTCTT AAGGTACCAG CAACAAAGCA GACAAAGCAG ACGAAGAAGC

661 TTACCATATA GCCCATACAG CCCGCATAGT CGGCCTAGAC GAGAAGAGC TGAATTTCGC

721 CCTCGAGGAC AGCACAGCCG CAGAGAACGA GCAGGACAAG AAGAAGAAGA CGAAGGTGGA

781 AACATCTTCA GCGGCTTCAC GCCGGAGTTC CTGGAACAAG CCTTCCAGGT TGACGACAGA

841 CAGATTGTGC AAAATCTGTG GGGCGAGAAC GAGAGTGAAG AAGAGGGAGC CATTGTGACG

901 GTGAGGGGAG GCCTCAGAAT CTTGAGCCCA GATGGAACGA GAGGTGCCGA CGAAGAAGAG

961 GAATACGATG AAGATCAATA TGAATACCAT GAACAGGATG GAAGGCGTGG CAGGGGAAGC

1021 AGAGGCGGGG GGAATGGTAT TGAAGAGACG ATCTGCACCG CATGTGTTAA AAAGAACATT

1081 GGTGGAAACA GATCCCCTCA CATCTACGAT CCTCAGCGCT GGTTCACTCA AAACTGCCAC

1141 GATCTCAACC TTCTAATCCT TAGGTGGCTT GGACTTAGTC CTGAATATGG AAATCTCTAC

1201 AGGAATGCAT TGTTTGTCCC TCACTACAAC ACCAACGCAC ACAGCATCAT ATATGCATTG

1261 AGGGGACGGG CTCACGTGCA AGTGGTGGAC AGCAACGGCA ACAGAGTGTA CGACGAGGAG

1321 CTTCAAGAGG GTCACGTTCT TGTGGTGCCA CAGAACTTCG CCGTGGCTGG GAAGTCCCAG

1381 AGCGAGAACT TCGAATACGT GGCATTCAAG ACAGATTCAA GGCCCAGCAT AGCCAACTTT

1441 GCCGGTGAAA ACTCCTTCAT AGATAACCTG CCGGAGGAGG TGGTTGCAAA TTCATATGGC

1501 CTCCCAAGGG AGCAGGCAAG GCAGCTTAAG AACAACAACC CCTTCAAGTT CTTCGTTCCA

1561 CCTTTTCAGC AGTCTCCGAG GGCTGTGGCT TAAAAACGAC CAGTATCTTT TGCAAGCGTG

1621 TTATCCACTA ACATAACTTT TTGCCACAAA TGAATAATAT AATAATAAGA AGAATAATGT

1681 AGTTTTAATT TTTAGTATGA ATAAGAATAC AAAGGGGCAT TGATGCCTTT TTGTTTAAGA
```

-continued

```
1741 TCGGAATGTA ACATATGTGC AATGAGCAGA TATGGAGAAA ACCTTTTGCG GGAAAAACAT

1801 GAATAATAAA AGAAGTTATG GTCTCACGCA AAAAAAAAAA AAAAAAAAAA AAA
```

TABLE 6

Nucleic acid sequences in the Epitope
regions of SEQ ID NO: 4

| Epitope NO | Position | Nucleotide sequence (5'-3') | SEQ ID NO |
|---|---|---|---|
| 1 | 156-200 | CATTGAGACTTGGAACCCCAACA ACCAGGAGTTCGAATGCGCCGG | 40 |
| 2 | 781-825 | AACATCTTCAGCGGCTTCACGCC GGAGTTCCTGGAACAAGCCTTC | 41 |
| 3 | 897-935 | GACGGTGAGGGGAGGCCTCA GAATCTTGAGCCCAGATGG | 42 |
| 4 | 963-998 | ATACGATGAAGATCAATA TGAATACCATGAACAGGA | 43 |

Nucleotide sequence (cDNA) of peanut allergen protein Arah 5. IgE
epitopes are in bold and underlined. The boxed area indicates a
region that may be used in the Ara hFNA constructs.
Start codon (ATG) and stop codon (TAA) in bold italic.

SEQ ID NO: 5

```
AGAAAGAGAA GACAAGATGT CGTGGCAAAC CTACGTCGAT AACCACCTTC TCTGCGAAAT    60

TGAAGGCGAC CACCTCTCCT CCGCCGCAAT CCTCGGCCAA GACGGCGGTG TTTGGGCTCA   120

GAGCTCTCAT TTCCCTCAGT TCAAGCCTGA GGAAATTACT GCTATCATGA ACGACTTTGC   180

TGAGCCTGGA TCGCTCGCCC CTACCGGGTT GTACCTCGGT GGCACCAAAT ACATGGTTAT   240

CCAAGGTGAA CCCGGAGCTA TCATTCCAGG GAAGAAGGGT CCTGGTGGTG TTACCATTGA   300

GAAGACGAAT CAGGCGTTAA TCATCGGAAT CTACGATAAG CCAATGACTC CGGGGCAGTG   360

CAACATGATT GTTGAAAGGC TGGGTGATTA TCTCATTGAT ACGGGTCTTT AAGTCCTCTT   420

TGTTATTTCT TGTTATCTGC TTGCTTATTT CACTGGCTCC TATACGAGGC TTCGCATCGA   480

TGTGCCAAGA GAATGCTCGA TTGTAGTGTA ATAATATTAA TTGATGGGTA TTCAAAAGTC   540

ATGGGATCTG CGTCTAGGGA AGAAGTTATG GTGCTTGAGA AGTGAATGAT AACTATCATC   600

TCTGTTGTTG TGCTTTTTAG CGGGTATCTG TATACAATTT ACAAGTGGTT TTAATGCTGT   660

GGGCATAAAT GGGCATTAAA AAAAAAAAAA AAAAAAAAAA AAAAAAAAAA AAAAAAAAAA   720

AAAAAAAAAA AAAAAAAAA AAA
```

TABLE 7

Nucleic acid sequences in the Epitope
regions of SEQ ID NO: 5

| Epitope NO | Position | Nucleotide sequence (5'-3') | SEQ ID NO |
|---|---|---|---|
| 1 | 47-116 | CTTCTCTGCGAAATTGAAGG CGACCACCTCTCCTCCGCCG CAATCCTCGGCCAAGACGGC | 44 |

Nucleotide sequence (cDNA) of peanut allergen protein Ara h 6. IgE epitope
is in bold and underlined. The boxed area indicates a region that may be used in
the Ara hRNA constructs. Start codon (ATG) and stop codon (TAG) in bold italic.

SEQ ID NO: 6

```
  1 ATGGCCAAG TCCACCATCC TGGTAGCTCT CCTTGCCCTC GTCCTGGTGG CACACGCCTC

61 CGCAATGAGG CGCGAGAGGG GGAGACAGGG GGACTCATCA AGCTGCGAGA GGCAGGTAGA

121 CAGGGTTAAC CTCAAGCCCT GCGAGCAGCA CATAATGCAG AGGATCATGG GCGAGCAAGA

181 GCAGTACGAC TCCTACGATA TTAGGAGTAC TCGATCCTCC GACCAGCAAC AGAGGTGCTG

241 CGATGAGCTG AACGAGATGG AGAACACACA GAGATGCATG TGCGAGGCAT TGCAGCAGAT

301 AATGGAGAAC CAGTGCGATA GGTTGCAGGA CAGGCAAATG GTGCAGCAGT TCAAGAGAGA

361 GCTCATGAAC TTGCCCCAAC AGTGTAACTT TAGGGCACCA CAGCGTTGCG ATTTGGACGT

421 GAGTGGCGGC AGATGCTAG
```

TABLE 8

**Nucleic acid sequence in the
Epitope regions of SEQ ID NO: 6**

| Epitope NO | Position | Nucleotide sequence (5'-3') | SEQ ID NO |
|---|---|---|---|
| 1 | 1052-1111 | CTTGCCCTCGTCCTGGTGGCA CACGCCTCCGCAATGAGGCG CGAGAGGG GGAGACAGGG | 45 |

Nucleotide sequence (cDNA) of peanut allergen protein Ara h 7. IgE epitope
is in bold and underlined. The boxed area indicates a region that may be used in
the Ara hRNA constructs. Start codon (ATG-position 1) and stop codon (TAG-position
483) in bold italic.

SEQ ID NO: 7

```
  1 ATGATGGTCA AGCTCAGCAT CCTGGTAGCC CTCCTGGGCG CCCTTCTTGT CGTAGCCTCC

61 GCGACAAGAT GGGATCCCGA TCGAGGGTCC AGAGGGTCGA GATGGGACGC ACCGAGCAGA

121 GGGGATGACC AGTGCCAGAG GCAGTTGCAG AGGGCAAACC TGAGGCCCTG TGAGGAACAC

181 ATGAGGCGAA GGGTGGAGCA GGAGCAAGAG CAAGAGCAAG ACGAGTACCC GTACAGCCGA

241 CGGGGATCCA GAGGACGACA ACCCGGCGAA TCTGACGAAA ATCAAGAGCA GAGGTGCTGC

301 AACGAGCTCA ACCGGTTCCA GAATAACCAA AGGTGCATGT GCCAGGCACT TCAACAGATC

361 CTCCAGAACC AGAGCTTTTG GGTTCCAGCA GGACAGGAGC CAGTTGCATC AGATGGAGAG

421 GGAGCTCAGG AACTTGCCCC AGAACTGCGG GTTCAGGTCA CCAAGCCGTT GCGACCTTTG

481 TAGCCGCACG CCCTACTAAA CAGACGAGCA CTTTGCGTTT TAATTTGCTT ACCCCACAAG

541 AGAAATCCAA TGATGATGAT TGATTGCTTT TTTACAAGCT ATTTCTATGT CTATGGTGTT

601 GTGGTAACAA TAAAGATCAT CACCATTTTA TGTAATGATG ATCGTATTGT CCGTGGCGAA

661 GTTGTATGGG GCACTTTGAA ATGTGCTTTT ATGGCAAAAA AA
```

TABLE 9

**Nucleic acid sequence in the
Epitope regions of SEQ ID NO: 7**

| Epitope NO | Position | Nucleotide sequence (5'-3') | SEQ ID NO |
|---|---|---|---|
| 1 | 31-90 | CTCCTGGGCGCCCTTCTTGTCG TAGCCTCCGCGACAAGATGGG ATCCCGA TCGAGGGTCC | 46 |

Nucleotide sequence (cDNA) of peanut allergen protein Ara h 8. IgE epitope
is in bold and underlined. The boxed area indicates a region that may be used in
the Ara hFLNA constructs. Start codon (ATG) and stop codon (TAG) in bold italic.

SEQ ID NO: 8

```
  1 ATTCCTCTCT TCATCAACCA CACACACACT ACAAAACTAA TTTAACCTCA CTTCTTACCA

61 TCTACTTCTC ATTCCTTCCC TTAGCTTCTT AATTCACAAT CATGGCCGTC TTCACTTTCG

121 AGGATGAAAT CACCTCCACC CTACCCCCTG CTAAGCTTTA CAATGCTATG AAGGATGCCG

181 ACTCCCTCAC CCCTAAGATT ATTGATGACG TCAAGAGTGT TGAAATCGTC GAGGGAAACG

241 GTGGTCCTGG AACCATCAAG AAACTCACCA TTGTCGAGGA TGGAGAAACC AAGTTTATCT

301 TACACAAAGT GGAGGCAATA GATGAGGCTA ACTATGCATA CAACTACAGC GTGGTTGGAG

361 GAGTGGCGCT GCCTCCCACG GCGGAGAAGA TAACATTTGA GACAAAGCTG GTAGAAGGAC

421 CCAACGGAGG ATCCATCGGG AAGCTGAGTG TGAAGTTCCA CTCGAAAGGA GAAGCGAAGC

481 CAGAGGAGGA AGACATGAAG AAGGGTAAGG CCAAGGGTGA AGCTCTCTTC AAGGCTATTG

541 AGGGTTACGT CTTGGCCAAC CCTGCTCAAT ATTAGAACAC TTTGCTCCAT CTTGATATGC

601 ACTTCTTCTT TTGAGCATGT TTGTGTGTGC GTATGCTTCA AGTAATTGGT TTTTTTCTAT

661 GTAATAAGAA AAATAAGTGT TGCTTTTCTT TGTTTTTTTG AT
```

TABLE 10

|         | Nucleic acid sequence in the Epitope regions of SEQ ID NO: 8 | | |
| --- | --- | --- | --- |
| Epitope NO | Position | Nucleotide sequence (5'-3') | SEQ ID NO |
| 1 | 115-262 | AGTGTTGAAATCGTCGAG GGAAACGGTGGTCCTGGA ACCATCAAGAA | 47 |

Nucleotide sequence (cDNA) of peanut allergen protein Ara h 9. IgE epitope
is in bold and underlined. The boxed area indicates a region that may be used in
the Ara hRNA constructs. Start codon (ATG) and stop codon (TGA) in bold italic.

SEQ ID NO: 9

```
  1 GACCAAATTC AAGCTTTCAA CACTCCAAAA CACACTTAGC TTTTATTTCA CATACATCAC

61 CACTTCCTCT TCTTCTTCTT GTTCATATTA TAACTAATGG CAGGCCTCAA GTTTGCATTT

121 GTGATGCTTG TGTGCATGGC CATGGTGGGA GCACCAATGG TGAATGCCCT ATCATGTGGC

181 CAAGTGAACA GTGCCCTAGC ACCATGCATC ACTTTCCTCA CAAAGGGTGG AGCTCCTTCT

241 CCGCCTTGTT GTAGCGGAGT TAGAGGCCTT CTCGGTGCTG CAAAAACCAC CGCGGACCGC

301 CAGGCCGCCT GTAACTGCCT CAAAGCCGCT GCCGGTTCCG TTCATGGCCT CAACCAAGGC

361 AACGCCGCCG CCCTCCCTGG AAGATGCGGT GTCAGCATTC CTTACAAGAT CAGCACCTCC

421 ACCAACTGTG CTACCATTAA GTTCTGAGGA GAGGAAGATG AAGAAGGTGG CTCTAGCCAG

481 CACTGGACAC AACAAGTAGT TATGTGAAAG CAGCTTATAT TAATTATTAA TTAATGAGAA

541 TAAACATGAG GGTGATGATG AGGGCTATAT ATATACTTAT ATATATATAT ATGCCCCTCT

601 CCTCTTGTAG TCTTTGTATG AGGTGGAAAT GGATTCTCTT ATTTCTTTTT TTTTTTGTTA

661 TGCATATGGA GTTGTTACTT GTTTCAACTT CCAACTACCT ATAGCAATCA ATGAAGCTGC

721 TTTTATTTGG TTAAAAAAAA AAAAAAAAAA AAAAAAA
```

TABLE 11

| | | Nucleic acid sequence in the Epitope regions of SEQ ID NO: 9 | | |
|---|---|---|---|
| Epitope NO | Position | Nucleotide sequence (5'-3') | SEQ ID NO |
| 1 | 351-441 | AACCAAGGCAACGCCGCCGCCCT CCCTGGAAGATGCGGTGTCAGC ATTCCTTACAAGATCAGCACCT CCACCAACTGTGCTACCATTAG | 48 |

Nucleotide sequence (cDNA) of peanut allergen protein Ara h 10. IgE epitope is in bold and underlined. The boxed area indicates a region that may be used in the Ara hRNA constructs. Start codon (ATG) and stop codon (TGA) in bold italic.

SEQ ID NO: 10

```
  1 GACGTCACAT GCATACACAA ACCAAATTAA ATATCTTTCC TTCTCTTTAC CTCTTCTCCC

61 TCAAACCTGC TTCATTCAGA GTAAAACAAA CATAAGGAAG AAAAGGGAGC TTCCTGCAAC

121 CATCAGCCAT GACTGACCGT ACCCAACCAC ACACTGTCCA AGTCCACACC ACAGCTGGCC

181 GTTTCGGCGA CACCGCTGCT GGAACTAACC GCTATCCCGA CAGAGGCCCG TCAACATCTA

241 AGGTTATCGC CGTCATCACT GGACTCCCTA TCGGCGGCAC GTTGCTATTG TTCGCGGGGC

301 TTGCCCTTGC CGGAACCCTG CTTGGGCTGG CGGTGACCAC CCCGCTTTTC ATCCTCTTCA

361 GCCCTGTCAT AGTTCCGGCC ATCATTGTCG TTGGGCTCTC GGTGGCGGGG TTCTTGACGT

421 CAGGTGCATG TGGGCTGACG GGGCTGTCTT CGTTCTCGTG GGTCATGAAT TACATCCGGC

481 AGACCCACGG ATCGGTGCCG GAGCAGCTGG AAATGGCAAA GCACCGCATG GCTGACGTGG

541 CCGGTTACGT TGGACAGAAG ACGAAGGATG TAGGACAGAA GACCAAGGAA GTTGGGCAAG

601 AGATACAGAC CAAGGCTCAG GATTCAAAGA GAACTTGATA GAATAGTGGT TTAAGCTTAA

661 GGATGAAAGG GGTCTATGGG TTTTGATGGT GATACGCAAA TAAATTATGT TCTCCTTGTA

721 GTTGAAGTTG TGAGCATTTT GTGTCTTTCT ATGATCTTGT AGGTAGCGGT TTGGTTTGTT

781 TATGTTCTTG TTGATTTGCT TTTTTAATGA GAGAAGTGAT TTTTCTTTTT TTTTGGTCAG

841 AGAAGTGGTT TGTTTGTCAT CAAGAGGTGC TGCTACCAGC TTTGTTTGTG TGTCAGTATG

901 CATGTAGGTT TGGTTCACTT CAATTGTTTA ATTTCAATGC GAGTGTTTTC TGTT
```

TABLE 12

| | | Nucleic acid sequence in the Epitope regions of SEQ ID NO: 10 | | |
|---|---|---|---|
| Epitope NO | Position | Nucleotide sequence (5'-3') | SEQ ID NO |
| 1 | 490-580 | ATCGGTGCCGGAGCAGCTGGAA ATGGCAAAGCACCGCATGGCTG ACGTGGCCGGTTACGTTGGACA GAAGACGAAGGATGTAGGACAG AA | 49 |

Nucleotide sequence (cDNA) of peanut allergen protein Ara h 11. IgE epitope is in bold and underlined. The boxed area indicates a region that may be used in the Ara hRNA constructs. Start codon (ATG) and stop codon (TGA) in bold italic.

SEQ ID NO: 11

```
  1 TTATGGCCGG GGATTCGCAT TAGCATTAGC CCTTTCATTT CACTTCATAA TTAATTAATA

61 ACATGGCTGA AGCACTCTAC TACGGCGGCC GCCAACGCCA AGAGCAACCA AGGTCCACCC

121 AGCTTGTCAA GGCCACCACC GCTGTTGTCG CCGGAGGCTC CCTCTTGATC CTCGCCGGCC

181 TTGTGCTGGC CGGCACCGTC ATTGGCCTCA CAACGATCAC ACCGCTCTTC GTGATCTTCA

241 GCCCGGTGCT TGTGCCAGCT GTCATCACTG TGGCACTCTT AGGCTTGGGG TTCTTGGCCT
```

-continued

```
301 CTGGAGGCTT CGGCGTGGCG GCAATAACAG TGCTGACGTG GATCTATAGG TACGTAACAG

361 GTAAGCATCC ACCTGGCGCC AACCAATTGG ACACAGCCCG CCACAAGCTG ATGGGCAAGG

421 CGCGTGAGAT TAAGGACTTT GGTCAACAAC AAACCAGTGG GGCCCAGGCT TCT*TGA*GCAT

481 ACCATCTTCG TTTGCATCTT TGTTTGCACG CACGTCCACG CCATCATTTA TCTTTTTCGA

541 ATTGTTATGG TTTATTTTAT TTTATTTAAT TTTTTTATGA GTCTGGGGTT TCCTTGAAAT

601 TAACCGTTGG TTTAAAATAT TTTCCCTGGG TTATCCAATC CCATTCAAAT TTTTA
```

TABLE 13                                                                15

Nucleic acid sequence in the
Epitope regions of SEQ ID NO: 11

| Epitope NO | Position | Nucleotide sequence (5'-3') | SEQ ID NO | |
|---|---|---|---|---|
| 1 | 108-164 | CCAAGGTCCACCCAGCTTG TCAAGGCCACCACCGCTGT TGTCGCCGGAGGCTCCCTC | 50 | 20 |

Nucleotide sequence (cDNA) of peanut allergen protein Arah 12. IgE
epitope region not identified. Any part of this sequence may be used
in hRNA constructs. Start codon (ATG) and stop codon (TGA) in bold italic.

SEQ ID NO: 12

```
  1 CAGCCTTTTT GTTGATAACA ATCTCTGCAT GCGTCCACAC TACTACTAGT CTACTACACT

61 TAGATGTACA TTGTTGACTT TTCTTCACTT TCAAAATAAA TTGACACCCA CATCATACAC

121 TGGAATTGAA ATCTCATGCC ACGTGTTTAT TTCTTAGTAT GGCACCTACG TACTTAAATC

181 TCTCTTGTTC ATAGTCCGAA ACTGTGTATA TAAATAGATC ACACACATAA ACCTCAACGA

241 TCGGTACAAA TCGAAACAGC AATA*ATG*GAG AAGAAAACAG TTGCTGGATT CTGCATCTTC

301 TTCCTCGTTC TCTTTCTTGC TCAGGAGGGA GTGGTGAAAA CAGAGGCAAA GCTATGCAAC

361 CACCTGGCAG ATACATACAG AGGACCATGC TTTACCAATG CAAGCTGCGA TGATCATTGC

421 AAGAACAAAG AGCACTTTGT TAGTGGAACC TGCATGAAAA TGGCGTGTTG GTGTGCTCAC

481 AACTGT*TGA*T GTAA
```

Nucleotide sequence (cDNA) of peanut allergen protein Ara h 13.
Incomplete mRNA sequence. IgE epitope region not identified. Any part of
this sequence may be used in hRNA constructs

SEQ ID NO: 13

```
CAGTACAAAAACGAACGATAATAATGGAGAAGAAATGGCTGGATTCTGCATCTTTTTCCTCATTCTCTTTCTTG

CTCAGGAATATGGCGTGGAGGGAAAGGAGTGTTTGAACCTAAGTGACAAATTCAAGGGACCGTGTTTGGGTTCAA

AGAACTGCGATCATCACTGCAGGGACATAGAGCACTTGCTCAGCGGAGTTTGCAGGGACGATTTCCGCTGCTGGT

GCAACAGAAAGTGTTAAAACTACTCCATCATCATCAAACCTCTAAAACCATATGATATAATAATAATAATAATAA

TATATGAATAATAAATGCTTAGCTTGCATTATATTGGATCCCCACGATGCGTTAGACGCATGCACCTAGC
```

Nucleotide sequence (cDNA) of peanut allergen protein Ara h 14. IgE
epitope region not identified. Any part of this sequence may be used
in hRNA constructs. Start codon (ATG) and stop codon (TAA) in bold
and italic.

SEQ ID NO: 14

```
  1 *ATG*GCTACTG CTACTGATCG TGCACCTCAC CAGGTTCAAG TTCACACCCC CACCACACAA

61 CGCGTCGACG TTCCACGCCG CGGCTACGAT GTTAGTGGTG GTGGTATTAA GACTCTTCTC

121 CCCGAGAGAG GTCCGTCCAC CTCTCAAATC ATCGCCGTCC TCGTCGGCGT CCCCACTGGG

181 GGCACTCTGT TGCTCCTCTC CGGCCTTTCA CTTCTCGGAA CCATAATCGG GCTGGCAATT
```

-continued

```
241 GCCACCCCGG TTTTTACTTT CTTCAGCCCG GTTATAGTTC CCGCGGTCGT TACCATTGGA

301 CTTGCAGTCA CTGGTATTCT CACGGCGGGA GCATGTGGAC TAACCGGGCT GATGTCTTTG

361 TCATGGATGA TTAACTTCAT CCGACAGGTA CATGGGACGA CGGTGCCGGA TCAGCTGGAC

421 TCAGTGAAGC GGCGCATGGC GGACATGGCG GATTACGTGG GGCAGAAGAC AAAGGATGCT

481 GGCCAACAGA TACAGACTAA GGCCCAGGAT GTTAAGAGGT CATCATCA*TA A*;
```

Nucleotide sequence (cDNA) of peanut allergen protein Ara h 15. IgE
epitope region not identified. Any part of this sequence may be used
in hRNA constructs. Start codon (ATG) and stop codon (TGA) in
bold italic.

SEQ ID NO: 15

```
  1 GAAACCCCAT CACTTCTTGT CTAAAAATTC TCAAAAGTCA CCAGCCACCA AAAACCCATT

61 TACCATT*ATG* TCTGATCAAA CAAGGACAGG CTATGGAGGA GGAGGGTCCT ATGGATCATC

121 CTATGGTGGA GGAGGCACCT ATGGTTCATC TTATGGAACC TCCTATGACC CCAGTACTAA

181 CCAACCTATA CGCCAAGCCA TCAAGTTCAT GACAGCATCA ACCATTGGTG TCTCATTCTT

241 GATCCTGTCT GGGTTGATCC TCACTGGAAC TGTCATAGGT TTGATCATTG CAACACCACT

301 TCTTGTTATC TTCAGTCCTA TCCTTGTCCC TGCTGCCATA ACCCTTGCAC TGGCTGCTGG

361 TGGATTTTTG TTCTCTGGTG GCTGTGGTGT TGCTGCCATT GCTGCATTGT CATGGTTGTA

421 CAGCTATGTC ACTGGGAAAC ACCCTGCTGG CTCTGATAGG CTTGATTATG CTAAAGGGGT

481 GATTGCTGAT AAGGCTAGGG ATGTTAAGGA CAGGGCCAAG GATTATGCTG GTGCTGGTAG

541 GGCTCAGGAG GGCACCCCAG **GGTAT*TGATC***CTCATTGTGA TGAAAAAAAA TGGAAGCTTT

601 TGTGTGTAAT GTGTGGGTGA AGTGAAGGTC TGAAAGGTGA CACCCCC
```

TABLE 14 / TABLE 14-continued

Example of sgRNA pair sequences for deletions in the allergen Ara h 1 (SEQ ID NO: 2), targeting *A. duranensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO: | Genome position |
|---|---|---|
| CCTTTCTACTTCCCGTCAAGGCG GTTTAGCACCC*GCTACGGGAAC* *CAAAACGGTAGG* | 51 | 569 |
| CCGGCGAGCAGCCGAGACCAATC ATCCTACTTGCA*CCAACGTATT* *CCTGCTGAAGCCC* | 52 | 956 |
| AGAGGTTTGACCAAAGGTCAAGG CAGTTTCAGAATCTCCAGAATCA *CCGTATTGTGCAGATCGAGGCCA* | 53 | 639 |
| CCGAGACCAATCATCCTACTTGC AGGGCTTCAGCAGGAATAC*CC* *GCATTGAAGGCGGCCTCCAAC* | 54 | 967 |
| CCTTTCTACTTCCCGTCAAGGCG GTTTAGCACCCGCTACGG*GAAC* *CAAAACGGTAGGATCCGGG* | 55 | 569 |
| CCGGCCAGTTTGAGGATTTCTT CCCGGCGAGCAGCCGA*CCCTGC* *AAGTAGGATGATTGGTC* | 56 | 933 |
| CCCTTTCTACTTCCCGTCAAGG CGGTTTAGCACCC*GCTACGGGA* *ACCAAAACGGTAGG* | 57 | 568 |
| CCATGTGAGGGAAGAAACATCTC GGAACAACCCTTTCTACTTCCCG TCAA*GGCGGTTTAGCACCCGCTA* *CGGG* | 58 | 538 |
| CCTCGAGGATCATAGACACAACG ACACACTGGCACCACCAACCAAC GTTCCCCT*CCAGGGGAGCGGACA* *CGTGGCCG* | 59 | 257 |
| CCCGGAGACTACGATGATGAC CGCCGTCAACCCCGAAGAGAG GAA*GGAGGCCGATGGGGACCAG* *CTGG* | 60 | 338 |
| CCTCTTTCTCAGGAGACTCTTT CATCAAGAGGAGGAAAA*CCAAG* *GAGGGAAGGGTCCACTCC* | 61 | 1843 |

TABLE 14-continued

Example of sgRNA pair sequences for deletions
in the allergen Ara h 1 (SEQ ID NO: 2),
targeting *A. duranensis* genome in peanut using
the Online CHOCHOP sgRNA design tool. The
distance between the two sgRNAs is underlined
bold. sgRNA1 and sgRNA2 are on the left and
right side of the underlined area respectively.
Ideally, the pair of nickase sgRNA Sequences
that have Zero (0) Off-target in the
peanut genome are selected.

| Nickase sgRNA Pair Sequence (5' to 3') Deletions with Zero (0) Off-target Nickase Pair | SEQ ID NO: | Genome position |
|---|---|---|
| CCAAGCACGCTGATGCTGATAAC ATCCTTGTTATCCAGCAAGGGCA *A*GCCACCGTGACCGTAGCAAATGG | 62 | 729 |
| AGAGAAGGAGAACAAGAGTGGGG AACACCAGGTAG*CCATGTGA* *GGGAAGAAACATCTC* | 63 | 503 |
| GAAGCTCATCAAAAACCAGAAG GAATCTCACTTTGTGAGTGCT CGT*CCTCAATCTCAATCTCAAT* *CTCC* | 64 | 1762 |

TABLE 15

Example of sgRNA pair sequences for
deletions in the allergen Ara h 1 (SEQ ID
NO: 2), targeting *A. ipaensis* genome in
peanut using the Online CHOCHOP sgRNA
design tool. The distance between the two
sgRNAs is underlined bold. sgRNA1 and
sgRNA2 are on the left and right side of
the underlined area respectively. Ideally,
the pair of nickase sgRNA Sequences that
have Zero (0) Off-target in the peanut
genome are selected.

| Nickase sgRNA Pair Sequence (5' to 3') Deletions with Zero (0) Off-target Nickase Pair | SEQ ID NO | Genome position |
|---|---|---|
| CCGGCGAGCAGCCGAGACCAAT CATCCTACTTGCA*CCAACGTAT* *TCCTGCTGAAGCCC* | 65 | 956 |
| CCGAGACCAATCATCCTACTTGC AGGGCTTCAGCAGGAATAC*GTT* *GGAGGCCGCCTTCAATGCGG* | 66 | 967 |
| CCGGCCAGTTTGAGGATTTCTT CCCGGCGAGCAGCCG*CCTGCA* *AGTAGGATGATTGGTCT* | 67 | 933 |
| GTTATCAGCATCAGCGTGCTTG GATCCTTGTTATCCAGCAAGGG CAA*CCATTTGCTACGGTCACGGT* *GGC* | 68 | 729 |
| CCCCACTCTTGTTCTCCTTCTC TAACACCAGGTAG*GAGATGTTT* *CTTCCCTCACATGG* | 69 | 503 |
| CGGTCATCATCGTAGTCTCCGG GCCGTCAACCCCC*CATCGGCCT* *CCTTCCTCTCTTC* | 70 | 338 |
| CCTTCTGGTTTTTGATGAGCTT CAATCTCACTTTGTGAGTGCTC GT*CCTCAATCTCAATCTCAATC* *TCC* | 71 | 1762 |

TABLE 15-continued

Example of sgRNA pair sequences for
deletions in the allergen Ara h 1 (SEQ ID
NO: 2), targeting *A. ipaensis* genome in
peanut using the Online CHOCHOP sgRNA
design tool. The distance between the two
sgRNAs is underlined bold. sgRNA1 and
sgRNA2 are on the left and right side of
the underlined area respectively. Ideally,
the pair of nickase sgRNA Sequences that
have Zero (0) Off-target in the peanut
genome are selected.

| Nickase sgRNA Pair Sequence (5' to 3') Deletions with Zero (0) Off-target Nickase Pair | SEQ ID NO | Genome position |
|---|---|---|
| CCTCAATCTCAATCTCAATCTC CGTCGTCTCCTGA*CCTCTTTCT* *CAGGAGACTCTTTC* | 72 | 1808 |

TABLE 16

Example of sgRNA pair sequences for
deletions in the allergen Ara h 2 (SEQ ID
NO: 3), targeting *A. duranensis* genome
in peanut using the Online CHOCHOP sgRNA
design tool. The distance between the two
sgRNAs is underlined bold. sgRNA1 and sgRNA2
are on the left and right side of the
underlined area respectively. Ideally,
the pair of nickase sgRNA Sequences that
have Zero (0) Off-target in the peanut
genome are selected.

| Nickase sgRNA Pair Sequence (5' to 3') Deletions with Zero (0) Off-target Nickase Pair | SEQ ID NO | Genome position |
|---|---|---|
| TGGACGTCGAAAGTGGCGGCA GGCGGCCGCGAATTCCGCCGA TACTGACGGGCT*CCAGGAGTC* *GTCGCCACCAATCC* | 73 | 449 |
| CCGTCAGTATCGGCGGAATTC GCGCTCCAGGAGTCGTCGCC *ACCAATCCCCATATGGAAACC* | 74 | 477 |
| CCTTAGGGCACCACAGCGTTG CGACTTGGACGTCGAAAGTGG CGGCAGGCGGCC*CCGTCAGTA* *TCGGCGGAATTCGC* | 75 | 423 |
| CCCGTCAGTATCGGCGGAATTC GCTCCAGGAGTCGTCG*CCACC* *AATCCCCATATGGAAACC* | 76 | 478-a |
| CCATATGGGGATTGGTGGCGAC GAAACCGTCGATATTCAGCCA *TGTGCCTTCTTCCGCGTGCA* | 77 | 511 |
| CCCGTCAGTATCGGCGGAATTC GCTCCAGGAGTCGTCGCCA*CC* *AATCCCCATATGGAAACCGTC* | 78 | 478-b |
| CCTGGAGCCCGTCAGTATCGGC GAGTCGTCGCCA*CCAATCCCCA* *TATGGAAACCGTC* | 79 | 485 |

TABLE 17

Example of sgRNA pair sequences for deletions in the allergen Ara h 2 (SEQ ID NO: 3), targeting *A. ipaensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| TGGACGTCGAAAGTGGCGGCA GGCGGCCGCGAATTCCGCCGA TACTGACGGGCT*CCAGGAGTC* *GTCGCCACCAATCC* | 80 | 449 |
| CCGTCAGTATCGGCGGAATTC GCGCTCCAGGAGTCGTCG*CCA* *CCAATCCCCATATGGAAACC* | 81 | 477 |
| CCCGTCAGTATCGGCGGAATT CGCTCCAGGAGTCGTCG*CCAC* *CAATCCCCATATGGAAACC* | 82 | 478 |
| CCATATGGGGATTGGTGGCGA CGAAACCGTCGATATTCAGCC *ATGTGCCTTCTTCCGCGTGCA* | 83 | 511 |
| CCCGTCAGTATCGGCGGAATT CGCTCCAGGAGTCGTCGCCA*C* *CAATCCCCATATGGAAACCGT* *C* | 84 | 478 |
| CCTGGAGCCCGTCAGTATCGG CGAGTCGTCGCCA*CCAATCCC* *CATATGGAAACCGTC* | 85 | 485 |
| CCTCAACAGTGCGGCCTTAGG GCACCACAGCGTTGCGACT*TG* *GACGTCGAAAGTGGCGGCAGG* | 86 | 409 |
| CCTTAGGGCACCACAGCGTTG CGACTTGGACGTCGAAAGTGG CGGCAGGCGGCC*CCGTCAGTA* *TCGGCGGAATTCGC* | 87 | 423 |

TABLE 18

Example of sgRNA pair sequences for deletions in the allergen Ara h 3/3.02 (SEQ ID NO: 4), targeting *A. ipaensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| CCGTCACAATGGCTCCCTCTT CTTGAGGGGAGGCCTCAGAAT CTTGAGCGGCACCTCTCGTTC CATCTGGG | 88 | 879 |

TABLE 18-continued

Example of sgRNA pair sequences for deletions in the allergen Ara h 3/3.02 (SEQ ID NO: 4), targeting *A. ipaensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| GCCCATACAGCCCGCATAGTC GGCCTAGACGAGAAGAGCGTG AATTTCG*CCCTCGAGGACAGC* *ACAGCCGCA* | 89 | 671 |
| GTGCGTTGGTGTTGTAGTGAG GGACAGCATCATATATGCATT GAG*CCACTTGCACGTGAGCCC* *GTCCC* | 90 | 1218 |
| GACAGATTGTGCAAAATCTGT GGGGCGAGAACGAGAGTGAAG AAGAGGGAG*CCATTGTGACGG* *TGAGGGGAGGC* | 91 | 839 |
| TGGAGTAGAAAGGCCTACGAA GGATGCTCCCCAGG*CCTTCCT* *TGCTGGATGAAGATCT* | 92 | 237 |
| CCAGCAACAAAGCAGACAAAG CAGACGAAGAAGCTTACCATA *TAGCCCATACAGCCCGCATAG* *TCGG* | 93 | 627 |
| CCAAATTGAATCTCCTGGGGA ACCTGGGAACCACGAGCAAGA GTTCTTAAGGTA*CCAGCAACA* *AAGCAGACAAAGCA* | 94 | 573 |
| TGGAGTAGAAAGGCCTACGAA GGATGCTCCCCAGGA*CCCTTC* *CTTGCTGGATGAAGATC* | 95 | 237 |
| CCTTCCTTGCTGGATGAAGAT CTGGATACTTTGGGTTGATAT TCCCTGGTTGT*GCAGGCTCTT* *CATATGTGCTAGG* | 96 | 272 |
| GCATGTGTTAAAAAGAACATT GGTGGAAACAGATC*CCCTCAC* *ATCTACGATCCTCAGC* | 97 | 1060 |
| CCTTTCTACTCCAATGCTCCC CAGGAGATCTTCATCC*CCCAA* *AGTATCCCCTTCCTTGCT* | 98 | 247 |

TABLE 19

Example of sgRNA pair sequences for deletions in the allergen Ara h 3/3.02 (SEQ ID NO: 4), targeting A. duranensis genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| TGGACGTCGAAAGTGGCGGCA GGCGGCCGCGAATTCCGCCGA TACTGACGGGCT *CCAGGAGTCGTCGCCACCAATCC* | 99 | 449 |
| CCGTCAGTATCGGCGGAATTC GCGCTCCAGGAGTCGTCGCCA *CCAATCCCCATATGGAAACC* | 100 | 477 |
| CCTTAGGGCACCACAGCGTTG CGACTTGGACGTCGAAAGTGG CGGCAGGCGGCC*CCGTCAGTA* *TCGGCGGAATTCGC* | 101 | 423 |
| CCCGTCAGTATCGGCGGAATT CGCTCCAGGAGTCGTCGC*CAC* *CAATCCCCATATGGAAACC* | 102 | 478-a |
| CCATATGGGGATTGGTGGCGA CGAAACCGTCGATATTCAGCC *ATGTGCCTTCTTCCGCGTGCA* | 103 | 511 |
| CCCGTCAGTATCGGCGGAATT CGCTCCAGGAGTCGTCGCCAC *CAATCCCCATATGGAAACCGT* *C* | 104 | 478-b |
| CCTGGAGCCCGTCAGTATCGG CGAGTCGTCGCCA*CCAATCCC* *CATATGGAAACCGTC* | 105 | 485 |

TABLE 20

Example of sgRNA pair sequences for deletions in the allergen Ara h 5 (SEQ ID NO: 5), targeting A. duranensis genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| GGTGCCACCGAGGTACAACC CGGAAATACATGGTTATCCA AGGTGAACCCGGA *GCTATCATTCCAGGGAAGAAGGG* | 106 | 204 |
| CGCCTTCAATTTCGCAGAGAA GGACCACCTCTCCTCCGCCGC *AATCCTCGGCCAAGACGGCGG* | 107 | 48 |

TABLE 20 -continued

Example of sgRNA pair sequences for deletions in the allergen Ara h 5 (SEQ ID NO: 5), targeting A. duranensis genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| GCTATCATTCCAGGGAAGAAG GGTCCTGGTGGTGTTA*CCATT* *GAGAAGACGAATCAGGCG* | 108 | 257 |
| GAACCCGGAGCTATCATTCCA GGGAAGAAGGGTCCTGGTGGT GTTA*CCATTGAGAAGACGAAT* *CAGGCG* | 109 | 248 |

TABLE 21

Example of sgRNA pair sequences for deletions in the allergen Ara h 5 (SEQ ID NO: 5), targeting A. ipaensis genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| CGCCTTCAATTTCGCAGAG AAGGACCACCTCTCCTCCG CG*CCGCCG* *TCTTGGCCGAGGATTGC* | 110 | 46 |
| CCCTTCTTCCCTGGAATGA TAGCTCCTGGTGGTGTTAC *CATTGAGAAGACGAATCAG* *GCG* | 111 | 257 |
| GGTGCCACCGAGGTACAAC CCGGAAATACATGGTTATC CAAGGTGAACCCGGA*CCCT* *TCTTCCCTGGAATGATAGC* | 112 | 204 |
| CCTGGAATGATAGCTCCGG GTTCGAAGAAGGGTCCTGG TGGTGTTA*CCATTGAGAAG* *ACGAATCAGGCG* | 113 | 248 |

TABLE 22

Example of sgRNA pair sequences for deletions in the allergen Ara h 6 (SEQ ID NO: 6), targeting *A. duranensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| CCTTGCCCTCGTCCTGGTGG CACACGCCTCCGCAATG *AGGCGCGAGAGGGGGAGACAGGG* | 114 | 30 |
| CCATCCTGGTAGCTCTCCTTG CCCTCGTCCTGGTGGCACACG CCTCCGCAATGAGGCGCGAG AGGGGGAGACAGGG | 115 | 14 |
| CCTGGTAGCTCTCCTTGCCCT CGTCCTGGTGGCACACGCCTC CGCAATGAGGCGCGAGAGGGG GAGACAGGG | 116 | 18 |

TABLE 23

Example of sgRNA pair sequences for deletions in the allergen Ara h 7 (SEQ ID NO: 7), targeting *A. duranensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| CCTCCTGGGCGCCCTTCTTGTCG TAGCCTCCGCGACAAGATGGGA *TCCCGATCGAGGGTCCAGAGG* | 117 | 30 |
| CCCTCCTGGGCGCCCTTCTTGT CGTAGCCTCCGCGACAAGATGG *GATCCCGATCGAGGGTCCAGAGG* | 118 | 29 |
| GATGGTCAAGCTCAGCATCCTG GTAGCCCTCCTGGGCGCCCTTC TTGTCGTAGCCTCCGCGACAAGA *TGGGATCCC* | 119 | 3 |

TABLE 24

Example of sgRNA pair sequences for deletions in the allergen Ara h 7 (SEQ ID NO: 7), targeting *A. ipaensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| GATGGTCAAGCTCAGCATCCT GGTAGCCCTCCTGGGCGCCCT TCTTGTCGTAG *CCTCCGCGACAAGATGGGATCCC* | 120 | 3 |

TABLE 25

Example of sgRNA pair sequences for deletions in the allergen Ara h 8 (SEQ ID NO: 8), targeting *A. duranensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| GTCGAGGGAAACGGTGGTCC TGGAACCATCAAGAAACTCA *CCATTGTCGAGGATGGAGAAACC* | 121 | 228 |
| CCGTTTCCCTCGACGATTTCAACTG GTCCTGGAACCATCAAGAAACTCA *CCATTGTCGAGGATGGAGAAACC* | 122 | 219 |
| CCTGGAACCATCAAGAAACTCAC CATTGTCGAGGATGGAGAAACCA AGTTTATCTTACACAAAGTGGAGG | 123 | 248 |
| CCTCAATAGCCTTGAAGA GAGCTGTTACGTCTTGG *GTTCTAATATTGAGCAGGGTTGG* | 124 | 521 |

TABLE 26

Example of sgRNA pair sequences for deletions in the allergen Ara h 8 (SEQ ID NO: 8), targeting *A. ipaensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| GTCGAGGGAAACGGTGGTCCT GGAACCATCAAGAAACTCA CCATTGTCGAGGATGGAGAA ACC | 125 | 228 |
| CCGTTTCCCTCGACGATTTC AACTGGTCCTGGAACCATCA AGAAACTCA *CCATTGTCGAGGATGGAGAAACC* | 126 | 219 |
| CCTGGAACCATCAAGAAACT CACCATTGTCGAGGATGGAG AAACCAA *GTTTATCTTACACAAAGTGGAGG* | 127 | 246 |
| CCTCAATAGCCTTGAAGAGA GCTGTTACGTCTTGG *CCAACCCTGCTC* *AATATTAGAAC* | 128 | 521 |

TABLE 27

Example of sgRNA pair sequences for deletions in the allergen Ara h 9 (SEQ ID NO: 9), targeting A .duranensis genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| CCCTGGAAGATGCGGTGTCAGCATTCC TTACAAGATCAGCACCTCCACCAAC *CCTCAGAACTTAATGGTAGCACA* | 129 | 375 |

TABLE 28

Example of sgRNA pair sequences for deletions in the allergen Ara h 9 (SEQ ID NO: 9), targeting *A. ipaensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| CCGCGGTGGTTTTTGCAGCACCG ACCGCCAGGCCG*AGCGGCTTTG* *AGGCAGTTACAGG* | 130 | 273 |
| CCACCATGGCCATGCACACAAGC GAGCACCAATGGTGAATG*GTT* *CACTTGGCCACATGATAGGG* | 131 | 128 |
| CCATGGCCATGCACACAAGCATC TGGGAGCACCAATGGTGAATG *GTTCACTTGGCCACATGATAGGG* | 132 | 123 |
| TGCTGACACCGCATCTTCCAGGG TTCCTTACAAGATCAGCACCTC CACCAACTGTGCTACCATTAAGT *TCTGAGG* | 133 | 375 |
| CCGCGGTGGTTTTTGCAGCACCG ACCGCCAGGCCGCCTGTAACTG CCTCAAAGGCCATGAACGGAACC *GGCAGCGG* | 134 | 273 |
| GTTCACTTGGCCACATGATAGGG AGTGCCCTAGCACCA*CCCTTTG* *TGAGGAAAGTGATGCA* | 135 | 167 |
| GTGGAGGTGCTGATCTTGTAAGG CAACTGTGCTACCATTAAGTTC TGA*CCACCTTCTTCATCTTCCTC* *TCC* | 136 | 400 |

TABLE 29

TABLE 29 Example of sgRNA pair sequences for deletions in the allergen Ara h 10 (SEQ ID NO: 10), targeting *A. ipaensis* genome in peanut using the Online CHOCHOP sgRNA design tool. The distance between the two sgRNAs is underlined bold. sgRNA1 and sgRNA2 are on the left and right side of the underlined area respectively. Ideally, the pair of nickase sgRNA Sequences that have Zero (0) Off-target in the peanut genome are selected.

| Nickase sgRNA Pair Sequence (5' to 3') Deletions with Zero (0) Off-target Nickase Pair | SEQ ID NO | Genome position |
|---|---|---|
| CCATGACTGACCGTACCCAACC ACACACTGTCCAAGTCCACACC ACAGCTGGC*CGTTTCGGCGAC* *ACCGCTGCTGG* | 137 | 67 |
| CCGGCCATCATTGTCGTTGGGCT CTCGGTGGCGGGGTTCTTGAC*G* *TCAGGTGCATGTGGGCTGACGG* | 138 | 315 |

TABLE 29-continued

TABLE 29 Example of sgRNA pair sequences for
deletions in the allergen Ara h 10 (SEQ ID
NO: 10), targeting *A. ipaensis* genome in
peanut using the Online CHOCHOP sgRNA design
tool. The distance between the two sgRNAs
is underlined bold. sgRNA1 and sgRNA2 are on
the left and right side of the underlined
area respectively. Ideally, the pair of
nickase sgRNA Sequences that have
Zero (0) Off-target in the peanut
genome are selected.

| Nickase sgRNA Pair Sequence (5' to 3') Deletions with Zero (0) Off-target Nickase Pair | SEQ ID NO | Genome position |
|---|---|---|
| CGTTTCGGCGACACCGCTGCTG GAACTAACCGCTATCCCGACAG AGGCCCGTCAACATCTAAGGTT ATCG | 139 | 120 a |
| CCAACCACACACTGTCCAAGTCC ACACCACAGCTGGCCGTTTCGG CGACACCGCTGCTGG | 140 | 83 |
| CCCAACCACACACTGTCCAAGTC CACACCACAGCTGGCCGTTTCG GCGACACCGCTGCTGG | 141 | 82 |
| CGTTTCGGCGACACCGCTGCTGG AACTAACCGCTATCCCGACAGA GGCCCGTCAACATCT | 142 | 120b |

TABLE 30

Example of sgRNA pair sequences for
deletions in the allergen Ara h 11 (SEQ ID
NO: 11), targeting *A. duranensis* genome in
peanut using the Online CHOCHOP sgRNA
design tool. The distance between the
two sgRNAs is underlined bold.
sgRNA1 and sgRNA2 are on the left
and right side of the underlined
area respectively. Ideally, the pair
of nickase sgRNA Sequences that have
Zero (0) Off-target in the peanut
genome are selected.

| Nickase sgRNA Pair Sequence (5' to 3') Deletions with Zero (0) Off-target Nickase Pair | SEQ ID NO | Genome position |
|---|---|---|
| CCTCACAACGATCACACCGCT CTTCGTGATCTTCAGCCCGGT GCTTGTGCCAGCTGTCATCAC TGTGG | 143 | 206 |
| CCCGGTGCTTGTGCCAGCTGT CATCACTGTGGCACTCTTACC AGAGGCCAAGAACCCCAAGCC | 144 | 242 |
| TGTGAGGCCAATGACGGTGCC GGACGATCACACCGCTCTTCG TGATCTTCAGCCCGG | 145 | 190 |
| GTTTCCTTGAAATTAACCGTT GGTTTAAAATATTTTGAATGG GATTGGATAACCCAGGG | 146 | 588 |
| TGTGCCAGCTGTCATCACTGT GGCACTCTTAGGCTTGGGGTT CTTGGCCTCTGGAGGCTTCGG CGTGGCG | 147 | 251 |

TABLE 30-continued

Example of sgRNA pair sequences for
deletions in the allergen Ara h 11 (SEQ ID
NO: 11), targeting *A. duranensis* genome in
peanut using the Online CHOCHOP sgRNA
design tool. The distance between the
two sgRNAs is underlined bold.
sgRNA1 and sgRNA2 are on the left
and right side of the underlined
area respectively. Ideally, the pair
of nickase sgRNA Sequences that have
Zero (0) Off-target in the peanut
genome are selected.

| Nickase sgRNA Pair Sequence (5' to 3') Deletions with Zero (0) Off-target Nickase Pair | SEQ ID NO | Genome position |
|---|---|---|
| CCTAAGAGTGCCACAGTGATG ACCTTGGGGTTCTTGGCCTCT GGAGGCTTCGGCGTGGCG | 148 | 261 |
| CCGGCGAGGATCAAGAGGGAG CCCCTTGTGCTGGTGTGAGGC CAATGACGGTGCCGG | 149 | 156 |
| CCAGCACAAGGCCGGCGAGGA TCCCGGCACCGTCATTGGCCT CACAACGATCACACCGCTCT | 150 | 167 |
| CCGGCGAGGATCAAGAGGGAG CCCCTTGTGCTGGCCGGCACC GTCATTGGCCTCACAACGATC ACACCGCTCT | 151 | 156 |
| CCTCTGGAGGCTTCGGCGTGG CGGCAATAACAGTGCTGACGC CTGTTACGTACCTATAGATCCA | 152 | 298 |
| TGACGGTGCCGGCCAGCACAA GGTTGGCCTCACAACGATCAC ACCGCTCTTCGTGATCTTCAG CCCGG | 153 | 179 |

TABLE 31

Example of sgRNA pair sequences for
deletions in the allergen Ara h 11 (SEQ ID
NO 11), targeting *A. ipaensis* genome in
peanut using the Online CHOCHOP sgRNA
design tool. The distance between the
two sgRNAs is underlined bold. sgRNA1 and
sgRNA2 are on the left and right side of
the underlined area respectively.
Ideally, the pair of nickase sgRNA
Sequences that have Zero (0)
Off-target in the peanut genome
are selected.

| Nickase sgRNA Pair Sequence (5' to 3') Deletions with Zero (0) Off-target Nickase Pair | SEQ ID NO | Genome position |
|---|---|---|
| CCTCACAACGATCACACCGCT CTTCGTGATCTTCAGCCCGGT GCTTGTGCCAGCTGTCATCAC TGTGG | 154 | 206 |
| CCGGCACCGTCATTGGCCTCA CAACGATCACACCCCGGGCTG AAGATCACGAAGAGC | 155 | 190 |
| CCGGCGAGGATCAAGAGGGAG CCCCTTGTGCTGGCCGGCACC GTCATTGGCCTCACA | 156 | 156 |

TABLE 31-continued

Example of sgRNA pair sequences for
deletions in the allergen Ara h 11 (SEQ ID
NO 11), targeting *A. ipaensis* genome in
peanut using the Online CHOCHOP sgRNA
design tool. The distance between the
two sgRNAs is underlined bold. sgRNA1 and
sgRNA2 are on the left and right side of
the underlined area respectively.
Ideally, the pair of nickase sgRNA
Sequences that have Zero (0)
Off-target in the peanut genome
are selected.

| Nickase sgRNA Pair Sequence (5' to 3') Deletions with Zero (0) Off-target Nickase Pair | SEQ ID NO | Genome position |
|---|---|---|
| CCAGCACAAGGCCGGCGAGGA TCCCGGCACCGTCATTGG*CCT CACAACGATCACACCGCTCT* | 157 | 167 |
| CCTTGTGCTGGCCGGCACCGT CATTGGCCTCACAACGATCAC *ACCCCGGGCTGAAGATCACGA AGAGC* | 158 | 179 |
| GGTGGCCTTGACAAGCTGGGT GGACCGCTGTTGTCGCCGGAG GC*TCCCTCTTCCAGCACAAGG CCGGCGAGGATC* | 159 | 115 |
| CCGGCGAGGATCAAGAGGGAG CCCCTTGTGCTGGCCGGCACC *GTCATTGGCCTCACAACGATC* | 160 | 156 |
| CGGTGGTGGCCTTGACAAGCT GGCTGTTGTCGCCGGAGGCTC *CCTCTTCCAGCACAAGGCCGG CGAGGATC* | 161 | 119 |
| CCCGGTGCTTGTGCCAGCTGT CATCACTGTGGCACTCTTA*CC AGAGGCCAAGAACCCCAAGCC* | 162 | 242 |
| GGTGGTGGCCTTGACAAGCTG GGGCTGTTGTCGCCGGAGGCT *CCCTCTTCCAGCACAAGGCCG GCGAGGATC* | 163 | 118 |
| TGTGCCAGCTGTCATCACTGT GGCACTCTTAGGCTTGGGGTT *CTTGGCCTCTGGAGGCTTCGG CGTGGCG* | 164 | 251 |
| CCTCTGGAGGCTTCGGCGTGG CGGCAATAACAGTGCTGACGC *CTGTTACGTACCTATAGATCC A* | 165 | 298 |
| CCTAAGAGTGCCACAGTGATG ACCTTGGGGTTCTTGG*CCTCT GGAGGCTTCGGCGTGGCG* | 166 | 261 |
| CCGGCGACAACAGCGGTGGTG GCAGGCTCCCTCTTGATCCTC *GCCGGCCTTGTGCTGGCCGGC ACCGTCA* | 167 | 132a |
| CCGGCGACAACAGCGGTGGTG GCAGGCTCCCTCTTGATCCTC *GCCGGCCTTGTGCTGGCCGGC ACC* | 168 | 132b |
| GTTTCCTTGAAATTAACCGTT GGTTTAAAATATTTT*GAATGG GATTGGATAACCCAGGG* | 169 | 588 |

TABLE 32

Example of sgRNA pair sequences for
deletions in the allergen Ara h 14 (SEQ ID
NO 14), targeting *A. ipaensis* genome in
peanut using the Online CHOCHOP sgRNA
design tool. The distance between the
two sgRNAs is underlined bold. sgRNA1
and sgRNA2 are on the left and right
side of the underlined area
respectively. Ideally, the pair of
nickase sgRNA Sequences that have
Zero (0) Off-target in the peanut
genome are selected.

| Nickase sgRNA Pair Sequence (5' to 3') Deletions with Zero (0) Off-target Nickase Pair | SEQ ID NO | Genome position |
|---|---|---|
| CGACCGCGGGAACTATAACCG GGTTACCATTGGACT*CCGTGA GAATACCAGTGACTGCA* | 170 | 207 |
| GACGGCGATGATTTGAGAGGTG GCTCGTCGGCGTCCCCACTGGG *CCGGAGAGGAGCAACAGAGTGCC* | 171 | 137 |

TABLE 33

Example of sgRNA pair sequences for
deletions in the allergen Ara h 15 (SEQ ID
NO 15), targeting *A. duranensis* genome
in peanut using the Online CHOCHOP sgRNA
design tool. The distance between the two
sgRNAs is underlined bold. sgRNA1 and sgRNA2
are on the left and right side of the
underlined area respectively. Ideally,
the pair of nickase sgRNA Sequences
that have Zero (0) Off-target in the
peanut genome are selected.

| Nickase sgRNA Pair Sequence (5' to 3') Deletions with Zero (0) Off-target Nickase Pair | SEQ ID NO | Genome position |
|---|---|---|
| CCAGCCACCAAAAACCCATTTA CCATTATGTCTGATCAAACAAC *CCTCCTCCTCCATAGCCTGTCC* | 172 | 41 |

TABLE 34

Example of sgRNA pair sequences for
deletions in the allergen Ara h 15 (SEQ ID
NO 15), targeting *A. ipaensis* genome in
peanut using the Online CHOCHOP sgRNA
design tool. The distance between the
two sgRNAs is underlined bold. sgRNA1
and sgRNA2 are on the left and right
side of the underlined area
respectively. Ideally, the pair
of nickase sgRNA Sequences that
have Zero (0) Off-target in
the peanut genome are selected.

| Nickase sgRNA Pair Sequence (5' to 3') Deletions with Zero (0) Off-target Nickase Pair | SEQ ID NO | Genome position |
|---|---|---|
| CCAGCCACCAAAAACCCATTTA CCATTATGTCTGATCAAACAA *CCCTCCTCCTCCATAGCCTGTCC* | 173 | 41 |

The invention will now be described with reference to the
following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Figure 8:
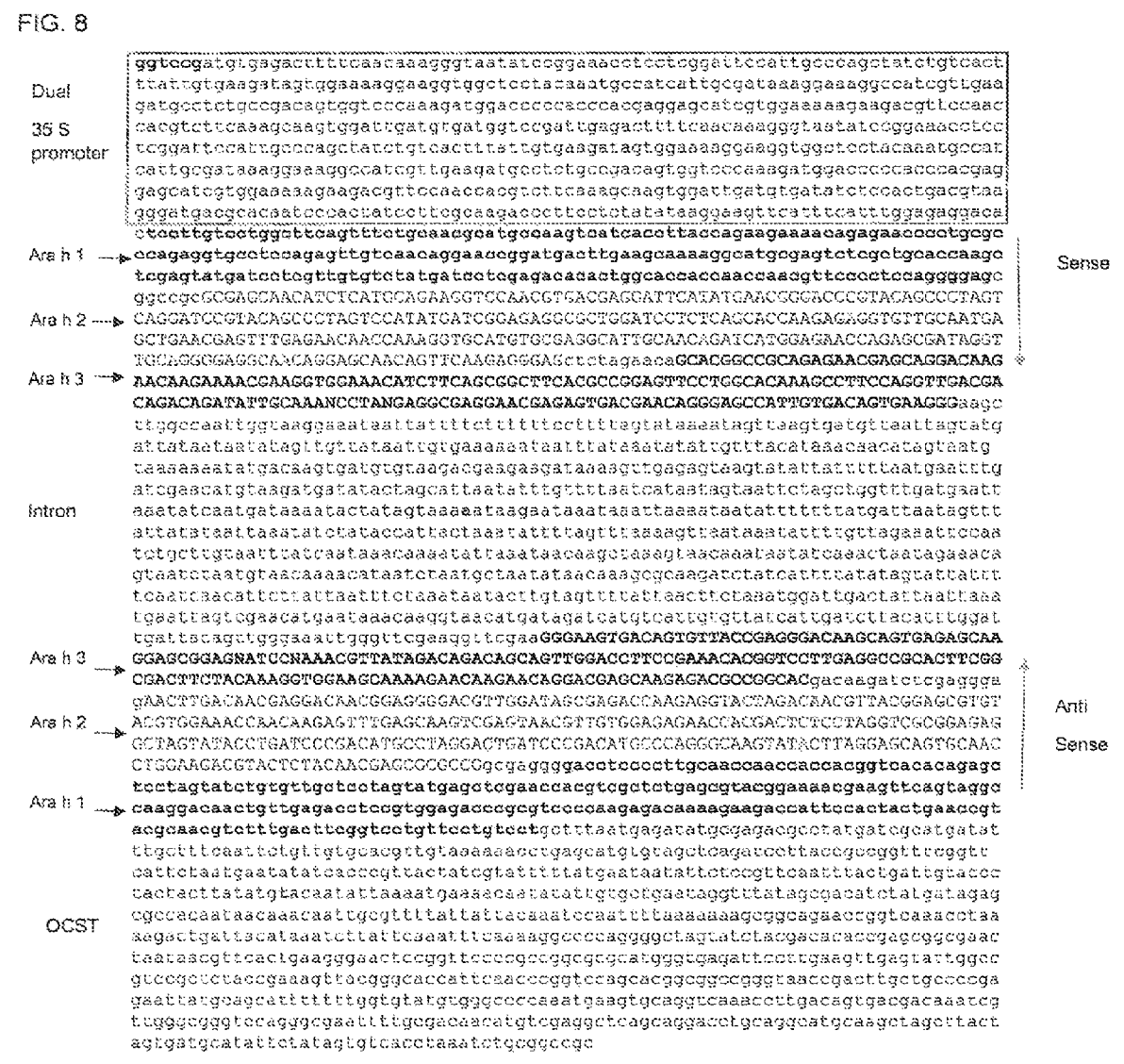
Figure 28:
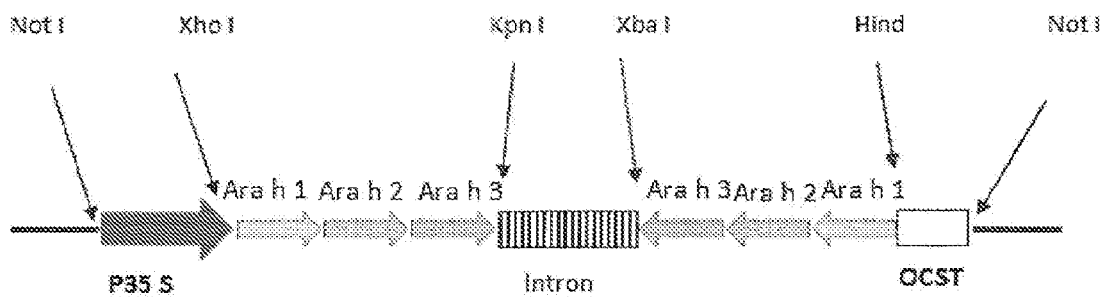
FIG. 28. A schematic diagram of IGG-NR-17.

A DNA construct was synthesized that encodes a DS-RNA stem-and-loop structure, having the structure shown in FIG. 8. As shown in FIG. 28, the construct comprises a promoter, a sense region with three Ara h homology sequences (to Ara h1, h2, and h3), a loop-forming intron, an antisense region that hybridizes with the sense region, and a terminator. This construct was cloned into a plasmid (see FIG. 27 for the structure of the plasmid). For the sequence of Ara h 2, a portion was selected which has nucleotide sequence homology with Ara h6 and Ara h 7. Therefore, the chimeric Ara h DNA was designed to target the downregulation of the five allergens Ara h 1, Ara h 2, Ara h 3, Ara h 6 and Ara h 7 concomitantly. This chimeric gene was cloned into the plasmid pHannibal (Wesley et al, 2001) in sense and antisense, separated by an intron. This inverted repeat structure was under the control of the regulatory elements CaMV 35s promoter and OCST Terminator. Cloning in pHannibal linked the Ara h RNAi expression cassette to the neomycin phosphotransferase II (NPT II) selection marker expression cassette. Both the Ara h RNAi expression cassette and the NPT II selection marker expression cassette were subcloned into the binary vector pART27 (Gleave, 1992) to make the genetic construct pDK30.

The genetic construct pDK30 was mobilized into *Agrobacterium tumefaciens* strain EHA105. Peanut genetic transformation was performed by inoculating (co-culture) peanut cells with EHA105 containing pDK30. Following the co-culture period of 3-5 days, peanut cells were transferred onto a selection medium supplemented with the antibiotic kanamycin. Peanut cells which were found resistant to kanamycin grew to regenerate plants which were considered putatively transgenic. Southern blot experiments confirmed the stable transformation of peanut.

Figure 29:
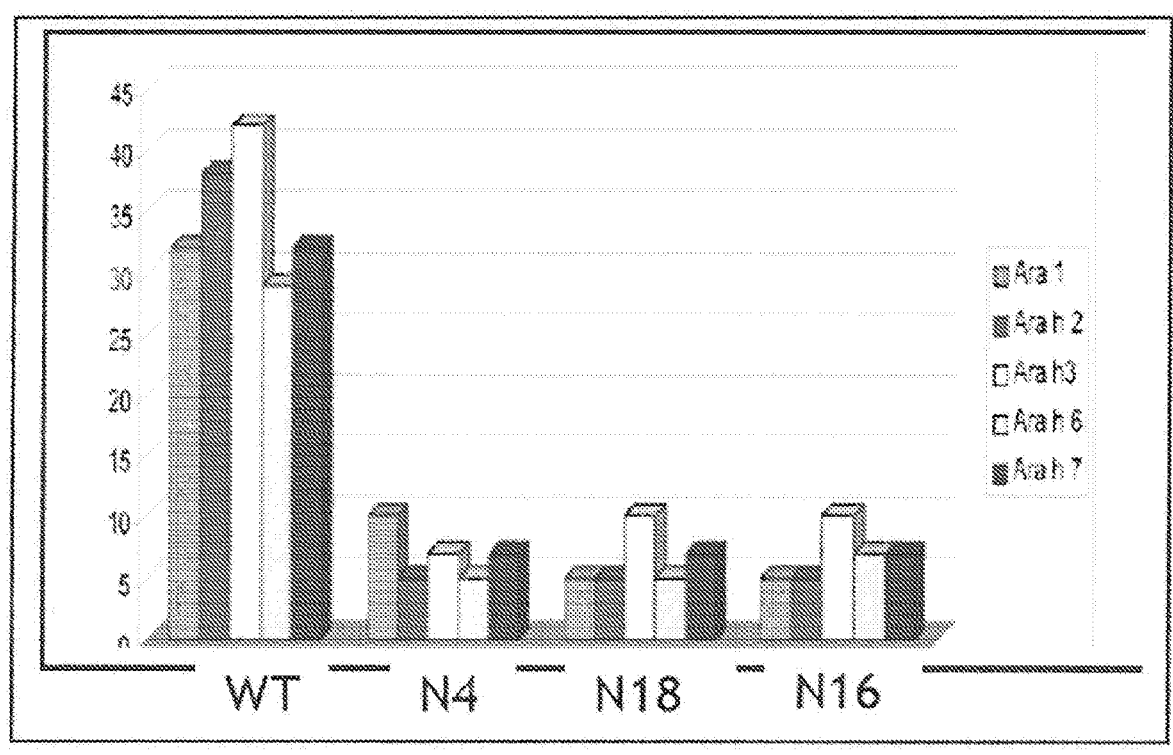
FIG. 29. Quantitative real time PCR of RNA transcripts for Ara h 1, Ara h 2, Ara h 3, Ara h 6 and Ara h 7, showing significant reduction in transgenic peanut lines N4, N18 and N16 compared to control WT.

FIG. 29 shows quantitative RT PCR to quantify the amount of messenger RNA present in seeds of the first generation of transformant plants using primers for Ara h1-3, 6, and 7. Bars average values of seeds from a single plant. N4, N18, and N16 all show lower levels of Ara h expression than the wild type. Seeds were collected from the control non transgenic peanut plant (WT), and from three (3) different plant lines (N4, N16, N18) of the transgenic plants obtained from transformation using pDK30. N4, N16 and N18 are three individual plant lines obtained from different transformation experiments performed using pDK30. RNA was extracted from the seeds of N4, N16 and N18 and RT-qPCR was performed. The levels of messenger RNA in seeds from N4, N16 and N18 were significantly lower compared to that of the control WT plant.

Figure 30:
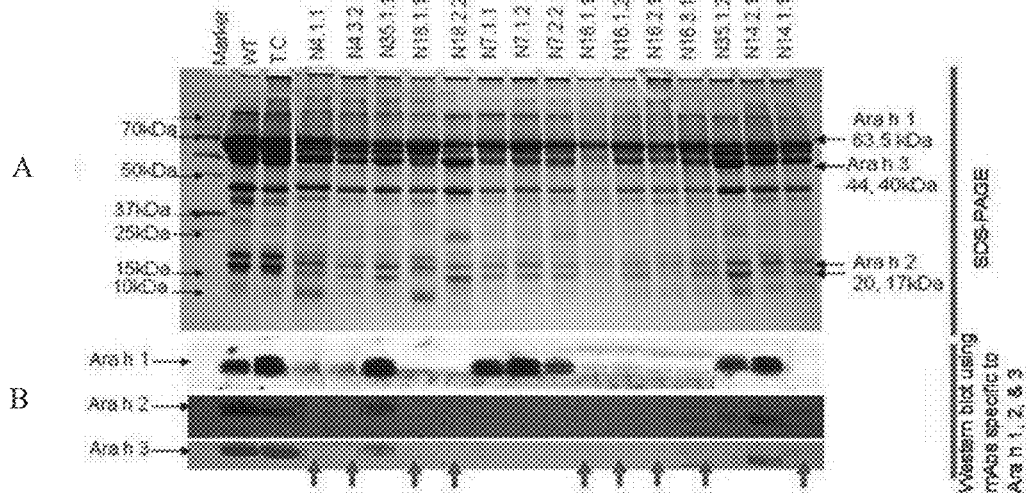
FIG. 30. SDS page (panel A) and Western blots (panel B) of protein extracts of peanut seeds from first generation genetically modified peanuts.
Figure 32:
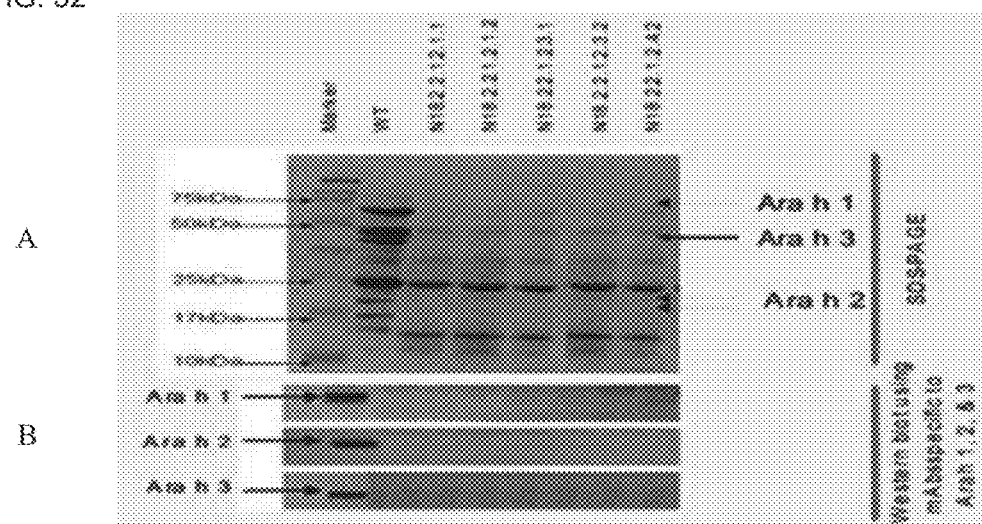
FIG. 32. SDS page (panel A) and Western blots (panel B) of protein extracts of peanut seeds from third generation genetically modified peanuts.
Figure 34A:
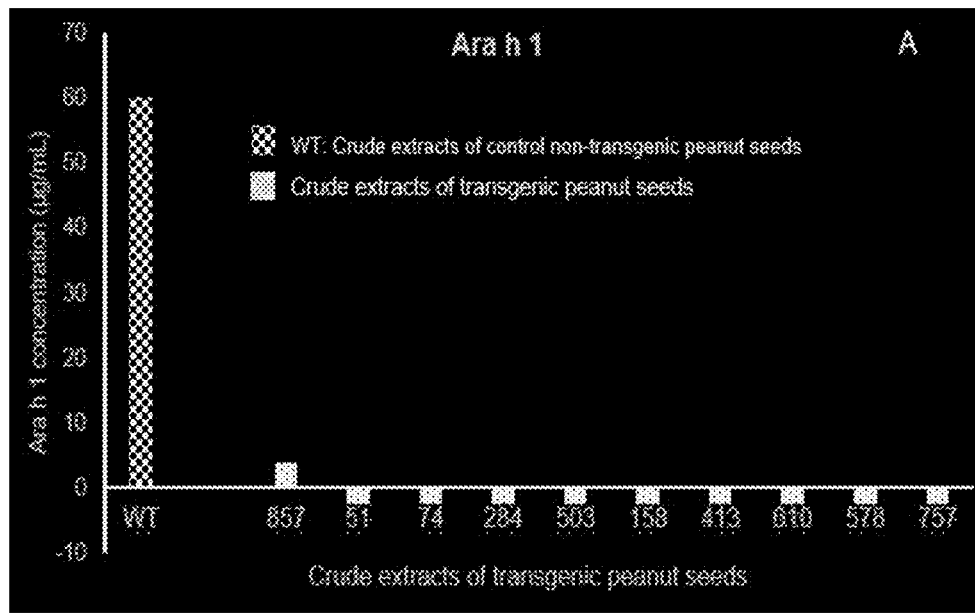
FIG. 34. Quantification of allergens Ara h 1 (panel A) and Ara h 2 (panel B) in crude extract of the peanut seeds of genetically modified peanut using Arah-siRNA constructs.
Figure 34B:
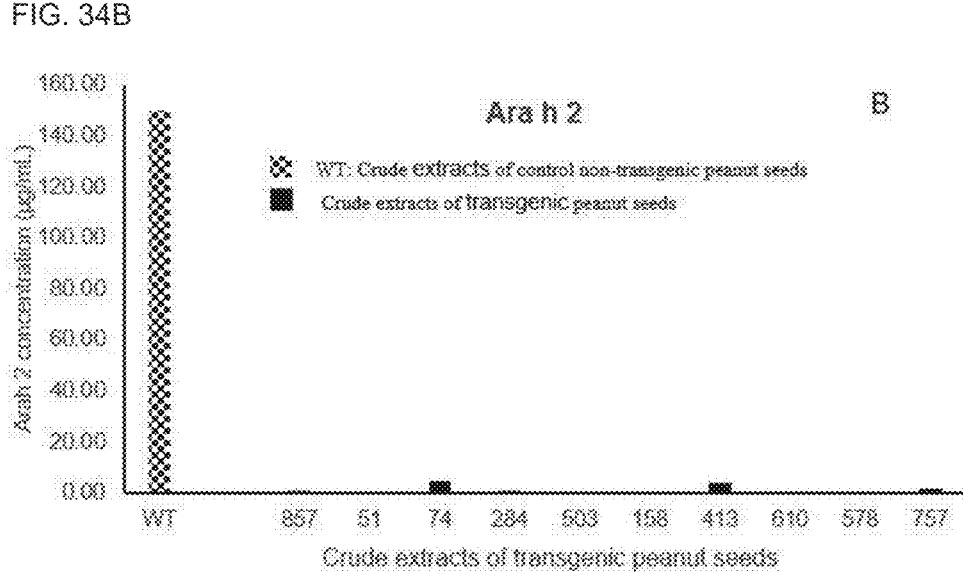

FIG. 30 is a Western blot of Ara h1, 2, and 3 concentrations in peanut seeds using SDSPAGE (top gel) and antibody probes (bottom gel). The lanes each contain crude extract from peanut seeds of one individual plant. The N4 plants, N18 plants, and N16 plants show reduced Ara h protein, as does one of two N14 plants. FIG. 32 shows Western blots of the progeny of a self-cross of N18.2.2 (second generation). FIG. 34 shows Western blots of the progeny of a self-cross of N18.2.2.1.2 (third generation). In each case, the amount of the Ara h peptides was reduced compared to WT.

Figure 31:
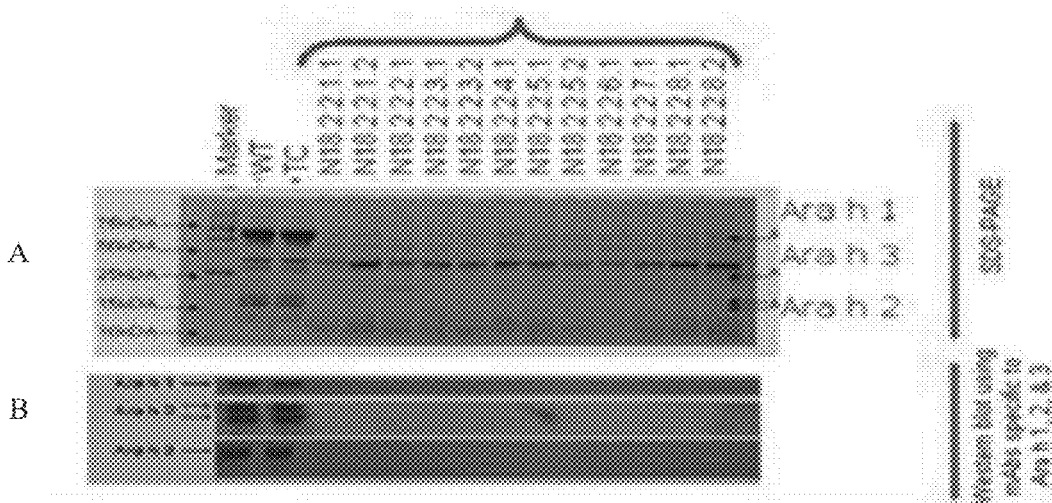
FIG. 31. SDS page (panel A) and Western blots (panel B) of protein extracts of peanut seeds from second generation genetically modified peanuts.

While FIG. 30 shows the levels of messenger RNA in the seeds, FIGS. 30-32 show the protein profile (SDS PAGE) in peanut seeds harvested from the 1st, 2nd and 3rd generations of transgenic plants respectively. The seed number N18.2.2 from the 1st generation of the N18 plant (FIG. 30) was sowed to produce a plant, the 2nd generation of plant. Seeds harvested from this 2nd generation plant were numbered N18.2.2.1.1 through N18.2.2.8.2. Similarly, the seed number N18.2.2.1.2 from the 2nd generation (FIG. 31) was sowed to produce a plant, the 3rd generation of plant. Seeds harvested from this 3rd generation plant (FIG. 32) were numbered (N18.2.2.1.2.1.1 through N18.2.2.1.2.4.2).

Then the seed proteins separated by SDS PAGE were transferred onto membranes for Western blots. Detection was performed using monoclonal antibodies specific to each one of the allergens Ara h 1, Ara h 2 and Ara h 3. Monoclonal antibodies against Ara h 6 and Ara h 7 were not available. In Western blots analyses the allergens Ara h 1, Ara h 2 and Ara h 3 were not detected in the 1st generation seed N18.2.2, or in the 2nd and 3rd generations of the progeny of this seed (FIGS. 30-32, respectively).

Example 2

Microprojectile-Mediated Genetic Transformation

Microprojectile-mediated genetic transformation of peanut Globular Repetitive Somatic Embryogenic tissue was performed. Peanut zygotic embryos were used to induce globular Repetitive Somatic Embryos (gRSEs). gRSEs were then transformed with the Arah-RNAi construct using the particle bombardment system. Transgenic tissue was submitted to hygromycin selection pressure, and transgenic somatic embryos were isolated and allowed to grow to maturity. First generation transgenic plants (TO plants) were recovered from the embryos (A), the plants flowered (B) and subsequently produced seeds (T1) seeds (C)

Example 3

Sandwich ELISA

Sandwich ELISA was performed (FIG. 33) and shows: Allergen Ara h 1 was 93.5% to 100% eliminated from the transgenic peanut seeds (FIG. 33, panel A). Similarly, while Ara h 2, concentration in the WT control sample was 1,667 µg/mL, the transgenic protein samples displayed concentrations ranging from 0.9 to 4.6 µg/mL, representing 360 to over 1000 times reduction (FIG. 33, panel B) in the Ara h 2 content of the transgenic seeds. Thus, a significant reduction and/or elimination of allergens Ara h 1 and Ara h 2 in the peanut seeds is demonstrated.

The foregoing description illustrates and describes the processes, manufactures, compositions of matter, and other teachings of the present disclosure. Additionally, the disclosure shows and describes only certain embodiments of the processes, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, manufactures, compositions of matter, and other teachings of the present disclosure and to enable others skilled in the art to utilize the teachings of the present disclosure in such, or 5 other, embodiments and with the various modifications required by the particular applications or uses. Accordingly, the processes, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

That which is claimed is:

1. A nucleic acid construct comprising:
   a CRISPR guide sequence targeting an Ara h2 gene of SEQ ID NO: 3, wherein the CRISPR guide sequence comprises one or more of a single guide RNA (sgRNA) pair, wherein the sgRNA pair comprises a first sgRNA and a second sgRNA, and wherein the sgRNA pair comprise
   a nucleotide sequence comprising the first sgRNA having at least 95% complementarity to nucleotides 1 to 23 and the second sgRNA having at least 95% complementarity to nucleotides 35 to 57 of SEQ ID NO: 77.

2. The nucleic acid construct of claim 1, wherein the CRISPR guide sequence comprises two or more copies of the first sgRNA and the second sgRNA.

3. The nucleic acid construct of claim 1, further comprising a scaffold sequence for binding a CRISPR Cas endonuclease.

4. The nucleic acid construct of claim 1, further comprising a polynucleotide encoding at least one CRISPR Cas endonuclease.

5. The nucleic acid construct of claim 4, wherein the CRISPR guide sequence and the polynucleotide encoding the at least one CRISPR Cas endonuclease are operably linked to a single promoter or are operably linked to separate promoters that are the same promoter or different promoters.

6. The nucleic acid construct of claim 1, further comprising a second CRISPR guide sequence targeting an Ara h1 gene of SEQ ID NO: 2,
   wherein the second CRISPR guide sequence targeting an Ara h1 gene of SEQ ID NO: 2 comprises one or more of a first sgRNA and a second sgRNA, and wherein the first sgRNA and second sgRNA are selected from:
   i) the first sgRNA having at least 95% complementarity to nucleotides 1 to 23 of SEQ ID NO: 51 and the second sgRNA having at least 95% complementarity to nucleotides 35 to 57 of SEQ ID NO: 51;
   ii) the first sgRNA having at least 95% complementarity to nucleotides 1 to 23 of SEQ ID NO: 53 and the second sgRNA having at least 95% complementarity to nucleotides 47 to 59 of SEQ ID NO: 53;
   iii) the first sgRNA having at least 95% complementarity to nucleotides 1 to 23 of SEQ ID NO: 60 and the second sgRNA having at least 95% complementarity to nucleotides 46 to 58 of SEQ ID NO: 60; or
   iv) the first sgRNA having at least 95% complementarity to nucleotides 1 to 23 of SEQ ID NO: 64 and the second sgRNA having at least 95% complementarity to nucleotides 47 to 69 of SEQ ID NO: 64.

7. The nucleic acid construct of claim 1, wherein the CRISPR guide sequence further comprises a CRISPR guide sequence targeting an Ara h6 gene of SEQ ID NO: 6,
   wherein the CRISPR guide sequence targeting an Ara h6 gene of SEQ ID NO: 6 comprises one or more of:
   i) a nucleotide sequence having at least 95% complementarity to 1 to 23 and nucleotides 38 to 60 of SEQ ID NO: 114; or
   ii) a nucleotide sequence having at least 95% complementarity to 1 to 23 and nucleotides 50 to 72 of SEQ ID NO: 116.

8. An expression cassette or vector comprising the nucleic acid construct of claim 1.

9. A method of reducing the production of at least one *Arachis hypogaea* allergen (Ara h) polypeptide in a peanut plant, plant part and/or cell, comprising:
   introducing into the peanut plant, plant part and/or cell at least one nucleic acid construct of claim 1 to produce a genetically modified peanut plant, plant part and/or cell comprising a mutation in at least one Ara h gene, thereby reducing production of the at least one Ara h polypeptides in the peanut plant, plant part and/or cell.

10. The method of claim 9, further comprising regenerating a genetically modified peanut plant from the genetically modified peanut cell and producing seed from the genetically modified peanut plant, wherein production of at least one *Arachis hypogaea* allergen (Ara h) polypeptide in the seed is reduced.

11. The method of claim 9, wherein peanut plant, plant part and/or cell is a plant part, and the plant part is a peanut seed comprising reduced production of the at least two Ara h polypeptides.

12. A peanut seed produced by the method of claim 9, wherein the seed comprises the mutations in the Ara h genes.

13. A product produced from the peanut seed of claim 12, wherein the product comprises the mutations in the Ara h genes.

14. The product of claim 13, wherein the product is a food product, wherein the food product is salted peanuts, roasted peanuts, boiled peanuts, candied peanuts, peanut meal, peanut butter, peanut milk, butter from peanut milk, peanut flour, peanuts coated with chocolate or other confections, peanut brittle, peanut protein hydrolysate, peanut nougat, peanut sauces, peanut pesto, peanut mole sauce, peanut marzipan, peanut cookies, peanut pies, peanut chikki, peanut hearts, peanut food bars, peanut granola, peanut brownies, peanut animal feed, and/or groundnut cake.

* * * * *